US008796275B2

(12) United States Patent
Scott et al.

(10) Patent No.: US 8,796,275 B2
(45) Date of Patent: Aug. 5, 2014

(54) ANTI-MALARIAL COMPOUNDS

(75) Inventors: Richard W. Scott, Radnor, PA (US);
Doron Greenbaum, Philadelphia, PA (US); Dahui Liu, Wynnewood, PA (US);
Xiaodong Fan, Center Valley, PA (US);
Yongjiang Xu, Wayne, PA (US);
Haizhong Tang, Lawrenceville, NJ (US); Ehab Khalil, Whitehouse Station, NJ (US)

(73) Assignees: The Trustees of the University of Pennsylvania, Philadelphia, PA (US);
Cellceutix Corporation, Beverly, MA (US)

( * ) Notice: Subject to any disclaimer, the term of this patent is extended or adjusted under 35 U.S.C. 154(b) by 489 days.

(21) Appl. No.: 12/510,593

(22) Filed: Jul. 28, 2009

(65) Prior Publication Data

US 2010/0081665 A1   Apr. 1, 2010

Related U.S. Application Data

(60) Provisional application No. 61/162,467, filed on Mar. 23, 2009, provisional application No. 61/083,972, filed on Jul. 28, 2008.

(51) Int. Cl.
| C07D 241/04 | (2006.01) |
| C07D 209/58 | (2006.01) |
| C07D 307/91 | (2006.01) |
| C07D 333/76 | (2006.01) |
| A61K 31/381 | (2006.01) |

(52) U.S. Cl.
USPC .................. 514/252.13; 514/253.01; 514/337; 514/443; 544/357; 544/360; 546/281.1; 549/43

(58) Field of Classification Search
USPC .................. 544/357, 360; 546/281.1; 549/43; 514/252.13, 253.01, 337, 443
See application file for complete search history.

(56) References Cited

U.S. PATENT DOCUMENTS

| 3,218,337 | A |   | 11/1965 | Bryson et al. |
| 3,450,772 | A |   | 6/1969 | Bridger et al. |
| 5,066,409 | A |   | 11/1991 | Nader |
| 5,310,726 | A | * | 5/1994 | Balkovec ...................... 514/3.3 |
| 5,641,737 | A |   | 6/1997 | Forster |
| 5,798,340 | A | * | 8/1998 | Bischofberger et al. ........ 514/45 |
| 6,172,104 | B1 |  | 1/2001 | Tidwell et al. |
| 6,229,012 | B1 |  | 5/2001 | Hu et al. |
| 6,548,483 | B2 | * | 4/2003 | Hageman et al. ............... 514/23 |
| 6,645,531 | B1 | * | 11/2003 | Antelman ...................... 424/635 |
| 2002/0165236 | A1 | | 11/2002 | Schenbrenner et al. |
| 2003/0109570 | A1 | | 6/2003 | Tsunoda et al. |
| 2005/0075460 | A1 | | 4/2005 | McHugh et al. |
| 2005/0287108 | A1 | | 12/2005 | DeGrado et al. |
| 2006/0041023 | A1 | | 2/2006 | DeGrado et al. |
| 2006/0134538 | A1 | * | 6/2006 | Radu et al. ................. 430/58.15 |
| 2007/0224446 | A1 | * | 9/2007 | Nakano et al. ................ 428/690 |
| 2008/0131731 | A1 | | 6/2008 | Igawa et al. |

FOREIGN PATENT DOCUMENTS

| CN | 1694591 | | 11/2005 |
| CN | 1701111 | | 11/2005 |
| JP | 2005-112765 | * | 4/2005 |
| JP | 2006-521355 | | 9/2006 |
| WO | 02/39987 A2 | | 5/2002 |
| WO | 2004082634 | | 9/2004 |
| WO | 2006093813 | | 9/2006 |
| WO | 2008/083256 A2 | | 7/2008 |

OTHER PUBLICATIONS

Dartiguelongue et al., CAPLUS Abstract 145:10769 (2005).*
Cho et al., CAPLUS Abstract 141:106226 (2004).*
Kumazoea et al., CAPLUS Abstract 139:149478 (2003).*
Monsanto Chemicals Ltd., CAPLUS Abstract 60:9678 (1964).*
Cushion et al., Effects of Atovaquone and Diospyrin-based Drugs on the Cellular ATP of *Pnemocystis carinii* f. sp. *carinii*, Antimicrobial Agents and Chemotherapy, vol. 44, No. 3, pp. 713-719 (Mar. 2000).*
Pearson, Atovaquone/Proguanil for the Treatment of Prevention of Malaria, Clinical Trials Report, pp. 47-49, 2001.*
Shimimura et al., CAPLUS Abstract 142:400323 (2005).*
Possani, L. D., et al., From noxiustoxin to Shiva-3, a peptide toxic to the sporogonic development of *Plasmodium berghei*, Toxicon, Nov. 1998;36(11):1683-92.
Gwadz, R. W., et al., Effects of magainins and cecropins on the sporogonic development of malaria parasites in mosquitoes, Infect Immun., Sep. 1989;57(9):2628-33.
Arrighi, R. B., et al., Design and activity of antimicrobial peptides against sporogonic-stage parasites causing murine malarias, Antimicrob Agents Chemother., Jul. 2002;46(7):2104-10.
Feder, R., et al., Structure-activity relationship study of antimicrobial dermaseptin S4 showing the consequences of peptide oligomerization on selective cytotoxicity, J Biol Chem., Feb. 11, 2000;275(6):4230-8.
Krugliak, M., et al., Antimalarial activities of dermaseptin S4 derivatives, Antimicrob Agents Chemother., Sep. 2000;44(9):2442-51.
Dagan, A., et al., In vitro antiplasmodium effects of dermaseptin S4 derivatives, Antimicrob Agents Chemother. Apr. 2002;46(4):1059-66.
Efron, L., et al., Direct interaction of dermaseptin S4 aminoheptanoyl derivative with intraerythrocytic malaria parasite leading to increased specific antiparasitic activity in culture, J Biol Chem., Jul. 5, 2002;277(27):24067-72. Epub Apr. 5, 2002.
International Search Report dated Nov. 25, 2009.
Choi, S., et al., The design and evaluation of heparin-binding foldamers, Angew Chem Int Ed Engl. Oct. 21, 2005;44 (41):6685-9.
Choi, S., et al., De novo design and in vivo activity of conformationally restrained antimicrobial arylamide foldamers, Proc Natl Acad Sci U S A. Apr. 28, 2009;106(17):6968-73.

(Continued)

*Primary Examiner* — Deepak Rao

(74) *Attorney, Agent, or Firm* — Pepper Hamilton LLP

(57) ABSTRACT

The present invention provides tricyclic compounds, arylamide compounds, and other compounds, and compositions comprising the same, for treating malaria, and methods of treating malaria comprising administering such compounds to an animal.

20 Claims, No Drawings

(56) References Cited

OTHER PUBLICATIONS

Bigdeli et al. "Ab initio study of atropisomers of 1,8-di-pyridine 9H-fluorene, dibenzo[b,d]furan, 9H-cabazole and dibenzo[b,d]thiophene", J. Molecular Structure: Theochem, (2008) vol. 860, 64-79.

Heikkila et al. "Design and synthesis of potent inhibitors of the malaria parasite dihydroorotate dehydrogenase", J. Med Chem. (2007) 50(2):186-191.

Cho, Yong-Hwan et al. "Asymmetric synthesis of axially chiral biaryls by nickel-catalyzed grignard cross-coupling of dibenzothiophenes", J Org. Chem. (2004) 69(11):3811-3823.

STN Registry No. 1623-91-2, (1984).

STN Registry No. 2914-39-8, (1984).

"CAS RN," CAS, STN-Registry (Oct. 7, 2008).

* cited by examiner

ANTI-MALARIAL COMPOUNDS

CROSS-REFERENCE TO RELATED APPLICATIONS

This application claims priority under 35 U.S.C. §119(e) to U.S. provisional application Ser. No. 61/162,467 filed Mar. 23, 2009 and to U.S. provisional application Ser. No. 61/083,972 filed Jul. 28, 2008, each of which is incorporated herein by reference in its entirety.

FIELD OF THE INVENTION

The present invention is directed, in part, to tricyclic compounds, arylamide compounds, and other compounds, and compositions comprising the same, for treating malaria, and methods of treating malaria comprising administering such compounds to an animal.

BACKGROUND OF THE INVENTION

World-wide, 41% of the population live in areas where malaria is transmitted, such as parts of Africa, Asia, Middle East, Central and South America, Hispaniola, and Oceania. Each year between 350 and 500 million cases of malaria occur worldwide, and over one million people die, most of them young children in sub-Saharan Africa. In areas of Africa with high malaria transmission, an estimated 990,000 people died of malaria in 1995. In 2002, malaria was the fourth cause of death in children in developing countries. In addition, malaria caused 10.7% of all children's deaths in developing countries.

Antimicrobial peptides (AMPs) represent a component of the innate immune system that provides resistance to a variety of pathogenic bacteria. AMPs have provided new leads for developing antibiotics, because they play a central role in the innate immune system. Some AMPs display very broad spectrum action against bacteria, yeast, fungus, and even viruses. Anti-parasitic activities have also been reported for a number of host defense peptides. The best studied organisms include *Plasmodium, Leishmania*, and *Trypanosoma* (Vizioli et al., Trends in Pharmacol., 2002, 18, 475-476; Jacobs et al., Antimicrob. Agents Chemother., 2003, 47, 607-613; and Brand et al., J. Biol. Chem., 2002, 277, 49332-49340), the parasitic agents of malaria, leishmaniasis and Chagas' disease, respectively. Additional protozoan parasites reported to be killed by the host defense peptides are *Cryptosporidium* (Giacometti et al., Antimicrob. Agents Chemother., 2000, 44, 3473-3475) and *Giardia* (Aley et al., Infect. Immun., 1994, 62, 5397-5403), human pathogens transmitted in contaminated drinking water. The peptides appear to kill protozoa by interacting with the cytoplasmic membrane causing excessive permeability, lysis and death; a mechanism which is similar to their mechanism of action against bacteria. Specificity for the parasite versus the host cell can be attributed to differences in phospholipid content and the lack of cholesterol in the protozoan membrane. Because the site of action is at the membrane and not to any specific receptor or intracellular target, the development of resistance to the cytotoxic properties of the antimicrobial peptides is highly unlikely.

With regard to anti-malarial activities, natural host defense proteins and their analogs have been shown to inhibit oocyst development of several *Plasmodium* species in various mosquito hosts (Gwadz et al., Infect. Immun., 1989, 57, 2628-2633; and Possani et al., Toxicon, 1998, 36, 1683-1692) and are directly cytotoxic against early sporogonic stages of *Plasmodium* in cell culture (Arrighi et al., Antimicrob. Agents Chemother., 2002, 46, 2104-2110). Furthermore, several antimicrobial peptides have been identified which selectively kill intraerthrocytic parasites (plasmodia life forms growing in red blood cells) by either attacking the infected erythrocyte while sparring normal erthrocytes (Feder et al., J. Biol. Chem., 2000, 275, 4230-4238; and Krugliak et al., Antimicrob. Agents Chemother., 2000, 44, 2442-2451) or interacting with and killing the intracellular parasite without harming the infected red blood cell (Dagan et al., Antimicrob. Agents Chemother., 2002, 46, 1059-1066; and Efron et al., J. Biol. Chem., 2002, 277, 24067-24072). Recognizing the significant therapeutic limitations of peptides, the development of nonpeptidic mimics of these anti-plasmodia peptides would represent a novel and powerful therapy to combat malaria.

SUMMARY OF THE INVENTION

The present invention provides compounds of Formula I:

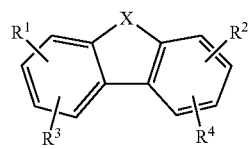

wherein: X is $C(R^7)C(R^8)$, $C(=O)$, $N(R^9)$, O, S, $S(=O)$, or $S(=O)_2$; $R^7$, $R^8$, and $R^9$ are, independently, H, $C_1$-$C_8$alkyl, $C_1$-$C_8$alkoxy, halo, OH, $CF_3$, or aromatic group; $R^1$ and $R^2$ are, independently, H, $C_1$-$C_8$alkyl, $C_1$-$C_8$alkoxy, halo, OH, halo$C_1$-$C_8$alkyl, or CN; $R^3$ and $R^4$ are, independently, carbocycle $(R^5)(R^6)$; each $R^5$ and each $R^6$ are, independently, H, $C_1$-$C_8$alkyl, $C_1$-$C_8$alkoxy, halo, OH, $CF_3$, aromatic group, heterocycle, or the free base or salt form of —$(CH_2)_n$—$NH_2$, —$(CH_2)_n$—NH—$(CH_2)_n$—$NH_2$, or —$(CH_2)_n$—NH—C($=$NH)$NH_2$, where each n is, independently, 1 to 8; or a pharmaceutically acceptable salt thereof, and compositions comprising the same and a pharmaceutically acceptable carrier.

The present invention also provides methods of treating malaria in an animal comprising administering to the animal a therapeutically effective amount of a compound of Formula I:

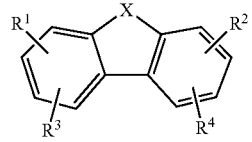

wherein: X is $C(R^7)C(R^8)$, $C(=O)$, $N(R^9)$, O, S, $S(=O)$, or $S(=O)_2$; $R^7$, $R^8$, and $R^9$ are, independently, H, $C_1$-$C_8$alkyl, $C_1$-$C_8$alkoxy, halo, OH, $CF_3$, or aromatic group; $R^1$ and $R^2$ are, independently, H, $C_1$-$C_8$alkyl, $C_1$-$C_8$alkoxy, halo, OH, halo$C_1$-$C_8$alkyl, or CN; $R^3$ and $R^4$ are, independently, carbocycle $(R^5)(R^6)$; each $R^5$ and each $R^6$ are, independently, H, $C_1$-$C_8$alkyl, $C_1$-$C_8$alkoxy, halo, OH, $CF_3$, aromatic group, heterocycle, or the free base or salt form of —$(CH_2)_n$—$NH_2$, —$(CH_2)_n$—NH—$(CH_2)_n$—$NH_2$, or —$(CH_2)_n$—NH—C($=$NH)$NH_2$, where each n is, independently, 1 to 8; or a pharmaceutically acceptable salt thereof.

The present invention also provides methods of killing or inhibiting the growth of a *Plasmodium* species comprising contacting the species with an effective amount of a compound of Formula I:

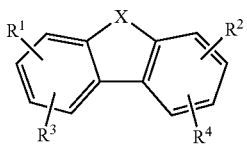

wherein: X is C(R$^7$)C(R$^8$), C(=O), N(R$^9$), O, S, S(=O), or S(=O)$_2$; R$^7$, R$^8$, and R$^9$ are, independently, H, C$_1$-C$_8$alkyl, C$_1$-C$_8$alkoxy, halo, OH, CF$_3$, or aromatic group; R$^1$ and R$^2$ are, independently, H, C$_1$-C$_8$alkyl, C$_1$-C$_8$alkoxy, halo, OH, haloC$_1$-C$_8$alkyl, or CN; R$^3$ and R$^4$ are, independently, carbocycle (R$^5$)(R$^6$); each R$^5$ and each R$^6$ are, independently, H, C$_1$-C$_8$alkyl, C$_1$-C$_8$alkoxy, halo, OH, CF$_3$, aromatic group, heterocycle, or the free base or salt form of —(CH$_2$)$_n$—NH$_2$, —(CH$_2$)$_n$—NH—(CH$_2$)$_n$—NH$_2$, or —(CH$_2$)$_n$—NH—C(=NH)NH$_2$, where each n is, independently, 1 to 8; or a pharmaceutically acceptable salt thereof.

The present invention also provides compounds of Formula II:

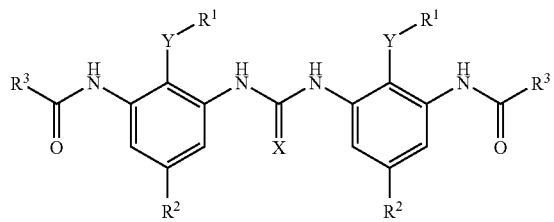

wherein: X is O or S; each Y is, independently, O, S, or N; each R$^1$ is, independently, H, 5- or 6-membered heterocycle, or the free base or salt form of —(CH$_2$)$_n$—NH$_2$ or —(CH$_2$)$_n$—NH—C(=NH)NH$_2$, where each n is, independently, 1 to 4; or each R$^1$ is, independently, together with Y a 5- or 6-membered heterocycle; each R$^2$ is, independently, H, CF$_3$, C(CH$_3$)$_3$, halo, or OH; and each R$^3$ is, independently, —(CH$_2$)$_n$—NH$_2$ or —(CH$_2$)$_n$—NH—C(=NH)NH$_2$, where each n is, independently, 1 to 4; or a pharmaceutically acceptable salt thereof, and compositions comprising the same and a pharmaceutically acceptable carrier.

The present invention also provides methods of treating malaria in an animal comprising administering to the animal a therapeutically effective amount of a compound of Formula II:

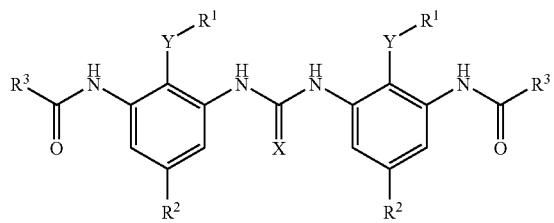

wherein: X is O or S; each Y is, independently, O, S, or N; each R$^1$ is, independently, H, 5- or 6-membered heterocycle, or the free base or salt form of —(CH$_2$)$_n$—NH$_2$ or —(CH$_2$)$_n$—NH—C(=NH)NH$_2$, where each n is, independently, 1 to 4; or each R$^1$ is, independently, together with Y a 5- or 6-membered heterocycle; each R$^2$ is, independently, H, CF$_3$, C(CH$_3$)$_3$, halo, or OH; and each R$^3$ is, independently, —(CH$_2$)$_n$—NH$_2$ or —(CH$_2$)$_n$—NH—C(=NH)NH$_2$, where each n is, independently, 1 to 4; or a pharmaceutically acceptable salt thereof.

The present invention also provides methods of killing or inhibiting the growth of a *Plasmodium* species comprising contacting the species with an effective amount of a compound of Formula II:

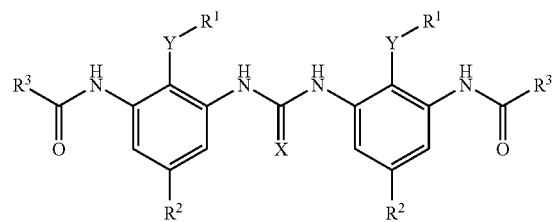

wherein: X is O or S; each Y is, independently, O, S, or N; each R$^1$ is, independently, H, 5- or 6-membered heterocycle, or the free base or salt form of —(CH$_2$)$_n$—NH$_2$ or —(CH$_2$)$_n$—NH—C(=NH)NH$_2$, where each n is, independently, 1 to 4; or each R$^1$ is, independently, together with Y a 5- or 6-membered heterocycle; each R$^2$ is, independently, H, CF$_3$, C(CH$_3$)$_3$, halo, or OH; and each R$^3$ is, independently, —(CH$_2$)$_n$—NH$_2$ or —(CH$_2$)$_n$—NH—C(=NH)NH$_2$, where each n is, independently, 1 to 4; or a pharmaceutically acceptable salt thereof.

The present invention also provides compounds of Formula III:

Q-X—Z—X-Q wherein: Z is

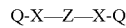

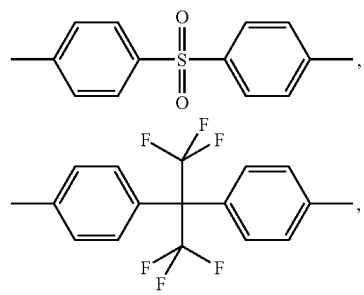

or phenyl; each Q is, independently,

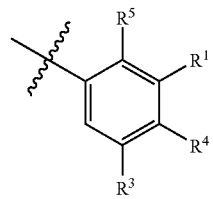

or —C(=O)—(CH$_2$)$_b$—NH—C(=NH)—NH$_2$, where each b is, independently, 1 to 4; each X is, independently, O, S, or N; each R$^1$ is, independently, H, CF$_3$, C(CH$_3$)$_3$, halo, or OH; each R$^3$ is, independently, H, —NH—R$^2$, (CH$_2$)$_r$—NH$_2$, —NH$_2$, —NH—(CH$_2$)$_w$—NH$_2$, or

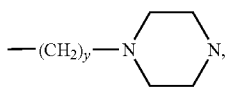

where each r is, independently, 1 or 2, each w is, independently, 1 to 3, and each y is, independently, 1 or 2; each $R^2$ is, independently, H, or the free base or salt form of —$(CH_2)_n$—$NH_2$ or —$(CH_2)_n$—NH—C(=NH)$NH_2$, where each n is, independently, 1 to 4; each $R^4$ is, independently, H, —NH—C(=O)—$(CH_2)_p$—NH—C(=NH)—$NH_2$ or

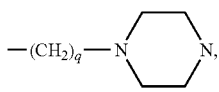

where each p is, independently, 1 to 6, and each q is, independently, 1 or 2; and each $R^5$ is, independently, H or $CF_3$; or a pharmaceutically acceptable salt thereof, and compositions comprising the same and a pharmaceutically acceptable carrier.

The present invention also provides methods of treating malaria in an animal comprising administering to the animal a therapeutically effective amount of a compound of Formula III:

Q-X—Z—X-Q wherein: Z is

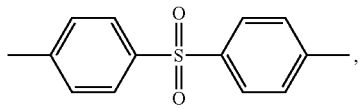

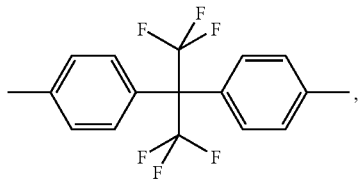

or phenyl; each Q is, independently,

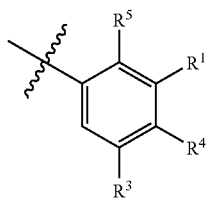

or —C(=O)—$(CH_2)_b$—NH—C(=NH)—$NH_2$, where each b is, independently, 1 to 4; each X is, independently, O, S, or N; each $R^1$ is, independently, H, $CF_3$, $C(CH_3)_3$, halo, or OH; each $R^3$ is, independently, H, —NH—$R^2$, —$(CH_2)_r$—$NH_2$, —$NH_2$, —NH—$(CH_2)_w$—$NH_2$, or

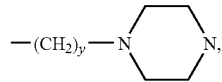

where each r is, independently, 1 or 2, each w is, independently, 1 to 3, and each y is, independently, 1 or 2; each $R^2$ is, independently, H, or the free base or salt form of —$(CH_2)_n$—$NH_2$ or —$(CH_2)_n$—NH—C(=NH)$NH_2$, where each n is, independently, 1 to 4; each $R^4$ is, independently, H, —NH—C(=O)—$(CH_2)_p$—NH—C(=NH)—$NH_2$ or

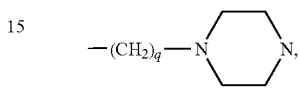

where each p is, independently, 1 to 6, and each q is, independently, 1 or 2; and each $R^5$ is, independently, H or $CF_3$, or a pharmaceutically acceptable salt thereof.

The present invention also provides methods of killing or inhibiting the growth of a *Plasmodium* species comprising contacting the species with an effective amount of a compound of Formula III:

Q-X—Z—X-Q wherein: Z is

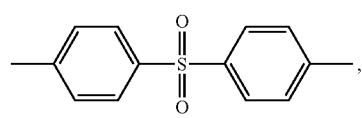

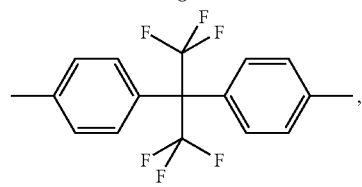

or phenyl; each Q is, independently,

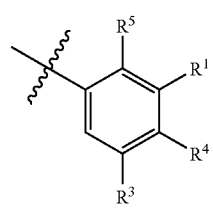

or —C(=O)—$(CH_2)_b$—NH—C(=NH)—$NH_2$, where each b is, independently, 1 to 4; each X is, independently, O, S, or N; each $R^1$ is, independently, H, $CF_3$, $C(CH_3)_3$, halo, or OH; each $R^3$ is, independently, H, —NH—$R^2$, —$(CH_2)_r$—$NH_2$, —$NH_2$, —NH—$(CH_2)_w$—$NH_2$, or

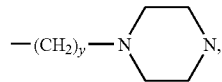

where each r is, independently, 1 or 2, each w is, independently, 1 to 3, and each y is, independently, 1 or 2; each $R^2$ is, independently, H, or the free base or salt form of —$(CH_2)_n$—$NH_2$ or —$(CH_2)_n$—NH—C(=NH)$NH_2$, where each n is, independently, 1 to 4; each $R^4$ is, independently, H, —NH—C(=O)—$(CH_2)_p$—NH—C(=NH)—$NH_2$ or

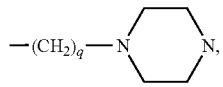

where each p is, independently, 1 to 6, and each q is, independently, 1 or 2; and each $R^5$ is, independently, H or $CF_3$, or a pharmaceutically acceptable salt thereof.

The present invention also provides compounds of Formula IV:

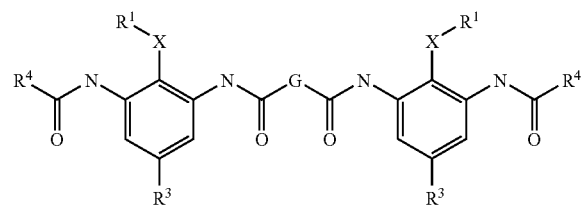

wherein: G is

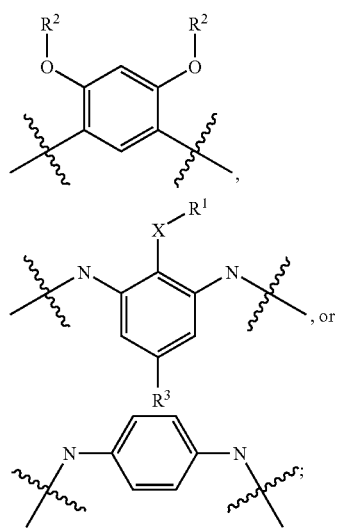

each X is, independently, O or S; each $R^1$ is, independently,

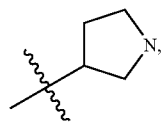

or the free base or salt form of —$(CH_2)_n$—$NH_2$ or —$(CH_2)_n$—NH—C(=NH)$NH_2$, where each n is, independently, 1 to 4; each $R^2$ is, independently, H, $C_1$-$C_8$alkyl, or the free base or salt form of —$(CH_2)_n$—$NH_2$ or —$(CH_2)_n$—NH—C(=NH)$NH_2$, where each n is, independently, 1 to 4; each $R^3$ is, independently, H, $CF_3$, $C(CH_3)_3$, halo, or OH; and each $R^4$ is, independently, —$(CH_2)_n$—$NH_2$ or —$(CH_2)_n$—NH—C(=NH)$NH_2$, where each n is, independently, 1 to 4, or a pharmaceutically acceptable salt thereof, and compositions comprising the same and a pharmaceutically acceptable carrier.

The present invention also provides methods of treating malaria in an animal comprising administering to the animal a therapeutically effective amount of a compound of Formula IV:

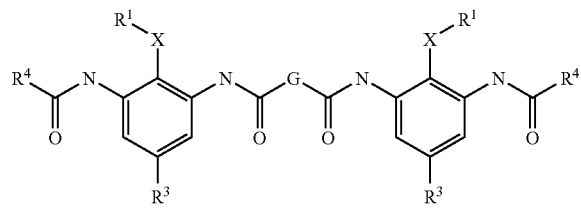

wherein: G is

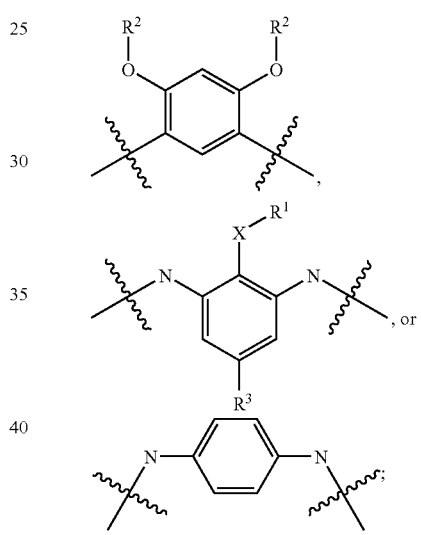

each X is, independently, O or S; each $R^1$ is, independently

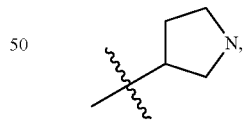

or the free base or salt form of —$(CH_2)_n$—$NH_2$ or —$(CH_2)_n$—NH—C(=NH)$NH_2$, where each n is, independently, 1 to 4; each $R^2$ is, independently, H, $C_1$-$C_8$alkyl, or the free base or salt form of —$(CH_2)_n$—$NH_2$ or —$(CH_2)_n$—NH—C(=NH)$NH_2$, where each n is, independently, 1 to 4; each $R^3$ is, independently, H, $CF_3$, $C(CH_3)_3$, halo, or OH; and each $R^4$ is, independently, —$(CH_2)_n$—$NH_2$ or —$(CH_2)_n$—NH—C(=NH)$NH_2$, where each n is, independently, 1 to 4, or a pharmaceutically acceptable salt thereof.

The present invention also provides methods of killing or inhibiting the growth of a *Plasmodium* species comprising contacting the species with an effective amount of a compound of Formula IV:

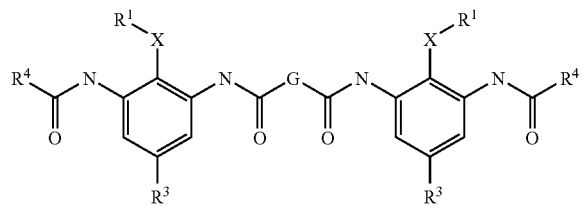

wherein: G is

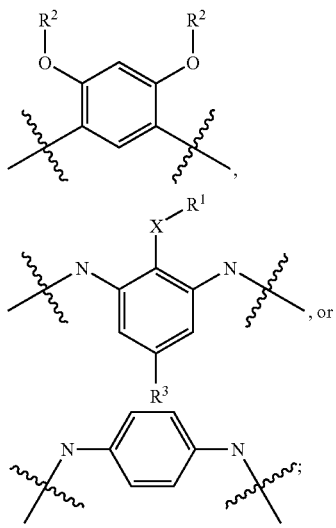

each X is, independently, O or S; each $R^1$ is, independently,

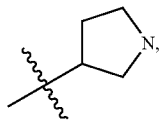

or the free base or salt form of $-(CH_2)_n-NH_2$ or $-(CH_2)_n-NH-C(=NH)NH_2$, where each n is, independently, 1 to 4; each $R^2$ is, independently, H, $C_1$-$C_8$alkyl, or the free base or salt form of $-(CH_2)_n-NH_2$ or $-(CH_2)_n-NH-C(=NH)NH_2$, where each n is, independently, 1 to 4; each $R^3$ is, independently, H, $CF_3$, $C(CH_3)_3$, halo, or OH; and each $R^4$ is, independently, $-(CH_2)_n-NH_2$ or $-(CH_2)_n-NH-C(=NH)NH_2$, where each n is, independently, 1 to 4, or a pharmaceutically acceptable salt thereof.

The present invention also provides compounds of Formula V:

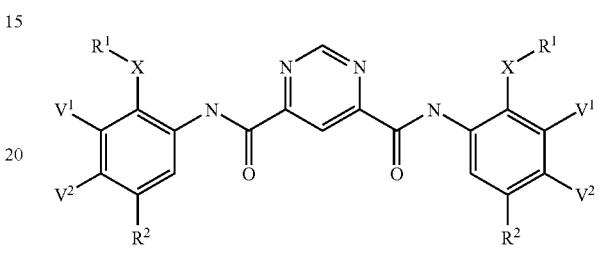

wherein: each X is, independently, O, S, or $S(=O)_2$; each $R^1$ is, independently, $-(CH_2)_n-NH_2$, $-(CH_2)_n-NH-C(=NH)NH_2$, or $-(CH_2)_n-NH-C(=O)-R^4$, where each n is, independently, 1 to 4, and each $R^4$ is, independently, H, $C_1$-$C_3$alkyl, or $-(CH_2)_p-NH_2$, where each p is, independently, 1 or 2; each $R^2$ is, independently, H, halo, $CF_3$, or $C(CH_3)_3$; and each $V^2$ is H, and each $V^1$ is, independently, $-N-C(=O)-R^3$, where each $R^3$ is, independently, $-(CH_2)_n-NH_2$ or $-(CH_2)_n-NH-C(=NH)NH_2$, where each n is, independently, 1 to 4; or each $V^1$ is H and each $V^2$ is, independently, $-S-R^5$, where each $R^5$ is, independently, $-(CH_2)_n-NH_2$ or $-(CH_2)_n-NH-C(=NH)NH_2$, where each n is, independently, 1 to 4; or a pharmaceutically acceptable salt thereof, and compositions comprising the same and a pharmaceutically acceptable carrier, provided that the compound is not:

a)

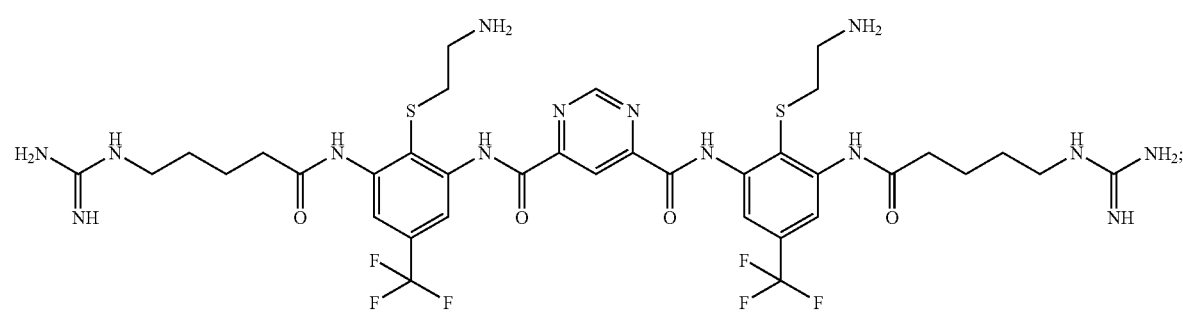 [SMILES: N=C(N)NCCCCC(=O)Nc1cc(C(F)(F)F)cc(NC(=O)c2cc(C(=O)Nc3cc(C(F)(F)F)cc(NC(=O)CCCCNC(=N)N)c3SCCN)ncn2)c1SCCN]

b)

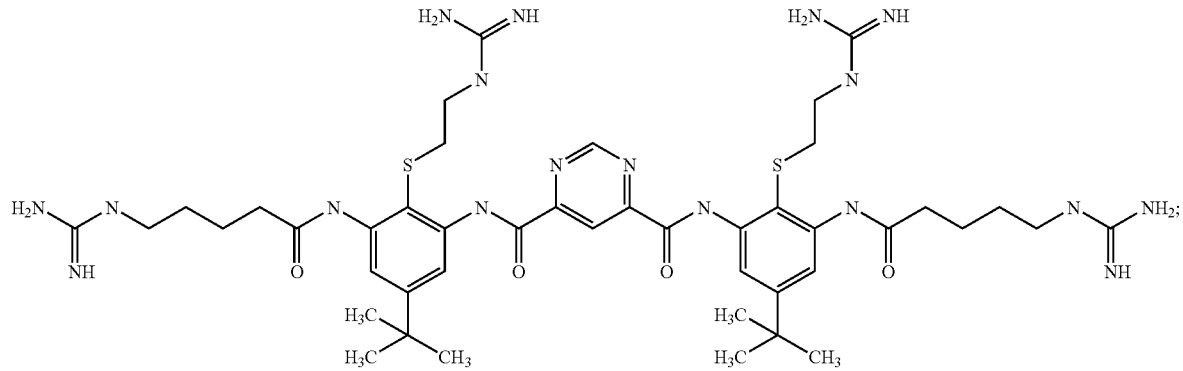 [SMILES: CC(C)(C)c1cc(NC(=O)CCCCNC(=N)N)c(SCCNC(=N)N)c(NC(=O)c2cc(C(=O)Nc3cc(C(C)(C)C)cc(NC(=O)CCCCNC(=N)N)c3SCCNC(=N)N)ncn2)c1]

or c)

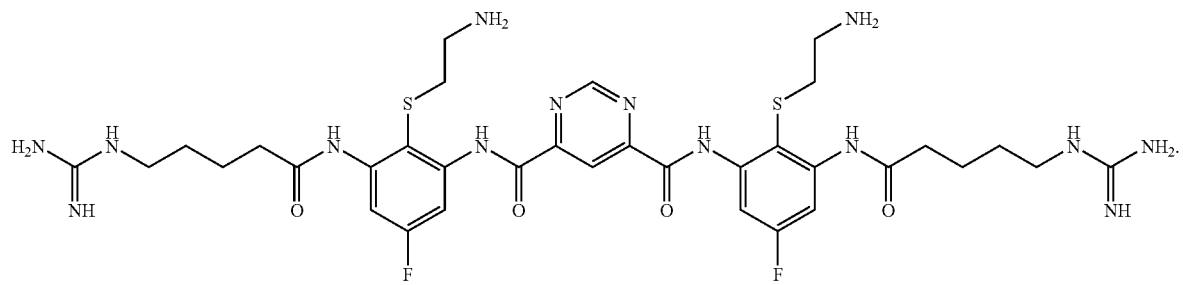 [SMILES: N=C(N)NCCCCC(=O)Nc1cc(F)cc(NC(=O)c2cc(C(=O)Nc3cc(F)cc(NC(=O)CCCCNC(=N)N)c3SCCN)ncn2)c1SCCN]

The present invention also provides methods of treating malaria in an animal comprising administering to the animal a therapeutically effective amount of a compound of Formula V:

The present invention also provides methods of killing or inhibiting the growth of a *Plasmodium* species comprising contacting the species with an effective amount of a compound of Formula V:

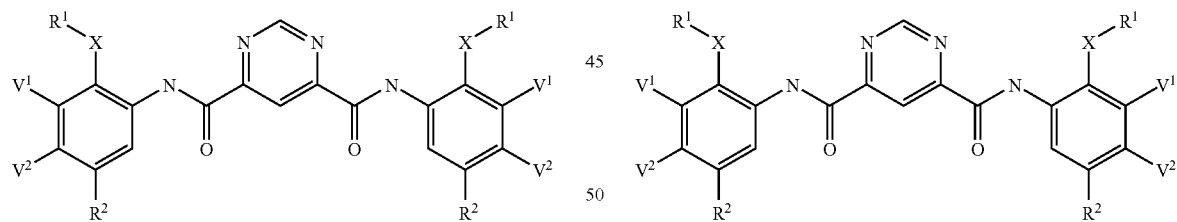

wherein: each X is, independently, O, S, or $S(=O)_2$; each $R^1$ is, independently, $-(CH_2)_n-NH_2$, $-(CH_2)_n-NH-C(=NH)NH_2$, or $-(CH_2)_n-NH-C(=O)-R^4$ where each n is, independently, 1 to 4, and each $R^4$ is, independently, H, $C_1$-$C_3$alkyl, or $-(CH_2)_p-NH_2$, where each p is, independently, 1 or 2; each $R^2$ is, independently, H, halo, $CF_3$, or $C(CH_3)_3$; and each $V^2$ is H, and each $V^1$ is, independently, $-N-C(=O)-R^3$, where each $R^3$ is, independently, $-(CH_2)_n-NH_2$ or $-(CH_2)_n-NH-C(=NH)NH_2$, where each n is, independently, 1 to 4; or each $V^1$ is H and each $V^2$ is, independently, $-S-R^5$, where each $R^5$ is, independently, $-(CH_2)_n-NH_2$ or $-(CH_2)_n-NH-C(=NH)NH_2$, where each n is, independently, 1 to 4; or a pharmaceutically acceptable salt thereof.

wherein: each X is, independently, O, S, or $S(=O)_2$; each $R^1$ is, independently, $-(CH_2)_n-NH_2$, $-(CH_2)_n-NH-C(=NH)NH_2$, or $-(CH_2)_n-NH-C(=O)-R^4$ where each n is, independently, 1 to 4, and each $R^4$ is, independently, H, $C_1$-$C_3$alkyl, or $-(CH_2)_p-NH_2$, where each p is, independently, 1 or 2; each $R^2$ is, independently, H, halo, $CF_3$, or $C(CH_3)_3$; and each $V^2$ is H, and each $V^1$ is, independently, $-N-C(=O)-R^3$, where each $R^3$ is, independently, $-(CH_2)_n-NH_2$ or $-(CH_2)_n-NH-C(=NH)NH_2$, where each n is, independently, 1 to 4; or each $V^1$ is H and each $V^2$ is, independently, $-S-R^5$, where each $R^5$ is, independently, $-(CH_2)_n-NH_2$ or $-(CH_2)_n-NH-C(=NH)NH_2$, where each n is, independently, 1 to 4; or a pharmaceutically acceptable salt thereof.

The present invention also provides compounds of Formula VI:

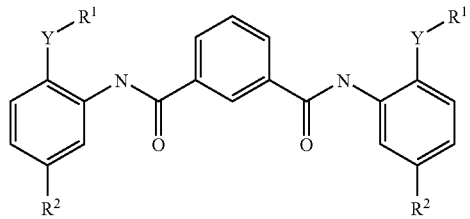

wherein: each Y is, independently, O, S, or NH; each $R^1$ is, independently, $-(CH_2)_n-NH_2$ or $-(CH_2)_n-NH-C(=NH)NH_2$, where each n is, independently, 1 to 4; and each $R^2$ is, independently, H, halo, $CF_3$, or $C(CH_3)_3$; or a pharmaceutically acceptable salt thereof, and compositions comprising the same and a pharmaceutically acceptable carrier.

The present invention also provides methods of treating malaria in an animal comprising administering to the animal a therapeutically effective amount of a compound of Formula VI:

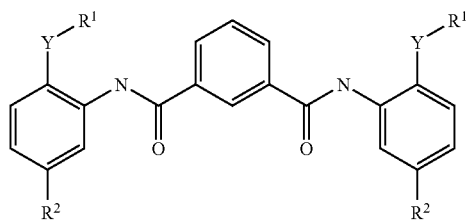

wherein: each Y is, independently, O, S, or NH; each $R^1$ is, independently, $-(CH_2)_n-NH_2$ or $-(CH_2)_n-NH-C(=NH)NH_2$, where each n is, independently, 1 to 4; and each $R^2$ is, independently, H, halo, $CF_3$, or $C(CH_3)_3$; or a pharmaceutically acceptable salt thereof.

The present invention also provides methods of killing or inhibiting the growth of a *Plasmodium* species comprising contacting the species with an effective amount of a compound of Formula VI:

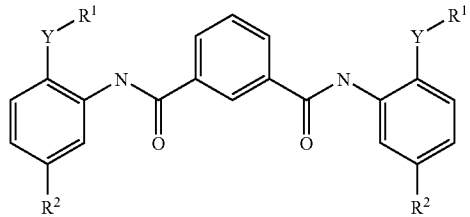

wherein: each Y is, independently, O, S, or NH; each $R^1$ is, independently, $-(CH_2)_n-NH_2$ or $-(CH_2)_n-NH-C(=NH)NH_2$, where each n is, independently, 1 to 4; and each $R^2$ is, independently, H, halo, $CF_3$, or $C(CH_3)_3$; or a pharmaceutically acceptable salt thereof.

The present invention also provides method of treating malaria in an animal comprising administering to the animal a therapeutically effective amount of a compound of Formula VII:

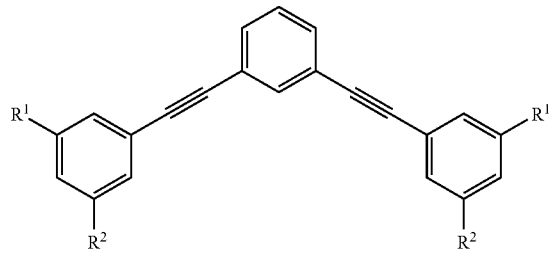

wherein: each $R^1$ is, independently, H, $C_1$-$C_8$alkyl, $C_1$-$C_8$alkoxy, halo, OH, $CF_3$, or CN; each $R^2$ is, independently, $-(CH_2)_n-NH_2$ or $-(CH_2)_n-NH-C(=NH)NH_2$, where each n is, independently, 1 to 4; or a pharmaceutically acceptable salt thereof.

The present invention also provides methods of killing or inhibiting the growth of a *Plasmodium* species comprising contacting the species with an effective amount of a compound of Formula VII:

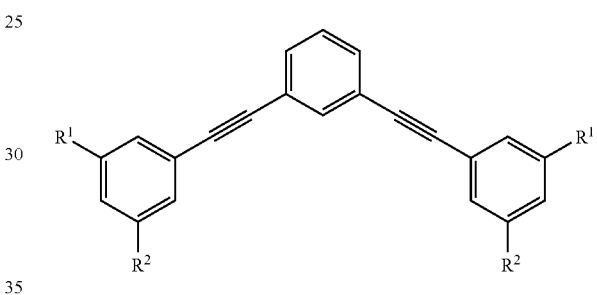

wherein: each $R^1$ is, independently, H, $C_1$-$C_8$alkyl, $C_1$-$C_8$alkoxy, halo, OH, $CF_3$, or CN; each $R^2$ is, independently, $-(CH_2)_n-NH_2$ or $-(CH_2)_n-NH-C(=NH)NH_2$, where each n is, independently, 1 to 4; or a pharmaceutically acceptable salt thereof.

The present invention also provides compounds of Formula VIII:

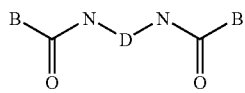

wherein: D is

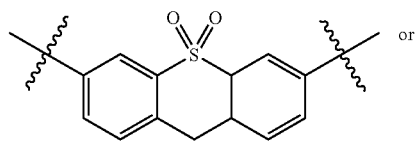 or

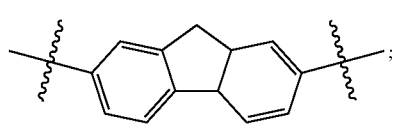 ;

each B is, independently, —(CH$_2$)$_n$—NH—C(=NH)NH$_2$, where each n is, independently, 1 to 4,

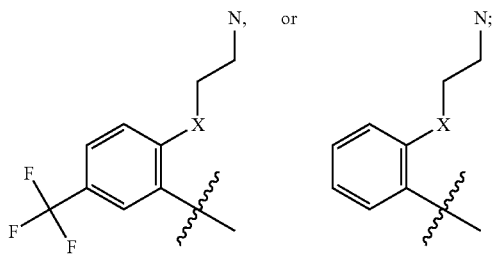

and each X is, independently, O or S, or a pharmaceutically acceptable salt thereof, and compositions comprising the same and a pharmaceutically acceptable carrier.

The present invention also provides methods of treating malaria in an animal comprising administering to the animal a therapeutically effective amount of a compound of Formula VIII:

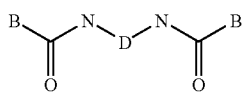

wherein: D is

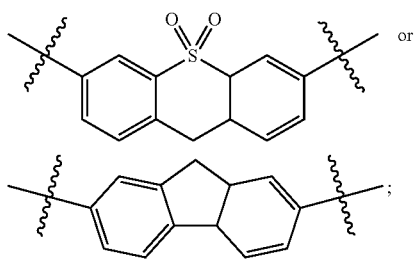

each B is, independently, —(CH$_2$)$_n$—NH—C(=NH)NH$_2$, where each n is, independently, 1 to 4,

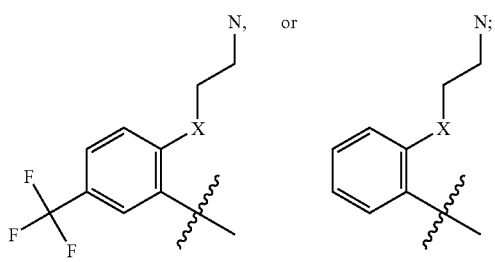

and each X is, independently, O or S, or a pharmaceutically acceptable salt thereof.

The present invention also provides methods of killing or inhibiting the growth of a *Plasmodium* species comprising contacting the species with an effective amount of a compound of Formula VIII:

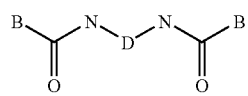

wherein: D is

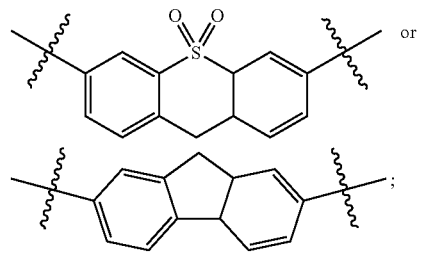

each B is, independently, —(CH$_2$)$_n$—NH—C(=NH)NH$_2$, where each n is, independently, 1 to 4,

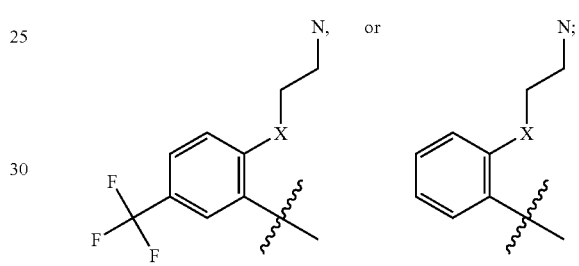

and each X is, independently, O or S, or a pharmaceutically acceptable salt thereof.

DESCRIPTION OF EMBODIMENTS

Collectively and individually, each of the compounds described herein are also referred to herein as "anti-malarial compounds."

As used herein and unless otherwise indicated, the term "animal" is intended to include, but not be limited to, humans and non-human vertebrates such as wild, domestic and farm animals.

As used herein and unless otherwise indicated, the term "about" is intended to mean±5% of the value it modifies. Thus, about 100 means 95 to 105.

As used herein and unless otherwise indicated, the term "alkyl" is intended to include branched and straight-chain saturated aliphatic hydrocarbon groups having the specified number of carbon atoms. For example, $C_1$-$C_8$, as in "$C_1$-$C_8$ alkyl" is intended to include groups having 1, 2, 3, 4, 5, 6, 7, or 8 carbons in a linear or branched arrangement. "$C_1$-$C_6$ alkyl" is intended to include groups having 1, 2, 3, 4, 5, or 6 carbons in a linear or branched arrangement. "$C_1$-$C_3$ alkyl" is intended to include groups having 1, 2, or 3 carbons in a linear or branched arrangement. Examples of alkyl groups include, but are not limited to, methyl, ethyl, n-propyl, i-propyl, n-butyl, t-butyl, i-butyl, 2-methyl-1-propyl, 2-methyl-2-propyl, pentyl, 2-methyl-1-butyl, 3-methyl-1-butyl, 2-methyl-3-butyl, 2,2-dimethyl-1-propyl, isopentyl, neopentyl, hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, heptyl, and octyl, or any combination thereof. An alkyl group can be unsubstituted or substituted with one, two, or three suitable substituents. These same alkyl groups can be used in connection with "alkoxy" groups, "haloalkyl" groups, "alkenyl" groups, "alkynyl" groups, and "cycloalkyl" groups as appropriate.

As used herein and unless otherwise indicated, the term "halo" means fluorine, chlorine, bromine, or iodine.

As used herein and unless otherwise indicated, the phrase "5- or 6-membered heterocycle" means a monocyclic ring comprising carbon atoms, hydrogen atoms, and one or more heteroatoms, such as 1 to 3 heteroatoms, independently chosen from nitrogen, oxygen, and sulfur. 5-membered heterocycles include, but are not limited to, thienyl, 2-thienyl, 3-thienyl, furyl, 2-furyl, 3-furyl, pyrrolyl, 2-pyrrolyl, 3-pyrrolyl, imidazolyl, pyrazolyl, isothiazolyl, pyrrolinyl, imidazolidinyl, imidazolinyl, pyrazolidinyl, and pyrazolinyl. 6-membered heterocycles include, but are not limited to, pyranyl, pyridyl, pyrazinyl, pyrimidinyl, pyridazinyl, piperidyl, piperazinyl, and morpholinyl. The 5- and 6-membered heterocycles can be unsubstituted or substituted with one, two, or three suitable substituents.

As used herein and unless otherwise indicated, the phrase "carbocycle" means a 5- or 6-membered, saturated or unsaturated cyclic ring, optionally containing O, S, or N atoms as part of the ring. Examples of carbocycles include, but are not limited to, cyclopentyl, cyclohexyl, cyclopenta-1,3-diene, phenyl, and any of the heterocycles recited above.

As used herein and unless otherwise indicated, the term "phenyl" means $—C_6H_5$. A phenyl group can be unsubstituted or substituted with one, two, or three suitable substituents.

As used herein and unless otherwise indicated, the phrase "therapeutically effective amount" of a composition or compound is measured by the therapeutic effectiveness of the administered compound, wherein at least one adverse effect is ameliorated or alleviated. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, prevention or elimination of a disorder, or side-effects. The amount needed to elicit the therapeutic response can be determined based on the age, health, size and sex of the subject. Optimal amounts can also be determined based on monitoring of the subject's response to treatment.

When administered to a mammal (e.g., to an animal for veterinary use or to a human for clinical use) the anti-malarial compounds described herein can be administered in isolated form. As used herein and unless otherwise indicated, the term "isolated" means that the anti-malarial compounds described herein are separated from other components of either (a) a natural source, such as a plant or cell, such as a bacterial culture, or (b) a synthetic organic chemical reaction mixture, such as by conventional techniques.

As used herein and unless otherwise indicated, the term "purified" means that when isolated, the isolate contains at least 90%, at least 95%, at least 98%, or at least 99% of an anti-malarial compound described herein by weight of the isolate.

As used herein and unless otherwise indicated, the phrase "pharmaceutically acceptable salt(s)," includes, but is not limited to, salts of acidic or basic groups. Compounds that are basic in nature are capable of forming a wide variety of salts with various inorganic and organic acids. Acids that may be used to prepare pharmaceutically acceptable acid addition salts of such basic compounds are those that form non-toxic acid addition salts, i.e., salts containing pharmacologically acceptable anions including, but not limited to, sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds that include an amino moiety may form pharmaceutically acceptable salts with various amino acids, in addition to the acids mentioned above. Compounds that are acidic in nature are capable of forming base salts with various pharmacologically acceptable cations. Examples of such salts include, but are not limited to, alkali metal or alkaline earth metal salts and, particularly, calcium, magnesium, sodium lithium, zinc, potassium, and iron salts.

As used herein and unless otherwise indicated, the phrase "suitable substituent" means a group that does not nullify the synthetic or pharmaceutical utility of the anti-malarial compounds described herein or the intermediates useful for preparing them. Examples of suitable substituents include, but are not limited to: $(C_1-C_6)$alkyl, $(C_1-C_6)$alkenyl, $(C_1-C_6)$alkynyl, $(C_5-C_6)$aryl, $(C_3-C_5)$heteroaryl, $(C_3-C_6)$cycloalkyl, $(C_1-C_6)$alkoxy, $(C_5-C_6)$aryloxy, —CN, —OH, oxo, halo, $—NO_2$, $—CO_2H$, $—NH_2$, $—NH((C_1-C_8)$alkyl$)$, $—N((C_1-C_8)$alkyl$)_2$, $—NH((C_6)$aryl$)$, $—N((C_5-C_6)$aryl$)_2$, —CHO, $—CO((C_1-C_6)$alkyl$)$, $—CO((C_5-C_6)$aryl$)$, $—CO_2((C_1-C_6)$alkyl$)$, and $—CO_2((C_5-C_6)$aryl$)$. One of skill in art can readily choose a suitable substituent based on the stability and pharmacological and synthetic activity of the anti-malarial compounds described herein.

As used herein and unless otherwise indicated, the terms "treatment" or "treating" refers to an amelioration of malaria, or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of malaria, either physically, e.g., stabilization of a discernible symptom, physiologically, e.g., stabilization of a physical parameter, or both. In yet another embodiment, "treatment" or "treating" refers to delaying the onset of malaria.

In some embodiments, the anti-malarial compound, or composition comprising the same, are administered to a patient, such as a human, as a preventative measure against malaria. As used herein and unless otherwise indicated, "prevention" or "preventing" refers to a reduction of the risk of acquiring malaria.

The anti-malarial compounds described herein may contain one or more chiral centers and/or double bonds and, therefore, exist as stereoisomers, such as double-bond isomers (i.e., geometric isomers), enantiomers, or diastereomers. Therefore, the anti-malarial compounds described herein encompass all of the corresponding compound's enantiomers and stereoisomers, that is, both the stereomerically pure form (e.g., geometrically pure, enantiomerically pure, or diastereomerically pure) and enantiomeric and stereoisomeric mixtures. Enantiomeric and stereoisomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically- or enantiomerically-pure intermediates, reagents, and catalysts by well known asymmetric synthetic methods.

The present invention provides compounds of Formula I:

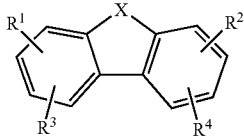

wherein:

X is $C(R^7)C(R^8)$, $C(=O)$, $N(R^9)$, O, S, $S(=O)$, or $S(=O)_2$;

$R^7$, $R^8$, and $R^9$ are, independently, H, $C_1$-$C_8$alkyl, $C_1$-$C_8$alkoxy, halo, OH, $CF_3$, or aromatic group;

$R^1$ and $R^2$ are, independently, H, $C_1$-$C_8$alkyl, $C_1$-$C_8$alkoxy, halo, OH, halo$C_1$-$C_8$alkyl, or CN;

$R^3$ and $R^4$ are, independently, carbocycle$(R^5)(R^6)$;

each $R^5$ and each $R^6$ are, independently, H, $C_1$-$C_8$alkyl, $C_1$-$C_8$alkoxy, halo, OH, $CF_3$, aromatic group, heterocycle, or the free base or salt form of —$(CH_2)_n$—$NH_2$, —$(CH_2)_n$—NH—$(CH_2)_n$—$NH_2$, or —$(CH_2)_n$—NH—$C(=NH)NH_2$, where each n is, independently, 1 to 8;

or a pharmaceutically acceptable salt thereof.

In some embodiments, X is $N(R^9)$, O, S, or $S(=O)_2$; or X is NH, O, or S; or X is NH or S.

In any of the above embodiments, $R^1$ and $R^2$ are, independently, H, $C_1$-$C_3$alkyl, $C_1$-$C_3$alkoxy, halo, OH, halo$C_1$-$C_3$alkyl, or CN; or $R^1$ and $R^2$ are, independently, H, $C_1$-$C_3$alkyl, $C_1$-$C_3$alkoxy, halo, or OH; or $R^1$ and $R^2$ are, independently, H, $C_1$-$C_3$alkyl, or halo; or $R^1$ and $R^2$ are H.

In any of the above embodiments, $R^3$ and $R^4$ are, independently, carbocycle $(R^5)(R^6)$, where $R^5$ and $R^6$ can be positioned anywhere on the carbocycle. In any of the above embodiments, $R^3$ and $R^4$ are, independently,

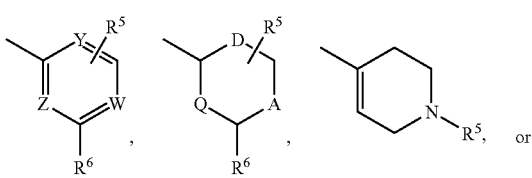

wherein each W, Y, and Z are, independently, C or N, each A, D, and Q are, independently, $C(R^{10})C(R^{11})$, $C(=O)$, $N(R^{12})$, O, or S, and each $R^{10}$, $R^{11}$, and $R^{12}$ are, independently, H, $C_1$-$C_8$alkyl, $C_1$-$C_8$alkoxy, halo, OH, $CF_3$, or aromatic group.

In any of the above embodiments, $R^3$ and $R^4$ are, independently,

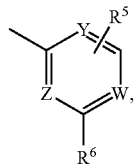

wherein each W, Y, and Z are, independently, C or N; or $R^3$ and $R^4$ are, independently,

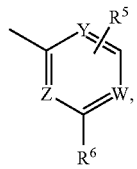

wherein each W, Y, and Z are C, or each Y and Z are C and each W is N.

In any of the above embodiments, each $R^5$ is, independently, H, $C_1$-$C_8$alkyl, $C_1$-$C_8$alkoxy, halo, OH, $CF_3$, or the free base or salt form of —$(CH_2)_n$—$NH_2$, —$(CH_2)_n$—NH—$(CH_2)_n$—$NH_2$, or —$(CH_2)_n$—NH—$C(=NH)NH_2$, where each n is, independently, 1 to 8, and each $R^6$ is, independently, heterocycle or the free base or salt form of —$(CH_2)_n$—$NH_2$, —$(CH_2)_n$—NH—$(CH_2)_n$—$NH_2$, or —$(CH_2)_n$—NH—$C(=NH)NH_2$, where each n is, independently, 1 to 8; or each $R^5$ is, independently, H, $C_1$-$C_3$alkyl, $C_1$-$C_3$alkoxy, halo, OH, or $CF_3$, and each $R^6$ is, independently, heterocycle or the free base or salt form of —$(CH_2)_n$—$NH_2$, where each n is, independently, 1 to 8; or each $R^5$ is, independently, H, $C_1$-$C_3$alkyl, halo, or OH; and each $R^6$ is, independently, heterocycle or the free base or salt form of —$(CH_2)_n$—$NH_2$, where each n is, independently, 1 to 4; or each $R^5$ is, independently, H, $C_1$-$C_3$alkyl, halo, or OH; and each $R^6$ is, independently, 6-membered heterocycle or the free base or salt form of —$(CH_2)_n$—$NH_2$, where each n is, independently, 1 to 3; or each $R^5$ is, independently, H or halo; and each $R^6$ is piperazinyl or the free base or salt form of —$(CH_2)_n$—$NH_2$ where each n is, independently, 1 to 3; or each $R^5$ is piperazinyl; and each $R^6$ is, independently, H, $C_1$-$C_3$alkyl, $C_1$-$C_3$alkoxy, halo, OH, or $CF_3$; or each $R^5$ is piperazinyl; and each $R^6$ is H, $C_1$-$C_3$alkyl, halo, OH, or $CF_3$.

In some embodiments, X is NH, O, S, or $S(=O)_2$; $R^1$ and $R^2$ are H; $R^3$ and $R^4$ are, independently,

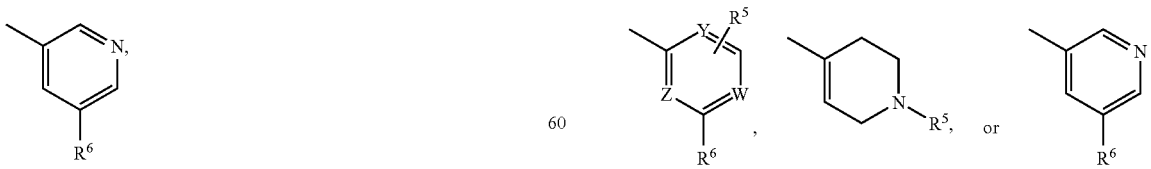

wherein: each W, Y, and Z are, independently, C or N; each $R^5$ and each $R^6$ are, independently, H, heterocycle, or the free base or salt form of —$(CH_2)_n$—$NH_2$, where each n is, independently, 1 to 3.

In some embodiments, X is NH, O, or S; $R^1$ and $R^2$ are H; $R^3$ and $R^4$ are

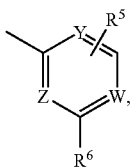

where each Z and Y are C, and each W is N; or each W, Y, and Z are C; each $R^5$ is, independently, H or halo, and each $R^6$ is piperazinyl or the free base or salt form of —$(CH_2)_n$—$NH_2$, where each n is, independently, 1 to 3; or each $R^5$ is piperazinyl, and each $R^6$ is, independently, H, $C_1$-$C_3$alkyl, $C_1$-$C_3$alkoxy, halo, OH, or $CF_3$.

In some embodiments, X is NH, O, or S; $R^1$ and $R^2$ are H; $R^3$ and $R^4$ are

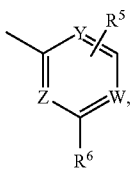

where each Z and Y are C, and each W is N; or each W, Y, and Z are C; each $R^5$ is H, and each $R^6$ is piperazinyl or the free base or salt form of —$(CH_2)_n$—$NH_2$, where n is, independently, 1 to 3; or each $R^5$ is piperazinyl; and each $R^6$ is H.

In some embodiments, the compound is chosen from:

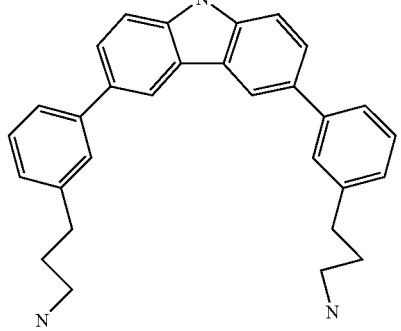

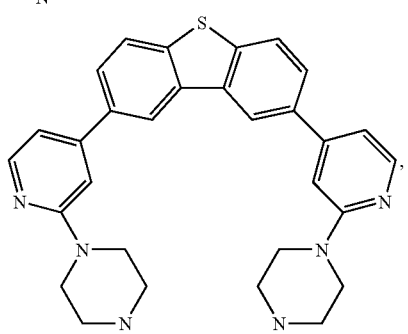

-continued

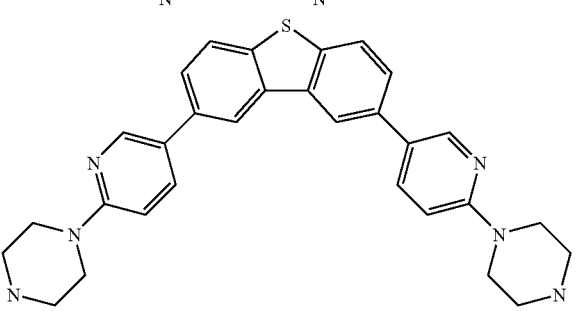

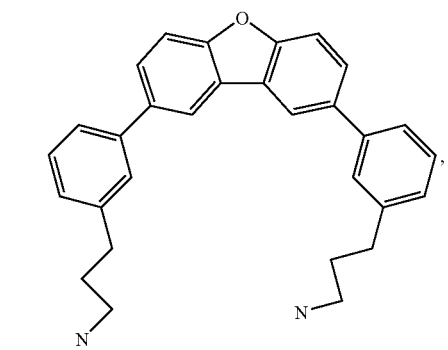

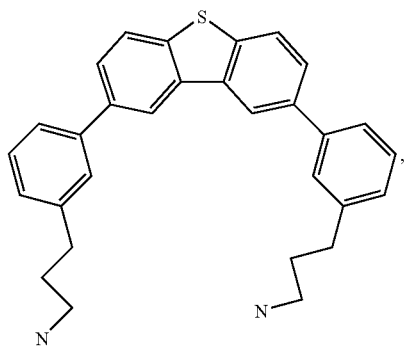

23
-continued
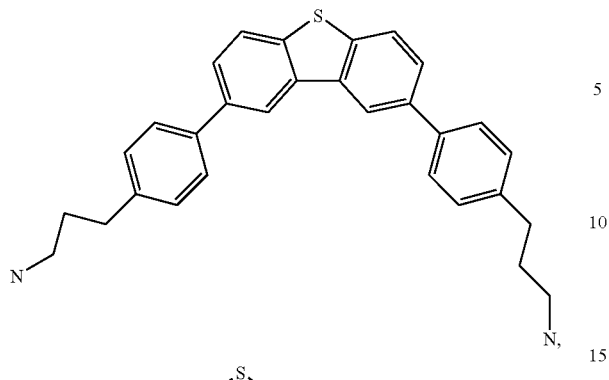
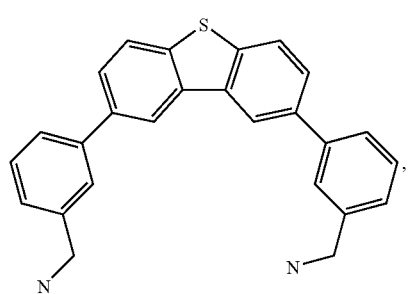
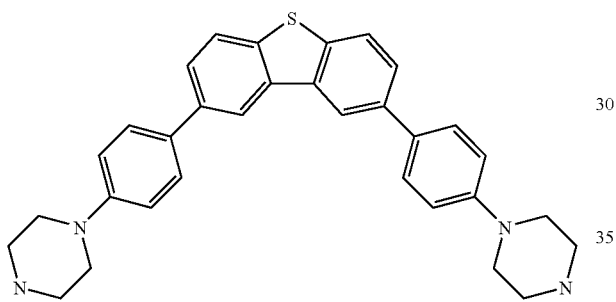
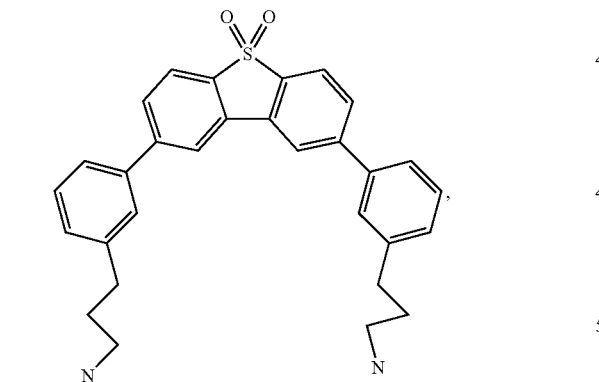
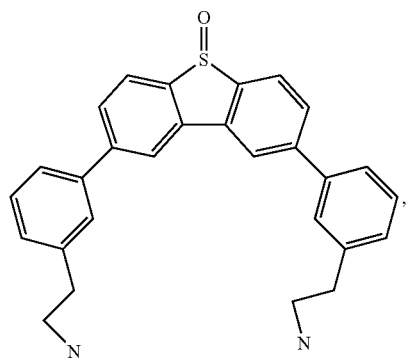
24
-continued
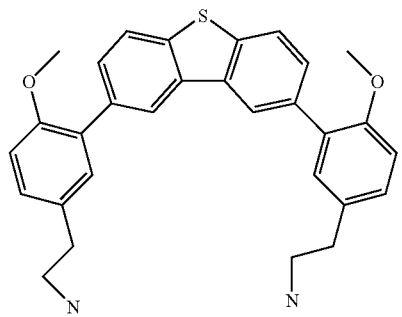
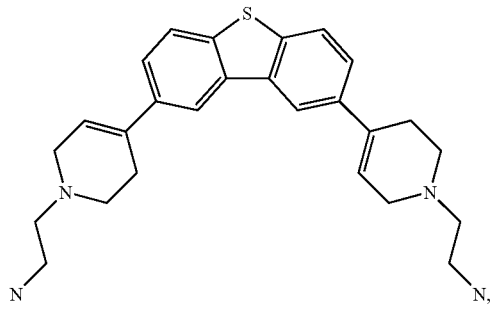
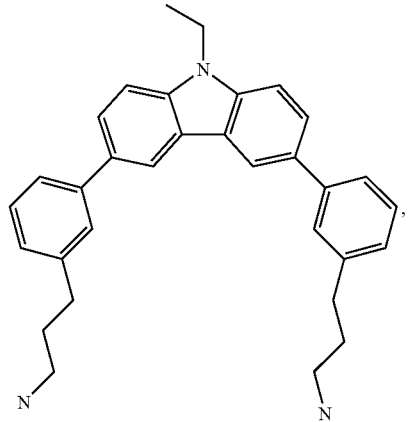
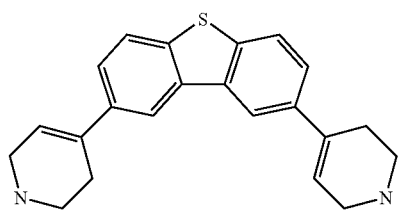
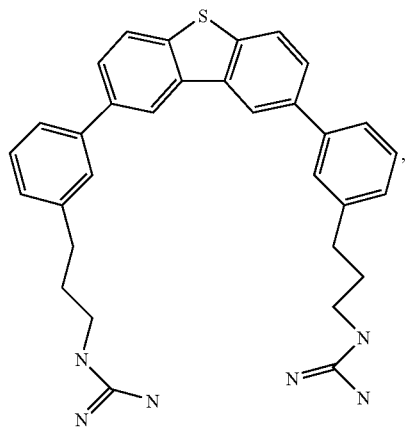

-continued

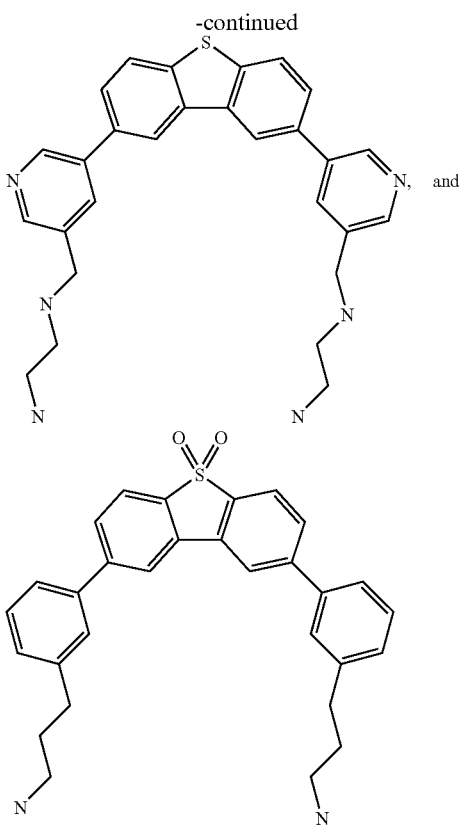

or pharmaceutically acceptable salt thereof.

In some embodiments, any one or more of the above compounds may be excluded from any of the genus of compounds described above.

The present invention also provides compositions comprising one or more of the compounds or salts described above and a pharmaceutically acceptable carrier.

The present invention also provides methods of treating malaria in an animal comprising administering to the animal a therapeutically effective amount of a compound of Formula I:

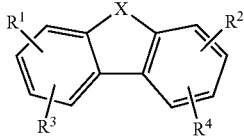

wherein:
X is $C(R^7)C(R^8)$, $C(=O)$, $N(R^9)$, O, S, $S(=O)$, or $S(=O)_2$;
$R^7$, $R^8$, and $R^9$ are, independently, H, $C_1$-$C_8$alkyl, $C_1$-$C_8$alkoxy, halo, OH, $CF_3$, or aromatic group;
$R^1$ and $R^2$ are, independently, H, $C_1$-$C_8$alkyl, $C_1$-$C_8$alkoxy, halo, OH, halo$C_1$-$C_8$alkyl, or CN;
$R^3$ and $R^4$ are, independently, carbocycle $(R^5)(R^6)$;
each $R^5$ and each $R^6$ are, independently, H, $C_1$-$C_8$alkyl, $C_1$-$C_8$alkoxy, halo, OH, $CF_3$, aromatic group, heterocycle, or the free base or salt form of —$(CH_2)_n$—$NH_2$, —$(CH_2)_n$—$NH$—$(CH_2)_n$—$NH_2$, or —$(CH_2)_n$—$NH$—$C(=NH)NH_2$, where each n is, independently, 1 to 8;
or a pharmaceutically acceptable salt thereof.

In some embodiments, X is $N(R^9)$, O, S, or $S(=O)_2$; or X is NH, O, or S; or X is NH or S.

In any of the above embodiments, $R^1$ and $R^2$ are, independently, H, $C_1$-$C_3$alkyl, $C_1$-$C_3$alkoxy, halo, OH, halo$C_1$-$C_3$alkyl, or CN; or $R^1$ and $R^2$ are, independently, H, $C_1$-$C_3$alkyl, $C_1$-$C_3$alkoxy, halo, or OH; or $R^1$ and $R^2$ are, independently, H, $C_1$-$C_3$alkyl, or halo; or $R^1$ and $R^2$ are H.

In any of the above embodiments, $R^3$ and $R^4$ are, independently,

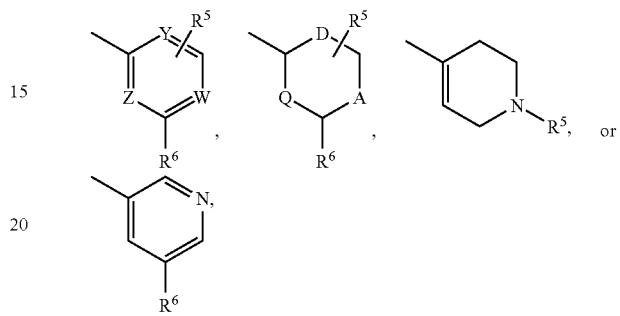

wherein each W, Y, and Z are, independently, C or N, each A, D, and Q are, independently, $C(R^{10})C(R^{11})$, $C(=O)$, $N(R^{12})$, O, or S, and each $R^{10}$, $R^{11}$, and $R^{12}$ are, independently, H, $C_1$-$C_8$alkyl, $C_1$-$C_8$alkoxy, halo, OH, $CF_3$, or aromatic group.

In any of the above embodiments, $R^3$ and $R^4$ are, independently,

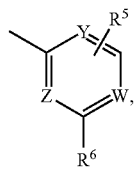

wherein each W, Y, and Z are, independently, C or N; or $R^3$ and $R^4$ are, independently,

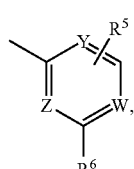

wherein each W, Y, and Z are C; or each Y and Z are C and each W is N.

In any of the above embodiments, each $R^5$ is, independently, H, $C_1$-$C_8$alkyl, $C_1$-$C_8$alkoxy, halo, OH, $CF_3$, or the free base or salt form of —$(CH_2)_n$—$NH_2$, $(CH_2)_n$—$NH$—$(CH_2)_n$—$NH_2$, or —$(CH_2)_n$—$NH$—$C(=NH)NH_2$, where each n is, independently, 1 to 8, and each $R^6$ is, independently, heterocycle or the free base or salt form of —$(CH_2)_n$—$NH_2$, —$(CH_2)_n$—$NH$—$(CH_2)_n$—$NH_2$, or —$(CH_2)_n$—$NH$—$C(=NH)NH_2$, where each n is, independently, 1 to 8; or each $R^5$ is, independently, H, $C_1$-$C_3$alkyl, $C_1$-$C_3$alkoxy, halo, OH, or $CF_3$, and each $R^6$ is, independently, heterocycle or the free base or salt form of —$(CH_2)_n$—$NH_2$, where each n is, independently, 1 to 8; or each $R^5$ is, independently, H, $C_1$-$C_3$alkyl, halo, or OH, and each $R^6$ is, independently, heterocycle or the free base or salt form of —(CH$_2$)$_n$—NH$_2$, where each n is, independently, 1 to 4; or each R$^5$ is, independently, H, C$_1$-C$_3$alkyl, halo, or OH, and each R$^6$ is, independently, 6-membered heterocycle or the free base or salt form of —(CH$_2$)$_n$—NH$_2$, where each n is, independently, 1 to 3; or each R$^5$ is, independently, H or halo, and each R$^6$ is piperazinyl or the free base or salt form of —(CH$_2$)$_n$—NH$_2$ where each n is, independently, 1 to 3; or each R$^5$ is piperazinyl, and each R$^6$ is, independently, H, C$_1$-C$_3$alkyl, C$_1$-C$_3$alkoxy, halo, OH, or CF$_3$; or each R$^5$ is piperazinyl, and each R$^6$ is H, C$_1$-C$_3$alkyl, halo, OH, or CF$_3$.

In some embodiments, X is NH, O, S, or S(=O)$_2$; R$^1$ and R$^2$ are H; R$^3$ and R$^4$ are, independently,

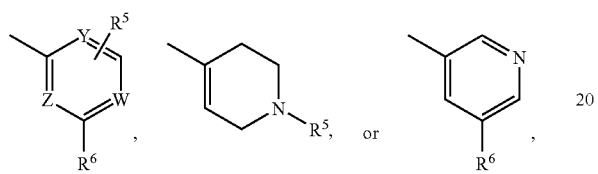

wherein each W, Y, and Z are, independently, C or N; and each R$^5$ and each R$^6$ are, independently, H, heterocycle, or the free base or salt form of —(CH$_2$)$_n$—NH$_2$, where each n is, independently, 1 to 3.

In some embodiments, X is NH, O, or S; R$^1$ and R$^2$ are H; R$^3$ and R$^4$ are

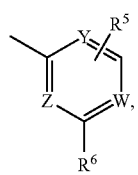

where each Z and Y are C, and each W is N; or each W, Y, and Z are C; each R$^5$ is, independently, H or halo, and each R$^6$ is piperazinyl or the free base or salt form of —(CH$_2$)$_n$—NH$_2$, where each n is, independently, 1 to 3; or each R$^5$ is piperazinyl, and each R$^6$ is, independently, H, C$_1$-C$_3$alkyl, C$_1$-C$_3$alkoxy, halo, OH, or CF$_3$.

In some embodiments, X is NH, O, or S; R$^1$ and R$^2$ are H; R$^3$ and R$^4$ are

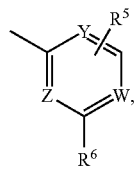

where each Z and Y are C, and each W is N; or each W, Y, and Z are C; each R$^5$ is H, and each R$^6$ is piperazinyl or the free base or salt form of —(CH$_2$)$_n$—NH$_2$, where each n is, independently, 1 to 3; or each R$^5$ is piperazinyl; and each R$^6$ is H.

In some embodiments, the compound is chosen from:

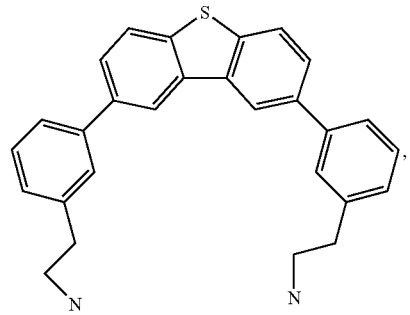

Compound 106

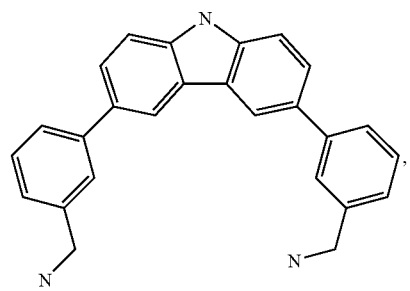

Compound 118

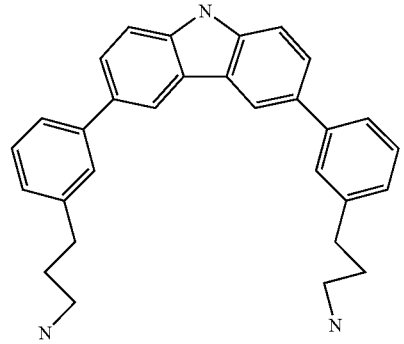

Compound 119

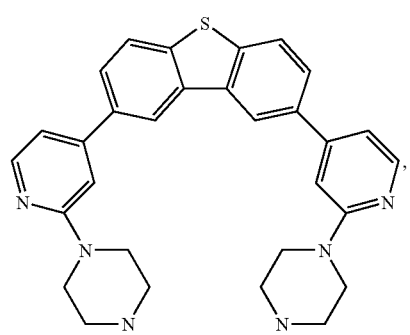

Compound 110

-continued
Compound 117
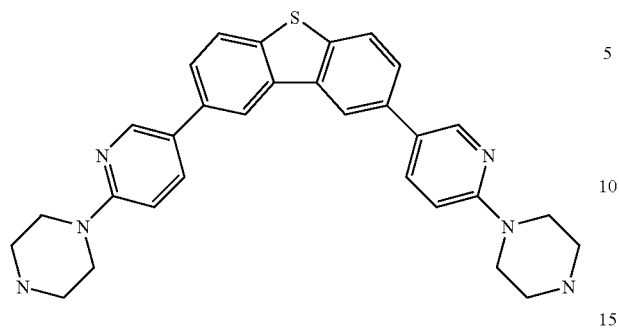
Compound 120
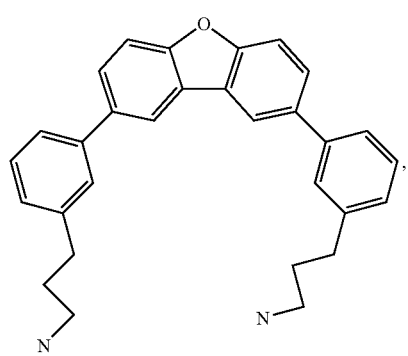
Compound 116
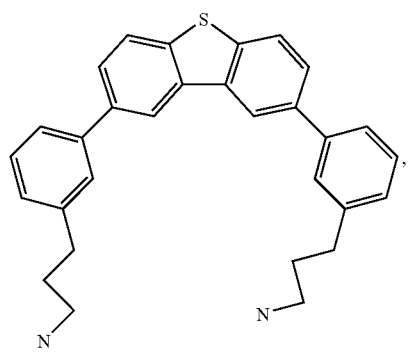
Compound 130
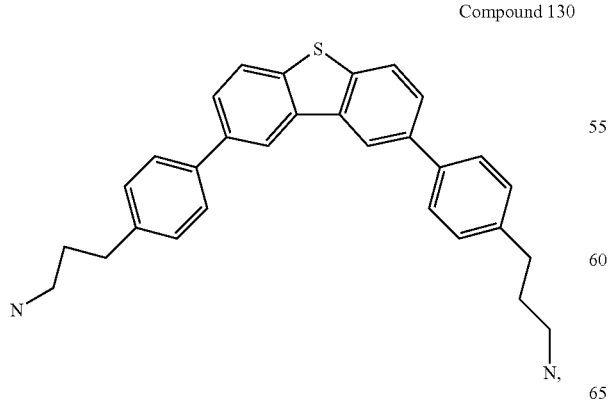
-continued
Compound 131
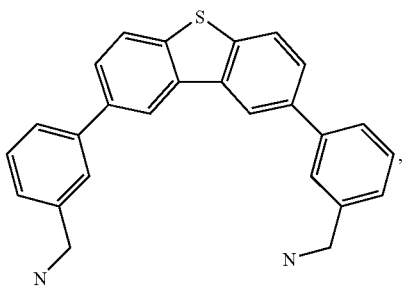
Compound 132
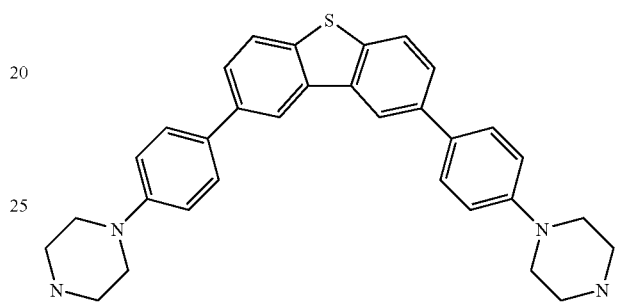
Compound 133
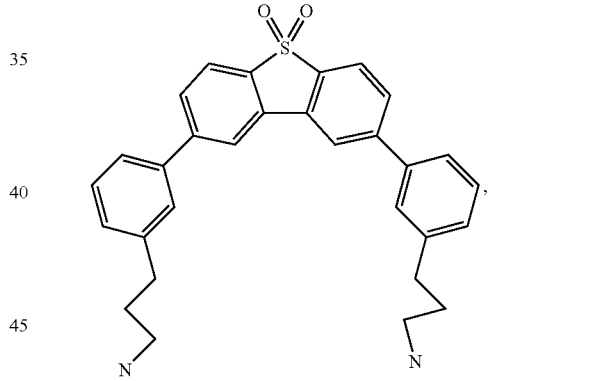
Compound 134
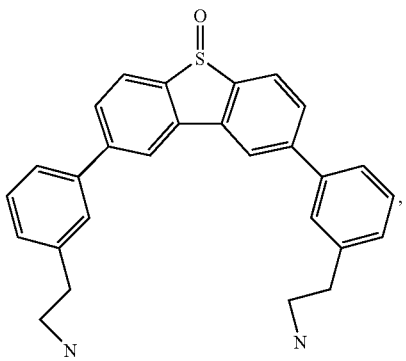

Compound 135
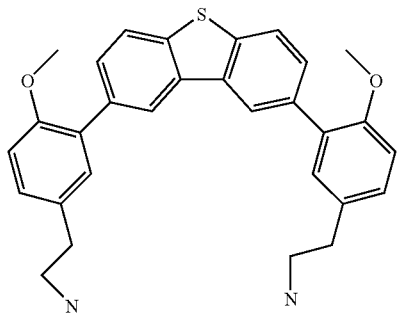

Compound 136
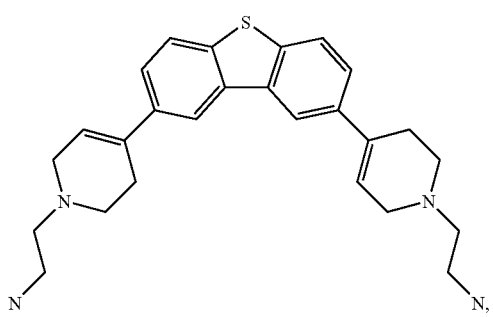

Compound 137
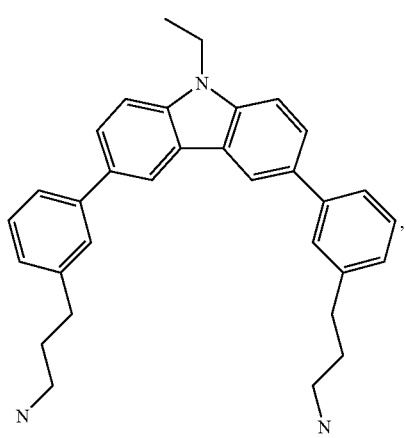

Compound 138
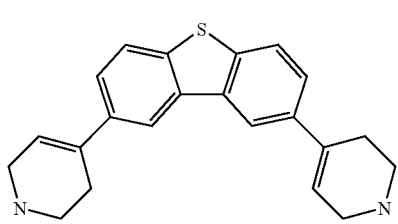

Compound 139
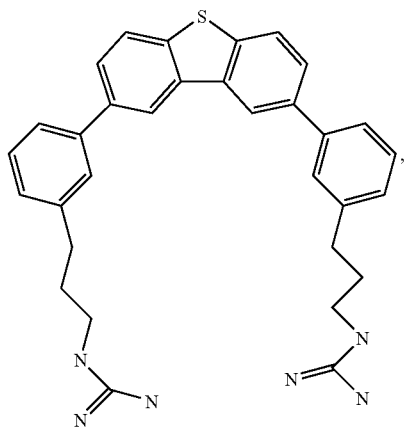

Compound 140
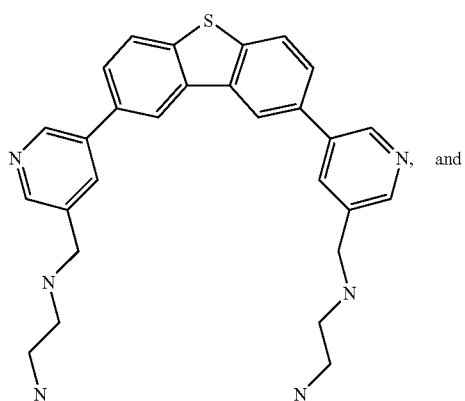

and

Compound 141
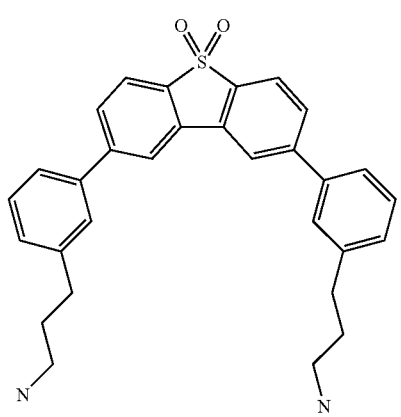

or pharmaceutically acceptable salt thereof.

In any of the above embodiments, the malaria can be chloroquine-sensitive or chloroquine-resistant.

The present invention also provides methods of killing or inhibiting the growth of a *Plasmodium* species comprising contacting the species with an effective amount of a compound of Formula I:

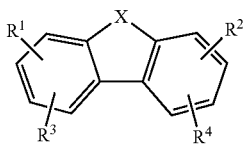

wherein:

X is $C(R^7)C(R^8)$, $C(=O)$, $N(R^9)$, O, S, $S(=O)$, or $S(=O)_2$;

$R^7$, $R^8$, and $R^9$ are, independently, H, $C_1$-$C_8$alkyl, $C_1$-$C_8$alkoxy, halo, OH, $CF_3$, or aromatic group;

$R^1$ and $R^2$ are, independently, H, $C_1$-$C_8$alkyl, $C_1$-$C_8$alkoxy, halo, OH, halo$C_1$-$C_8$alkyl, or CN;

$R^3$ and $R^4$ are, independently, carbocycle($R^5$)($R^6$);

each $R^5$ and each $R^6$ are, independently, H, $C_1$-$C_8$alkyl, $C_1$-$C_8$alkoxy, halo, OH, $CF_3$, aromatic group, heterocycle, or the free base or salt form of —$(CH_2)_n$—$NH_2$, —$(CH_2)_n$—NH—$(CH_2)_n$—$NH_2$, or —$(CH_2)_n$—NH—$C(=NH)NH_2$, where each n is, independently, 1 to 8;

or a pharmaceutically acceptable salt thereof.

In some embodiments, X is $N(R^9)$, O, S, or $S(=O)_2$; or X is NH, O, or S; or X is NH or S.

In any of the above embodiments, $R^1$ and $R^2$ are, independently, H, $C_1$-$C_3$alkyl, $C_1$-$C_3$alkoxy, halo, OH, halo$C_1$-$C_3$alkyl, or CN; or $R^1$ and $R^2$ are, independently, H, $C_1$-$C_3$alkyl, $C_1$-$C_3$alkoxy, halo, or OH; or $R^1$ and $R^2$ are, independently, H, $C_1$-$C_3$alkyl, or halo; or $R^1$ and $R^2$ are H.

In any of the above embodiments, $R^3$ and $R^4$ are, independently,

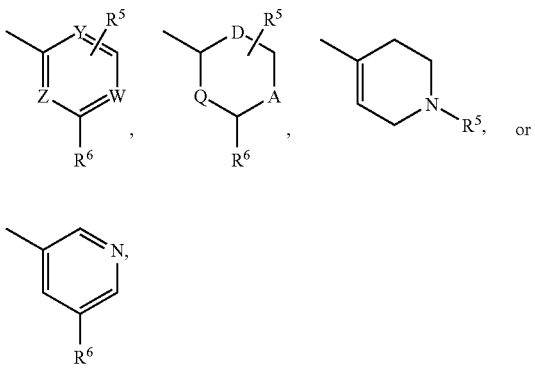

wherein each W, Y, and Z are, independently, C or N, each A, D, and Q are, independently, $C(R^{10})C(R^{11})$, $C(=O)$, $N(R^{12})$, O, or S, and each $R^{10}$, $R^{11}$, and $R^{12}$ are, independently, H, $C_1$-$C_8$alkyl, $C_1$-$C_8$alkoxy, halo, OH, $CF_3$, or aromatic group.

In any of the above embodiments, $R^3$ and $R^4$ are, independently,

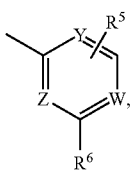

wherein each W, Y, and Z are, independently, C or N; or $R^3$ and $R^4$ are, independently,

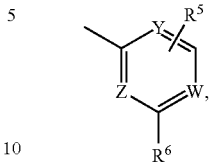

wherein each W, Y, and Z are C; or each Y and Z are C and each W is N.

In any of the above embodiments, each $R^5$ is, independently, H, $C_1$-$C_8$alkyl, $C_1$-$C_8$alkoxy, halo, OH, $CF_3$, or the free base or salt form of —$(CH_2)_n$—$NH_2$, —$(CH_2)_n$—NH—$(CH_2)_n$—$NH_2$, or —$(CH_2)_n$—NH—$C(=NH)NH_2$, where each n is, independently, 1 to 8, and each $R^6$ is, independently, heterocycle or the free base or salt form of —$(CH_2)_n$—$NH_2$, —$(CH_2)_n$—NH—$(CH_2)_n$—$NH_2$, or —$(CH_2)_n$—NH—$C(=NH)NH_2$, where each n is, independently, 1 to 8; or each $R^5$ is, independently, H, $C_1$-$C_3$alkyl, $C_1$-$C_3$alkoxy, halo, OH, or $CF_3$, and each $R^6$ is, independently, heterocycle or the free base or salt form of —$(CH_2)_n$—$NH_2$, where each n is, independently, 1 to 8; or each $R^5$ is, independently, H, $C_1$-$C_3$alkyl, halo, or OH, and each $R^6$ is, independently, heterocycle or the free base or salt form of —$(CH_2)_n$—$NH_2$, where each n is, independently, 1 to 4; or each $R^5$ is, independently, H, $C_1$-$C_3$alkyl, halo, or OH, and each $R^6$ is, independently, 6-membered heterocycle or the free base or salt form of —$(CH_2)_n$—$NH_2$, where each n is, independently, 1 to 3; or each $R^5$ is, independently, H or halo, and each $R^6$ is piperazinyl or the free base or salt form of —$(CH_2)_n$—$NH_2$ where each n is, independently, 1 to 3; or each $R^5$ is piperazinyl, and each $R^6$ is, independently, H, $C_1$-$C_3$alkyl, $C_1$-$C_3$alkoxy, halo, OH, or $CF_3$; or each $R^5$ is piperazinyl, and each $R^6$ is H, $C_1$-$C_3$alkyl, halo, OH, or $CF_3$.

In some embodiments, X is NH, O, S, or $S(=O)_2$; $R^1$ and $R^2$ are H; $R^3$ and $R^4$ are, independently,

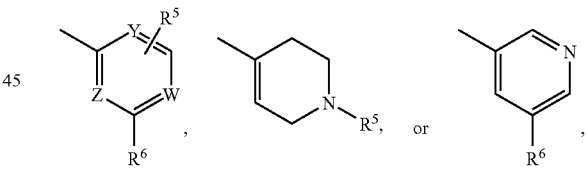

wherein each W, Y, and Z are, independently, C or N; and each $R^5$ and each $R^6$ are, independently, H, heterocycle, or the free base or salt form of —$(CH_2)_n$—$NH_2$, where each n is, independently, 1 to 3.

In some embodiments, X is NH, O, or S; $R^1$ and $R^2$ are H; $R^3$ and $R^4$ are

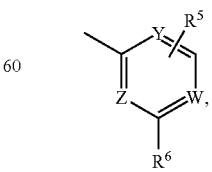

where each Z and Y are C, and each W is N; or each W, Y, and Z are C; each $R^5$ is, independently, H or halo, and each $R^6$ is piperazinyl or the free base or salt form of —(CH$_2$)$_n$—NH$_2$, where each n is, independently, 1 to 3; or each R$^5$ is piperazinyl, and each R$^6$ is, independently, H, C$_1$-C$_3$alkyl, C$_1$-C$_3$alkoxy, halo, OH, or CF$_3$.

In some embodiments, X is NH, O, or S; R$^1$ and R$^2$ are H; R$^3$ and R$^4$ are

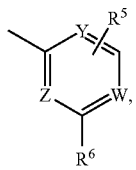

where each Z and Y are C, and each W is N; or each W, Y, and Z are C; each R$^5$ is H, and each R$^6$ is piperazinyl or the free base or salt form of —(CH$_2$)$_n$—NH$_2$, where each n is, independently, 1 to 3; or each R$^5$ is piperazinyl; and each R$^6$ is H.

In some embodiments, the compound is chosen from:

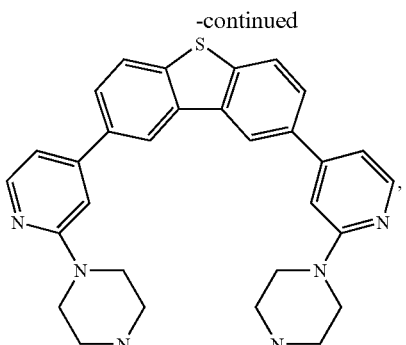

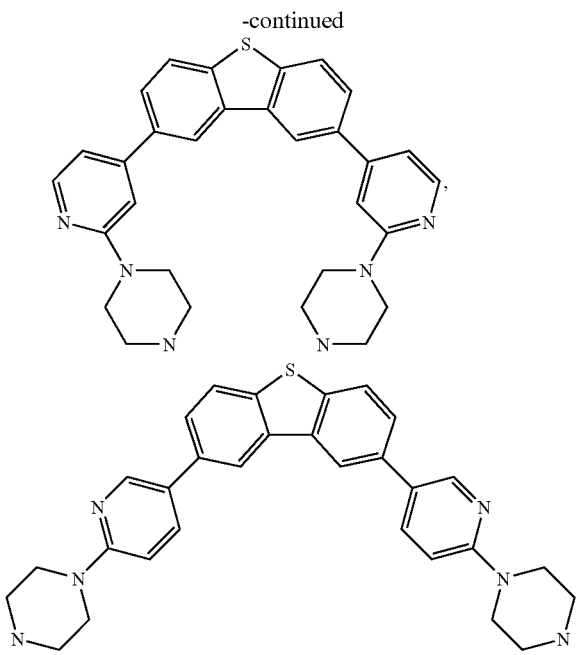

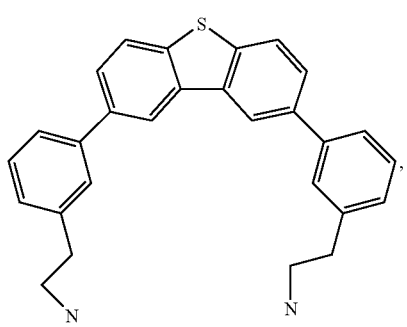

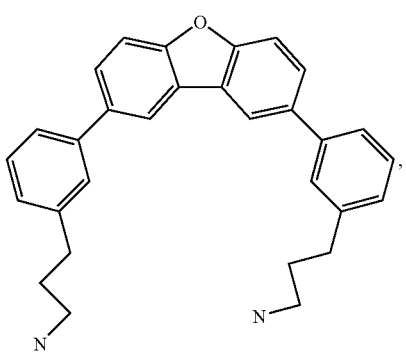

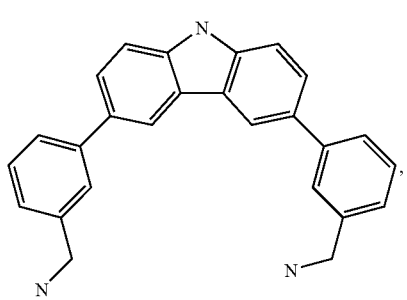

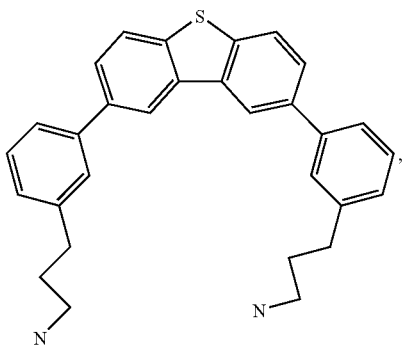

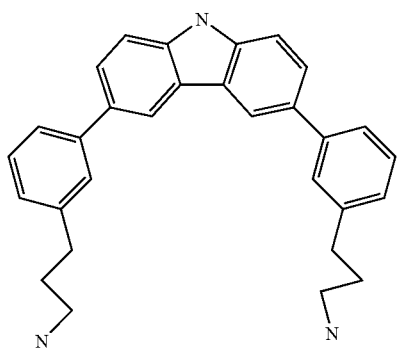

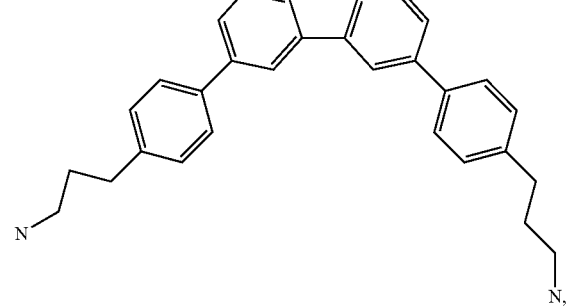

37
-continued
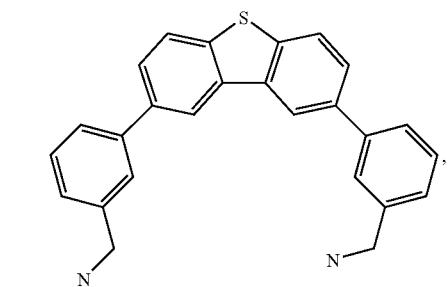
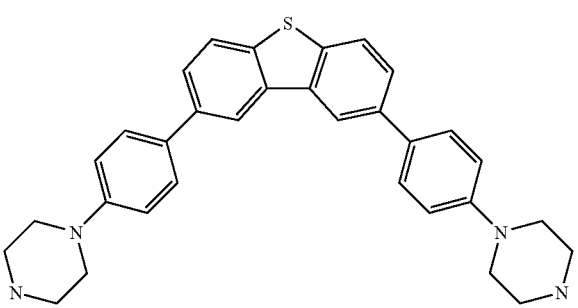
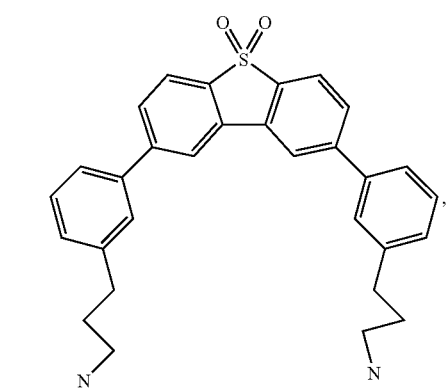
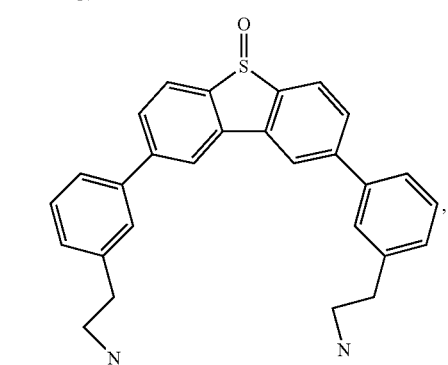
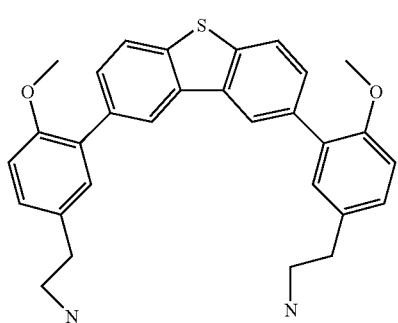
38
-continued
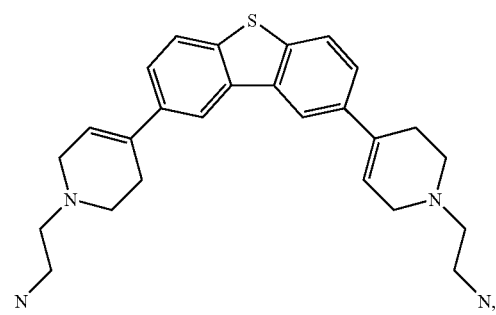
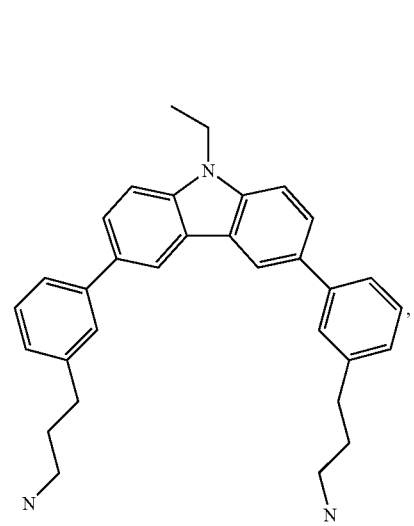
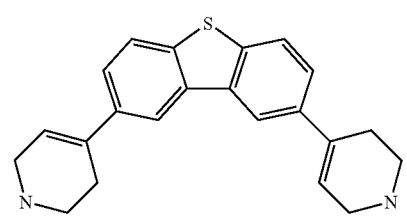
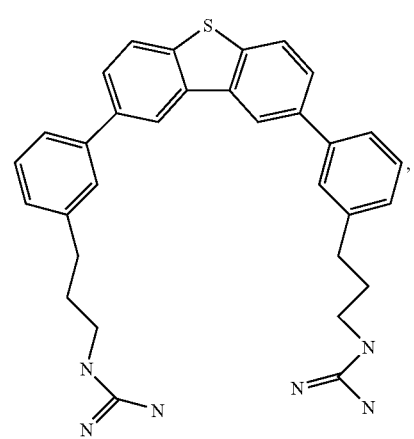

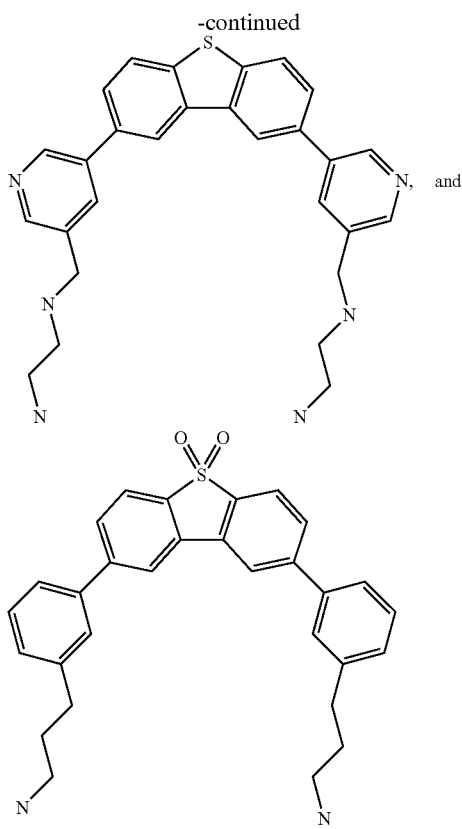

or pharmaceutically acceptable salt thereof.

The present invention also provides compounds of Formula II:

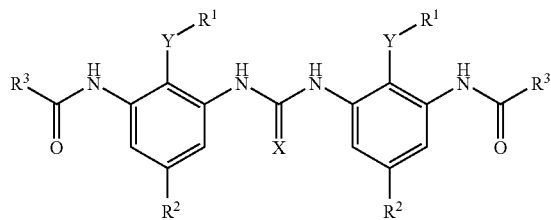

wherein:
X is O or S;
each Y is, independently, O, S, or N;
each $R^1$ is, independently, H, 5- or 6-membered heterocycle, or the free base or salt form of $-(CH_2)_n-NH_2$ or $-(CH_2)_n-NH-C(=NH)NH_2$, where each n is, independently, 1 to 4; or
each $R^1$ is, independently, together with Y a 5- or 6-membered heterocycle;
each $R^2$ is, independently, H, $CF_3$, $C(CH_3)_3$, halo, or OH; and
each $R^3$ is, independently, $-(CH_2)_n-NH_2$ or $-(CH_2)_n-NH-C(=NH)NH_2$, where each n is, independently, 1 to 4;
or a pharmaceutically acceptable salt thereof.

In some embodiments, X is O.

In any of the above embodiments, each Y is O or S.

In any of the above embodiments, each $R^1$ is, independently, 5-membered heterocycle or the free base or salt form of $-(CH_2)_n-NH_2$, where each n is, independently, 1 to 4; or each $R^1$ is, independently, 3-pyrrolyl or the free base or salt form of $-(CH_2)_n-NH_2$, where each n is, independently, 1 or 2.

In any of the above embodiments, each $R^2$ is, independently, $CF_3$, $C(CH_3)_3$, or halo.

In any of the above embodiments, each $R^3$ is, independently, $(CH_2)_n-NH-C(=NH)NH_2$, where each n is, independently, 1 to 4; or each $R^3$ is $-(CH_2)_n-NH-C(=NH)NH_2$, where each n is 4.

In some embodiments, X is O or S; each Y is, independently, O or S; each $R^1$ is, independently, 5-membered heterocycle, or the free base or salt form of $-(CH_2)_n-NH_2$, where each n is, independently, 1 to 4; each $R^2$ is, independently, $CF_3$ or $C(CH_3)_3$; and each $R^3$ is, independently, $-(CH_2)_n-NH-C(=NH)NH_2$, where each n is, independently, 1 to 4.

In some embodiments, X is O or S; each Y is O or S; each $R^1$ is 5-membered heterocycle, or the free base or salt form of $-(CH_2)_n-NH_2$, where each n is 1 to 4; each $R^2$ is $CF_3$ or $C(CH_3)_3$; and each $R^3$ is $-(CH_2)_n-NH-C(=NH)NH_2$, where each n is 1 to 4.

In some embodiments, X is O or S; each Y is O or S; each $R^1$ is 3-pyrrolyl, or the free base or salt form of $-(CH_2)_n-NH_2$, where each n is 2; each $R^2$ is $CF_3$ or $C(CH_3)_3$; and each $R^3$ is $-(CH_2)_n-NH-C(=NH)NH_2$, where each n is 4.

In some embodiments, the compound is chosen from:

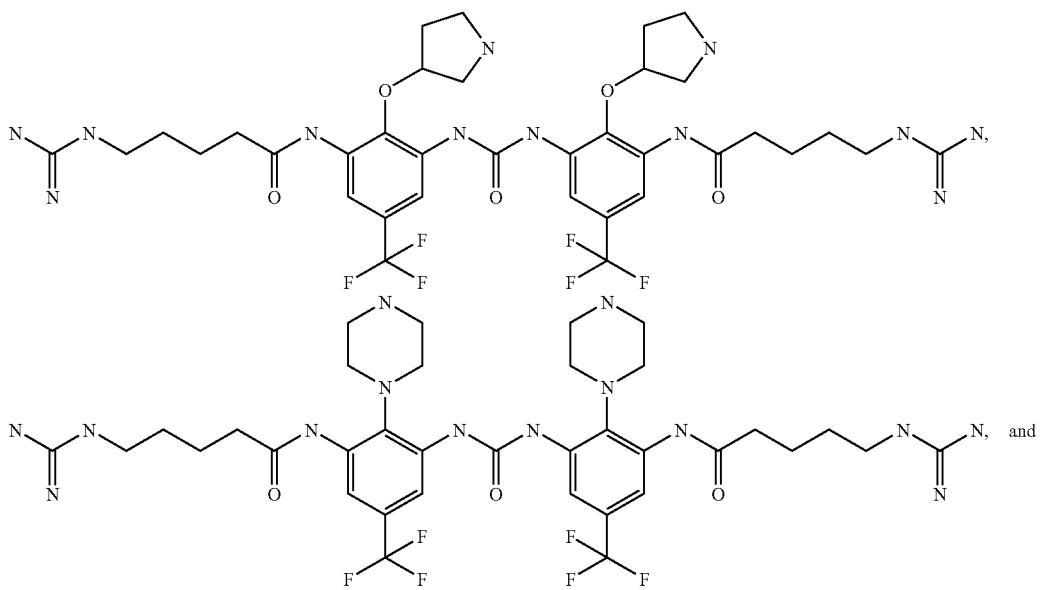

-continued

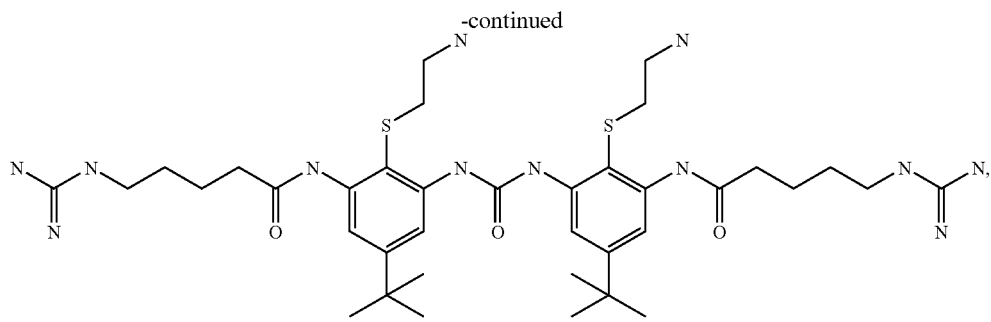

or a pharmaceutically acceptable salt thereof.

In some embodiments, any one or more of the above compounds may be excluded from any of the genus of compounds described above.

The present invention also provides compositions comprising one or more of the compounds or salts described above and a pharmaceutically acceptable carrier.

The present invention also provides methods of treating malaria in an animal comprising administering to the animal a therapeutically effective amount of a compound of Formula II:

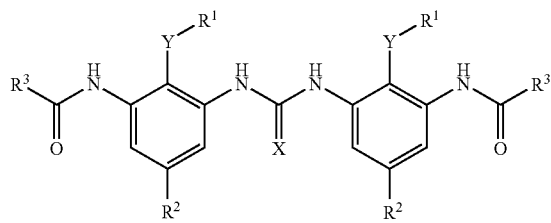

wherein:

X is O or S;

each Y is, independently, O, S, or N;

each $R^1$ is, independently, H, 5- or 6-membered heterocycle, or the free base or salt form of —$(CH_2)_n$—$NH_2$ or —$(CH_2)_n$—NH—C(=NH)$NH_2$, where each n is, independently, 1 to 4; or each $R^1$ is, independently, together with Y a 5- or 6-membered heterocycle;

each $R^2$ is, independently, H, $CF_3$, $C(CH_3)_3$, halo, or OH; and each $R^3$ is, independently, —$(CH_2)_n$—$NH_2$ or —$(CH_2)_n$—NH—C(=NH)$NH_2$, where each n is, independently, 1 to 4;

or a pharmaceutically acceptable salt thereof.

In some embodiments, X is O.

In any of the above embodiments, each Y is O or S.

In any of the above embodiments, each $R^1$ is, independently, 5-membered heterocycle or the free base or salt form of —$(CH_2)_n$—$NH_2$, where each n is, independently, 1 to 4; or each $R^1$ is, independently, 3-pyrrolyl or the free base or salt form of —$(CH_2)_n$—$NH_2$, where each n is, independently, 1 or 2.

In any of the above embodiments, each $R^2$ is, independently, $CF_3$, $C(CH_3)_3$, or halo.

In any of the above embodiments, each $R^3$ is, independently, —$(CH_2)_n$—NH—C(=NH)$NH_2$, where each n is, independently, 1 to 4; or each $R^3$ is —$(CH_2)_n$—NH—C(=NH)$NH_2$, where each n is 4.

In some embodiments, X is O or S; each Y is, independently, O or S; each $R^1$ is, independently, 5-membered heterocycle, or the free base or salt form of —$(CH_2)_n$—$NH_2$, where each n is, independently, 1 to 4; each $R^2$ is, independently, $CF_3$ or $C(CH_3)_3$; and each $R^3$ is, independently, —$(CH_2)_n$—NH—C(=NH)$NH_2$, where each n is, independently, 1 to 4.

In some embodiments, X is O or S; each Y is O or S; each $R^1$ is 5-membered heterocycle, or the free base or salt form of —$(CH_2)_n$—$NH_2$, where each n is 1 to 4; each $R^2$ is $CF_3$ or $C(CH_3)_3$; and each $R^3$ is —$(CH_2)_n$—NH—C(=NH)$NH_2$, where each n is 1 to 4.

In some embodiments, X is O or S; each Y is O or S; each $R^1$ is 3-pyrrolyl, or the free base or salt form of —$(CH_2)_n$—$NH_2$, where each n is 2; each $R^2$ is $CF_3$ or $C(CH_3)_3$; and each $R^3$ is —$(CH_2)_n$—NH—C(=NH)$NH_2$, where each n is 4.

In some embodiments, the compound is chosen from:

Compound 104

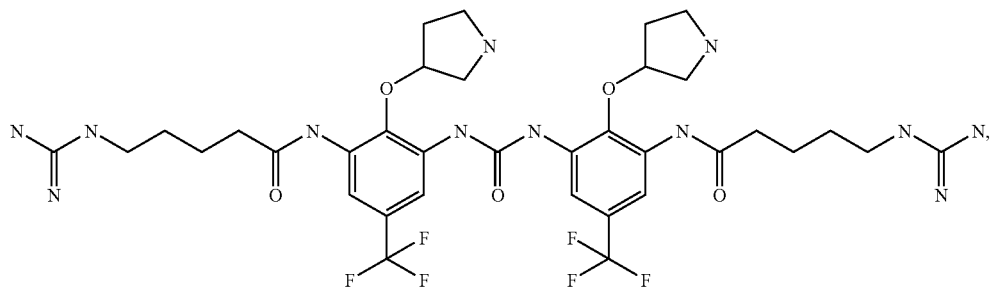

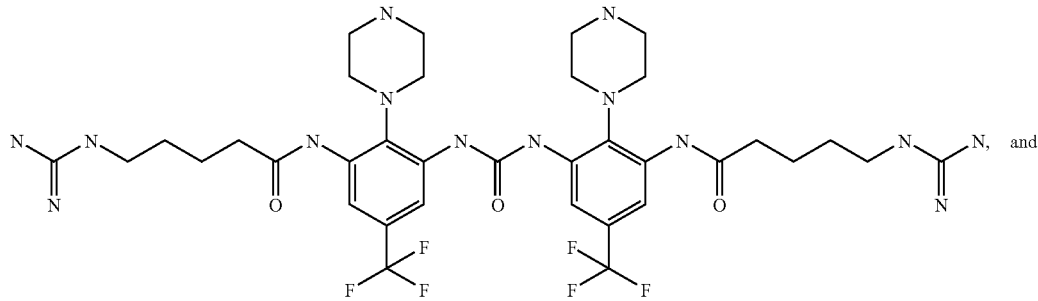

Compound 105

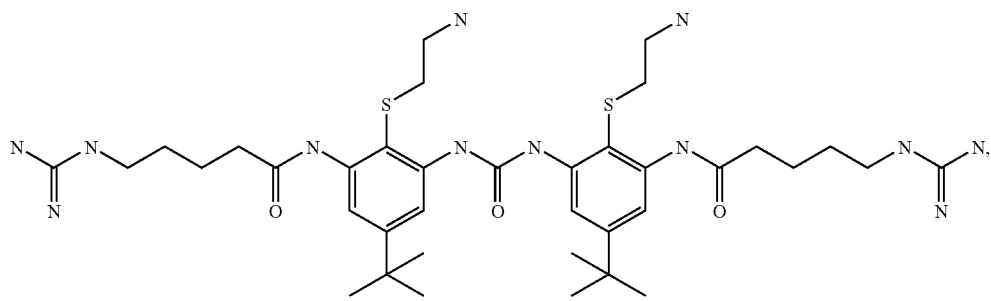

Compound 103 or a pharmaceutically acceptable salt thereof.

In any of the above embodiments, the malaria can be chloroquine-sensitive or chloroquine-resistant.

The present invention also provides methods of killing or inhibiting the growth of a *Plasmodium* species comprising contacting the species with an effective amount of a compound of Formula II:

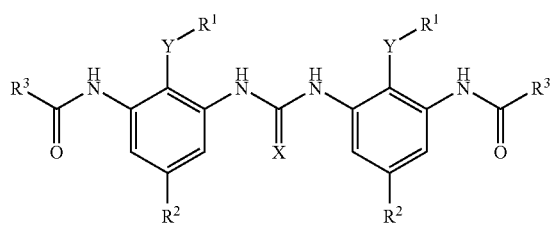

wherein:
X is O or S;
each Y is, independently, O, S, or N;
each $R^1$ is, independently, H, 5- or 6-membered heterocycle, or the free base or salt form of —$(CH_2)_n$—$NH_2$ or —$(CH_2)_n$—NH—C(=NH)$NH_2$, where each n is, independently, 1 to 4; or each $R^1$ is, independently, together with Y a 5- or 6-membered heterocycle;
each $R^2$ is, independently, H, $CF_3$, $C(CH_3)_3$, halo, or OH; and
each $R^3$ is, independently, —$(CH_2)_n$—$NH_2$ or —$(CH_2)_n$—NH—C(=NH)$NH_2$, where each n is, independently, 1 to 4;
or a pharmaceutically acceptable salt thereof.

In some embodiments, X is O.

In any of the above embodiments, each Y is O or S.

In any of the above embodiments, each $R^1$ is, independently, 5-membered heterocycle or the free base or salt form of —$(CH_2)_n$—$NH_2$, where each n is, independently, 1 to 4; or each $R^1$ is, independently, 3-pyrrolyl or the free base or salt form of —$(CH_2)_n$—$NH_2$, where each n is, independently, 1 or 2.

In any of the above embodiments, each $R^2$ is, independently, $CF_3$, $C(CH_3)_3$, or halo.

In any of the above embodiments, each $R^3$ is, independently, —$(CH_2)_n$—NH—C(=NH)$NH_2$, where each n is, independently, 1 to 4; or each $R^3$ is —$(CH_2)_n$—NH—C(=NH)$NH_2$, where each n is 4.

In some embodiments, X is O or S; each Y is, independently, O or S; each $R^1$ is, independently, 5-membered heterocycle, or the free base or salt form of —$(CH_2)_n$—$NH_2$, where each n is, independently, 1 to 4; each $R^2$ is, independently, $CF_3$ or $C(CH_3)_3$; and each $R^3$ is, independently, —$(CH_2)_n$—NH—C(=NH)$NH_2$, where each n is, independently, 1 to 4.

In some embodiments, X is O or S; each Y is O or S; each $R^1$ is 5-membered heterocycle, or the free base or salt form of —$(CH_2)_n$—$NH_2$, where each n is 1 to 4; each $R^2$ is $CF_3$ or $C(CH_3)_3$; and each $R^3$ is —$(CH_2)_n$—NH—C(=NH)$NH_2$, where each n is 1 to 4.

In some embodiments, X is O or S; each Y is O or S; each $R^1$ is 3-pyrrolyl, or the free base or salt form of —$(CH_2)_n$—$NH_2$, where each n is 2; each $R^2$ is $CF_3$ or $C(CH_3)_3$; and each $R^3$ is —$(CH_2)_n$—NH—C(=NH)$NH_2$, where each n is 4.

In some embodiments, the compound is chosen from:

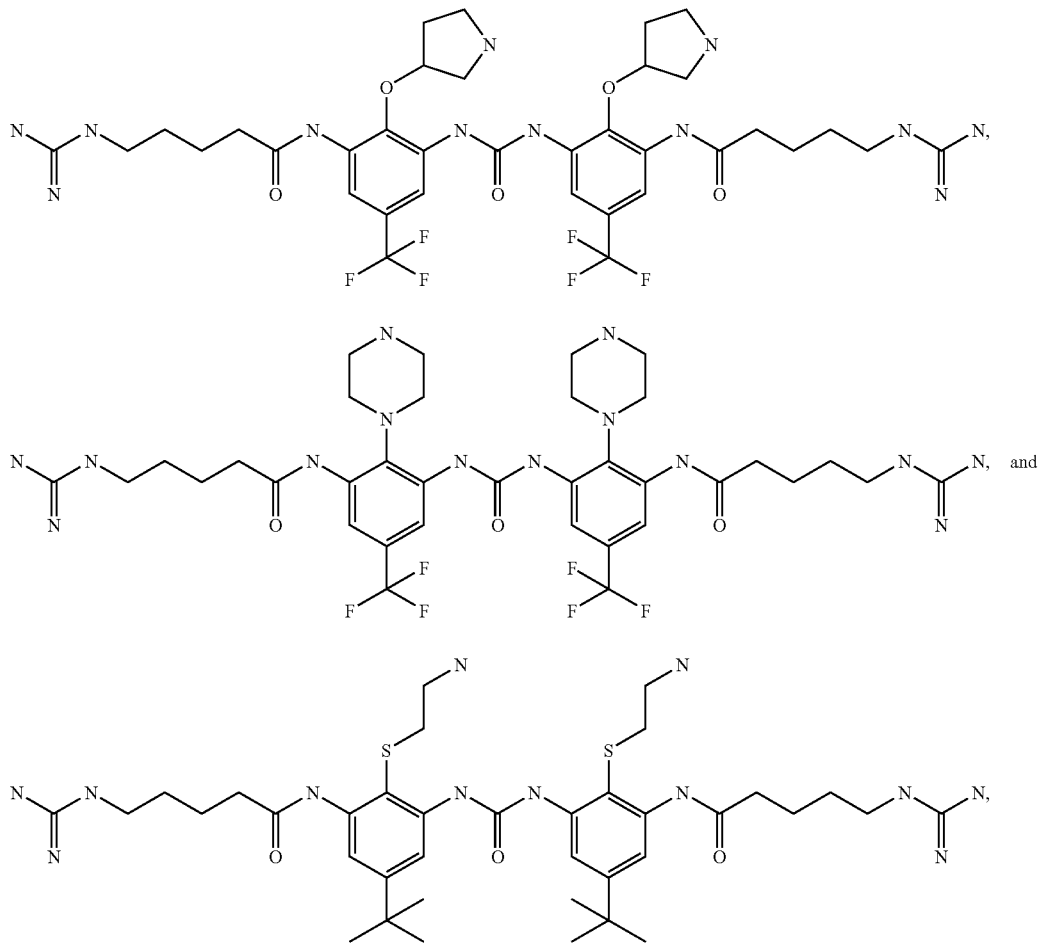

or a pharmaceutically acceptable salt thereof.

The present invention also provides compounds of Formula III:

Q-X—Z—X-Q wherein:

Z is

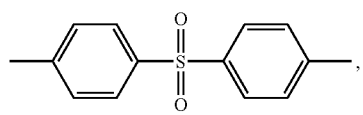

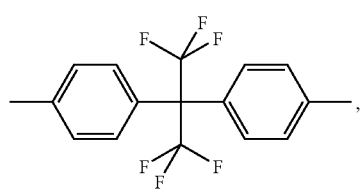

or phenyl;

each Q is, independently,

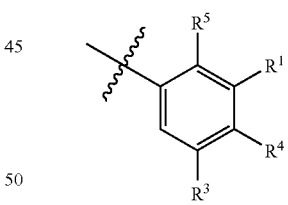

or —C(=O)—(CH$_2$)$_b$—NH—C(=NH)—NH$_2$, where each b is, independently, 1 to 4;

each X is, independently, O, S, or N;

each R$^1$ is, independently, H, CF$_3$, C(CH$_3$)$_3$, halo, or OH;

each R$^3$ is, independently, H, —NH—R$^2$, —(CH$_2$)$_r$—NH$_2$, —NH$_2$, —NH—(CH$_2$)$_w$—NH$_2$, or

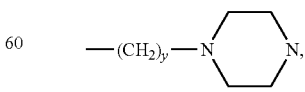

where each r is, independently, 1 or 2, each w is, independently, 1 to 3, and each y is, independently, 1 or 2;

each R$^2$ is, independently, H, or the free base or salt form of —(CH$_2$)$_n$—NH$_2$ or —(CH$_2$)$_n$—NH—C(=NH)NH$_2$, where each n is, independently, 1 to 4;

each $R^4$ is, independently, H, —NH—C(=O)—$(CH_2)_p$—NH—C(=NH)—$NH_2$ or

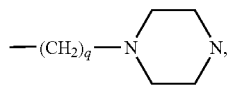

where each p is, independently, 1 to 6, and each q is, independently, 1 or 2; and each $R^5$ is, independently, H or $CF_3$;

or a pharmaceutically acceptable salt thereof.

In some embodiments, Z is

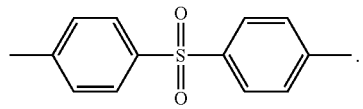

In any of the above embodiments, each Q is, independently,

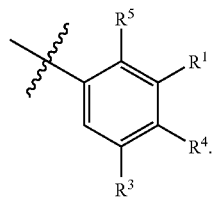

In any of the above embodiments, each X is O.

In any of the above embodiments, each $R^1$ is, independently, H, $CF_3$, or halo; or each $R^1$ is $CF_3$.

In any of the above embodiments, each $R^3$ is, independently, —NH—$R^2$.

In any of the above embodiments, each $R^2$ is, independently, H, or the free base or salt form of —$(CH_2)_n$—$NH_2$, where each n is, independently, 1 to 4; or each $R^2$ is, independently, the free base or salt form of —$(CH_2)_n$—$NH_2$, where each n is, independently, 1 or 2; or each $R^2$ is the free base or salt form of —$(CH_2)_n$—$NH_2$, where each n is 2.

In any of the above embodiments, each $R^4$ and each $R^5$ is H.

In some embodiments, Z is

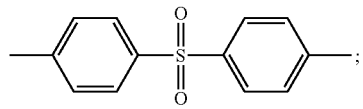

each Q is, independently,

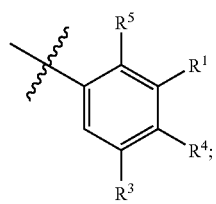

each X is O or S; each $R^1$ is, independently, $CF_3$, $C(CH_3)_3$, or halo; each $R^3$ is, independently, —NH—$R^2$; each $R^2$ is, independently, H, or the free base or salt form of —$(CH_2)_n$—$NH_2$, where each n is, independently, 1 to 4; and each $R^4$ and each $R^5$ is H.

In some embodiments, Z is

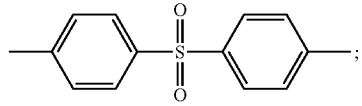

each Q is, independently,

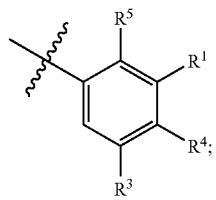

each X is O; each $R^1$ is $CF_3$, $C(CH_3)_3$, or halo; each $R^3$ is, independently, —NH—$R^2$; each $R^2$ is, independently, the free base or salt form of —$(CH_2)_n$—$NH_2$, where each n is 1 or 2; and each $R^4$ and each $R^5$ is H.

In some embodiments, Z is

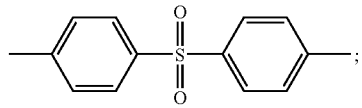

each Q is, independently,

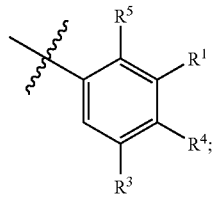

each X is O; each $R^1$ is $CF_3$ or halo; each $R^3$ is, independently, —NH—$R^2$; each $R^2$ is the free base or salt form of —$(CH_2)_n$—$NH_2$, where each n is 2; and each $R^4$ and each $R^5$ is H.

In some embodiments, Z is

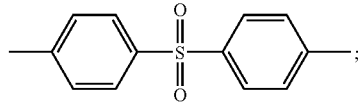

each Q is, independently,

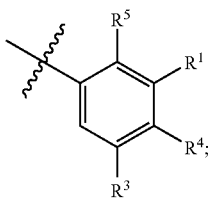

each X is, independently, O, or S; each $R^1$ is, independently, H, or $CF_3$; each $R^3$ is H; each $R^4$ is, independently, H or —NH—C(=O)—(CH$_2$)$_p$—NH—C(=NH)—NH$_2$, where each p is, independently, 3 or 4; and each $R^5$ is, independently, H or $CF_3$.

In some embodiments, Z is

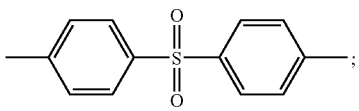

each Q is, independently, —C(=O)—(CH$_2$)$_b$—NH—C(=NH)—NH$_2$, where each b is, independently, 3 or 4; and each X is N.

In some embodiments, Z is

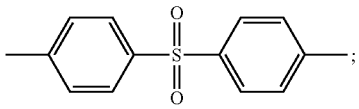

each Q is, independently,

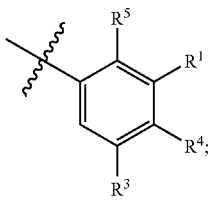

each X is O or S; each $R^1$ is, independently, H or $CF_3$; each $R^3$ is, independently, —(CH$_2$)$_r$—NH$_2$, —NH$_2$, —NH—(CH$_2$)$_w$—NH$_2$, or

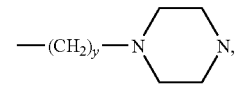

where each r is, independently, 1 or 2, each w is, independently, 1 to 3, and each y is, independently, 1 or 2; each $R^4$ is H; and each $R^5$ is, independently, H or $CF_3$.

In some embodiments, Z is

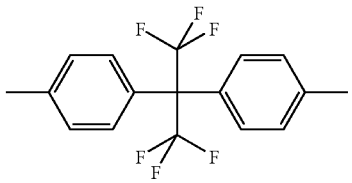

or phenyl; each Q is, independently,

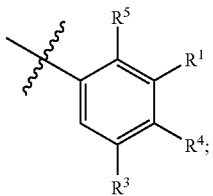

each X is, independently, O or S; each $R^1$ is, independently, H or $CF_3$; each $R^3$ is H; each $R^4$ is, independently,

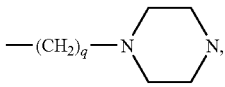

where each q is, independently, 1 or 2; and each $R^5$ is, independently, H or $CF_3$.

In some embodiments, the compound is chosen from:

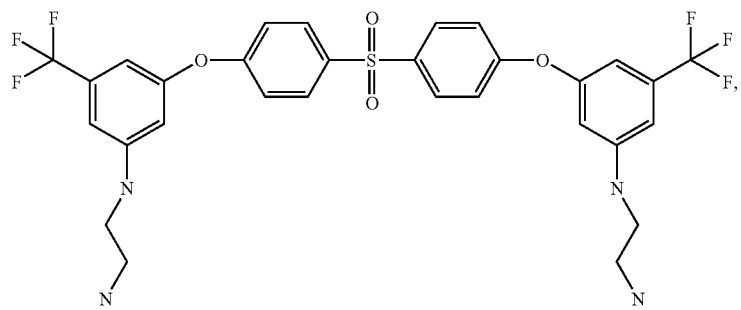

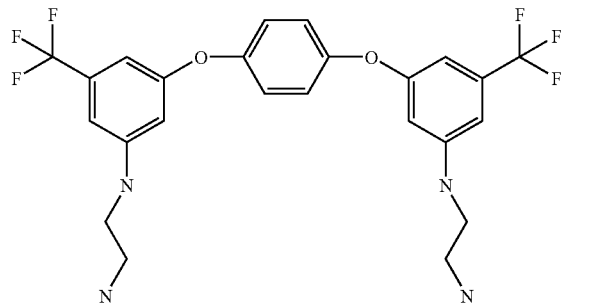
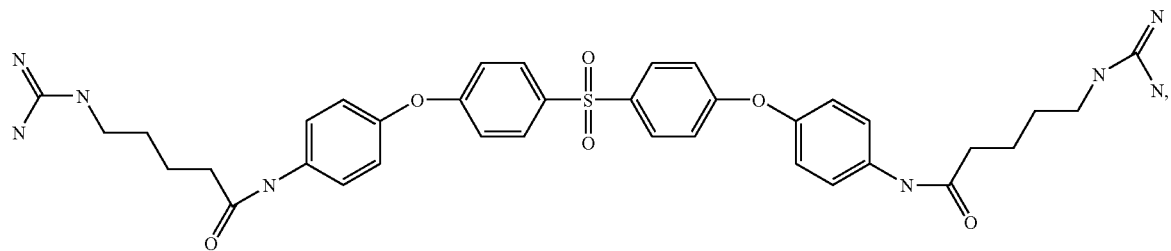
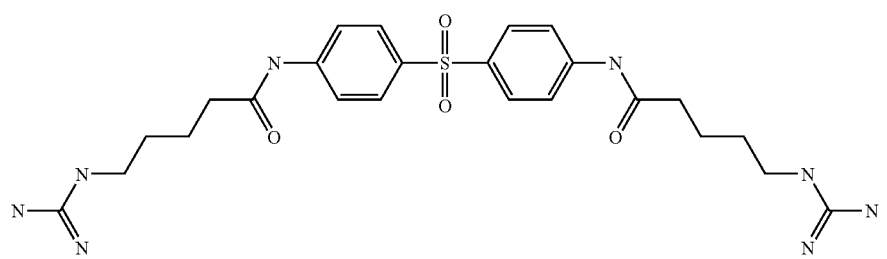
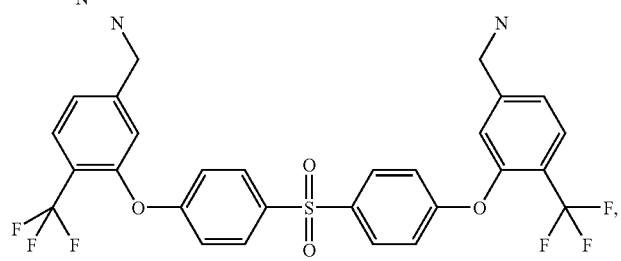
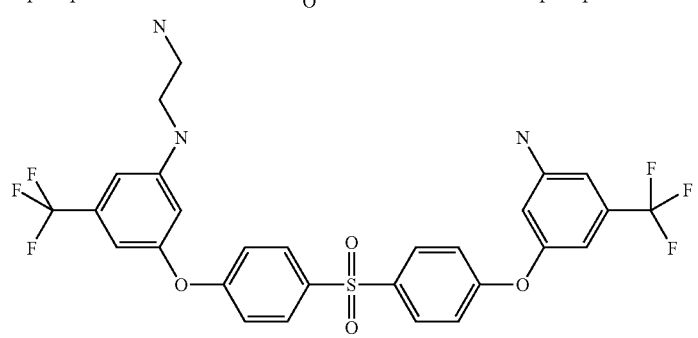
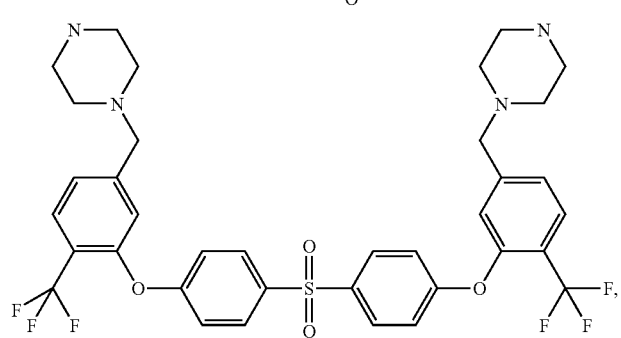

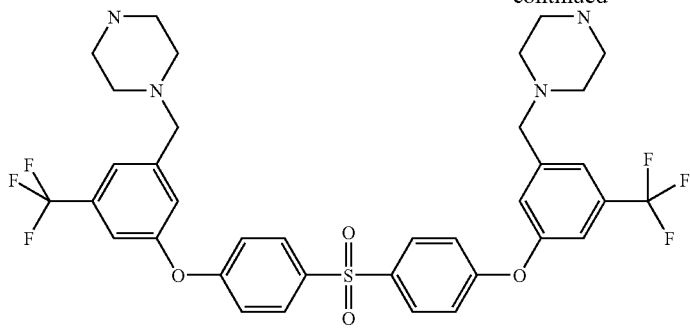

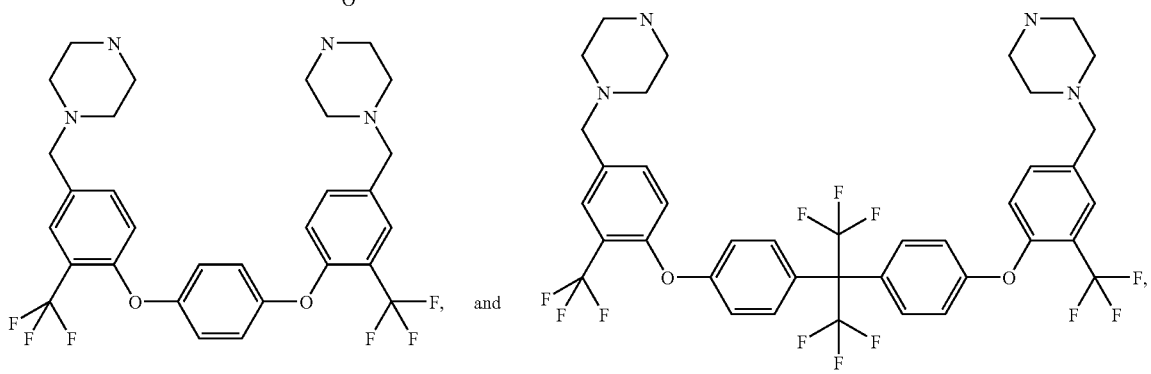

or a pharmaceutically acceptable salt thereof.

In some embodiments, any one or more of the above compounds may be excluded from any of the genus of compounds described above.

The present invention also provides compositions comprising one or more of the compounds or salts described above and a pharmaceutically acceptable carrier.

The present invention also provides methods of treating malaria in an animal comprising administering to the animal a therapeutically effective amount of a compound of Formula III:

Q-X—Z—X-Q wherein:
Z is

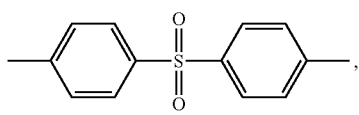

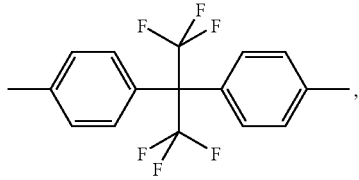

or phenyl;
each Q is, independently,

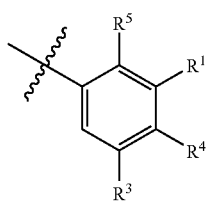

or —C(=O)—(CH$_2$)$_b$—NH—C(=NH)—NH$_2$, where each b is, independently, 1 to 4;
each X is, independently, O, S, or N;
each R$^1$ is, independently, H, CF$_3$, C(CH$_3$)$_3$, halo, or OH;
each R$^3$ is, independently, H, —NH—R$^2$, —(CH$_2$)$_r$—NH$_2$, —NH$_2$, —NH—(CH$_2$)$_w$—NH$_2$, or

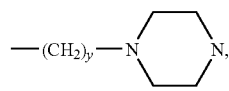

where each r is, independently, 1 or 2, each w is, independently, 1 to 3, and each y is, independently, 1 or 2;
each R$^2$ is, independently, H, or the free base or salt form of —(CH$_2$)$_n$—NH$_2$ or —(CH$_2$)$_n$—NH—C(=NH)NH$_2$, where each n is, independently, 1 to 4;
each R$^4$ is, independently, H, —NH—C(=O)—(CH$_2$)$_p$—NH—C(=NH)—NH$_2$ or

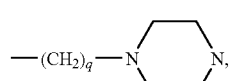

where each p is, independently, 1 to 6, and each q is, independently, 1 or 2; and
each R$^5$ is, independently, H or CF$_3$;
or a pharmaceutically acceptable salt thereof.

In some embodiments, Z is

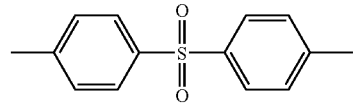

In any of the above embodiments, each Q is, independently,

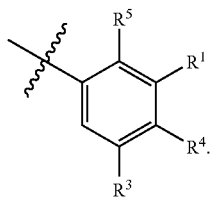

In any of the above embodiments, each X is O.
In any of the above embodiments, each $R^1$ is, independently, H, $CF_3$, or halo; or each $R^1$ is $CF_3$.
In any of the above embodiments, each $R^3$ is, independently, —NH—$R^2$.
In any of the above embodiments, each $R^2$ is, independently, H, or the free base or salt form of —$(CH_2)_n$—$NH_2$, where each n is, independently, 1 to 4; or each $R^2$ is, independently, the free base or salt form of —$(CH_2)_n$—$NH_2$, where each n is, independently, 1 or 2; or each $R^2$ is the free base or salt form of —$(CH_2)_n$—$NH_2$, where each n is 2.
In any of the above embodiments, each $R^4$ and each $R^5$ is H.
In some embodiments, Z is

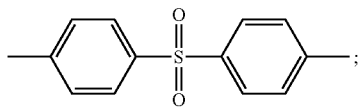

each Q is, independently,

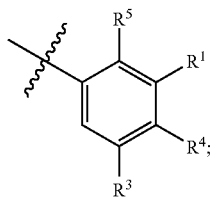

each X is O or S; each $R^1$ is, independently, $CF_3$, $C(CH_3)_3$, or halo; each $R^3$ is, independently, —NH—$R^2$; each $R^2$ is, independently, H, or the free base or salt form of —$(CH_2)_n$—$NH_2$, where each n is, independently, 1 to 4; and each $R^4$ and each $R^5$ is H.
In some embodiments, Z is

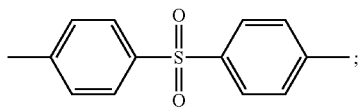

each Q is, independently,

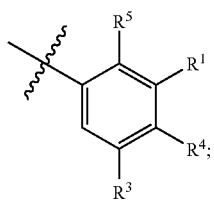

each X is O; each $R^1$ is $CF_3$, $C(CH_3)_3$, or halo; each $R^3$ is, independently, —NH—$R^2$; each $R^2$ is, independently, the free base or salt form of —$(CH_2)_n$—$NH_2$, where each n is 1 or 2; and each $R^4$ and each $R^5$ is H.
In some embodiments, Z is

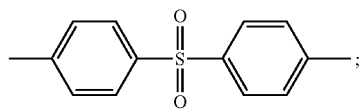

each Q is, independently,

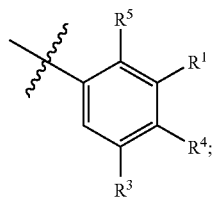

each X is O; each $R^1$ is $CF_3$ or halo; each $R^3$ is, independently, —NH—$R^2$; each $R^2$ is the free base or salt form of —$(CH_2)_n$—$NH_2$, where each n is 2; and each $R^4$ and each $R^5$ is H.
In some embodiments, Z is

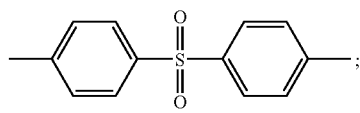

each Q is, independently,

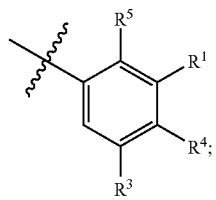

each X is, independently, O, or S; each $R^1$ is, independently, H, or $CF_3$; each $R^3$ is H; each $R^4$ is, independently, H or —NH—C(=O)—$(CH_2)_p$—NH—C(=NH)—$NH_2$, where each p is, independently, 3 or 4; and each $R^5$ is, independently, H or $CF_3$.
In some embodiments, Z is

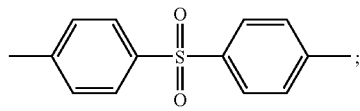

each Q is, independently, —C(=O)—$(CH_2)_b$—NH—C(=NH)—$NH_2$, where each b is, independently, 3 or 4; and each X is N.

In some embodiments, Z is

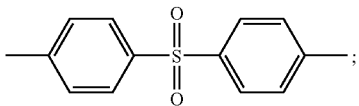

each Q is, independently,

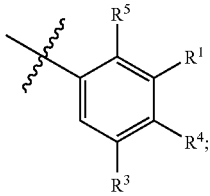

each X is O or S; each $R^1$ is, independently, H or $CF_3$; each $R^3$ is, independently, $-(CH_2)_r-NH_2$, $-NH_2$, $-NH-(CH_2)_w-NH_2$, or

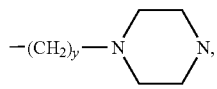

where each r is, independently, 1 or 2, each w is, independently, 1 to 3, and each y is, independently, 1 or 2; each $R^4$ is H; and each $R^5$ is, independently, H or $CF_3$.

In some embodiments, Z is

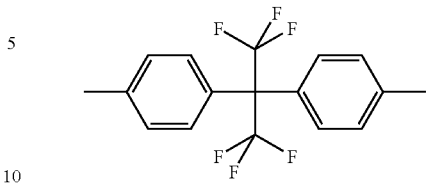

or phenyl; each Q is, independently,

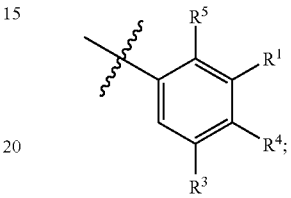

each X is, independently, O or S; each $R^1$ is, independently, H or $CF_3$; each $R^3$ is H; each $R^4$ is, independently,

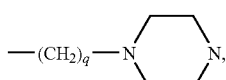

where each q is, independently, 1 or 2; and each $R^5$ is, independently, H or $CF_3$.

In some embodiments, the compound is chosen from:

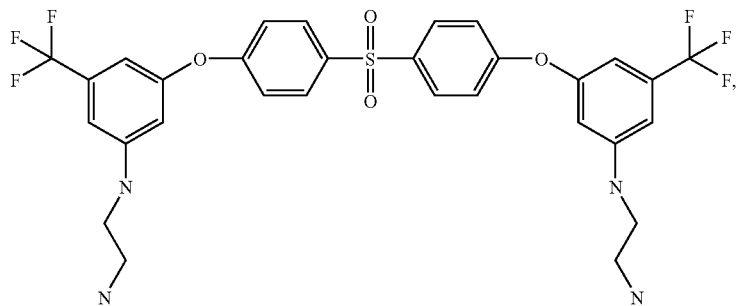

Compound 111

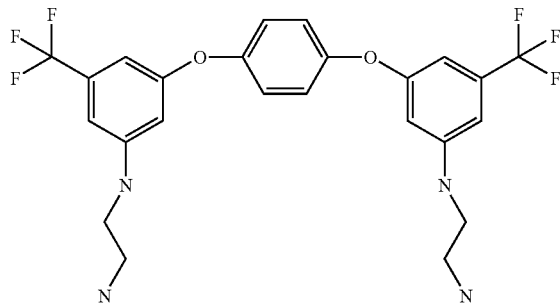

Compound 109

Compound 142
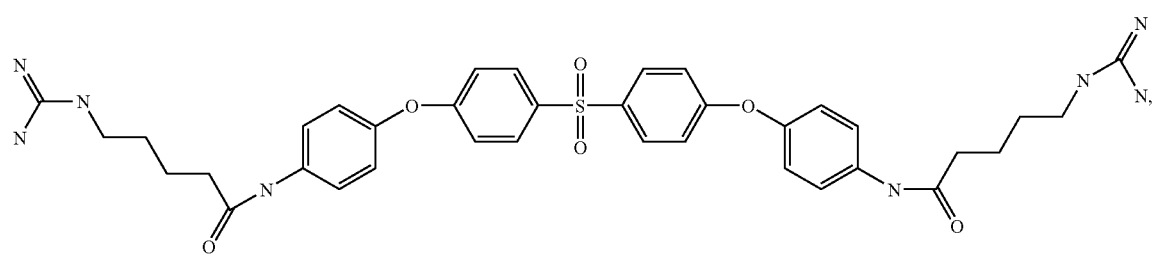
Compound 149
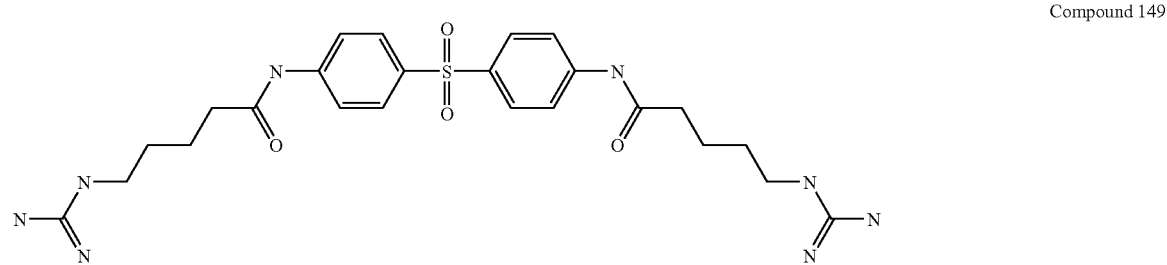
Compound 143
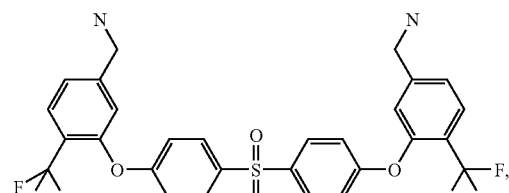
Compound 144
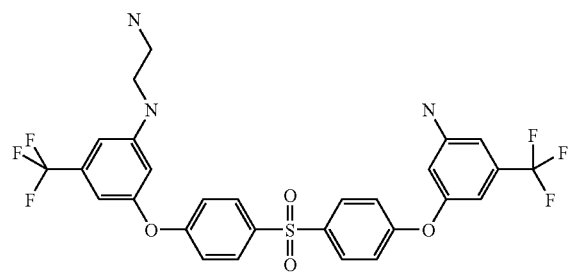
Compound 145
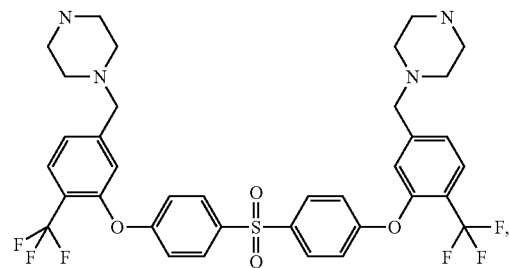
Compound 146
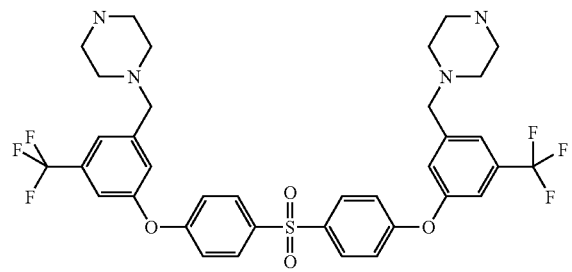
Compound 147
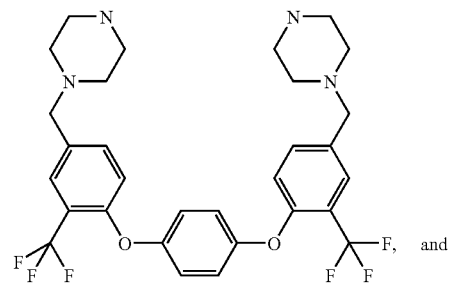
and
Compound 148
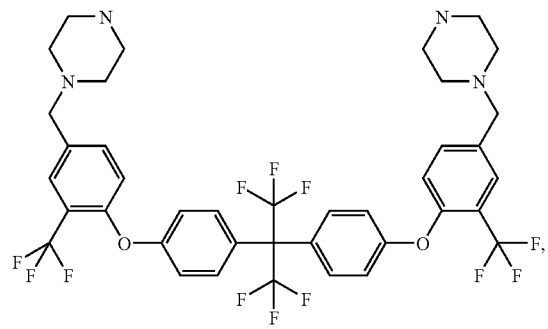
or a pharmaceutically acceptable salt thereof.

In any of the above embodiments, the malaria can be chloroquine-sensitive or chloroquine-resistant.

The present invention also provides methods of killing or inhibiting the growth of a *Plasmodium* species comprising contacting the species with an effective amount of a compound of Formula III:

Q-X—Z—X-Q wherein:

Z is

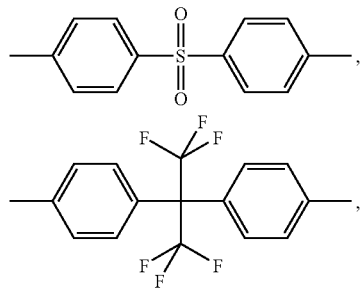

or phenyl;

each Q is, independently,

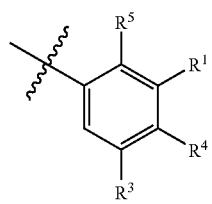

or —C(=O)—(CH$_2$)$_b$—NH—C(=NH)—NH$_2$, where each b is, independently, 1 to 4;

each X is, independently, O, S, or N;
each R$^1$ is, independently, H, CF$_3$, C(CH$_3$)$_3$, halo, or OH;
each R$^3$ is, independently, H, —NH—R$^2$, —(CH$_2$)$_r$—NH$_2$, —NH$_2$, —NH—(CH$_2$)$_w$—NH$_2$, or

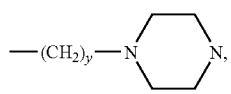

where each r is, independently, 1 or 2, each w is, independently, 1 to 3, and each y is, independently, 1 or 2;

each R$^2$ is, independently, H, or the free base or salt form of —(CH$_2$)$_n$—NH$_2$ or —(CH$_2$)$_n$—NH—C(=NH)NH$_2$, where each n is, independently, 1 to 4;

each R$^4$ is, independently, H, —NH—C(=O)—(CH$_2$)$_p$—NH—C(=NH)—NH$_2$ or

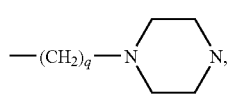

where each p is, independently, 1 to 6, and each q is, independently, 1 or 2; and each R$^5$ is, independently, H or CF$_3$;
or a pharmaceutically acceptable salt thereof.

In some embodiments, Z is

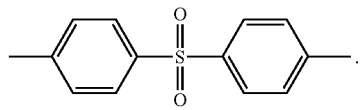

In any of the above embodiments, each Q is, independently,

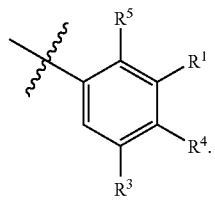

In any of the above embodiments, each X is O.

In any of the above embodiments, each R$^1$ is, independently, H, CF$_3$, or halo; or each R$^1$ is CF$_3$.

In any of the above embodiments, each R$^3$ is, independently, —NH—R$^2$.

In any of the above embodiments, each R$^2$ is, independently, H, or the free base or salt form of —(CH$_2$)$_n$—NH$_2$, where each n is, independently, 1 to 4; or each R$^2$ is, independently, the free base or salt form of —(CH$_2$)$_n$—NH$_2$, where each n is, independently, 1 or 2; or each R$^2$ is the free base or salt form of —(CH$_2$)$_n$—NH$_2$, where each n is 2.

In any of the above embodiments, each R$^4$ and each R$^5$ is H.

In some embodiments, Z is

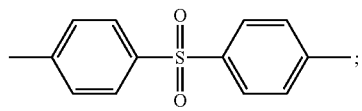

each Q is, independently,

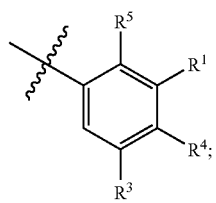

each X is O or S; each R$^1$ is, independently, CF$_3$, C(CH$_3$)$_3$, or halo; each R$^3$ is, independently, —NH—R$^2$; each R$^2$ is, independently, H, or the free base or salt form of —(CH$_2$)$_n$—NH$_2$, where each n is, independently, 1 to 4; and each R$^4$ and each R$^5$ is H.

In some embodiments, Z is

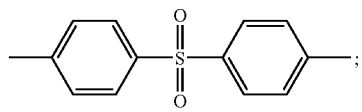

each Q is, independently,

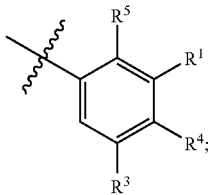

each X is O; each $R^1$ is $CF_3$, $C(CH_3)_3$, or halo; each $R^3$ is, independently, —NH—$R^2$; each $R^2$ is, independently, the free base or salt form of —$(CH_2)_n$—$NH_2$, where each n is 1 or 2; and each $R^4$ and each $R^5$ is H.

In some embodiments, Z is

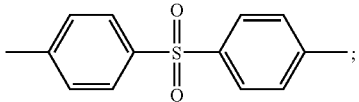

each Q is, independently,

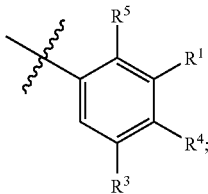

each X is O; each $R^1$ is $CF_3$ or halo; each $R^3$ is, independently, —NH—$R^2$; each $R^2$ is the free base or salt form of —$(CH_2)_n$—$NH_2$, where each n is 2; and each $R^4$ and each $R^5$ is H.

In some embodiments, Z is

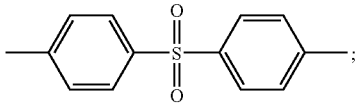

each Q is, independently,

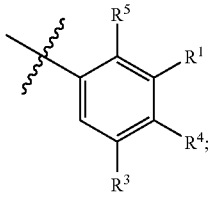

each X is, independently, O, or S; each $R^1$ is, independently, H, or $CF_3$; each $R^3$ is H; each $R^4$ is, independently, H or —NH—C(=O)—$(CH_2)_p$—NH—C(=NH)—$NH_2$, where each p is, independently, 3 or 4; and each $R^5$ is, independently, H or $CF_3$.

In some embodiments, Z is

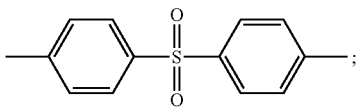

each Q is, independently, —C(=O)—$(CH_2)_b$—NH—C(=NH)—$NH_2$, where each b is, independently, 3 or 4; and each X is N.

In some embodiments, Z is

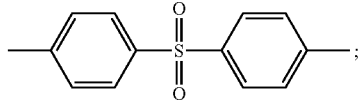

each Q is, independently,

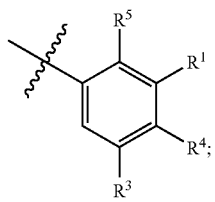

each X is O or S; each $R^1$ is, independently, H or $CF_3$; each $R^3$ is, independently, —$(CH_2)_r$—$NH_2$, —$NH_2$, —NH—$(CH_2)_w$—$NH_2$, or

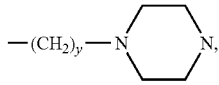

where each r is, independently, 1 or 2, each w is, independently, 1 to 3, and each y is, independently, 1 or 2; each $R^4$ is H; and each $R^5$ is, independently, H or $CF_3$.

In some embodiments, Z is

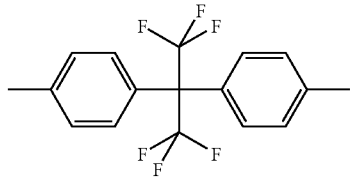

or phenyl; each Q is, independently,

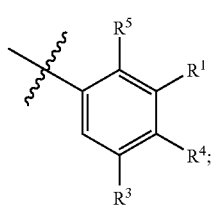

each X is, independently, O or S; each $R^1$ is, independently, H or $CF_3$; each $R^3$ is H; each $R^4$ is, independently,

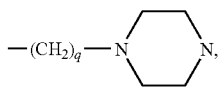

where each q is, independently, 1 or 2; and each $R^5$ is, independently, H or $CF_3$.

In some embodiments, the compound is chosen from:
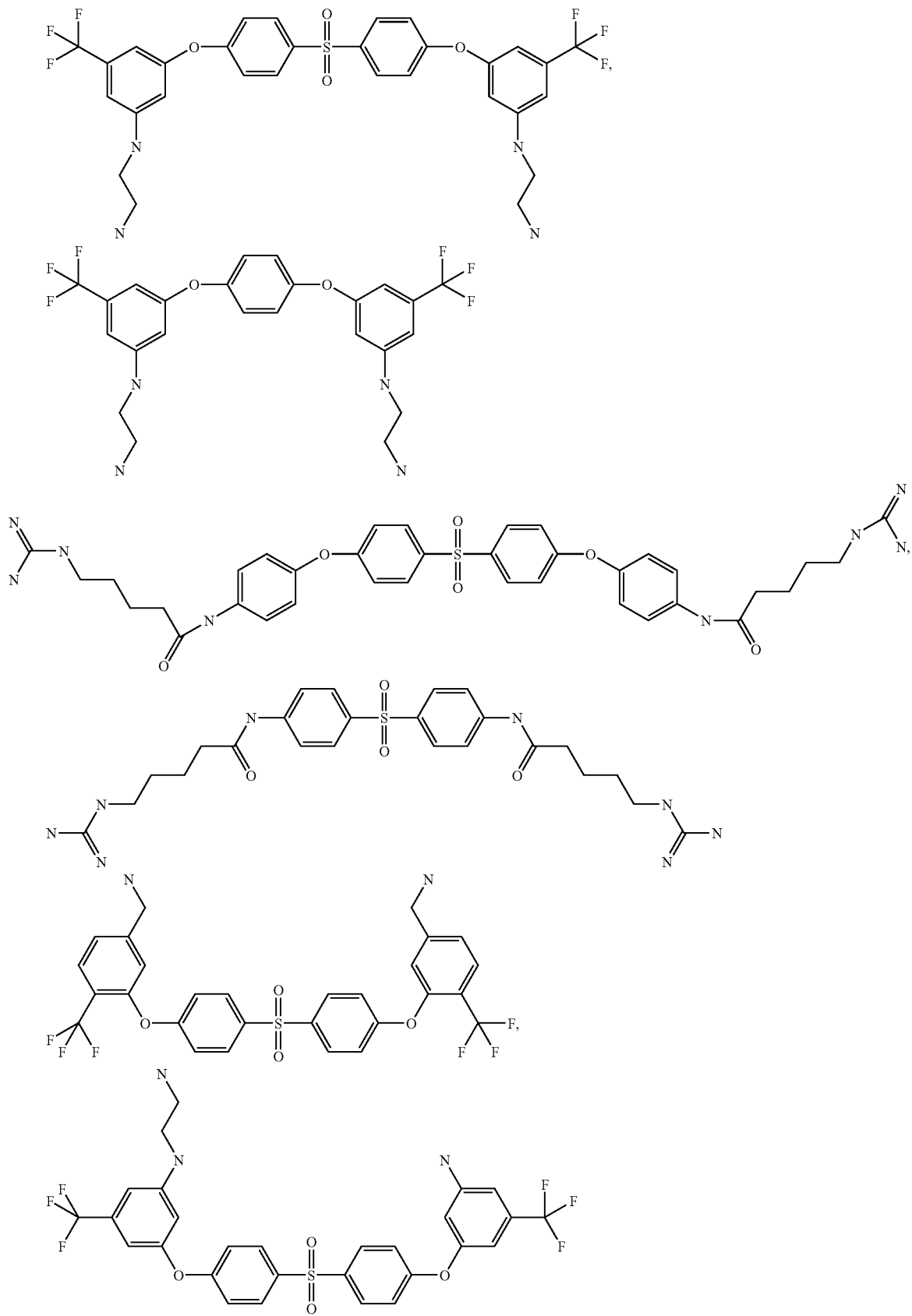

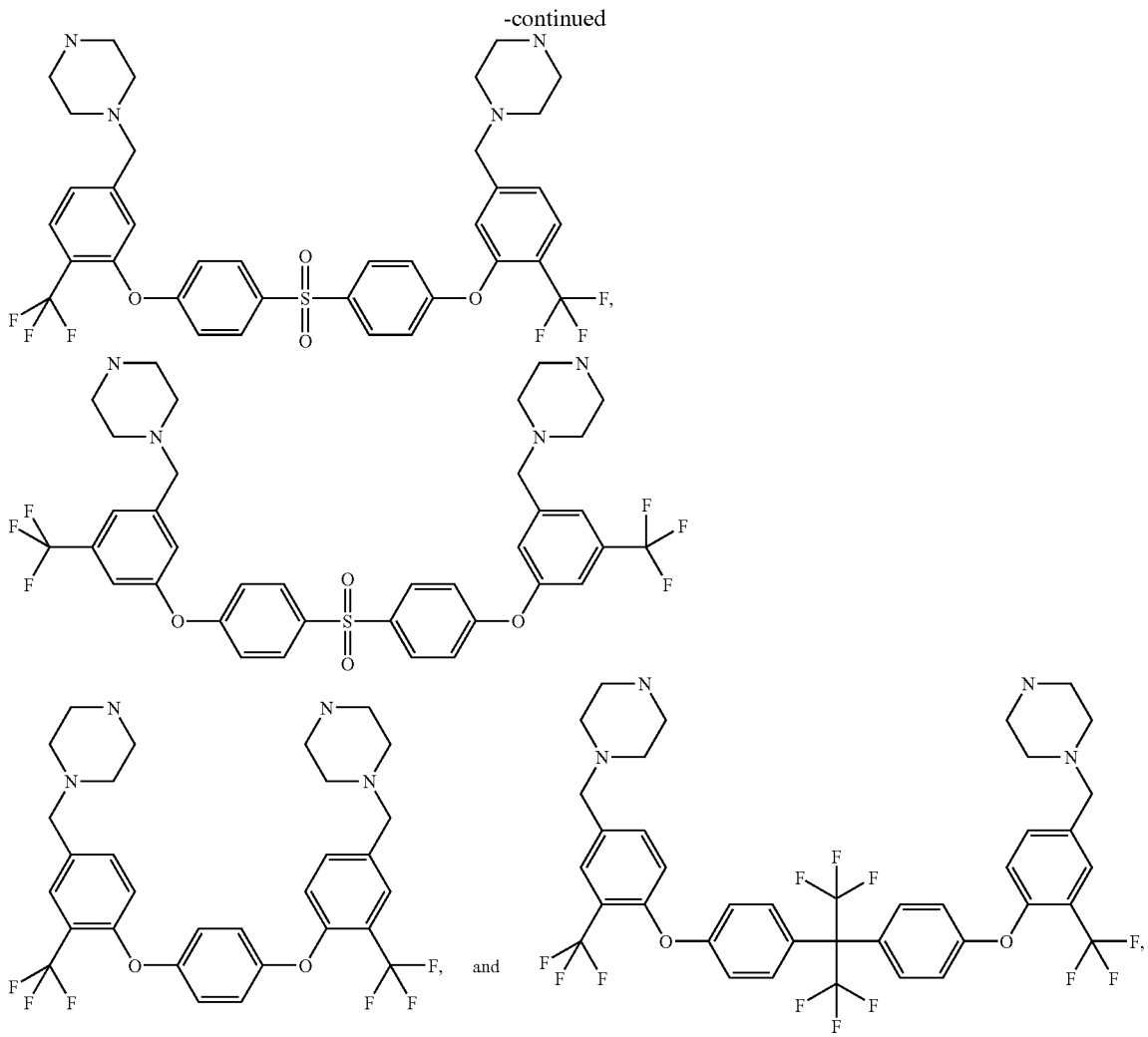
or a pharmaceutically acceptable salt thereof.
The present invention also provides compounds of Formula IV:
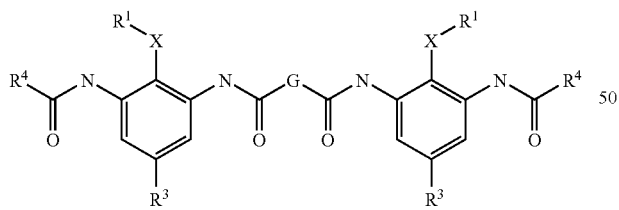
wherein:
G is
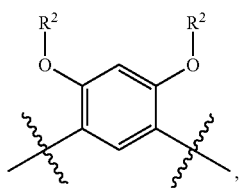
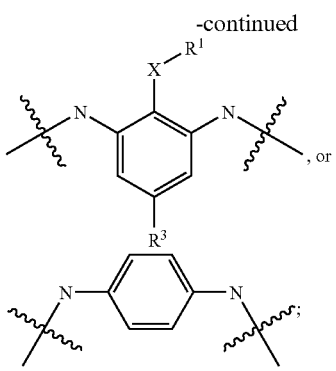
each X is, independently, O or S;
each $R^1$ is, independently,
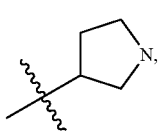

or the free base or salt form of —(CH$_2$)$_n$—NH$_2$ or —(CH$_2$)$_n$—NH—C(=NH)NH$_2$, where each n is, independently, 1 to 4;

each R$^2$ is, independently, H, C$_1$-C$_8$alkyl, or the free base or salt form of —(CH$_2$)$_n$—NH$_2$ or —(CH$_2$)$_n$—NH—C(=NH)NH$_2$, where each n is, independently, 1 to 4;

each R$^3$ is, independently, H, CF$_3$, C(CH$_3$)$_3$, halo, or OH; and each R$^4$ is, independently, —(CH$_2$)$_n$—NH$_2$ or —(CH$_2$)$_n$—NH—C(=NH)NH$_2$, where each n is, independently, 1 to 4; or a pharmaceutically acceptable salt thereof.

In some embodiments, G is

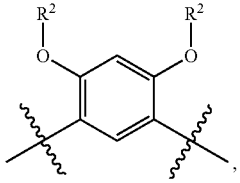

and each X is S.

In any of the above embodiments, each R$^1$ is, independently, the free base or salt form of —(CH$_2$)$_n$—NH$_2$, where each n is, independently, 1 to 4; or each R$^1$ is, independently, the free base or salt form of —(CH$_2$)$_n$—NH$_2$, where each n is, independently, 1 or 2; or each R$^1$ is the free base or salt form of —(CH$_2$)$_n$—NH$_2$, where each n is 2.

In any of the above embodiments, each R$^2$ is, independently, C$_1$-C$_3$alkyl or the free base or salt form of —(CH$_2$)$_n$—NH$_2$ where n is 1 to 4; or each R$^2$ is, independently, C$_1$-C$_3$alkyl or the free base or salt form of —(CH$_2$)$_n$—NH$_2$, where each n is, independently, 1 or 2; or each R$^2$ is, independently, methyl or the free base or salt form of —(CH$_2$)$_n$—NH$_2$, where each n is, independently, 2; or each R$^2$ is methyl or the free base or salt form of —(CH$_2$)$_n$—NH$_2$, where each n is 2.

In any of the above embodiments, each R$^3$ is, independently, CF$_3$, C(CH$_3$)$_3$, or halo; or each R$^3$ is CF$_3$.

In any of the above embodiments, each R$^4$ is, independently, —(CH$_2$)$_n$—NH—C(=NH)NH$_2$, where each n is, independently, 1 to 4; or each R$^4$ is —(CH$_2$)$_n$—NH—C(=NH)NH$_2$, where each n is 4.

In some embodiments, G is

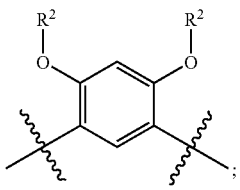

each X is S; each R$^1$ is, independently, the free base or salt form of —(CH$_2$)$_n$—NH$_2$, where each n is, independently, 1 or 2; each R$^2$ is, independently, C$_1$-C$_8$alkyl or the free base or salt form of —(CH$_2$)$_n$—NH$_2$, where each n is, independently, 1 or 2; each R$^3$ is, independently, CF$_3$, C(CH$_3$)$_3$, or halo; and each R$^4$ is, independently, —(CH$_2$)$_n$—NH—C(=NH)NH$_2$, where each n is, independently, 3 or 4.

In some embodiments, G is

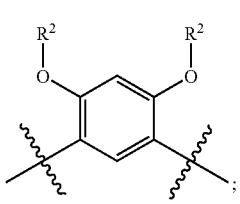

each X is S; each R$^1$ is the free base or salt form of —(CH$_2$)$_n$—NH$_2$, where each n is 1 or 2; each R$^2$ is, independently, C$_1$-C$_3$alkyl or the free base or salt form of —(CH$_2$)$_n$—NH$_2$, where each n is 2; each R$^3$ is, independently, CF$_3$ or C(CH$_3$)$_3$; and each R$^4$ is —(CH$_2$)$_n$—NH—C(=NH)NH$_2$, where each n is 3 or 4.

In some embodiments, G is

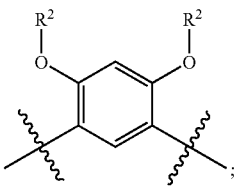

each X is S; each R$^1$ is the free base or salt form of —(CH$_2$)$_n$—NH$_2$, where each n is 2; each R$^2$ is, independently, methyl or the free base or salt form of —(CH$_2$)$_n$—NH$_2$, where each n is 2; each R$^3$ is, independently, CF$_3$ or C(CH$_3$)$_3$; and each R$^4$ is —(CH$_2$)$_n$—NH—C(=NH)NH$_2$, where each n is 4.

In some embodiments, G is

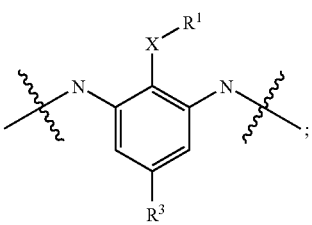

each X is, independently, O or S; each R$^1$ is, independently, the free base or salt form of —(CH$_2$)$_n$—NH$_2$ or —(CH$_2$)$_n$—NH—C(=NH)NH$_2$, where each n is, independently, 1 to 4; each R$^3$ is, independently, H or CF$_3$; and each R$^4$ is, independently, —(CH$_2$)$_n$—NH$_2$ or —(CH$_2$)$_n$—NH—C(=NH)NH$_2$, where each n is, independently, 1 to 4.

In some embodiments, G is

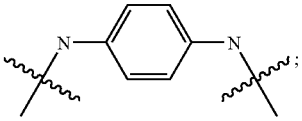

each X is, independently, O or S; each R$^1$ is

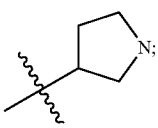

each R$^3$ is, independently, H or CF$_3$; and each R$^4$ is, independently, —(CH$_2$)$_n$—NH$_2$ or —(CH$_2$)$_n$—NH—C(=NH)NH$_2$, where each n is, independently, 1 to 4.

In some embodiments, the compound is chosen from:

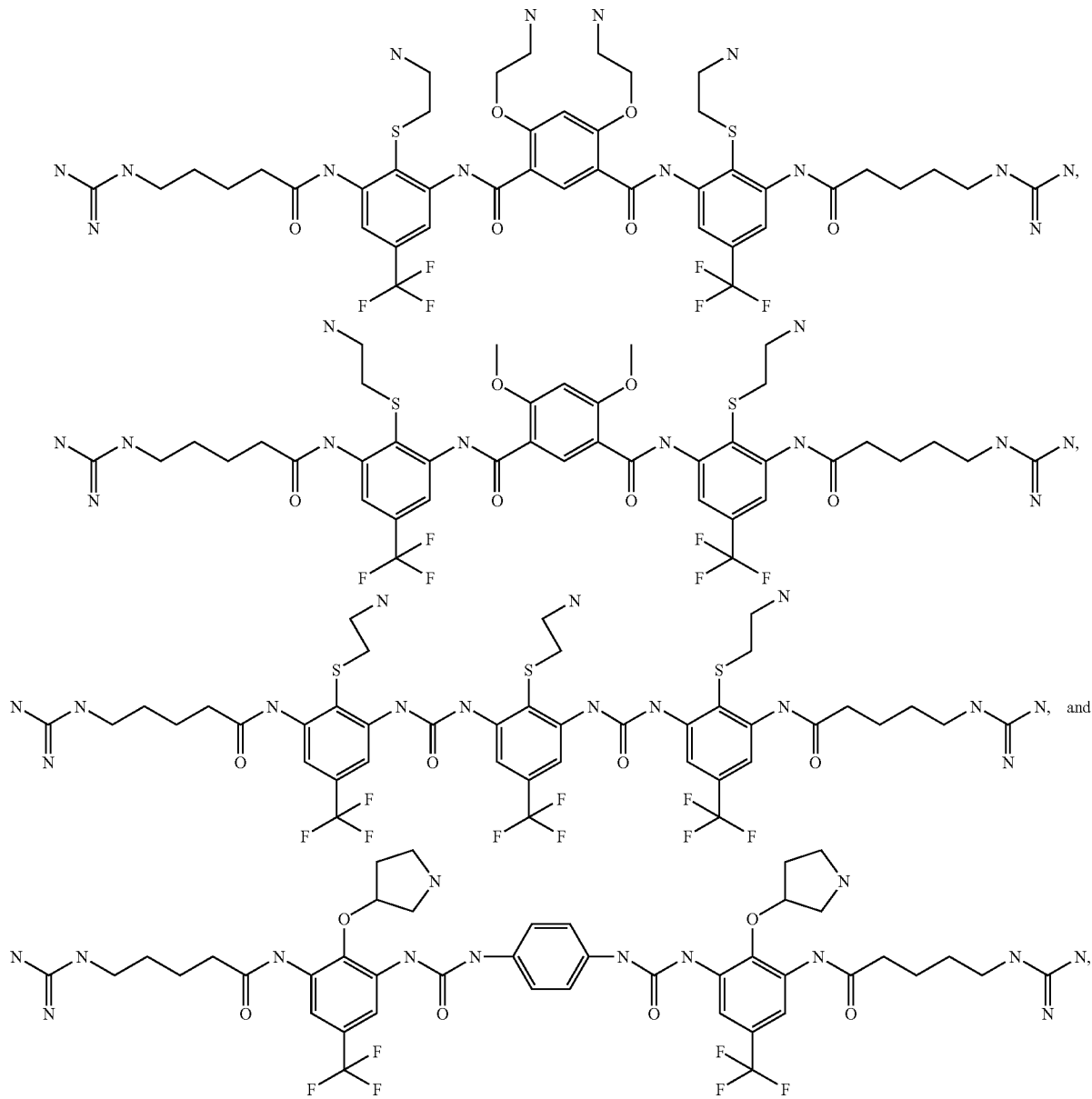

or a pharmaceutically acceptable salt thereof.

In some embodiments, any one or more of the above compounds may be excluded from any of the genus of compounds described above.

The present invention also provides compositions comprising one or more of the compounds or salts described above and a pharmaceutically acceptable carrier.

The present invention also provides methods of treating malaria in an animal comprising administering to the animal a therapeutically effective amount of a compound of Formula IV:

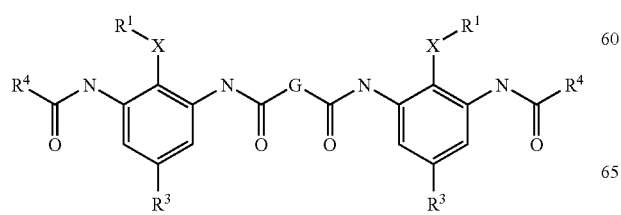

wherein:

G is

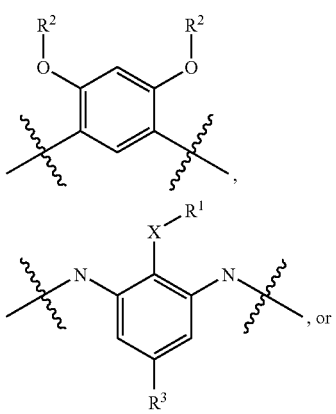

-continued

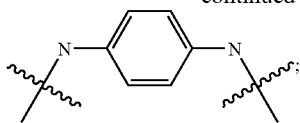

each X is, independently, O or S;
each R$^1$ is, independently,

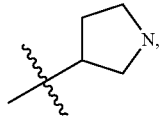

or the free base or salt form of —(CH$_2$)$_n$—NH$_2$ or —(CH$_2$)$_n$—NH—C(═NH)NH$_2$, where each n is, independently, 1 to 4;

each R$^2$ is, independently, H, C$_1$-C$_8$alkyl, or the free base or salt form of —(CH$_2$)$_n$—NH$_2$ or —(CH$_2$)$_n$—NH—C(═NH)NH$_2$, where each n is, independently, 1 to 4;

each R$^3$ is, independently, H, CF$_3$, C(CH$_3$)$_3$, halo, or OH; and each R$^4$ is, independently, —(CH$_2$)$_n$—NH$_2$ or —(CH$_2$)$_n$—NH—C(═NH)NH$_2$, where each n is, independently, 1 to 4;

or a pharmaceutically acceptable salt thereof.

In some embodiments, G is

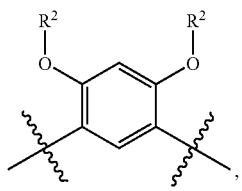

and each X is S.

In any of the above embodiments, each R$^1$ is, independently, the free base or salt form of —(CH$_2$)$_n$—NH$_2$, where each n is, independently, 1 to 4; or each R$^1$ is, independently, the free base or salt form of —(CH$_2$)$_n$—NH$_2$, where each n is, independently, 1 or 2; or each R$^1$ is the free base or salt form of —(CH$_2$)$_n$—NH$_2$, where each n is 2.

In any of the above embodiments, each R$^2$ is, independently, C$_1$-C$_3$alkyl or the free base or salt form of —(CH$_2$)$_n$—NH$_2$ where n is 1 to 4; or each R$^2$ is, independently, C$_1$-C$_3$alkyl or the free base or salt form of —(CH$_2$)$_n$—NH$_2$, where each n is, independently, 1 or 2; or each R$^2$ is, independently, methyl or the free base or salt form of —(CH$_2$)$_n$—NH$_2$, where each n is, independently, 2; or each R$^2$ is methyl or the free base or salt form of —(CH$_2$)$_n$—NH$_2$, where each n is 2.

In any of the above embodiments, each R$^3$ is, independently, CF$_3$, C(CH$_3$)$_3$, or halo; or each R$^3$ is CF$_3$.

In any of the above embodiments, each R$^4$ is, independently, —(CH$_2$)$_n$—NH—C(═NH)NH$_2$, where each n is, independently, 1 to 4; or each R$^4$ is (CH$_2$)$_n$—NH—C(═NH)NH$_2$, where each n is 4.

In some embodiments, G is

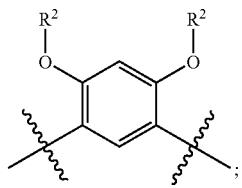

each X is S; each R$^1$ is, independently, the free base or salt form of —(CH$_2$)$_n$—NH$_2$, where each n is, independently, 1 or 2; each R$^2$ is, independently, C$_1$-C$_8$alkyl or the free base or salt form of —(CH$_2$)$_n$—NH$_2$, where each n is, independently, 1 or 2; each R$^3$ is, independently, CF$_3$, C(CH$_3$)$_3$, or halo; and each R$^4$ is, independently, —(CH$_2$)$_n$—NH—C(═NH)NH$_2$, where each n is, independently, 3 or 4.

In some embodiments, G is

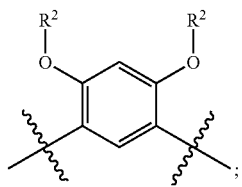

each X is S; each R$^1$ is the free base or salt form of —(CH$_2$)$_n$—NH$_2$, where each n is 1 or 2; each R$^2$ is, independently, C$_1$-C$_3$alkyl or the free base or salt form of —(CH$_2$)$_n$—NH$_2$, where n is 2; each R$^3$ is, independently, CF$_3$ or C(CH$_3$)$_3$; and each R$^4$ is —(CH$_2$)$_n$—NH—C(═NH)NH$_2$, where each n is 3 or 4.

In some embodiments, G is

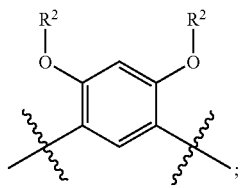

each X is S; each R$^1$ is the free base or salt form of —(CH$_2$)$_n$—NH$_2$, where each n is 2; each R$^2$ is, independently, methyl or the free base or salt form of —(CH$_2$)$_n$—NH$_2$, where each n is 2; each R$^3$ is, independently, CF$_3$ or C(CH$_3$)$_3$; and each R$^4$ is —(CH$_2$)$_n$—NH—C(═NH)NH$_2$, where each n is 4.

In some embodiments, G is

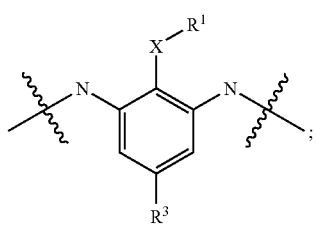

each X is, independently, O or S; each R¹ is, independently, the free base or salt form of —(CH$_2$)$_n$—NH$_2$ or —(CH$_2$)$_n$—NH—C(=NH)NH$_2$, where each n is, independently, 1 to 4; each R³ is, independently, H or CF$_3$; and each R⁴ is, independently, —(CH$_2$)$_n$—NH$_2$ or —(CH$_2$)$_n$—NH—C(=NH)NH$_2$, where each n is, independently, 1 to 4.

In some embodiments, G is

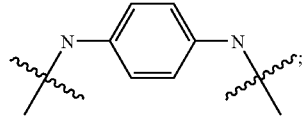 [SMILES: *Nc1ccc(N*)cc1 ; ";"]

each X is, independently, O or S; each R¹ is

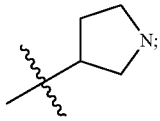

each R³ is, independently, H or CF$_3$; and each R⁴ is, independently, —(CH$_2$)$_n$—NH$_2$ or —(CH$_2$)$_n$—NH—C(=NH)NH$_2$, where each n is, independently, 1 to 4.

In some embodiments, the compound is chosen from:

Compound 102

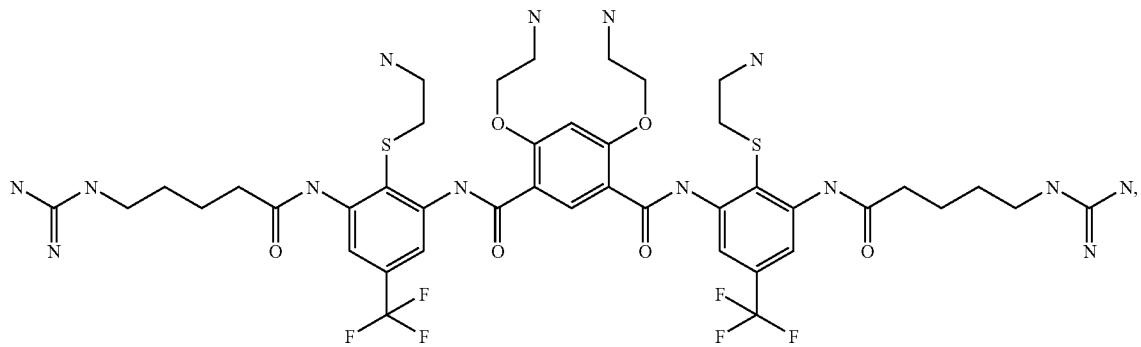

Compound 101

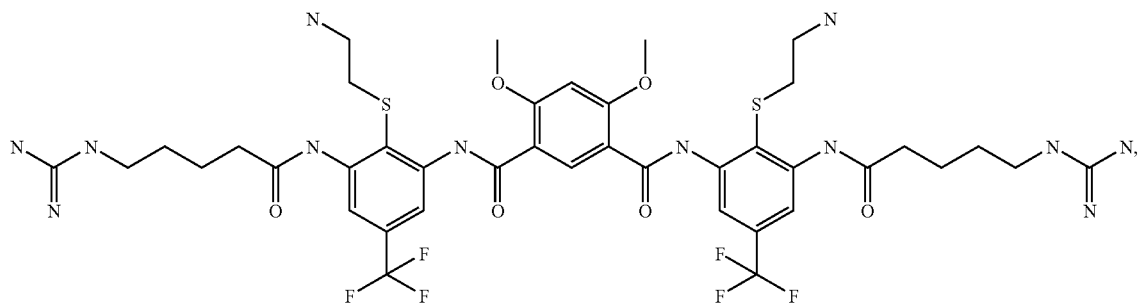

Compound 150

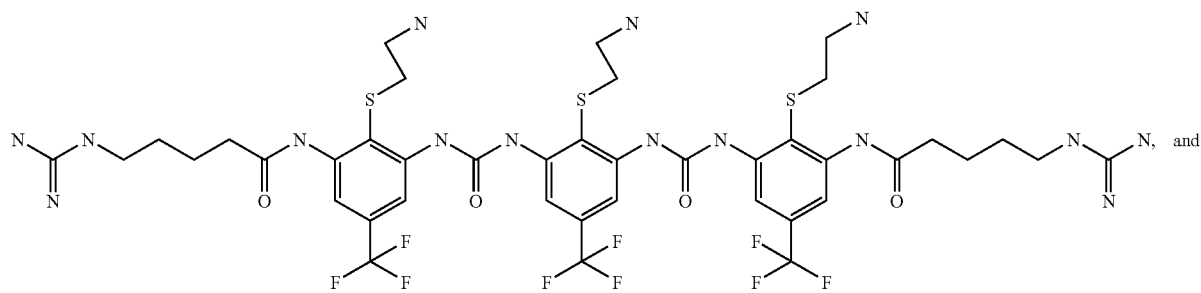

and

Compound 151

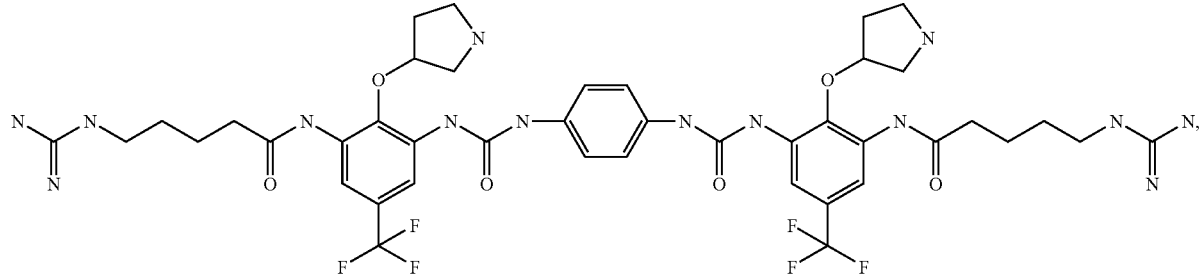

or a pharmaceutically acceptable salt thereof.

In any of the above embodiments, the malaria can be chloroquine-sensitive or chloroquine-resistant.

The present invention also provides methods of killing or inhibiting the growth of a *Plasmodium* species comprising contacting the species with an effective amount of a compound of Formula IV:

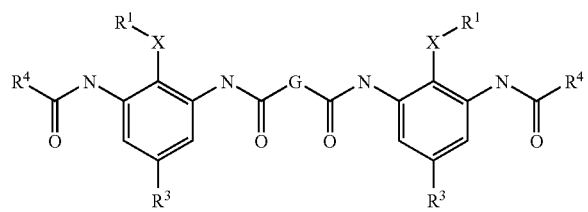

wherein:

G is

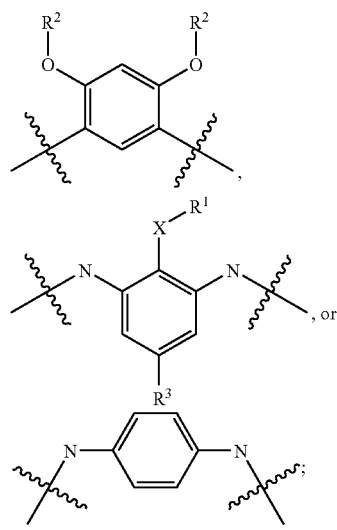

each X is, independently, O or S;
each $R^1$ is, independently,

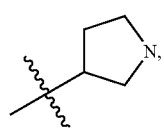

or the free base or salt form of —$(CH_2)_n$—$NH_2$ or —$(CH_2)_n$—NH—C(=NH)$NH_2$, where each n is, independently, 1 to 4;

each $R^2$ is, independently, H, $C_1$-$C_8$alkyl, or the free base or salt form of —$(CH_2)_n$—$NH_2$ or —$(CH_2)_n$—NH—C(=NH)$NH_2$, where each n is, independently, 1 to 4;

each $R^3$ is, independently, H, $CF_3$, C($CH_3$)$_3$, halo, or OH; and each $R^4$ is, independently, —$(CH_2)_n$—$NH_2$ or —$(CH_2)_n$—NH—C(=NH)$NH_2$, where each n is, independently, 1 to 4;

or a pharmaceutically acceptable salt thereof.

In some embodiments, G is

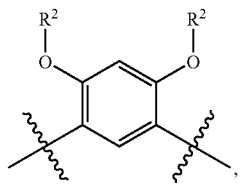

and each X is S.

In any of the above embodiments, each $R^1$ is, independently, the free base or salt form of —$(CH_2)_n$—$NH_2$, where each n is, independently, 1 to 4; or each $R^1$ is, independently, the free base or salt form of —$(CH_2)_n$—$NH_2$, where each n is, independently, 1 or 2; or each $R^1$ is the free base or salt form of —$(CH_2)_n$—$NH_2$, where each n is 2.

In any of the above embodiments, each $R^2$ is, independently, $C_1$-$C_3$alkyl or the free base or salt form of —$(CH_2)_n$—$NH_2$ where n is 1 to 4; or each $R^2$ is, independently, $C_1$-$C_3$alkyl or the free base or salt form of —$(CH_2)_n$—$NH_2$, where each n is, independently, 1 or 2; or each $R^2$ is, independently, methyl or the free base or salt form of —$(CH_2)_n$—$NH_2$, where each n is, independently, 2; or each $R^2$ is methyl or the free base or salt form of —$(CH_2)_n$—$NH_2$, where each n is 2.

In any of the above embodiments, each $R^3$ is, independently, $CF_3$, C($CH_3$)$_3$, or halo; or each $R^3$ is $CF_3$.

In any of the above embodiments, each $R^4$ is, independently, —$(CH_2)_n$—NH—C(=NH)$NH_2$, where each n is, independently, 1 to 4; or each $R^4$ is —$(CH_2)_n$—NH—C(=NH)$NH_2$, where each n is 4.

In some embodiments, G is

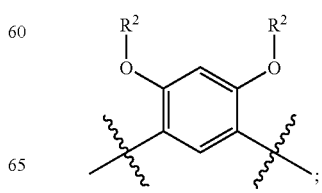

each X is S; each R$^1$ is, independently, the free base or salt form of —(CH$_2$)$_n$—NH$_2$, where each n is, independently, 1 or 2; each R$^2$ is, independently, C$_1$-C$_8$alkyl or the free base or salt form of —(CH$_2$)$_n$—NH$_2$, where each n is, independently, 1 or 2; each R$^3$ is, independently, CF$_3$, C(CH$_3$)$_3$, or halo; and each R$^4$ is, independently, —(CH$_2$)$_n$—NH—C(=NH)NH$_2$, where each n is, independently, 3 or 4.

In some embodiments, G is

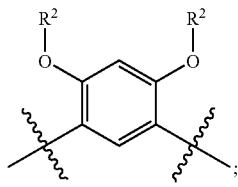

each X is S; each R$^1$ is the free base or salt form of —(CH$_2$)$_n$—NH$_2$, where each n is 1 or 2; each R$^2$ is, independently, C$_1$-C$_3$alkyl or the free base or salt form of —(CH$_2$)$_n$—NH$_2$, where each n is 2; each R$^3$ is, independently, CF$_3$ or C(CH$_3$)$_3$; and each R$^4$ is —(CH$_2$)$_n$—NH—C(=NH)NH$_2$, where each n is 3 or 4.

In some embodiments, G is

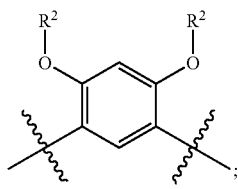

each X is S; each R$^1$ is the free base or salt form of —(CH$_2$)$_n$—NH$_2$, where each n is 2; each R$^2$ is, independently, methyl or the free base or salt form of —(CH$_2$)$_n$—NH$_2$, where each n is 2; each R$^3$ is, independently, CF$_3$ or C(CH$_3$)$_3$; and each R$^4$ is —(CH$_2$)$_n$—NH—C(=NH)NH$_2$, where each n is 4.

In some embodiments, G is

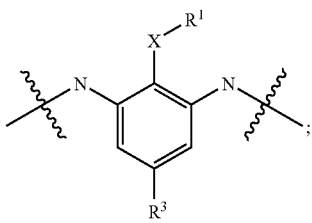

each X is, independently, O or S; each R$^1$ is, independently, the free base or salt form of —(CH$_2$)$_n$—NH$_2$ or —(CH$_2$)$_n$—NH—C(=NH)NH$_2$, where each n is, independently, 1 to 4; each R$^3$ is, independently, H or CF$_3$; and each R$^4$ is, independently, —(CH$_2$)$_n$—NH$_2$ or —(CH$_2$)$_n$—NH—C(=NH)NH$_2$, where each n is, independently, 1 to 4.

In some embodiments, G is

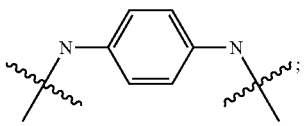 [SMILES: *Nc1ccc(N*)cc1 ; ";"]

each X is, independently, O or S; each R$^1$ is

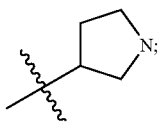

each R$^3$ is, independently, H or CF$_3$; and each R$^4$ is, independently, —(CH$_2$)$_n$—NH$_2$ or —(CH$_2$)$_n$—NH—C(=NH)NH$_2$, where each n is, independently, 1 to 4.

In some embodiments, the compound is chosen from:

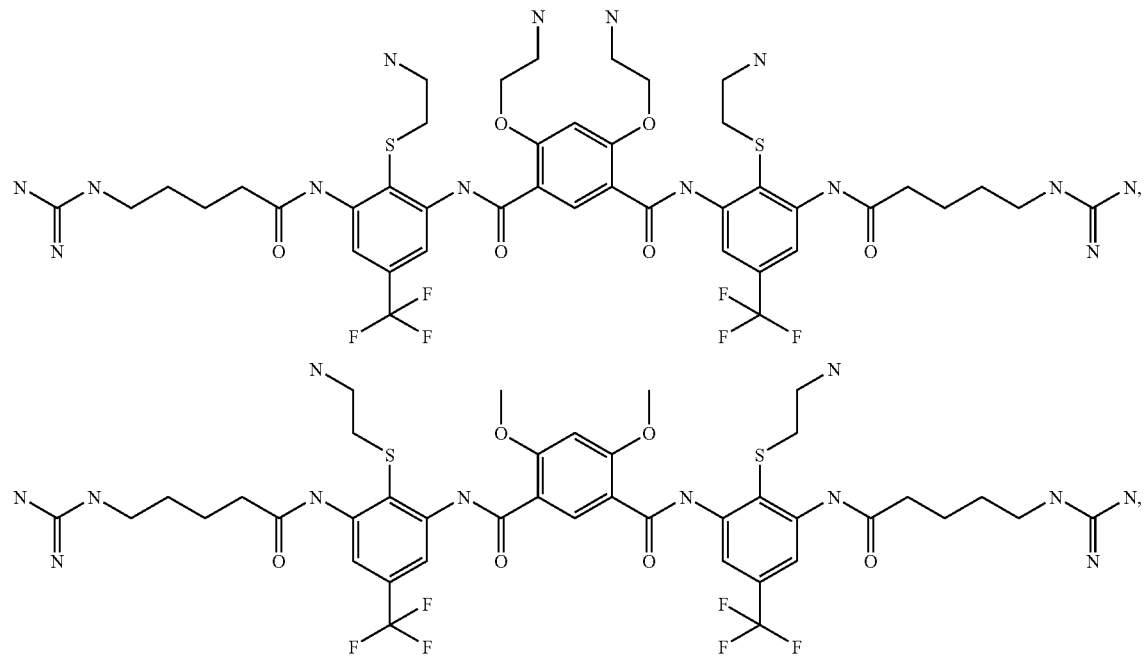

-continued

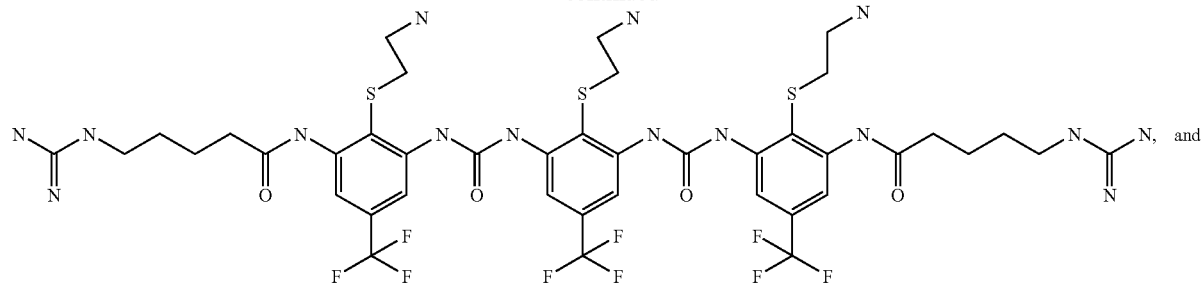

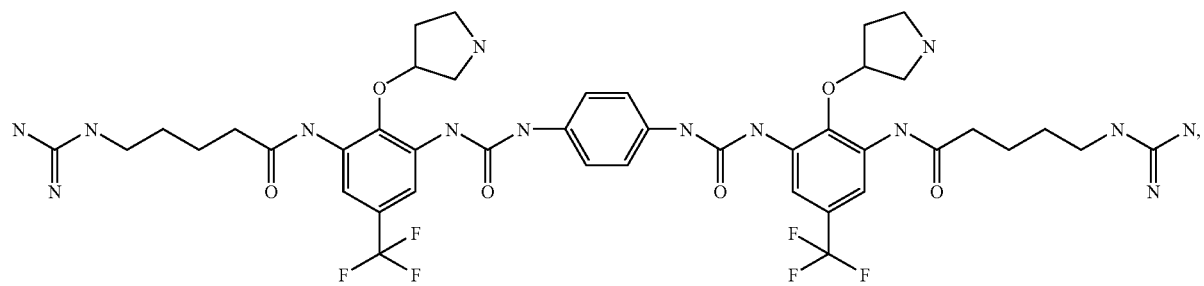

or a pharmaceutically acceptable salt thereof.

The present invention also provides compounds of Formula V:

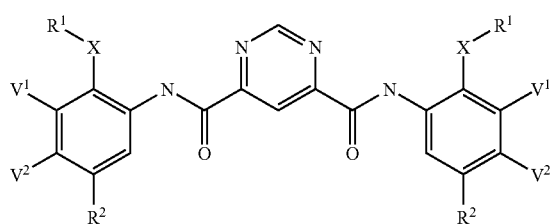

wherein:
each X is, independently, O, S, or S(=O)$_2$;
each R$^1$ is, independently, —(CH$_2$)$_n$—NH$_2$, —(CH$_2$)$_n$—NH—C(=NH)NH$_2$, or —(CH$_2$)$_n$—NH—C(=O)—R$^4$, where each n is, independently, 1 to 4, and each R$^4$ is, independently, H, C$_1$-C$_3$alkyl, or —(CH$_2$)$_p$—NH$_2$, where each p is, independently, 1 or 2;
each R$^2$ is, independently, H, halo, CF$_3$, or C(CH$_3$)$_3$; and
each V$^2$ is H, and each V$^1$ is, independently, —N—C(=O)—R$^3$, where each R$^3$ is, independently, —(CH$_2$)$_n$—NH$_2$ or —(CH$_2$)$_n$—NH—C(=NH)NH$_2$, where each n is, independently, 1 to 4; or each V$^1$ is H and each V$^2$ is, independently, —S—R$^5$, where each R$^5$ is, independently, —(CH$_2$)$_n$—NH$_2$ or —(CH$_2$)$_n$—NH—C(=NH)NH$_2$, where each n is, independently, 1 to 4;
or a pharmaceutically acceptable salt thereof,
provided that the compound is not:
a)

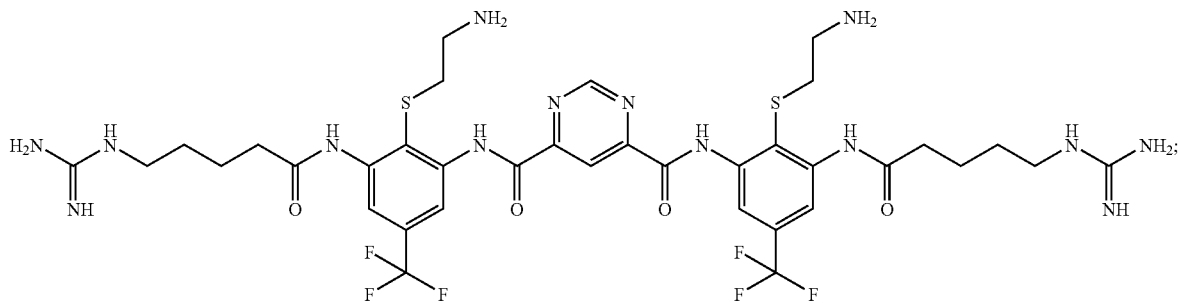 [SMILES: N=C(N)NCCCCC(=O)Nc1cc(C(F)(F)F)cc(NC(=O)c2cc(C(=O)Nc3cc(C(F)(F)F)cc(NC(=O)CCCCNC(=N)N)c3SCCN)ncn2)c1SCCN]

b)

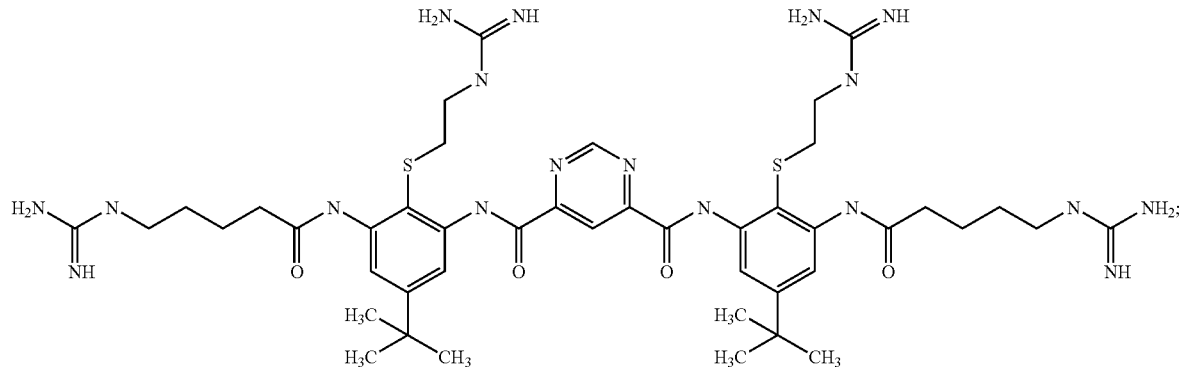 [SMILES: CC(C)(C)c1cc(NC(=O)CCCCNC(=N)N)c(SCCNC(=N)N)c(NC(=O)c2cc(C(=O)Nc3cc(C(C)(C)C)cc(NC(=O)CCCCNC(=N)N)c3SCCNC(=N)N)ncn2)c1]

or
c)

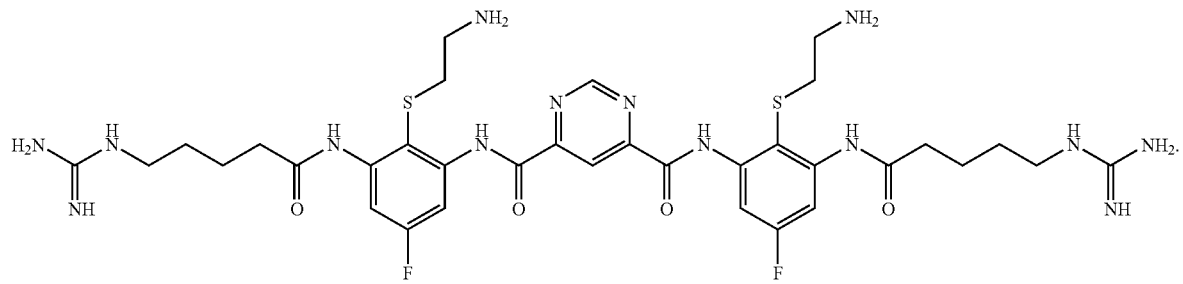 [SMILES: N=C(N)NCCCCC(=O)Nc1cc(F)cc(NC(=O)c2cc(C(=O)Nc3cc(F)cc(NC(=O)CCCCNC(=N)N)c3SCCN)ncn2)c1SCCN]

In some embodiments, each X is S.

In any of the above embodiments, each $R^1$ is, independently, —$(CH_2)_n$—$NH_2$, —$(CH_2)_n$—NH—C(=NH)$NH_2$, or —$(CH_2)_n$—NH—C(=O)—$R^4$, where each n is, independently, 1 or 2, and each $R^4$ is, independently, H or methyl; or each $R^1$ is, independently, —$(CH_2)_n$—$NH_2$, —$(CH_2)_n$—NH—C(=NH)$NH_2$, or —$(CH_2)_n$—NH—C(=O)—$R^4$, where each n is 2 and each $R^4$ is H; or each $R^1$ is, independently, —$(CH_2)_n$—$NH_2$ or —$(CH_2)_n$—NH—C(=NH)$NH_2$, where each n is 2; or each $R^1$ is —$(CH_2)_n$—$NH_2$ or —$(CH_2)_n$—NH—C(=NH)$NH_2$, where each n is 2.

In any of the above embodiments, each $R^2$ is, independently, H, Br, F, Cl, $CF_3$, or $C(CH_3)_3$; or each $R^2$ is Br, F, Cl, $CF_3$, or $C(CH_3)_3$.

In any of the above embodiments, each $V^2$ is H and each $V^1$ is, independently, —N—C(=O)—$R^3$, where each $R^3$ is, independently, —$(CH_2)_n$—$NH_2$ or —$(CH_2)_n$—NH—C(=NH)$NH_2$, where each n is, independently, 1 to 4; or each $V^2$ is H and each $V^1$ is, independently, —N—C(=O)—$R^3$, where each $R^3$ is, independently, —$(CH_2)_n$—$NH_2$ or —$(CH_2)_n$—NH—C(=NH)$NH_2$, where each n is, independently, 1 or 2; or each $V^2$ is H and each $V^1$ is, independently, N—C(=O)—$R^3$, where each $R^3$ is, independently, —$(CH_2)_n$—$NH_2$ or —$(CH_2)_n$—NH—C(=NH)$NH_2$, where each n is 2; or each $V^2$ is H and each $V^1$ is —N—C(=O)—$R^3$, where each $R^3$ is —$(CH_2)_n$—$NH_2$ or —$(CH_2)_n$—NH—C(=NH)$NH_2$, where n is 2.

In any of the above embodiments, each $V^1$ is H and each $V^2$ is, independently, —S—$R^5$ where each $R^5$ is, independently, —$(CH_2)_n$—$NH_2$ or —$(CH_2)_n$—NH—C(=NH)$NH_2$, where each n is, independently, 1 to 4; or each $V^1$ is H and each $V^2$ is, independently, —S—$R^5$, where each $R^5$ is, independently, —$(CH_2)_n$—$NH_2$ or —$(CH_2)_n$—NH—C(=NH)$NH_2$, where each n is 1 or 2; or each $V^1$ is H and each $V^2$ is, independently, —S—$R^5$, where each $R^5$ is, independently, —$(CH_2)_n$—$NH_2$ or —$(CH_2)_n$—NH—C(=NH)$NH_2$, where each n is 2; or each $V^1$ is H and each $V^2$ is —S—$R^5$ where each $R^5$ is —$(CH_2)_n$—$NH_2$ or —$(CH_2)_n$—NH—C(=NH)$NH_2$ where each n is 2.

In some embodiments, each X is S; each $R^1$ is, independently, —$(CH_2)_n$—$NH_2$ or —$(CH_2)_n$—NH—C(=NH)$NH_2$, where each n is, independently, 1 to 4; each $R^2$ is, independently, halo, $CF_3$, or $C(CH_3)_3$; and each $V^1$ is H and each $V^2$ is, independently, —S—$R^5$, where each $R^5$ is, independently, —$(CH_2)_n$—$NH_2$, where each n is, independently, 1 to 4.

In some embodiments, each X is S; each $R^1$ is, independently, —$(CH_2)_n$—$NH_2$, where each n is, independently, 1 or 2; each $R^2$ is, independently, $CF_3$ or $C(CH_3)_3$; and each $V^1$ is H and each $V^2$ is, independently, —S—$R^5$, where each $R^5$ is, independently, —$(CH_2)_n$—$NH_2$, where each n is, independently, 1 or 2.

In some embodiments, each X is S; each $R^1$ is —$(CH_2)_n$—$NH_2$, where each n is 1 or 2; each $R^2$ is, independently, $CF_3$ or $C(CH_3)_3$; and each $V^1$ is H and each $V^2$ is —S—$R^5$, where each $R^5$ is —$(CH_2)_n$—$NH_2$, where each n is 1 or 2.

In some embodiments, each X is O or S; each $R^1$ is, independently, —$(CH_2)_n$—$NH_2$, or —$(CH_2)_n$—NH—C(=NH)$NH_2$, or —$(CH_2)_n$—NH—C(=O)—$R^4$ where each n is, independently, 1 to 4, and each $R^4$ is, independently, H or methyl; each $R^2$ is, independently, halo, $CF_3$, or $C(CH_3)_3$; and each $V^1$ is H, and each $V^2$ is, independently, —N—C(=O)—$R^3$, where each $R^3$ is, independently, —$(CH_2)_n$—$NH_2$ or —$(CH_2)_n$—NH—C(=NH)$NH_2$, where each n is, independently, 1 to 4.

In some embodiments, each X is S; each $R^1$ is, independently, —$(CH_2)_n$—NH—C(=O)—$R^4$, where each n is, independently, 1 or 2, and each $R^4$ is, independently, H or methyl; each $R^2$ is, independently, halo; and each $V^2$ is H, and each $V^1$ is —N—C(=O)—$R^3$, where each $R^3$ is —$(CH_2)_n$—$NH_2$ or —$(CH_2)_n$—NH—C(=NH)$NH_2$, where each n is 4.

In some embodiments, each X is O or S; each $R^1$ is, independently, —$(CH_2)_n$—$NH_2$ or —$(CH_2)_n$—NH—C(=NH)$NH_2$, where each n is, independently, 1 to 4; each $R^2$ is, independently, halo, $CF_3$, or $C(CH_3)_3$; and each $V^2$ is H, and each $V^1$ is, independently, —N—C(=O)—$R^3$, where each $R^3$ is, independently, —$(CH_2)_n$—$NH_2$ or —$(CH_2)_n$—NH—C(=NH)$NH_2$, where each n is, independently, 1 to 4.

In some embodiments, each X is O or S; each $R^1$ is —$(CH_2)_n$—$NH_2$ or —$(CH_2)_n$—NH—C(=NH)$NH_2$, where each n is 1 or 2; each $R^2$ is halo, $CF_3$, or $C(CH_3)_3$; and each $V^2$ is H, and each $V^1$ is —N—C(=O)—$R^3$, where each $R^3$ is —$(CH_2)_n$—$NH_2$ or —$(CH_2)_n$—NH—C(=NH)$NH_2$, where each n is 3 or 4.

In some embodiments, each X is, independently, S or S(=O)$_2$; each $R^1$ is, independently, —$(CH_2)_n$—$NH_2$ or —$(CH_2)_n$—NH—C(=O)—$R^4$, where each n is, independently, 1 or 2, and each $R^4$ is, independently, —$(CH_2)_p$—$NH_2$, where each p is, independently, 1 or 2; each $R^2$ is, independently, halo or $CF_3$; and each $V^2$ is H, and each $V^1$ is, independently, —N—C(=O)—$R^3$, where each $R^3$ is, independently, —$(CH_2)_n$—$NH_2$ or —$(CH_2)_n$—NH—C(=NH)$NH_2$, where each n is, independently, 3 or 4.

In some embodiments, the compound is chosen from:

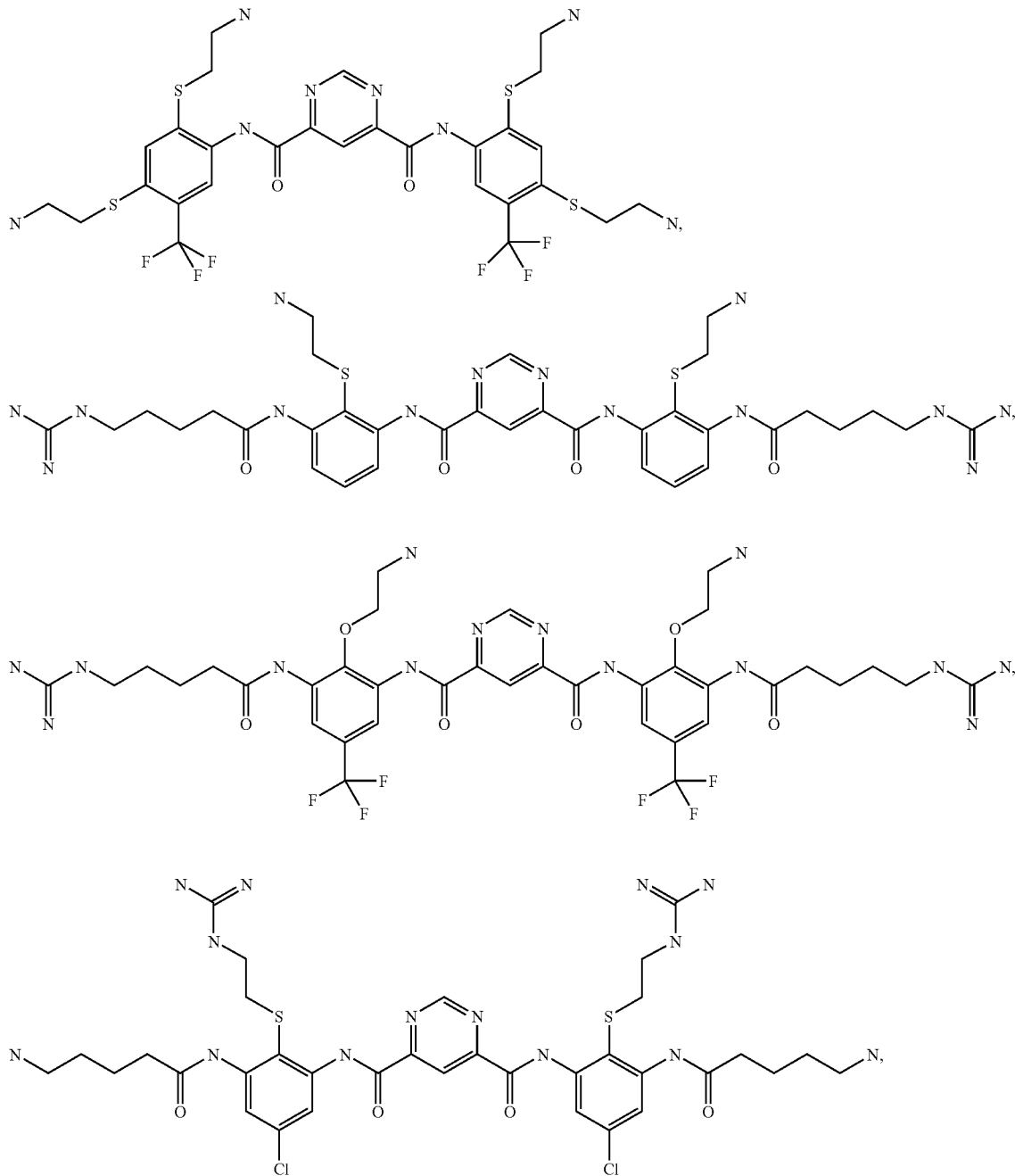

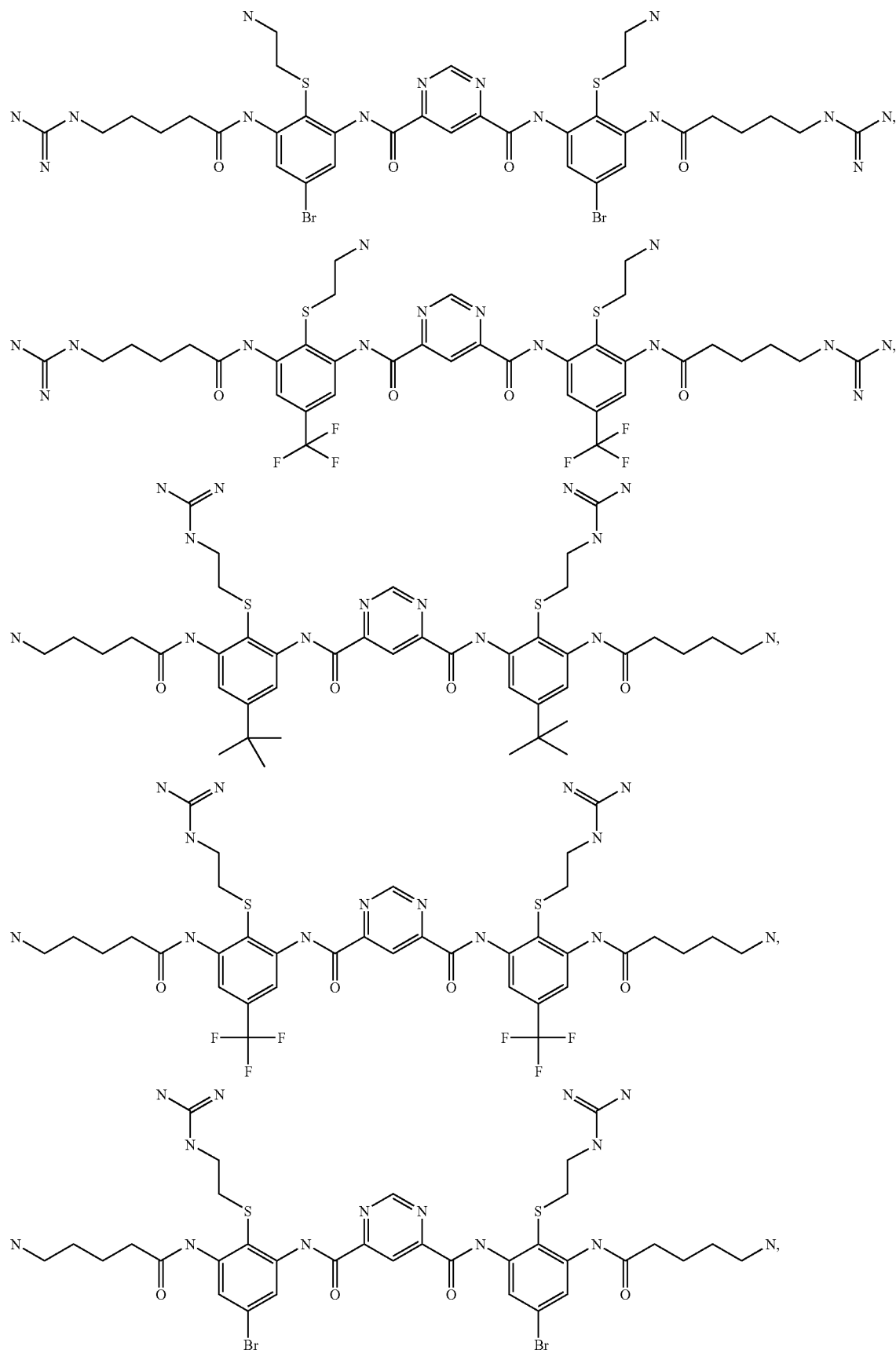

-continued
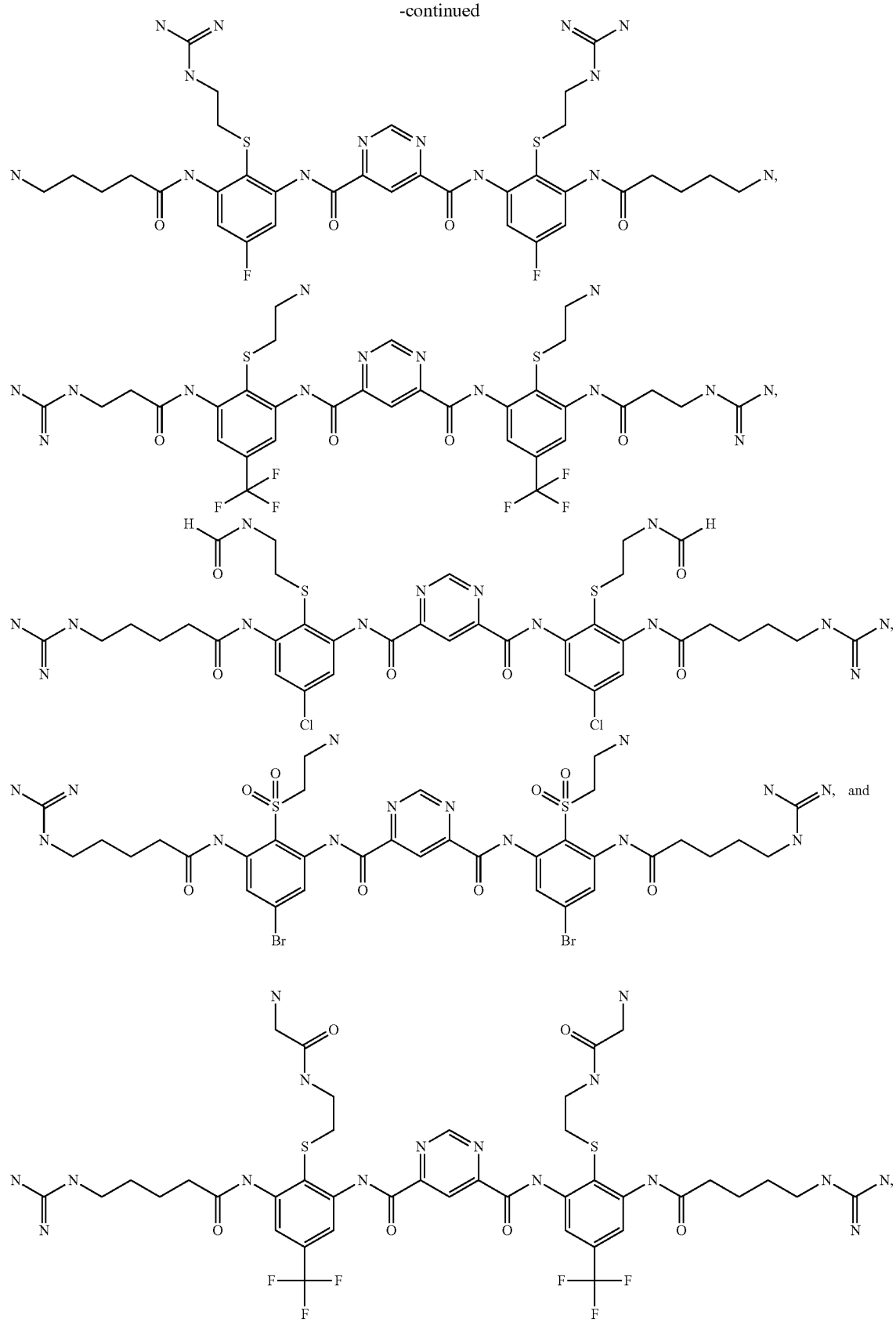
or a pharmaceutically acceptable salt thereof.

In some embodiments, any one or more of the above compounds may be excluded from any of the genus of compounds described above.

The present invention also provides compositions comprising one or more of the compounds or salts described above and a pharmaceutically acceptable carrier.

The present invention also provides methods of treating malaria in an animal comprising administering to the animal a therapeutically effective amount of a compound of Formula V:

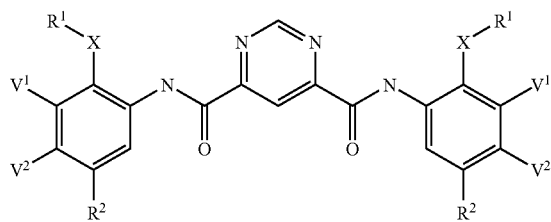

wherein:

each X is, independently, O, S, or S(=O)$_2$;

each R$^1$ is, independently, —(CH$_2$)$_n$—NH$_2$, —(CH$_2$)$_n$—NH—C(=NH)NH$_2$, or —(CH$_2$)$_n$—NH—C(=O)—R$^4$, where each n is, independently, 1 to 4, and each R$^4$ is, independently, H, C$_1$-C$_3$alkyl, or —(CH$_2$)$_p$—NH$_2$, where each p is, independently, 1 or 2;

each R$^2$ is, independently, H, halo, CF$_3$, or C(CH$_3$)$_3$; and each V$^2$ is H, and each V$^1$ is, independently, —N—C(=O)—R$^3$, where each R$^3$ is, independently, —(CH$_2$)$_n$—NH$_2$ or —(CH$_2$)$_n$—NH—C(=NH)NH$_2$, where each n is, independently, 1 to 4; or each V$^1$ is H and each V$^2$ is, independently, —S—R$^5$, where each R$^5$ is, independently, —(CH$_2$)$_n$—NH$_2$ or —(CH$_2$)$_n$—NH—C(=NH)NH$_2$, where each n is, independently, 1 to 4;

or a pharmaceutically acceptable salt thereof.

In some embodiments, each X is S.

In any of the above embodiments, each R$^1$ is, independently, —(CH$_2$)$_n$—NH$_2$, —(CH$_2$)$_n$—NH—C(=NH)NH$_2$, or —(CH$_2$)$_n$—NH—C(=O)—R$^4$ where each n is, independently, 1 or 2, and each R$^4$ is, independently, H or methyl; or each R$^1$ is, independently, —(CH$_2$)$_n$—NH$_2$, —(CH$_2$)$_n$—NH—C(=NH)NH$_2$, or —(CH$_2$)$_n$—NH—C(=O)—R$^4$ where each n is 2 and each R$^4$ is H; or each R$^1$ is, independently, —(CH$_2$)$_n$—NH$_2$ or —(CH$_2$)$_n$—NH—C(=NH)NH$_2$, where each n is 2; or each R$^1$ is —(CH$_2$)$_n$—NH$_2$ or, where each n is 2.

In any of the above embodiments, each R$^2$ is, independently, H, Br, F, Cl, CF$_3$, or C(CH$_3$)$_3$; or each R$^2$ is Br, F, Cl, CF$_3$, or C(CH$_3$)$_3$.

In any of the above embodiments, each V$^2$ is H and each V$^1$ is, independently, —N—C(=O)—R$^3$, where each R$^3$ is, independently, —(CH$_2$)$_n$—NH$_2$ or —(CH$_2$)$_n$—NH—C(=NH)NH$_2$, where each n is, independently, 1 to 4; or each V$^2$ is H and each V$^1$ is, independently, —N—C(=O)—R$^3$, where each R$^3$ is, independently, —(CH$_2$)$_n$—NH$_2$ or —(CH$_2$)$_n$—NH—C(=NH)NH$_2$, where each n is, independently, 1 or 2; or each V$^2$ is H and each V$^1$ is, independently, —N—C(=O)—R$^3$, where each R$^3$ is, independently, —(CH$_2$)$_n$—NH$_2$ or —(CH$_2$)$_n$—NH—C(=NH)NH$_2$, where each n is 2; or each V$^2$ is H and each V$^1$ is —N—C(=O)—R$^3$, where each R$^3$ is —(CH$_2$)$_n$—NH$_2$ or —(CH$_2$)$_n$—NH—C(=NH)NH$_2$, where n is 2.

In any of the above embodiments, each V$^1$ is H and each V$^2$ is, independently, —S—R$^5$ where each R$^5$ is, independently, —(CH$_2$)$_n$—NH$_2$ or —(CH$_2$)$_n$—NH—C(=NH)NH$_2$ where each n is, independently, 1 to 4; or each V$^1$ is H and each V$^2$ is, independently, —S—R$^{55}$ where each R$^5$ is, independently, —(CH$_2$)$_n$—NH$_2$ or —(CH$_2$)$_n$—NH—C(=NH)NH$_2$, where each n is 1 or 2; or each V$^1$ is H and each V$^2$ is, independently, —S—R$^{55}$ where each R$^5$ is, independently, —(CH$_2$)$_n$—NH$_2$ or —(CH$_2$)$_n$—NH—C(=NH)NH$_2$, where each n is 2; or each V$^1$ is H and each V$^2$ is —S—R$^5$ where each R$^5$ is —(CH$_2$)$_n$—NH$_2$ or —(CH$_2$)$_n$—NH—C(=NH)NH$_2$ where each n is 2.

In some embodiments, each X is S; each R$^1$ is, independently, —(CH$_2$)$_n$—NH$_2$ or —(CH$_2$)$_n$—NH—C(=NH)NH$_2$, where each n is, independently, 1 to 4; each R$^2$ is, independently, halo, CF$_3$, or C(CH$_3$)$_3$; and each V$^1$ is H and each V$^2$ is, independently, —S—R$^{55}$ where each R$^5$ is, independently, —(CH$_2$)$_n$—NH$_2$, where each n is, independently, 1 to 4.

In some embodiments, each X is S; each R$^1$ is, independently, —(CH$_2$)$_n$—NH$_2$, where each n is, independently, 1 or 2; each R$^2$ is, independently, CF$_3$ or C(CH$_3$)$_3$; and each V$^1$ is H and each V$^2$ is, independently, —S—R$^{55}$ where each R$^5$ is, independently, —(CH$_2$)$_n$—NH$_2$, where each n is, independently, 1 or 2.

In some embodiments, each X is S; each R$^1$ is —(CH$_2$)$_n$—NH$_2$, where each n is 1 or 2; each R$^2$ is, independently, CF$_3$ or C(CH$_3$)$_3$; and each V$^1$ is H and each V$^2$ is —S—R$^5$, where each R$^5$ is —(CH$_2$)$_n$—NH$_2$, where each n is 1 or 2.

In some embodiments, each X is O or S; each R$^1$ is, independently, —(CH$_2$)$_n$—NH$_2$, or —(CH$_2$)$_n$—NH—C(=NH)NH$_2$, or —(CH$_2$)$_n$—NH—C(=O)—R$^4$, where each n is, independently, 1 to 4, and each R$^4$ is, independently, H or methyl; each R$^2$ is, independently, halo, CF$_3$, or C(CH$_3$)$_3$; and each V$^2$ is H, and each V$^1$ is, independently, —N—C(=O)—R$^3$, where each R$^3$ is, independently, —(CH$_2$)$_n$—NH$_2$ or —(CH$_2$)$_n$—NH—C(=NH)NH$_2$, where each n is, independently, 1 to 4.

In some embodiments, each X is S; each R$^1$ is, independently, —(CH$_2$)$_n$—NH—C(=O)—R$^4$, where each n is, independently, 1 or 2, and each R$^4$ is, independently, H or methyl; each R$^2$ is, independently, halo; and each V$^2$ is H, and each V$^1$ is —N—C(=O)—R$^3$, where each R$^3$ is —(CH$_2$)$_n$—NH$_2$ or —(CH$_2$)$_n$—NH—C(=NH)NH$_2$, where each n is 4.

In some embodiments, each X is O or S; each R$^1$ is, independently, —(CH$_2$)$_n$—NH$_2$ or —(CH$_2$)$_n$—NH—C(=NH)NH$_2$, where each n is, independently, 1 to 4; each R$^2$ is, independently, halo, CF$_3$, or C(CH$_3$)$_3$; and each V$^2$ is H, and each V$^1$ is, independently, —N—C(=O)—R$^3$, where each R$^3$ is, independently, —(CH$_2$)$_n$—NH$_2$ or —(CH$_2$)$_n$—NH—C(=NH)NH$_2$, where each n is, independently, 1 to 4.

In some embodiments, each X is O or S; each R$^1$ is —(CH$_2$)$_n$—NH$_2$ or —(CH$_2$)$_n$—NH—C(=NH)NH$_2$, where each n is 1 or 2; each R$^2$ is halo, CF$_3$, or C(CH$_3$)$_3$; and each V$^2$ is H, and each V$^1$ is —N—C(=O)—R$^3$, where each R$^3$ is —(CH$_2$)—NH$_2$ or —(CH$_2$)$_n$—NH—C(=NH)NH$_2$, where each n is 3 or 4.

In some embodiments, each X is, independently, S or S(=O)$_2$; each R$^1$ is, independently, —(CH$_2$)$_n$—NH$_2$ or —(CH$_2$)$_n$—NH—C(=O)—R$^4$, where each n is, independently, 1 or 2, and each R$^4$ is, independently, —(CH$_2$)$_p$—NH$_2$, where each p is, independently, 1 or 2; each R$^2$ is, independently, halo or CF$_3$; and each V$^2$ is H, and each V$^1$ is, independently, —N—C(=O)—R$^3$, where each R$^3$ is, independently, —(CH$_2$)$_n$—NH$_2$ or —(CH$_2$)$_n$—NH—C(=NH)NH$_2$, where each n is, independently, 3 or 4.

In some embodiments, the compound is chosen from:
Compound 112
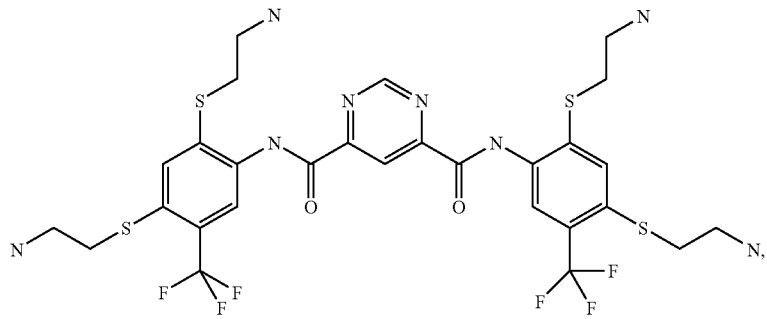
Compound 113
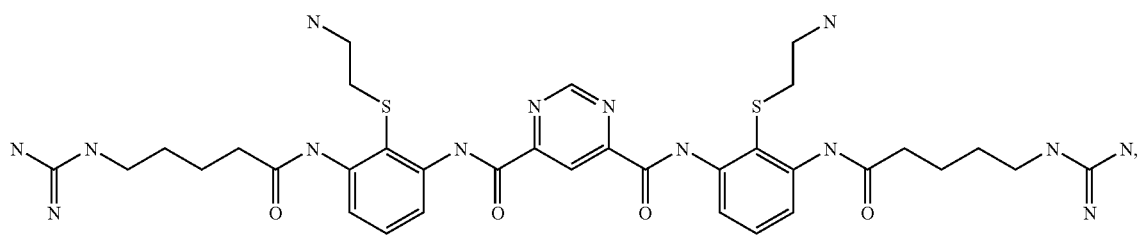
Compound 121
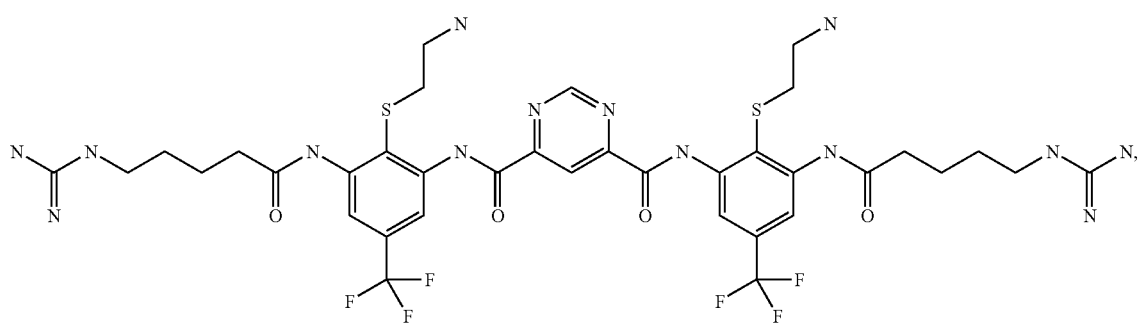
Compound 114
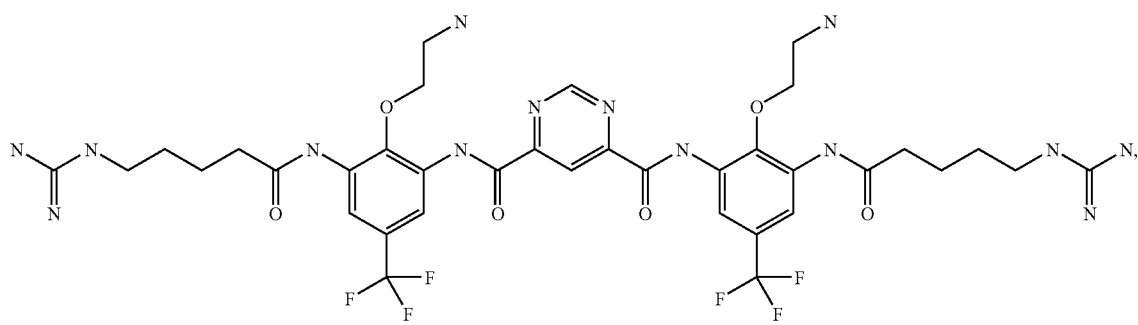
Compound 107
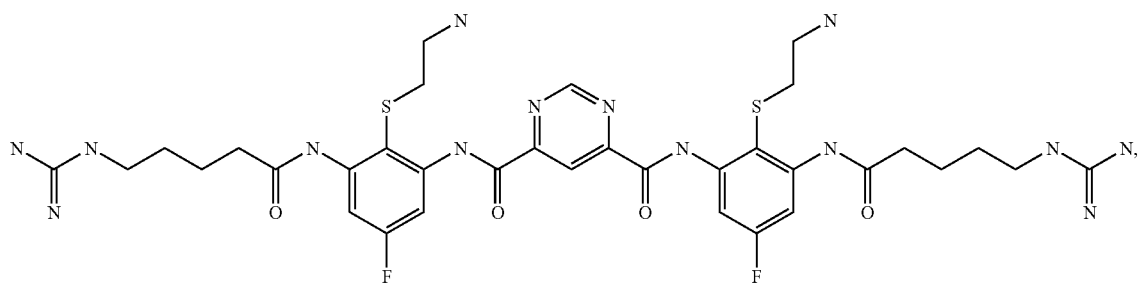

Compound 122
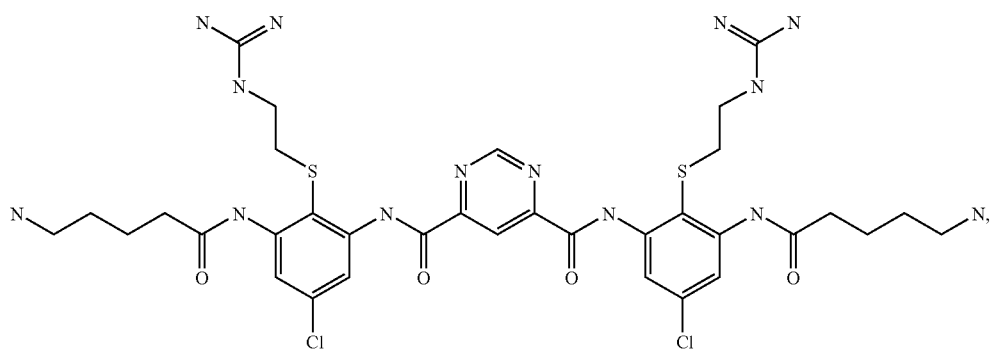
Compound 123
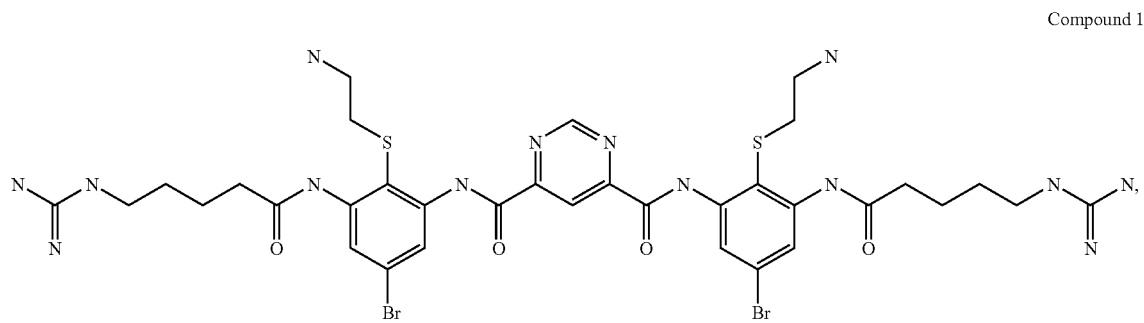
Compound 124
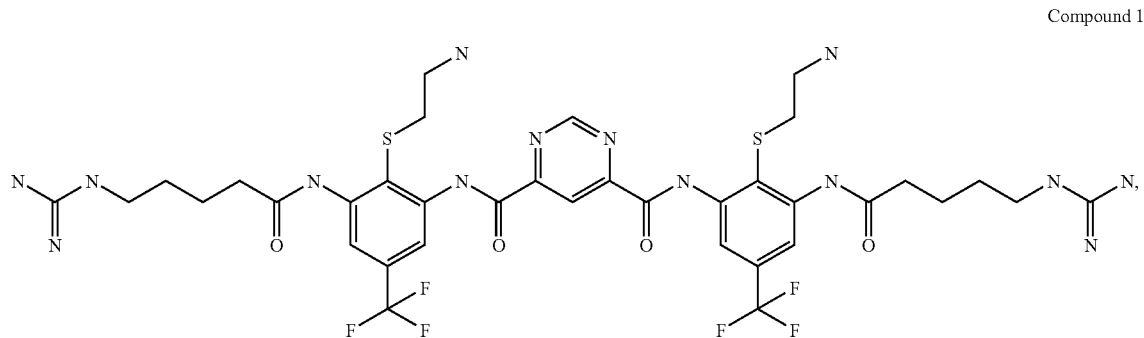
Compound 129
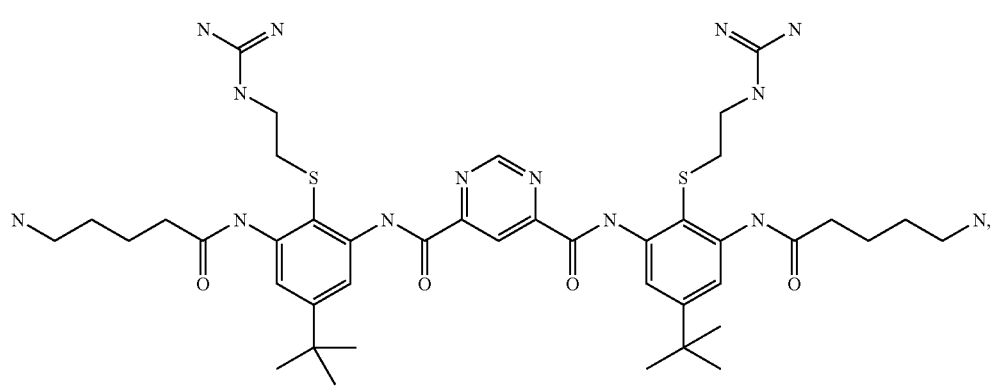

-continued
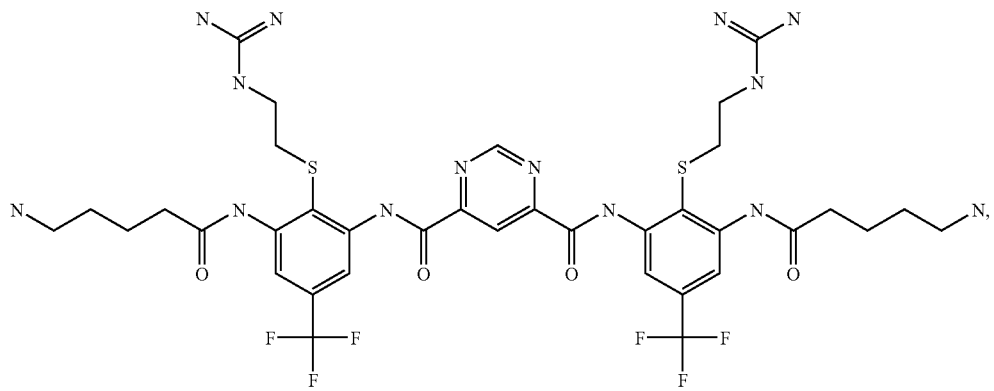
Compound 128
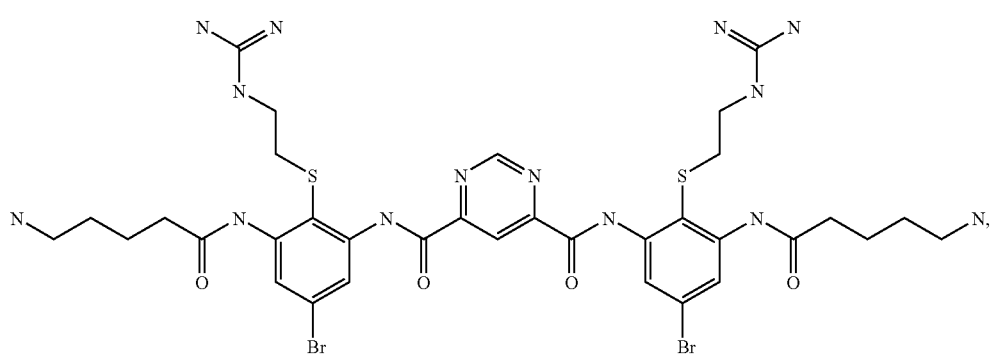
Compound 127
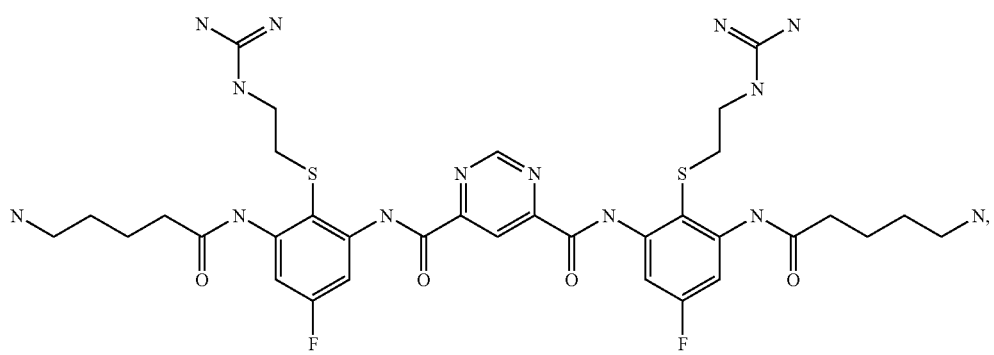
Compound 126
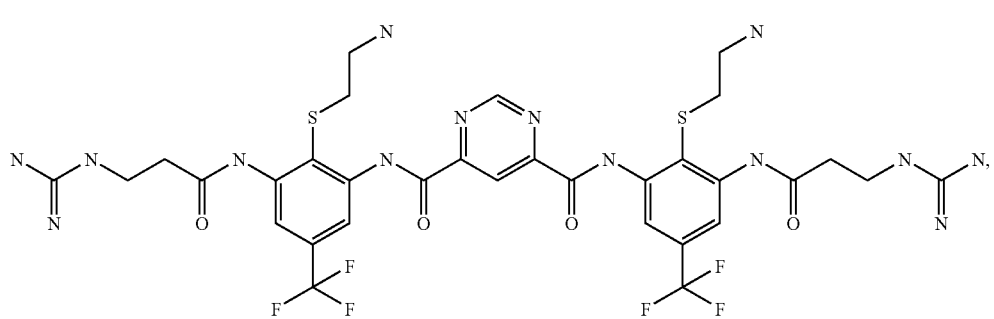
Compound 108

-continued

Compound 125

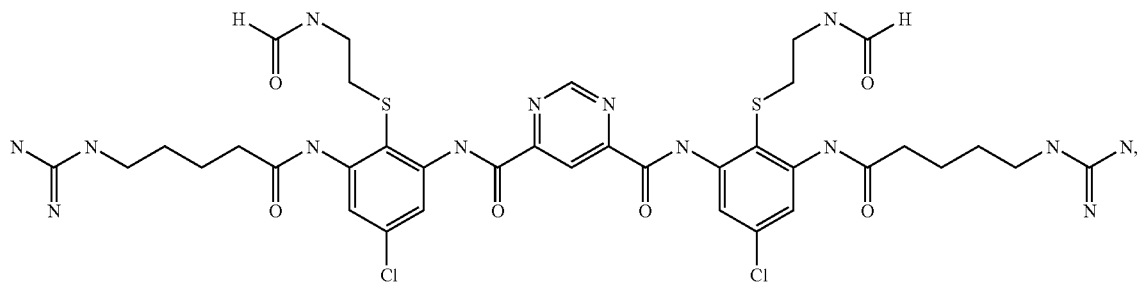

Compound 152

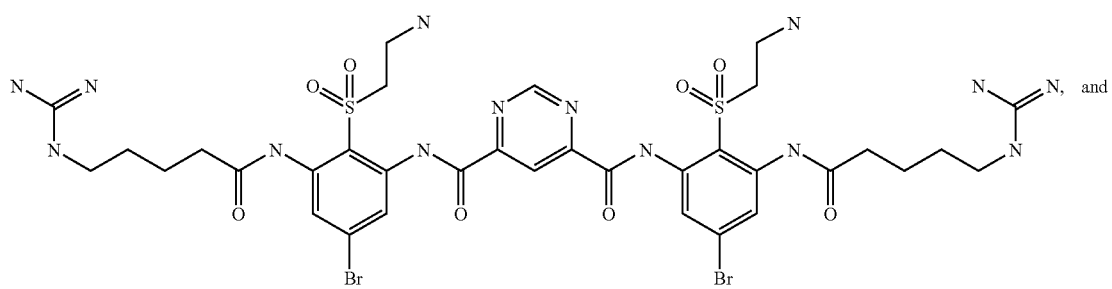

Compound 153

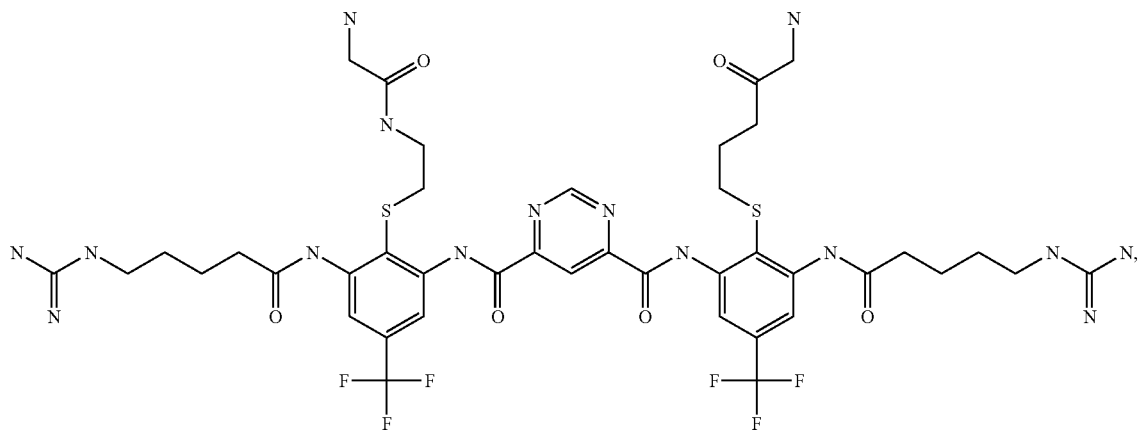

or a pharmaceutically acceptable salt thereof.

In any of the above embodiments, the malaria can be chloroquine-sensitive or chloroquine-resistant.

The present invention also provides methods of killing or inhibiting the growth of a *Plasmodium* species comprising contacting the species with an effective amount of a compound of Formula V:

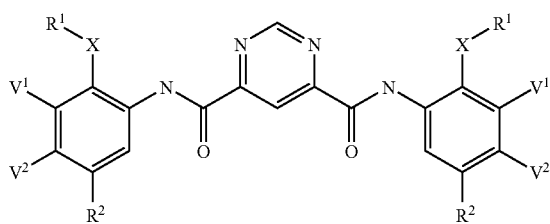

wherein:
each X is, independently, O, S, or S(=O)$_2$;
each R$^1$ is, independently, —(CH$_2$)$_n$—NH$_2$, —(CH$_2$)$_n$—NH—C(=NH)NH$_2$, or —(CH$_2$)$_n$—NH—C(=O)—R$^4$, where each n is, independently, 1 to 4, and each R$^4$ is, independently, H, C$_1$-C$_3$alkyl, or —(CH$_2$)$_p$—NH$_2$, where each p is, independently, 1 or 2;
each R$^2$ is, independently, H, halo, CF$_3$, or C(CH$_3$)$_3$; and
each V$^2$ is H, and each V$^1$ is, independently, —N—C(=O)—R$^3$, where each R$^3$ is, independently, —(CH$_2$)$_n$—NH$_2$ or —(CH$_2$)$_n$—NH—C(=NH)NH$_2$, where each n is, independently, 1 to 4; or each V$^1$ is H and each V$^2$ is, independently, —S—R$^5$, where each R$^5$ is, independently, —(CH$_2$)$_n$—NH$_2$ or —(CH$_2$)$_n$—NH—C(=NH)NH$_2$, where each n is, independently, 1 to 4;
or a pharmaceutically acceptable salt thereof.

In some embodiments, each X is S.

In any of the above embodiments, each R$^1$ is, independently, —(CH$_2$)$_n$—NH$_2$, —(CH$_2$)$_n$—NH—C(=NH)NH$_2$, or —(CH$_2$)$_n$—NH—C(=O)—R$^4$ where each n is, independently, 1 or 2, and each R$^4$ is, independently, H or methyl; or each R$^1$ is, independently, —(CH$_2$)$_n$—NH$_2$, —(CH$_2$)$_n$—NH—C(=NH)NH$_2$, or —(CH$_2$)$_n$—NH—C(=O)—R$^4$ where each n is 2 and each R$^4$ is H; or each R$^1$ is, independently, —(CH$_2$)$_n$—NH$_2$ or —(CH$_2$)$_n$—NH—C(=NH)NH$_2$, where each n is 2; or each R$^1$ is —(CH$_2$)$_n$—NH$_2$ or —(CH$_2$)$_n$—NH—C(=NH)NH$_2$, where each n is 2.

In any of the above embodiments, each $R^2$ is, independently, H, Br, F, Cl, $CF_3$, or $C(CH_3)_3$; or each $R^2$ is Br, F, Cl, $CF_3$, or $C(CH_3)_3$.

In any of the above embodiments, each $V^2$ is H and each $V^1$ is, independently, —N—C(=O)—$R^3$, where each $R^3$ is, independently, —$(CH_2)_n$—$NH_2$ or —$(CH_2)_n$—NH—C(=NH)$NH_2$, where each n is, independently, 1 to 4; or each $V^2$ is H and each $V^1$ is, independently, —N—C(=O)—$R^3$, where each $R^3$ is, independently, —$(CH_2)_n$—$NH_2$ or —$(CH_2)_n$—NH—C(=NH)$NH_2$, where each n is, independently, 1 or 2; or each $V^2$ is H and each $V^1$ is, independently, —N—C(=O)—$R^3$, where each $R^3$ is, independently, —$(CH_2)_n$—$NH_2$ or —$(CH_2)_n$—NH—C(=NH)$NH_2$, where each n is 2; or each $V^2$ is H and each $V^1$ is —N—C(=O)—$R^3$, where each $R^3$ is —$(CH_2)_n$—$NH_2$ or —$(CH_2)_n$—NH—C(=NH)$NH_2$, where n is 2.

In any of the above embodiments, each $V^1$ is H and each $V^2$ is, independently, —S—$R^5$ where each $R^5$ is, independently, —$(CH_2)$—$NH_2$ or —$(CH_2)_n$—NH—C(=NH)$NH_2$, where each n is, independently, 1 to 4; or each $V^1$ is H and each $V^2$ is, independently, —S—$R^5$, where each $R^5$ is, independently, —$(CH_2)_n$—$NH_2$ or —$(CH_2)_n$—NH—C(=NH)$NH_2$, where each n is 1 or 2; or each $V^1$ is H and each $V^2$ is, independently, —S—$R^5$, where each $R^5$ is, independently, —$(CH_2)_n$—$NH_2$ or —$(CH_2)_n$—NH—C(=NH)$NH_2$, where each n is 2; or each $V^1$ is H and each $V^2$ is —S—$R^5$ where each $R^5$ is —$(CH_2)_n$—$NH_2$ or —$(CH_2)_n$—NH—C(=NH)$NH_2$ where each n is 2.

In some embodiments, each X is S; each $R^1$ is, independently, —$(CH_2)_n$—$NH_2$ or —$(CH_2)_n$—NH—C(=NH)$NH_2$, where each n is, independently, 1 to 4; each $R^2$ is, independently, halo, $CF_3$, or $C(CH_3)_3$; and each $V^1$ is H and each $V^2$ is, independently, —S—$R^5$, where each $R^5$ is, independently, —$(CH_2)_n$—$NH_2$, where each n is, independently, 1 to 4.

In some embodiments, each X is S; each $R^1$ is, independently, —$(CH_2)_n$—$NH_2$, where each n is, independently, 1 or 2; each $R^2$ is, independently, $CF_3$ or $C(CH_3)_3$; and each $V^1$ is H and each $V^2$ is, independently, —S—$R^5$, where each $R^5$ is, independently, —$(CH_2)_n$—$NH_2$, where each n is, independently, 1 or 2.

In some embodiments, each X is S; each $R^1$ is —$(CH_2)_n$—$NH_2$, where each n is 1 or 2; each $R^2$ is, independently, $CF_3$ or $C(CH_3)_3$; and each $V^1$ is H and each $V^2$ is —S—$R^5$, where each $R^5$ is —$(CH_2)_n$—$NH_2$, where each n is 1 or 2.

In some embodiments, each X is O or S; each $R^1$ is, independently, —$(CH_2)_n$—$NH_2$, or —$(CH_2)_n$—NH—C(=NH)$NH_2$, or —$(CH_2)_n$—NH—C(=O)—$R^4$, where each n is, independently, 1 to 4, and each $R^4$ is, independently, H or methyl; each $R^2$ is, independently, halo, $CF_3$, or $C(CH_3)_3$; and each $V^2$ is H, and each $V^1$ is, independently, —N—C(=O)—$R^3$, where each $R^3$ is, independently, —$(CH_2)_n$—$NH_2$ or —$(CH_2)_n$—NH—C(=NH)$NH_2$, where each n is, independently, 1 to 4.

In some embodiments, each X is S; each $R^1$ is, independently, —$(CH_2)_n$—NH—C(=O)—$R^4$, where each n is, independently, 1 or 2, and each $R^4$ is, independently, H or methyl; each $R^2$ is, independently, halo; and each $V^2$ is H, and each $V^1$ is —N—C(=O)—$R^3$, where each $R^3$ is —$(CH_2)_n$—$NH_2$ or —$(CH_2)_n$—NH—C(=NH)$NH_2$, where each n is 4.

In some embodiments, each X is O or S; each $R^1$ is, independently, —$(CH_2)_n$—$NH_2$ or —$(CH_2)_n$—NH—C(=NH)$NH_2$, where each n is, independently, 1 to 4; each $R^2$ is, independently, halo, $CF_3$, or $C(CH_3)_3$; and each $V^2$ is H, and each $V^1$ is, independently, —N—C(=O)—$R^3$, where each $R^3$ is, independently, —$(CH_2)_n$—$NH_2$ or —$(CH_2)_n$—NH—C(=NH)$NH_2$, where each n is, independently, 1 to 4.

In some embodiments, each X is O or S; each $R^1$ is —$(CH_2)_n$—$NH_2$ or —$(CH_2)_n$—NH—C(=NH)$NH_2$, where each n is 1 or 2; each $R^2$ is halo, $CF_3$, or $C(CH_3)_3$; and each $V^2$ is H, and each $V^1$ is —N—C(=O)—$R^3$, where each $R^3$ is —$(CH_2)_n$—$NH_2$ or —$(CH_2)_n$—NH—C(=NH)$NH_2$, where each n is 3 or 4.

In some embodiments, each X is, independently, S or $S(=O)_2$; each $R^1$ is, independently, —$(CH_2)_n$—$NH_2$ or —$(CH_2)_n$—NH—C(=O)—$R^4$, where each n is, independently, 1 or 2, and each $R^4$ is, independently, —$(CH_2)_p$—$NH_2$, where each p is, independently, 1 or 2; each $R^2$ is, independently, halo or $CF_3$; and each $V^2$ is H, and each $V^1$ is, independently, —N—C(=O)—$R^3$, where each $R^3$ is, independently, —$(CH_2)_n$—$NH_2$ or —$(CH_2)_n$—NH—C(=NH)$NH_2$, where each n is, independently, 3 or 4.

In some embodiments, the compound is chosen from:

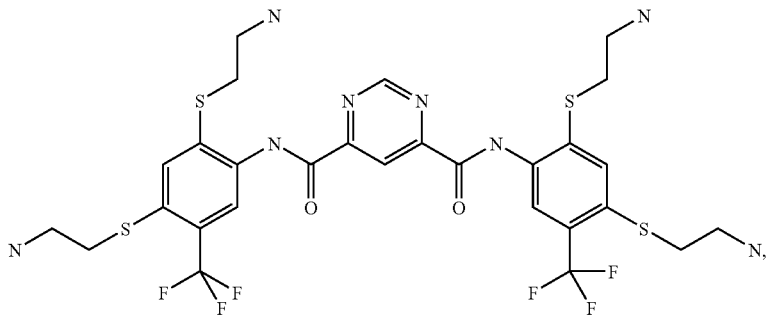

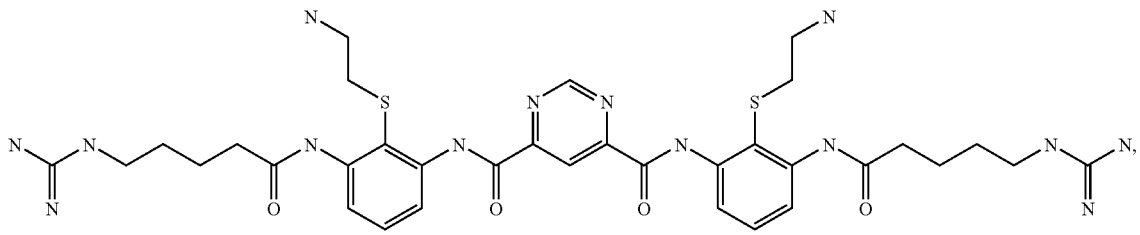

-continued
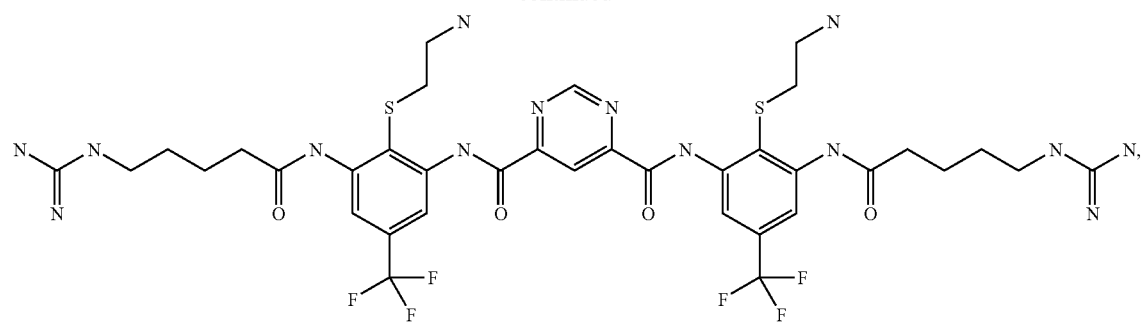
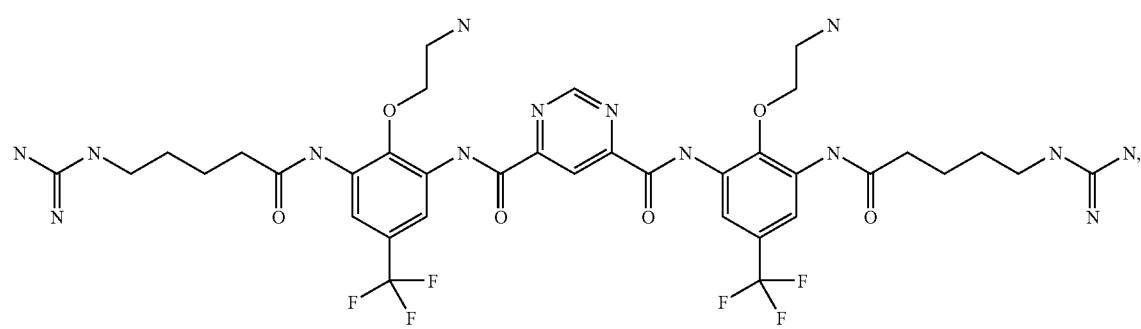
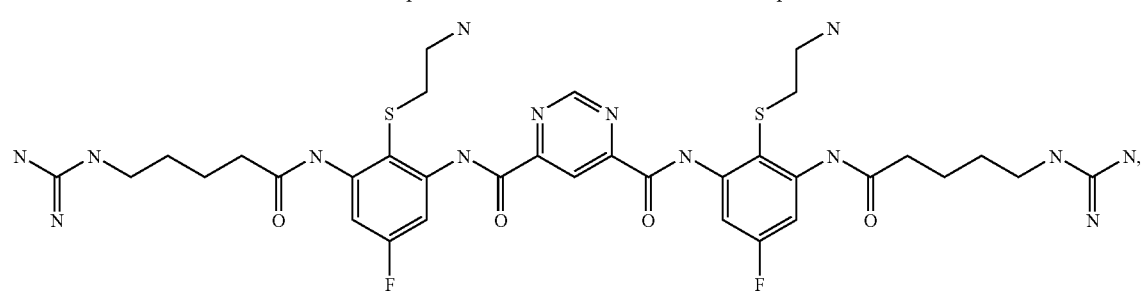
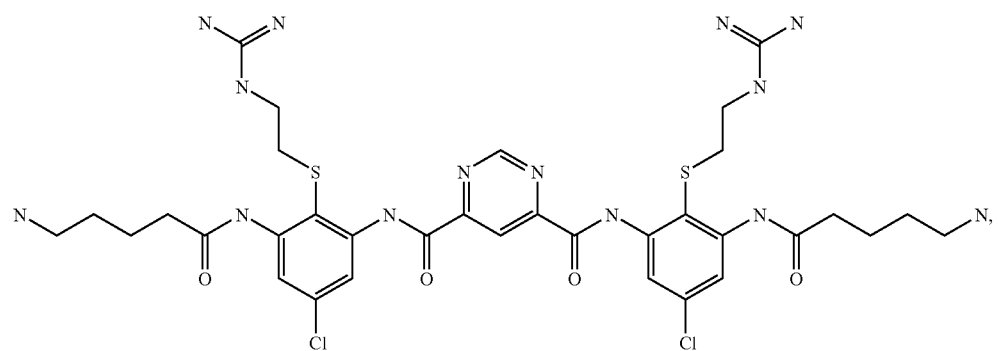
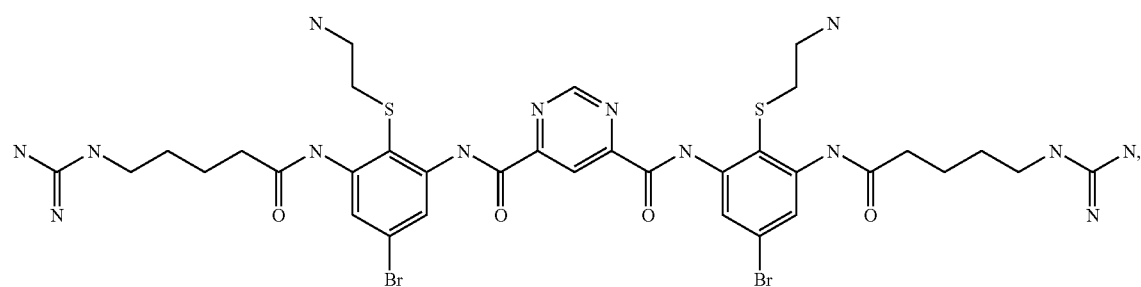

-continued
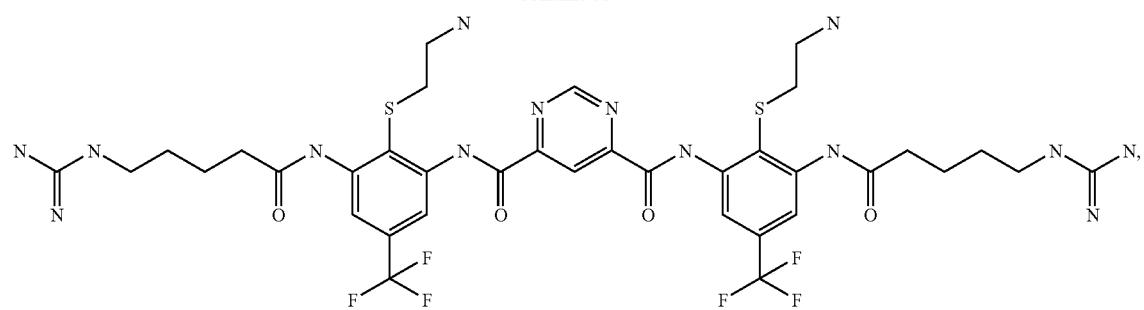
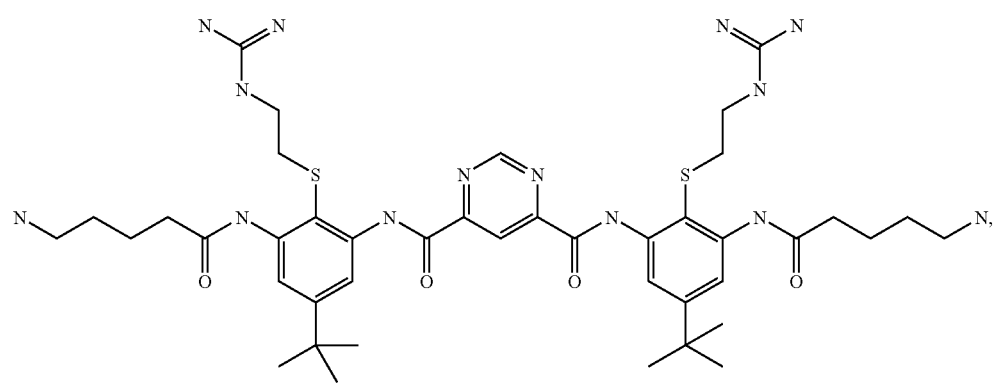
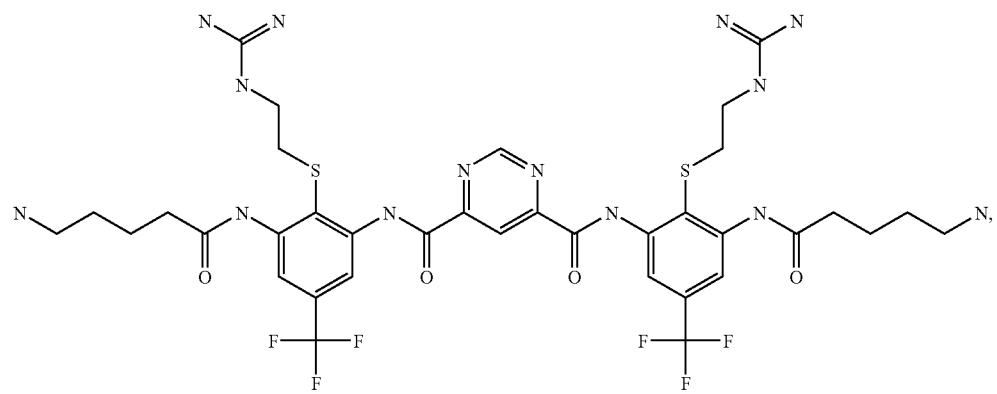
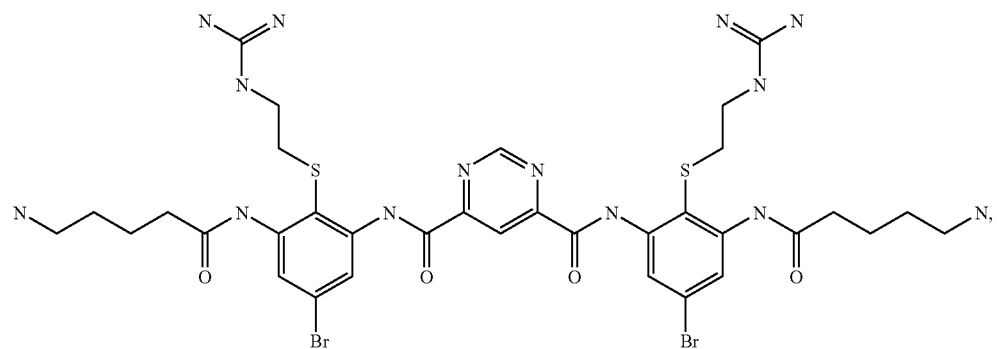

107 108
-continued
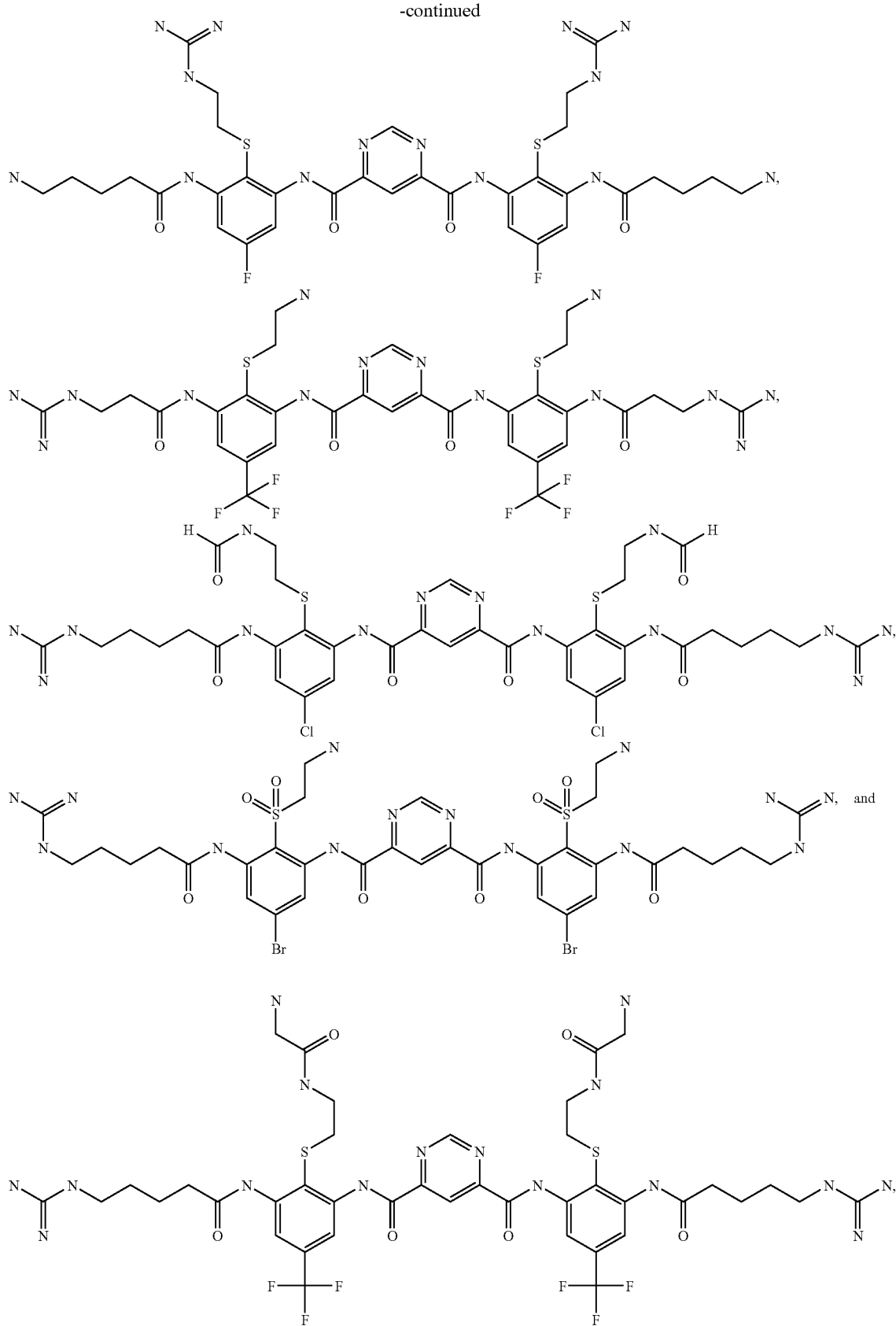
or a pharmaceutically acceptable salt thereof.

The present invention also provides compounds of Formula VI:

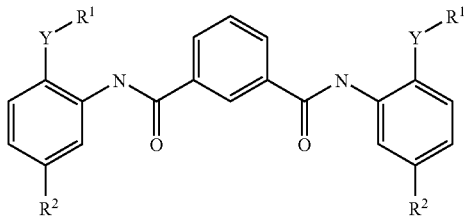

wherein:
each Y is, independently, O, S, or NH;
each $R^1$ is, independently, —$(CH_2)_n$—$NH_2$ or —$(CH_2)_n$—NH—C(=NH)$NH_2$, where each n is, independently, 1 to 4; and
each $R^2$ is, independently, H, halo, $CF_3$, or $C(CH_3)_3$;
or a pharmaceutically acceptable salt thereof.

In some embodiments, each Y is, independently, O, or S; or each Y is O or S.

In any of the above embodiments, each $R^1$ is, independently, —$(CH_2)_n$—$NH_2$, where each n is, independently, 2 to 4; or each $R^1$ is —$(CH_2)_n$—$NH_2$, where each n is 2 to 4.

In any of the above embodiments, each $R^2$ is, independently, halo, $CF_3$, or $C(CH_3)_3$; or each $R^2$ is halo, $CF_3$, or $C(CH_3)_3$.

In some embodiments, the compound is

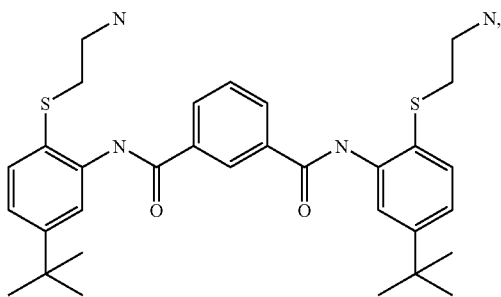

or pharmaceutically acceptable salt thereof.

In some embodiments, any one or more of the above compounds may be excluded from any of the genus of compounds described above.

The present invention also provides compositions comprising one or more of the compounds or salts described above and a pharmaceutically acceptable carrier.

The present invention also provides methods of treating malaria in an animal comprising administering to the animal a therapeutically effective amount of a compound of Formula VI:

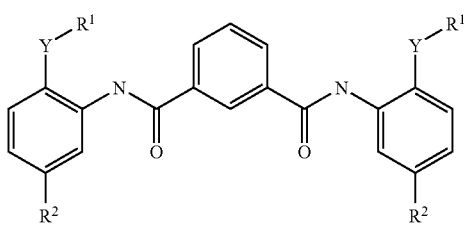

wherein:
each Y is, independently, O, S, or NH;
each $R^1$ is, independently, —$(CH_2)_n$—$NH_2$ or —$(CH_2)_n$—NH—C(=NH)$NH_2$, where each n is, independently, 1 to 4; and
each $R^2$ is, independently, H, halo, $CF_3$, or $C(CH_3)_3$;
or a pharmaceutically acceptable salt thereof.

In some embodiments, each Y is, independently, O, or S; or each Y is O or S.

In any of the above embodiments, each $R^1$ is, independently, —$(CH_2)_n$—$NH_2$, where each n is, independently, 2 to 4; or each $R^1$ is —$(CH_2)_n$—$NH_2$, where each n is 2 to 4.

In any of the above embodiments, each $R^2$ is, independently, halo, $CF_3$, or $C(CH_3)_3$; or each $R^2$ is halo, $CF_3$, or $C(CH_3)_3$.

In some embodiments, the compound is

Compound 100

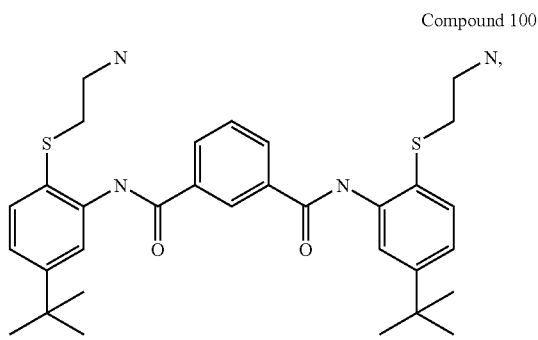

or pharmaceutically acceptable salt thereof.

In any of the above embodiments, the malaria can be chloroquine-sensitive or chloroquine-resistant.

The present invention also provides methods of killing or inhibiting the growth of a *Plasmodium* species comprising contacting the species with an effective amount of a compound of Formula VI:

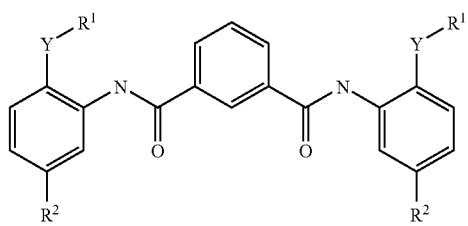

wherein:
each Y is, independently, O, S, or NH;
each $R^1$ is, independently, —$(CH_2)_n$—$NH_2$ or —$(CH_2)_n$—NH—C(=NH)$NH_2$, where each n is, independently, 1 to 4; and
each $R^2$ is, independently, H, halo, $CF_3$, or $C(CH_3)_3$;
or a pharmaceutically acceptable salt thereof.

In some embodiments, each Y is, independently, O, or S; or each Y is O or S.

In any of the above embodiments, each $R^1$ is, independently, —$(CH_2)_n$—$NH_2$, where each n is, independently, 2 to 4; or each $R^1$ is —$(CH_2)_n$—$NH_2$, where each n is 2 to 4.

In any of the above embodiments, each $R^2$ is, independently, halo, $CF_3$, or $C(CH_3)_3$; or each $R^2$ is halo, $CF_3$, or $C(CH_3)_3$.

In some embodiments, the compound is

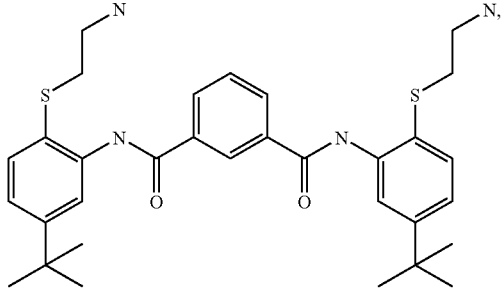

or pharmaceutically acceptable salt thereof.

The present invention also provides methods of treating malaria in an animal comprising administering to the animal a therapeutically effective amount of a compound of Formula VII:

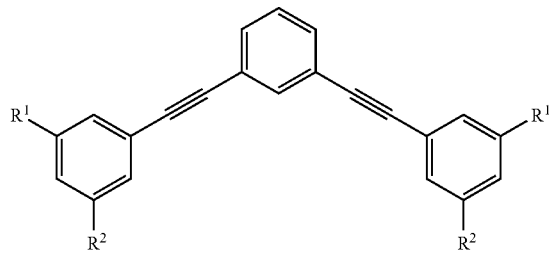

wherein:

each $R^1$ is, independently, H, $C_1$-$C_8$alkyl, $C_1$-$C_8$alkoxy, halo, OH, $CF_3$, or CN;

each $R^2$ is, independently, —$(CH_2)_n$—$NH_2$ or —$(CH_2)_n$—NH—C(=NH)$NH_2$, where each n is, independently, 1 to 4;

or a pharmaceutically acceptable salt thereof.

In some embodiments, each $R^1$ is, independently, $C_1$-$C_8$alkyl, halo, OH, $CF_3$, or CN; or each $R^1$ is, independently, $C_1$-$C_3$alkyl, halo, $CF_3$, or CN; or each $R^1$ is methyl or halo; or each $R^1$ is Br, F, or Cl.

In any of the above embodiments, each $R^2$ is, independently, —$(CH_2)_n$—NH—C(=NH)$NH_2$, where each n is, independently, 1 to 4; or each $R^2$ is —$(CH_2)_n$—NH—C(=NH)$NH_2$, where each n is 1 to 4; or each $R^2$ is —$(CH_2)_n$—NH—C(=NH)$NH_2$, where each n is 1 or 2.

In some embodiments, each $R^1$ is, independently, $C_1$-$C_8$alkyl, halo, OH, $CF_3$, or CN; and each $R^2$ is, independently, —$(CH_2)_n$—NH—C(=NH)$NH_2$, where each n is, independently, 1 to 4.

In some embodiments, each $R^1$ is, independently, $C_1$-$C_3$alkyl, halo, $CF_3$, or CN; and each $R^2$ is —$(CH_2)_n$—NH—C(=NH)$NH_2$, where each n is 1 to 4.

In some embodiments, each $R^1$ is methyl or halo; and each $R^2$ is —$(CH_2)_n$—NH—C(=NH)$NH_2$, where each n is 1 or 2.

In some embodiments, the compound is

Compound 115

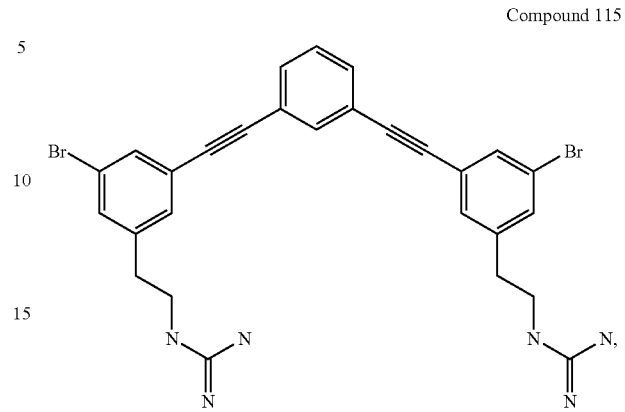

or a pharmaceutically acceptable salt thereof.

In any of the above embodiments, the malaria can be chloroquine-sensitive or chloroquine-resistant.

The present invention also provides methods of killing or inhibiting the growth of a *Plasmodium* species comprising contacting the species with an effective amount of a compound of Formula VII:

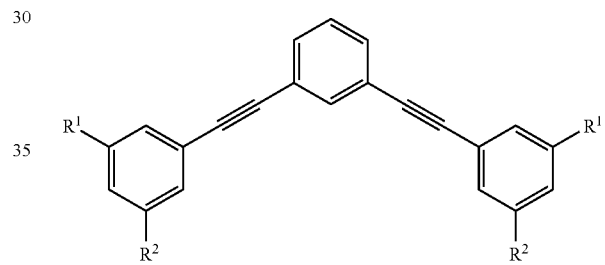

wherein:

each $R^1$ is, independently, H, $C_1$-$C_8$alkyl, $C_1$-$C_8$alkoxy, halo, OH, $CF_3$, or CN;

each $R^2$ is, independently, —$(CH_2)_n$—$NH_2$ or —$(CH_2)_n$—NH—C(=NH)$NH_2$, where each n is, independently, 1 to 4;

or a pharmaceutically acceptable salt thereof.

In some embodiments, each $R^1$ is, independently, $C_1$-$C_8$alkyl, halo, OH, $CF_3$, or CN; or each $R^1$ is, independently, $C_1$-$C_3$alkyl, halo, $CF_3$, or CN; or each $R^1$ is methyl or halo; or each $R^1$ is Br, F, or Cl.

In any of the above embodiments, each $R^2$ is, independently, —$(CH_2)_n$—NH—C(=NH)$NH_2$, where each n is, independently, 1 to 4; or each $R^2$ is $(CH_2)_n$—NH—C(=NH)$NH_2$, where each n is 1 to 4; or each $R^2$ is —$(CH_2)_n$—NH—C(=NH)$NH_2$, where each n is 1 or 2.

In some embodiments, each $R^1$ is, independently, $C_1$-$C_8$alkyl, halo, OH, $CF_3$, or CN; and each $R^2$ is, independently, —$(CH_2)_n$—NH—C(=NH)$NH_2$, where each n is, independently, 1 to 4.

In some embodiments, each $R^1$ is, independently, $C_1$-$C_3$alkyl, halo, $CF_3$, or CN; and each $R^2$ is —$(CH_2)_n$—NH—C(=NH)$NH_2$, where each n is 1 to 4.

In some embodiments, each $R^1$ is methyl or halo; and each $R^2$ is —$(CH_2)_n$—NH—C(=NH)$NH_2$, where each n is 1 or 2.

In some embodiments, the compound is

[structure]

or a pharmaceutically acceptable salt thereof.

The present invention also provides compounds of Formula VIII:

[structure: B-C(=O)-N-D-N-C(=O)-B]

wherein:
D is

[structure] or

[structure];

each B is, independently, —(CH$_2$)$_n$—NH—C(=NH)NH$_2$, where each n is, independently, 1 to 4,

[structure], or [structure];

and
each X is, independently, O or S;
or a pharmaceutically acceptable salt thereof.

In some embodiments, D is

[structure].

In any of the above embodiments, each B is, independently, —(CH$_2$)$_n$—NH—C(=NH)NH$_2$, where each n is, independently, 1 to 4.

In any of the above embodiments, each X is S.

In some embodiments, D is

[structure];

each B is, independently, —(CH$_2$)$_n$—NH—C(=NH)NH$_2$, where each n is, independently, 3 or 4, or

[structure];

and each X is S.

In some embodiments, D is

[structure];

each B is, independently,

[structure];

and each X is, independently, O or S.

In some embodiments, the compound is chosen from:

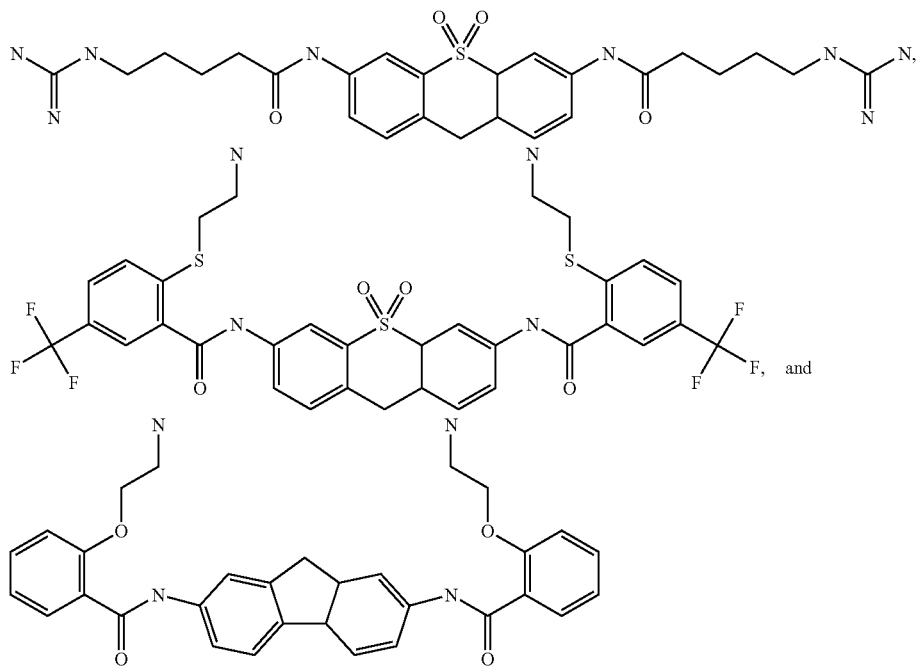

or pharmaceutically acceptable salt thereof.

In some embodiments, any one or more of the above compounds may be excluded from any of the genus of compounds described above.

The present invention also provides compositions comprising one or more of the compounds or salts described above and a pharmaceutically acceptable carrier.

The present invention also provides methods of treating malaria in an animal comprising administering to the animal a therapeutically effective amount of a compound of Formula VIII:

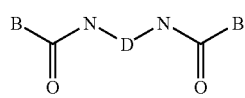

wherein:

D is

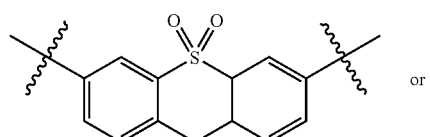  or

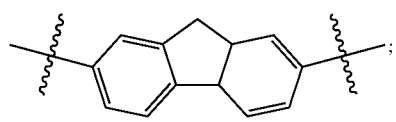 [SMILES: *C1=CC2Cc3cc(*)ccc3C2C=C1 ; ";"]

each B is, independently, —$(CH_2)_n$—NH—C(=NH)$NH_2$, where each n is, independently, 1 to 4,

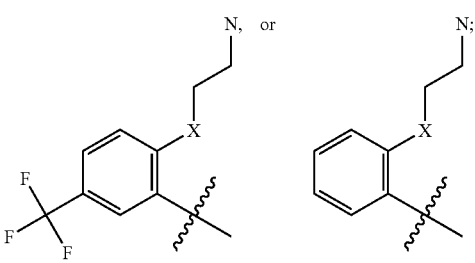

and each X is, independently, O or S;
or a pharmaceutically acceptable salt thereof.

In some embodiments, D is

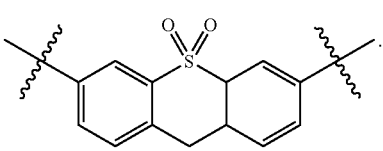 [SMILES: *C1=CC2C(C=C1)Cc1ccc(*)cc1S2(=O)=O ; ";"]

In any of the above embodiments, each B is, independently, —$(CH_2)_n$—NH—C(=NH)$NH_2$, where each n is, independently, 1 to 4.

In any of the above embodiments, each X is S.

In some embodiments, D is

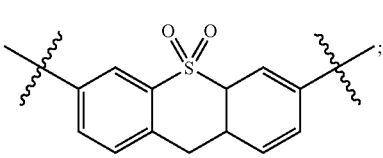 [SMILES: *C1=CC2C(C=C1)Cc1ccc(*)cc1S2(=O)=O ; ";"]

each B is, independently, —(CH$_2$)$_n$—NH—C(=NH)NH$_2$, where each n is, independently, 3 or 4, or

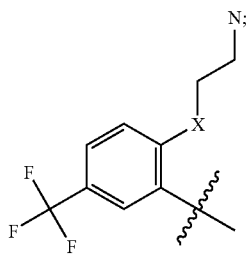

and each X is S.

In some embodiments, D is

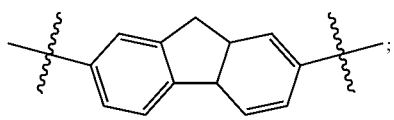

each B is, independently,

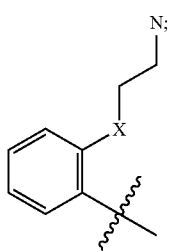

and each X is, independently, O or S.

In some embodiments, the compound is chosen from:

In any of the above embodiments, the malaria can be chloroquine-sensitive or chloroquine-resistant.

The present invention also provides methods of killing or inhibiting the growth of a *Plasmodium* species comprising contacting the species with an effective amount of a compound of Formula VIII:

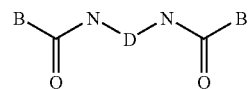

wherein:

D is

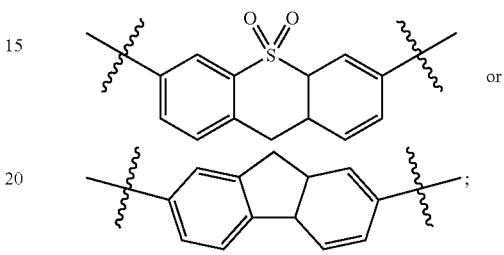

each B is, independently, —(CH$_2$)$_n$—NH—C(=NH)NH$_2$, where each n is, independently, 1 to 4,

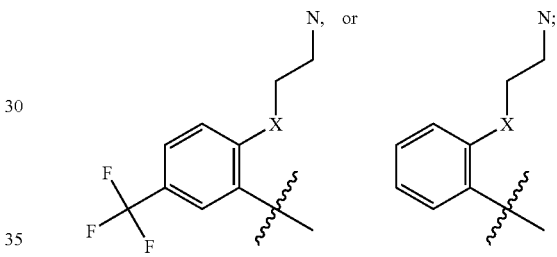

Compound 154

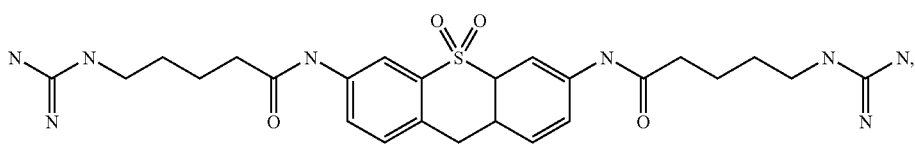

Compound 155

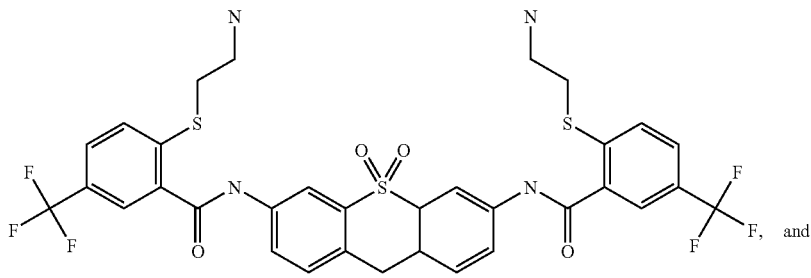

, and

Compound 156

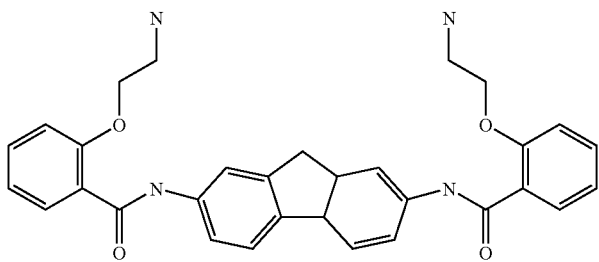

or pharmaceutically acceptable salt thereof.

and
each X is, independently, O or S;
or a pharmaceutically acceptable salt thereof.
In some embodiments, D is

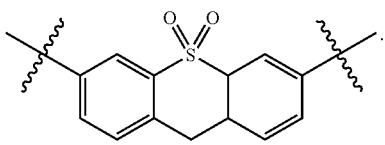

In any of the above embodiments, each B is, independently, —(CH$_2$)$_n$—NH—C(=NH)NH$_2$, where each n is, independently, 1 to 4.

In any of the above embodiments, each X is S.

In some embodiments, D is

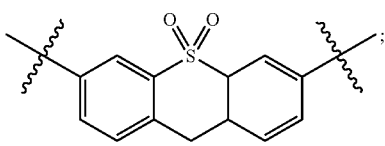

each B is, independently, —(CH$_2$)$_n$—NH—C(=NH)NH$_2$, where each n is, independently, 3 or 4, or

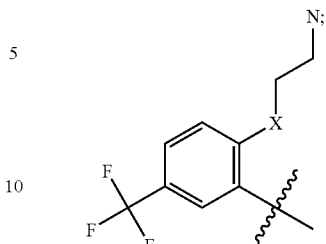

and each X is S.

In some embodiments, D is

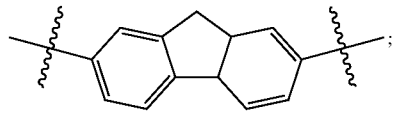 [SMILES: *C1=CC2Cc3cc(*)ccc3C2C=C1 ; ";"]

each B is, independently,

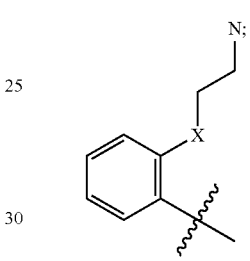

and each X is, independently, O or S.

In some embodiments, the compound is chosen from:

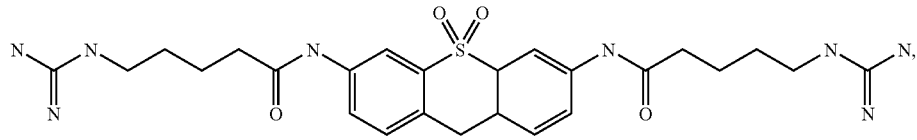

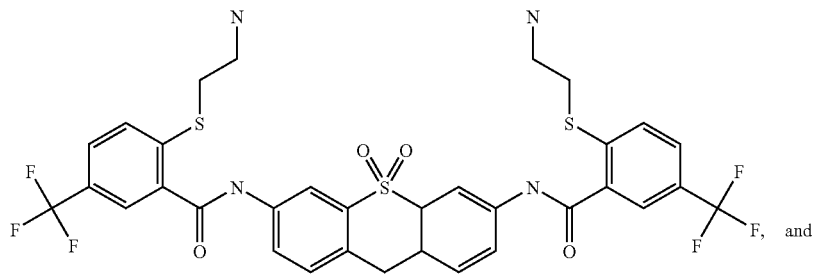

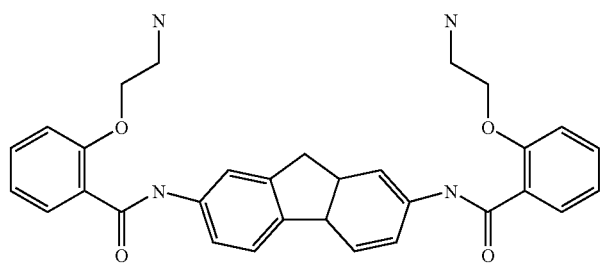

or pharmaceutically acceptable salt thereof.

It is to be understood that within any particular Formula, any one embodiment can be combined with any other embodiment(s), as deemed appropriate.

In some embodiments, the anti-malarial compound(s) can be chosen from one or more of the compounds (i.e., genuses, sub-genuses, and species) disclosed in U.S. Patent Application Publication Nos. US 2005/0287108 and/or US 2006/0041023, each of which is incorporated herein by reference in its entirety. The methods described herein can also be carried out using any one or more of the compounds disclosed as a genus, sub-genus, or species of U.S. Patent Application Publication Nos. US 2005/0287108 and/or US 2006/0041023.

Some of the compounds of the present invention may be capable of adopting amphiphilic conformations that allow for the segregation of polar and nonpolar regions of the molecule into different spatial regions and provide the basis for a number of uses. For example, some anti-malarial compounds may adopt amphiphilic conformations that are capable of disrupting the integrity of the cell membrane of microorganisms, resulting in the inhibition of growth or the death of, for example, *Plasmodium* species.

The anti-malarial compounds can be useful as anti-malarial agents in a number of applications. For example, anti-malarial compounds can be used therapeutically to treat malaria in animals, including humans and non-human vertebrates such as wild, domestic and farm animals. The malarial infection in an animal can be treated by administering to the animal an effective amount of an anti-malarial compound, or a pharmaceutical composition comprising the same. The anti-malarial compound, or composition thereof, can be administered systemically or topically and can be administered to any body site or tissue.

Although the anti-malarial compounds are suitable, other functional groups can be incorporated into the compound with an expectation of similar results. In particular, thioamides and thioesters are anticipated to have very similar properties. The distance between aromatic rings can impact the geometrical pattern of the compound and this distance can be altered by incorporating aliphatic chains of varying length, which can be optionally substituted or can comprise an amino acid, a dicarboxylic acid or a diamine. The distance between and the relative orientation of monomers within the compounds can also be altered by replacing the amide bond with a surrogate having additional atoms. Thus, replacing a carbonyl group with a dicarbonyl alters the distance between the monomers and the propensity of dicarbonyl unit to adopt an anti arrangement of the two carbonyl moiety and alter the periodicity of the compound. Pyromellitic anhydride represents still another alternative to simple amide linkages which can alter the conformation and physical properties of the compound. Modern methods of solid phase organic chemistry (E. Atherton and R. C. Sheppard, Solid Phase Peptide Synthesis A Practical Approach IRL Press Oxford 1989) now allow the synthesis of homodisperse compounds with molecular weights approaching 5,000 Daltons. Other substitution patterns are equally effective.

The term "malarialcidal" as used herein means that the compound inhibits, prevents, or destroys the growth or proliferation of a *Plasmodium* species.

The anti-malarial compounds can be incorporated into polishes, paints, sprays, or detergents formulated for application to surfaces to inhibit the growth of a *Plasmodium* species thereon. These surfaces include, but are not limited to, surfaces such as, countertops, desks, chairs, laboratory benches, tables, floors, bed stands, tools or equipment, doorknobs, and windows. The anti-malarial compounds can also be incorporated into soaps and hand lotions. The present cleansers, polishes, paints, sprays, soaps, or detergents contain an anti-malarial compound that provides a malarialstatic property to them. The anti-malarial compounds can optionally contain suitable solvent(s), carrier(s), thickeners, pigments, fragrances, deodorizers, emulsifiers, surfactants, wetting agents, waxes, or oils. For example, in some aspects, the anti-malarial compounds can be incorporated into a formulation for external use as a pharmaceutically acceptable skin cleanser, particularly for the surfaces of human hands. Cleansers, polishes, paints, sprays, soaps, hand lotions, and detergents and the like containing the anti-malarial compounds can be useful in homes and institutions, particularly but not exclusively, in hospital settings for the prevention of nosocomial infections.

In some aspects, the anti-malarial compounds include derivatives referred to as prodrugs. The expression "prodrug" denotes a derivative of a known direct acting drug, which derivative has enhanced delivery characteristics and therapeutic value as compared to the drug, and is transformed into the active drug by an enzymatic or chemical process.

It is understood that the present invention encompasses the use, where applicable, of stereoisomers, diastereomers and optical isomers of the anti-malarial compounds, as well as mixtures thereof, for treating malarial infections, an/or killing or inhibiting the growth of a *Plasmodium* species. Additionally, it is understood that stereoisomers, diastereomers, and optical isomers of the anti-malarial compounds, and mixtures thereof, are within the scope of the invention. By way of non-limiting example, the mixture may be a racemate or the mixture may comprise unequal proportions of one particular stereoisomer over the other. Additionally, the anti-malarial compounds can be provided as a substantially pure stereoisomers, diastereomers and optical isomers.

In another aspect, the anti-malarial compounds can be provided in the form of an acceptable salt (i.e., a pharmaceutically acceptable salt) for treating malarial infections, and/or killing or inhibiting the growth of a *Plasmodium* species. Salts can be provided for pharmaceutical use, or as an intermediate in preparing the pharmaceutically desired form of the anti-malarial compounds. One salt that can be considered to be acceptable is the hydrochloride acid addition salt. Hydrochloride acid addition salts are often acceptable salts when the pharmaceutically active agent has an amine group that can be protonated. Since an anti-malarial compound may be polyionic, such as a polyamine, the acceptable salt can be provided in the form of a poly(amine hydrochloride).

Polyamides and polyesters that are useful can be prepared by typical condensation polymerization and addition polymerization processes. See, for example, G. Odian, Principles of Polymerization, John Wiley & Sons, Third Edition (1991), M. Steven, Polymer Chemistry, Oxford University Press (1999). Most commonly the polyamides are prepared by (a) thermal dehydration of amine salts of carboxylic acids, (b) reaction of acid chlorides with amines and (c) aminolysis of esters. Methods (a) and (c) are of limited use in polymerizations of aniline derivatives which are generally prepared utilizing acid chlorides. The skilled chemist, however, will recognize that there are many alternative active acylating agents, for example phosphoryl anhydrides, active esters or azides, which may replace an acid chloride and which, depending of the particular polymer being prepared, may be superior to an acid chloride. The acid chloride route is probably the most versatile and baa been used extensively for the synthesis of aromatic polyamides.

Homopolymers derived from substituted aminobenzoic acid derivatives can also prepared in a stepwise fashion. A stepwise process comprises coupling an N-protected amino acid to an amine (or hydroxy group) and subsequently removing the amine-protecting group and repeating the process. These techniques have been highly refined for synthesis of specific peptides, allow for the synthesis of specific sequences, and both solid-phase and solution techniques for peptide synthesis are directly applicable to the present invention. An alternative embodiment of the present invention is the corresponding polysulfonamides that can be prepared in analogous fashion by substituting sulfonyl chlorides for carboxylic acid chlorides.

The most common method for the preparation of polyureas is the reaction of diamines with diisocyanates (Yamaguchi, et al., Polym. Bull., 2000, 44, 247). This exothermic reaction can be carried out by solution techniques or by interfacial techniques. One skilled in organic and polymer chemistry will appreciate that the diisocyanate can be replaced with a variety of other bis-acylating agents e.g., phosgene or N,N'-(diimidazolyl)carbonyl, with similar results. Polyurethanes are prepared by comparable techniques using a diisocyanate and a dialcohol or by reaction of a diamine with a bis-chloroformate.

The syntheses of the anti-malarial compounds can be carried out by routine and/or known methods such as those disclosed in, for example, U.S. Patent Application Publication Nos. US 2005/0287108 and US 2006/0041023, each of which is incorporated herein by reference in its entirety. Numerous pathways are available to incorporate polar and nonpolar side chains. Phenolic groups on the monomer can be alkylated. Alkylation of the commercially available phenol will be accomplished with standard Williamson ether synthesis for the non-polar side chain with ethyl bromide as the alkylating agent. Polar sidechains can be introduced with bifunctional alkylating agents such as BOC—NH(CH$_2$)$_2$Br. Alternatively, the phenol group can be alkylated to install the desired polar side chain function by employing the Mitsonobu reaction with BOC—NH(CH$_2$)$_2$—OH, triphenyl phosphine, and diethyl acetylenedicarboxylate. Standard conditions for reduction of the nitro groups and hydrolysis of the ester afford the amino acid. With the aniline and benzoic acid in hand, coupling can be effected under a variety of conditions. Alternatively, the hydroxy group of the (di)nitrophenol can be converted to a leaving group and a functionality introduced under nucleophilic aromatic substitution conditions. Other potential scaffolds that can be prepared with similar sequences are methyl 2-nitro-4-hydroxybenzoate and methyl 2-hydroxy-4-nitrobenzoate.

The anti-malarial compounds can also be designed using computer-aided computational techniques, such as de novo design techniques, to embody the amphiphilic properties. In general, de novo design of anti-malarial compounds is performed by defining a three-dimensional framework of the backbone assembled from a repeating sequence of monomers using molecular dynamics and quantum force field calculations. Next, side groups are computationally grafted onto the backbone to maximize diversity and maintain drug-like properties. The best combinations of functional groups are then computationally selected to produce a cationic, amphiphilic structures. Representative compounds can be synthesized from this selected library to verify structures and test their biological activity. Novel molecular dynamic and coarse grain modeling programs have also been developed for this approach because existing force fields developed for biological molecules, such as peptides, were unreliable in these oligomer applications (Car, R., and Parrinello, M., Phys. Rev. Lett., 55:2471-2474 (1985); Siepmann, J. I., and Frenkel, D., Mol. Phys. 75:59-70 (1992); Martin, M. G., and Siepmann, J. I., J. Phys. Chem. B 103:4508-4517 (1999); Brooks, B. R., et al., J. Comp. Chem. 4:187-217 (1983)). Several chemical structural series of compounds have been prepared. See, for example, WO 02/100295 A2, which is incorporated herein by reference in its entirety. The anti-malarial compounds can be prepared in a similar manner. Molecular dynamic and coarse grain modeling programs can be used for a design approach. See, for example, U.S. Patent Application No. US 2004-0107056, and U.S. Patent Application No. US 2004-0102941, each of which is incorporated herein by reference in its entirety.

After verifying the suitability of the force field by comparing computed predictions of the structure and thermodynamic properties to molecules that have similar torsional patterns and for which experimental data are available, the fitted torsions can then be combined with bond stretching, bending, one-four, van der Waals, and electrostatic potentials borrowed from the CHARMM (Brooks, B. R., et al., J. Comp. Chem. 4:187-217 (1983)) and TraPPE (Martin, M. G., and Siepmann, J. I., J. Phys. Chem. B 103:4508-4517 (1999); Wick, C. D., et al., J. Phys. Chem. B 104:3093-3104 (2000)) molecular dynamics force fields. To identify conformations that can adopt periodic folding patterns with polar groups and apolar groups lined up on the opposite sides, initial structures can be obtained with the Gaussian package (Frisch, M., et al., Gaussian 98 (revision A.7) Gaussian Inc., Pittsburgh, Pa. 1998). Then, the parallelized plane-wave Car-Parrinello CP-MD (Car, R., and Parrinello, M., Phys. Rev. Lett. 55:2471-2474 (1985)) program, (cf. Rothlisberger, U., et al., J. Chem. Phys. 3692-3700 (1996)) can be used to obtain energies at the minimum and constrained geometries. The conformations of the compounds without side-chains can be investigated in the gas phase. Both MD and MC methods can be used to sample the conformations. The former is useful for global motions of the compound. With biasing techniques (Siepmann, J. I., and Frenkel, D., Mol. Phys. 75:59-70 (1992); Martin, M. G., and Siepmann, J. I., J. Phys. Chem. B 103:4508-4517 (1999); Vlugt, T. J. H., et al. Mol. Phys. 94:727-733 (1998)), the latter allows efficient sampling for compounds with multiple local minimum configurations that are separated by relatively large barriers.

The potential conformations are examined for positions to attach pendant groups that will impart amphiphilic character to the secondary structure. Compounds selected from the gas phase studies with suitable backbone conformations and with side-chains at the optimal positions to introduce amphiphilicity can be further evaluated in a model interfacial system. n-hexane/water can be chosen because it is simple and cheap for calculations while it mimics well the lipid/water bilayer environment. Compound secondary structures that require inter-compound interactions can be identified by repeating the above-mentioned calculations using a periodically repeated series of unit cells of various symmetries (so called variable cell molecular dynamics or Monte Carlo technique) with or without solvent. The results of these calculations can guide the selection of candidates for synthesis.

An example of the design, synthesis, and testing of arylamide polymers and oligomers, a related group of compounds of the invention, is presented in Tew, G. N., et al., Proc. Natl. Acad. Sci. USA 99:5110-5114 (2002), which is incorporated herein by reference in its entirety.

The anti-malarial compounds can be synthesized by solid-phase synthetic procedures well know to those of skill in the art. See, for example, Tew et al. (Tew, G. N., et al., Proc. Natl. Acad. Sci. USA 99:5110-5114 (2002)). See also Barany, G., et al., Int. J. Pept. Prot. Res. 30:705-739 (1987); Solid-phase Synthesis: A Practical Guide, Kates, S. A., and Albericio, F., eds., Marcel Dekker, New York (2000); and Dörwald, F. Z., Organic Synthesis on Solid Phase: Supports, Linkers, Reactions, 2nd Ed., Wiley-VCH, Weinheim (2002).

One of skill in the art will recognize that the anti-malarial compounds can be tested for anti-malarial activity by methods well known to those of skill in the art. Any compound found to be active can be purified to homogeneity and retested to obtain an accurate $IC_{50}$.

The anti-malarial compounds can be administered in any conventional manner by any route where they are active. Administration can be systemic, topical, or oral. For example, administration can be, but is not limited to, parenteral, subcutaneous, intravenous, intramuscular, intraperitoneal, transdermal, oral, buccal, or ocular routes, or intravaginally, by inhalation, by depot injections, or by implants. Thus, modes of administration for the anti-malarial compounds (either alone or in combination with other pharmaceuticals) can be, but are not limited to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams. The selection of the specific route of administration and the dose regimen is to be adjusted or titrated by the clinician according to methods known to the clinician to obtain the desired clinical response.

The amount of any particular anti-malarial compound to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician). The amount of an anti-malarial compound described herein that will be effective in the treatment of malaria will depend on the nature of the malaria, and can be determined by standard clinical techniques. In addition, in vitro or in vivo assays may optionally be employed to help identify optimal dosage ranges. The precise dose to be employed in the compositions will also depend on the route of administration, and the seriousness of the disorder, and should be decided according to the judgment of the practitioner and each patient's circumstances. However, a suitable dosage range for oral administration is, generally, from about 0.001 milligram to about 200 milligrams per kilogram body weight. In some embodiments, the oral dose is from about 0.01 milligram to 100 milligrams per kilogram body weight, from about 0.01 milligram to about 70 milligrams per kilogram body weight, from about 0.1 milligram to about 50 milligrams per kilogram body weight, from 0.5 milligram to about 20 milligrams per kilogram body weight, or from about 1 milligram to about 10 milligrams per kilogram body weight. In some embodiments, the oral dose is about 5 milligrams per kilogram body weight.

The pharmaceutical compositions and/or formulations containing the anti-malarial compounds and a suitable carrier can be solid dosage forms which include, but are not limited to, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of a anti-malarial compound. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, Modern Pharmaceutics, Banker & Rhodes, Marcel Dekker, Inc. (1979); and Goodman & Gilman's The Pharmaceutical Basis of Therapeutics, 6th Edition, MacMillan Publishing Co., New York (1980) can be consulted.

The anti-malarial compounds can be formulated for parenteral administration by injection, e.g., by bolus injection or continuous infusion. The anti-malarial compounds can be administered by continuous infusion subcutaneously over a period of about 15 minutes to about 24 hours. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

For oral administration, the anti-malarial compounds can be formulated readily by combining these compounds with pharmaceutically acceptable carriers well known in the art. Such carriers enable the anti-malarial compounds to be formulated as tablets, pills, dragees, capsules, liquids, gels, syrups, slurries, suspensions and the like, for oral ingestion by a patient to be treated. Pharmaceutical preparations for oral use can be obtained by, for example, adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of, e.g., tablets or lozenges formulated in a conventional manner.

For administration by inhalation, the anti-malarial compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The anti-malarial compounds can also be formulated in rectal compositions such as suppositories or retention enemas, e.g., containing conventional suppository bases such as cocoa butter or other glycerides.

In addition to the formulations described previously, the anti-malarial compounds can also be formulated as a depot preparation. Such long acting formulations can be administered by implantation (for example subcutaneously or intramuscularly) or by intramuscular injection. Depot injections can be administered at about 1 to about 6 months or longer intervals. Thus, for example, the anti-malarial compounds can be formulated with suitable polymeric or hydrophobic materials (for example as an emulsion in an acceptable oil) or ion exchange resins, or as sparingly soluble derivatives, for example, as a sparingly soluble salt.

In transdermal administration, the anti-malarial compounds can be applied to a plaster, or can be applied by transdermal, therapeutic systems that are consequently supplied to the organism.

The pharmaceutical compositions comprising the anti-malarial compounds also can comprise suitable solid or gel phase carriers or excipients. Examples of such carriers or excipients include, but are not limited to, calcium carbonate, calcium phosphate, various sugars, starches, cellulose derivatives, gelatin, and polymers such as, e.g., polyethylene glycols.

In another embodiment, the anti-malarial compounds described herein can be delivered in a vesicle, in particular a liposome (see, Langer, Science, 1990, 249, 1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the anti-malarial compounds described herein can be delivered in a controlled release system. In one embodiment, a pump may be used (see Langer, supra; Sefton, CRC Crit. Ref. Biomed. Eng., 1987, 14, 201; Buchwald et al., Surgery, 1980, 88, 507 Saudek et al., N. Engl. J. Med., 1989, 321, 574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger et al., J. Macromol. Sci. Rev. Macromol. Chem., 1983, 23, 61; see, also Levy et al., Science, 1985, 228, 190; During et al., Ann. Neurol., 1989, 25, 351; Howard et al., J. Neurosurg., 1989, 71, 105). In yet another embodiment, a controlled-release system can be placed in proximity of the target of the anti-malarial compounds described herein, e.g., the liver, thus requiring only a fraction of the systemic dose (see, e.g., Goodson, in Medical Applications of Controlled Release, supra, vol. 2, pp. 115-138 (1984)). Other controlled-release systems discussed in the review by Langer, Science, 1990, 249, 1527-1533) may be used.

The anti-malarial compounds can also be administered in combination with other active ingredients such as, for example, antibiotics, including, but not limited to, vancomycin, ciprofloxacin, merapenem, oxicillin, and amikacin. The anti-malarial compounds can also be administered in combination with other anti-malarial compounds such as, for example, any one or more of artemisinin, quinine, artesunate, sulfadoxine-pyrimethamine, hydroxychloroquine, chloroquine, amodiaquine, pyrimethamine, sulphadoxine, proguanil, mefloquine, atovaquone, primaquine, halofantrine, doxycycline, clindamycin.

Thus, the present invention also provides methods of treating malaria in an animal comprising administering to the animal in need thereof an effective amount of an anti-malarial compound or a slat thereof. The present invention also provides methods of treating malaria in an animal comprising administering to the animal in need thereof a composition comprising an anti-malarial compound, or a slat thereof. The present invention also provides methods of killing or inhibiting the growth of a *Plasmodium* species comprising contacting the species with an effective amount of an anti-malarial compound, or salt thereof. The present invention also provides methods of killing or inhibiting the growth of a *Plasmodium* species comprising contacting the species with a composition comprising an anti-malarial compound, or salt thereof. The present invention also provides methods of killing or inhibiting the growth of a chloroquine-sensitive or chloroquine-resistant *Plasmodium* species comprising contacting the species with an effective amount of an anti-malarial compound, or salt thereof. The present invention also provides methods of killing or inhibiting the growth of a chloroquine-sensitive or chloroquine-resistant *Plasmodium* species comprising contacting the species with a composition comprising an anti-malarial compound, or salt thereof. The present invention also provides methods of disrupting a food vacuole of a *Plasmodium* species comprising contacting the species with an effective amount of an anti-malarial compound, or salt thereof. The present invention also provides methods of disrupting a food vacuole of a *Plasmodium* species comprising contacting the species with a composition comprising an anti-malarial compound, or salt thereof.

An "animal in need thereof" is an animal that has been diagnosed with malaria, an animal who is suspected of having malaria, and/or an animal that is in an environment or will be traveling to an environment in which malaria is prevelant.

The present invention also provides anti-malarial compounds, or a salt thereof, or compositions comprising the same, for use in treating a malarial infection in an animal. The present invention also provides anti-malarial compounds, or a salt thereof, or compositions comprising the same, for use in killing or inhibiting the growth of a *Plasmodium* species. The present invention also provides anti-malarial compounds, or a salt thereof, or compositions comprising the same, for use in preparation of a medicament for treating a malarial infection in an animal. The present invention also provides anti-malarial compounds, or a salt thereof, or compositions comprising the same, for use in preparation of a medicament for killing or inhibiting the growth of a *Plasmodium* species.

The anti-malarial compounds described herein can be combined with one, two, or three other anti-malarial compounds described herein to form a cocktail. This cocktail can also include other anti-malarial compounds.

In order that the invention disclosed herein may be more efficiently understood, examples are provided below. It should be understood that these examples are for illustrative purposes only and are not to be construed as limiting the invention in any manner.

EXAMPLES
Example 1
Synthesis of Compounds 142 and 149
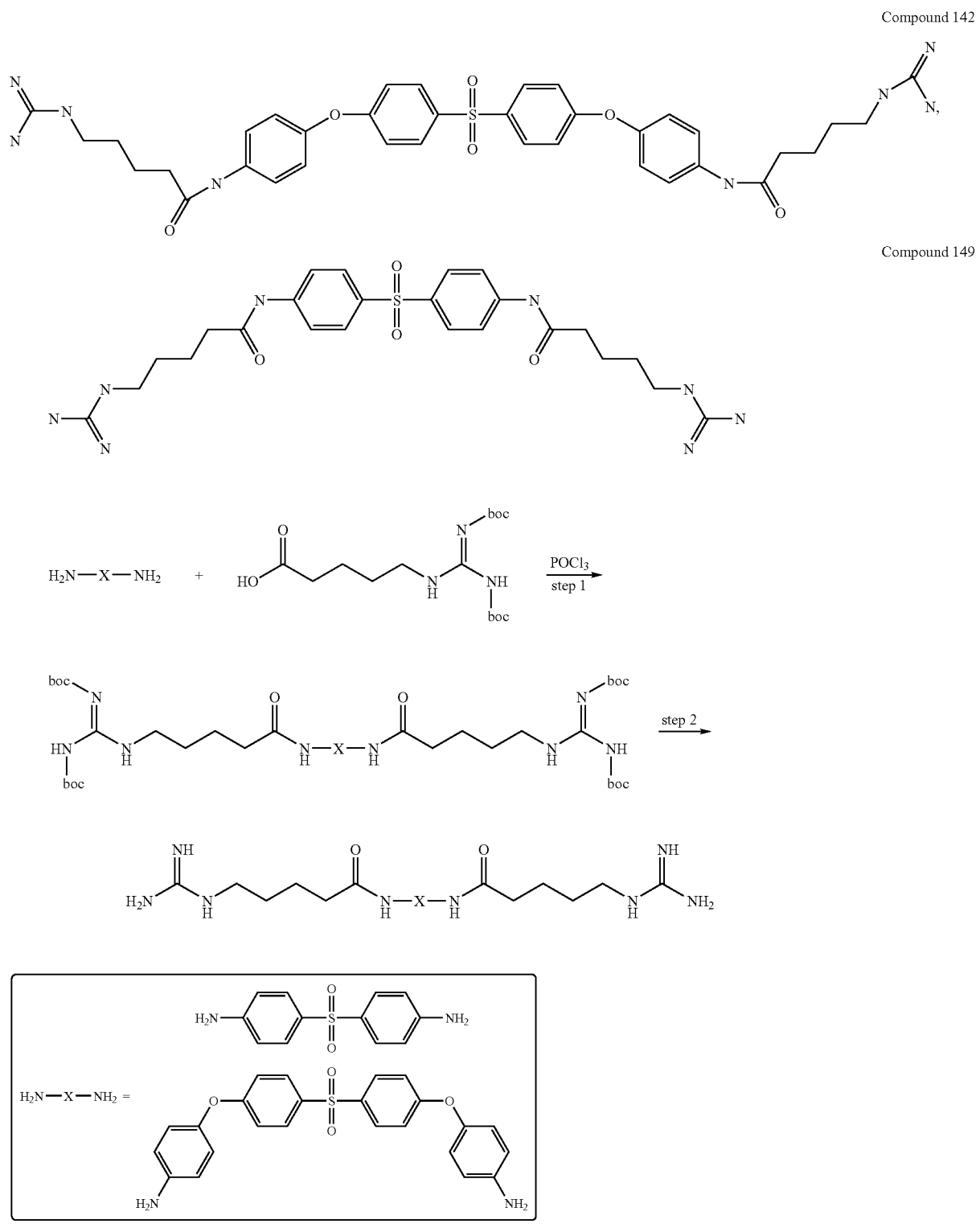

Step 1: The diamine (0.1 mmol) and ({[(tert-butoxycarbonyl)amino][(tert-butoxycarbonyl)imino]methyl}amino)pentanoic acid (4 equivalence) were dissolved in 3 mL of pyridine and cooled to 0° C. The solution was added POCl₃ (4 equiv.) dropwise and stirred at 0° C. for 1.5 hours. The reaction was quenched with ice water. The solvent was removed on a rotovap.

Step 2: The product from step 1 was treated with 50% trifluoroacetic acid (TFA) in dichloromethane (DCM). The product was purified by reverse phase chromatography.

Example 2

Synthesis of Compounds 109, 111, and 144

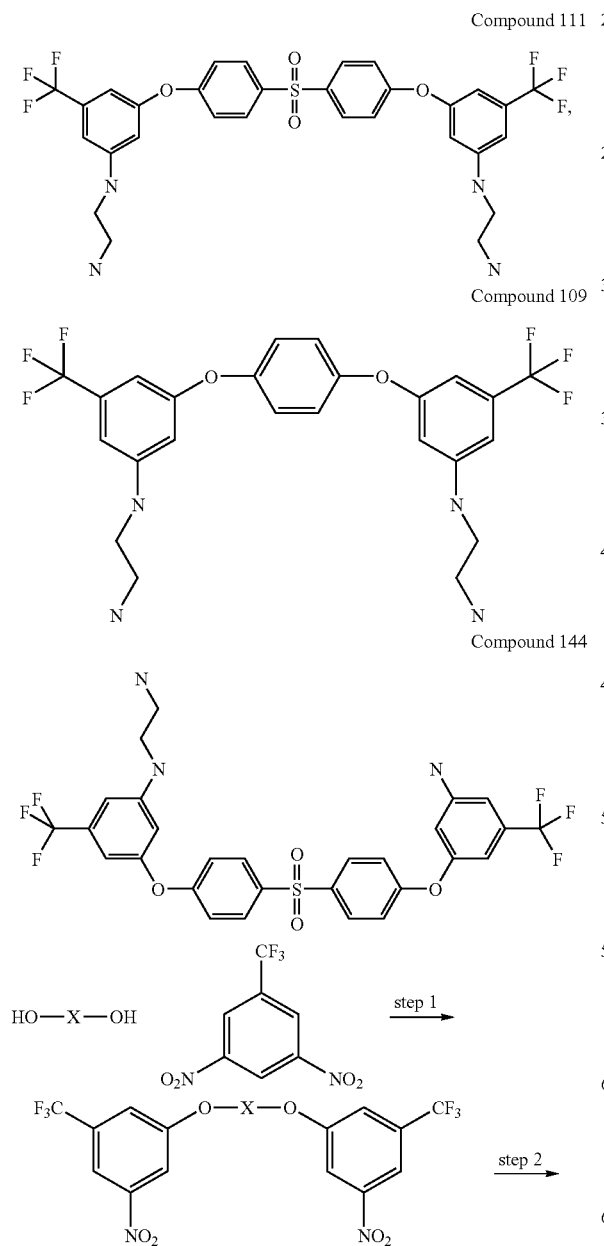

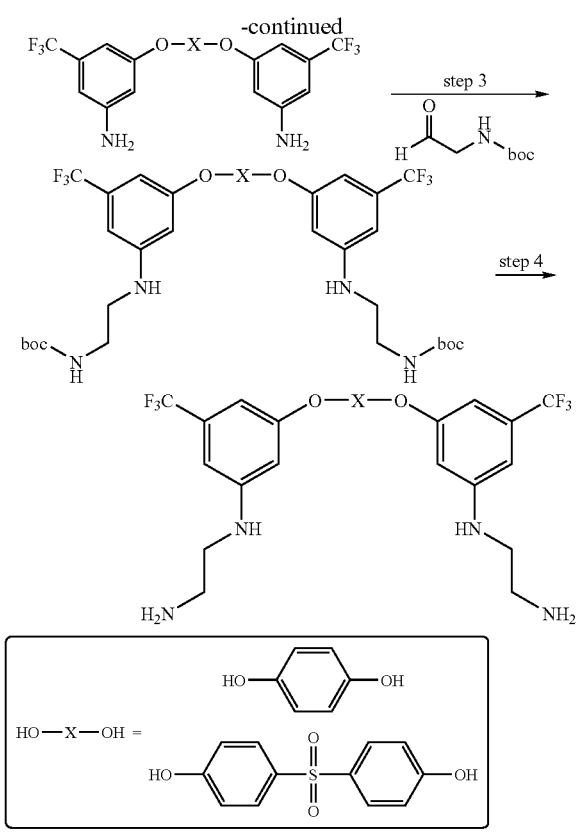

Step 1: 319.6 mg of 4,4-dihydroxyphenyl in 4.0 ml of dimethylformamide (DMF) were sequentially added to 839.0 mg of $K_2CO_3$, and 1.3166 g of 3,5-dinitrobenzotrifluoride. The reaction mixture was heated to 125° C. with stirring for overnight. TLC analysis indicated the starting material was consumed. The reaction was quenched with water and extracted with ethyl acetate (EtOAc) twice. The organic phase was washed with water, brine and dried with sodium sulfate before being concentrated under reduced pressure. The product was purified by column chromatography with a yield of 865.6 mg (69%).

Step 2: 312.3 mg of the product formed in step 1 in 5.0 ml of MeOH was sequentially added to 365.3 mg of $NH_4Cl$, and 400.2 mg of Zinc dust. The reaction mixture was irradiated under microwave at 115° C. for 20 minutes. LCMS analysis indicated the starting material was consumed. The reaction mixture was filtered and concentrated. The residue was quenched with water and extracted with EtOAc twice. The organic phase was washed with water, brine and dried with sodium sulfate before being concentrated under reduced pressure. The crude product was under high vacuum for 6 hours and was used without further purification.

Step 3: 44.9 mg of diamine formed in step 2 was added to (2-oxo-ethyl)-carbamic acid tert-butyl ester (2 equiv. for compounds 109 and 111, 1 equiv. for compound 144) in 1.5 ml of anhydrous EtOH. The reaction mixture was sequentially added 3 drops of HOAc and 78.6 mg of $NaCNBH_3$. The reaction mixture was stirred at room temperature overnight. LCMS analysis indicated the starting material was consumed. The reaction mixture was concentrated and the residue was quenched with water and extracted with EtOAc twice. The organic phase was washed with water, brine and dried with sodium sulfate before being concentrated under reduced pressure. The product was purified by column chromatography with a yield of 72.3 mg (97%).

Step 4: 41.3 mg of Boc-protected diamine formed in step 3 in 1.5 ml of DCM was added 1.5 ml of TFA and the reaction mixture was stirred at room temperature for 45 minutes. LCMS analysis indicated the starting material was consumed. The reaction mixture was concentrated and the residue was washed with ether twice. The white powder in 2 ml of ether was further sonicated for 10 minutes. The white solid was then washed with ether twice and was under high vacuum for 12 hours. The yield was 39.6 mg.

Example 3

Synthesis of Compounds 148 and 147

Compound 147

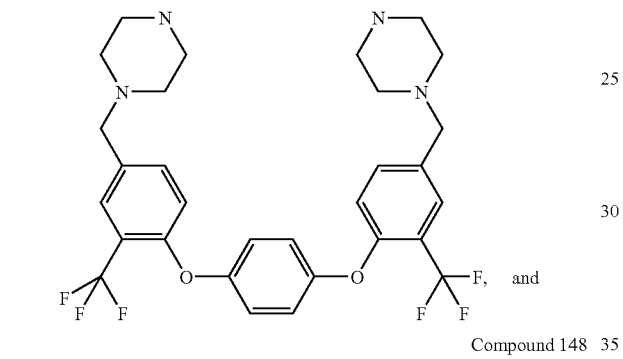

and

Compound 148

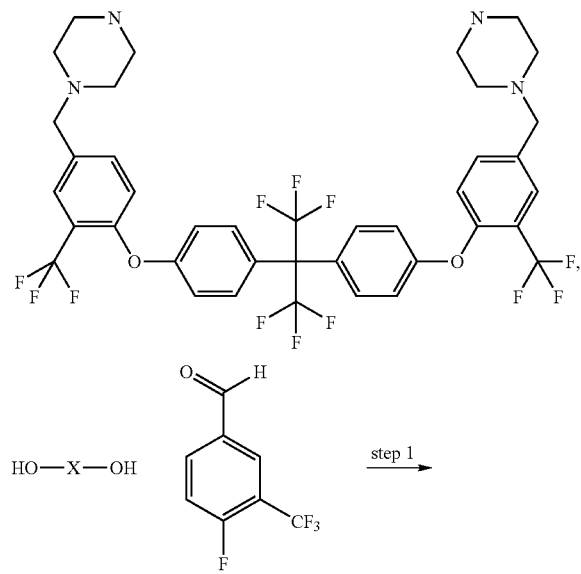

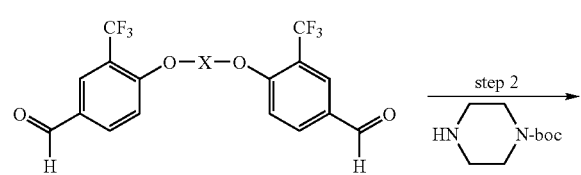

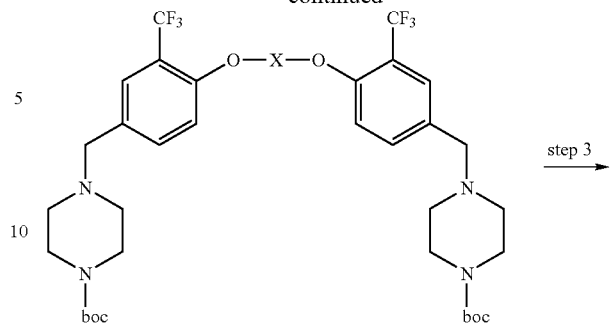

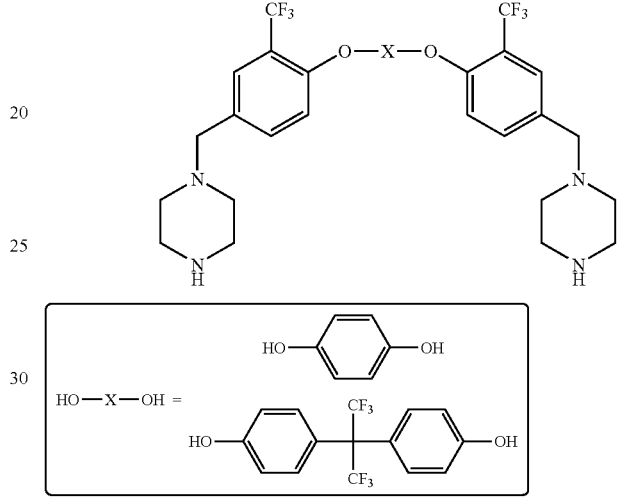

Step 1: 1.1071 g of bis-(4,4-dihydroxyphenyl)-bis-(trifluoromethyl)-methane in 4.0 ml of DMF were sequentially added 1.36 g of $K_2CO_3$, and 1.2777 g of 4-fluoro3-trifluoromethylbenzaldehyde. The reaction mixture was heated to 130° C. and stirred for 6 hours. The reaction was quenched with water and extracted with EtOAc twice. The organic phase was washed with water, brine and dried with sodium sulfate before was concentrated under reduced pressure. The product was purified by column chromatography with a yield of 400.0 mg.

Step 2: 71.4 mg of dialdehyde formed in step 1 in 3.0 ml of dichloroethane was sequentially added 241.8 mg of piperazine-1-carboxylic acid tert-butyl ester, and 257.8 mg of NaBH(OAc)$_3$. The reaction mixture was stirred at room temperature overnight. LCMS analysis indicated the starting material was consumed. The reaction mixture was concentrated and the residue was quenched with $Na_2CO_3$ solution and extracted with EtOAc twice. The organic phase was washed with water, brine and dried with sodium sulfate before being concentrated under reduced pressure. The product was purified by column chromatography with a yield of 113.7 mg (91%).

Step 3: 73.0 mg of Boc-protected diamine formed in step 2 in 2.0 ml of DCM was added 2.0 ml of TFA and the reaction mixture was stirred at room temperature for 45 minutes. LCMS analysis indicated the starting material was consumed. The reaction mixture was concentrated and the residue was washed with ether twice. The white powder in 2 ml of ether was further sonicated for 10 minutes. The white solid was then washed with ether twice and was under high vacuum for 12 hours. The yield was 70.3 mg.

Example 4

Synthesis of Compounds 145 and 146

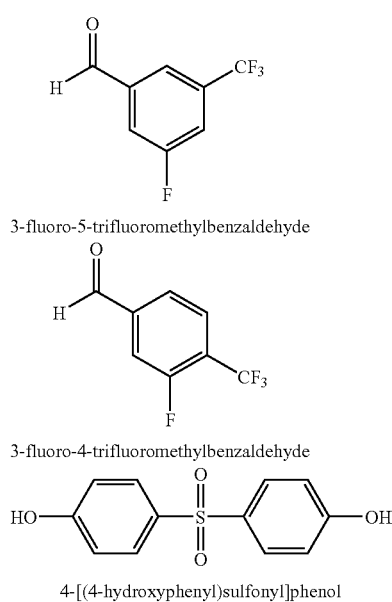

Compound 145 was synthesized using a similar procedure for compound 147. The starting materials for step 1 are 4-[(4-hydroxyphenyl)sulfonyl]phenol and 3-fluoro-4-trifluoromethylbenzaldehyde.

Compound 146 was synthesized using a similar procedure for compound 147. The starting materials for step 1 are 4-[(4-hydroxyphenyl)sulfonyl]phenol and 3-fluoro-5-trifluoromethylbenzaldehyde.

Example 5

Synthesis of Compound 143

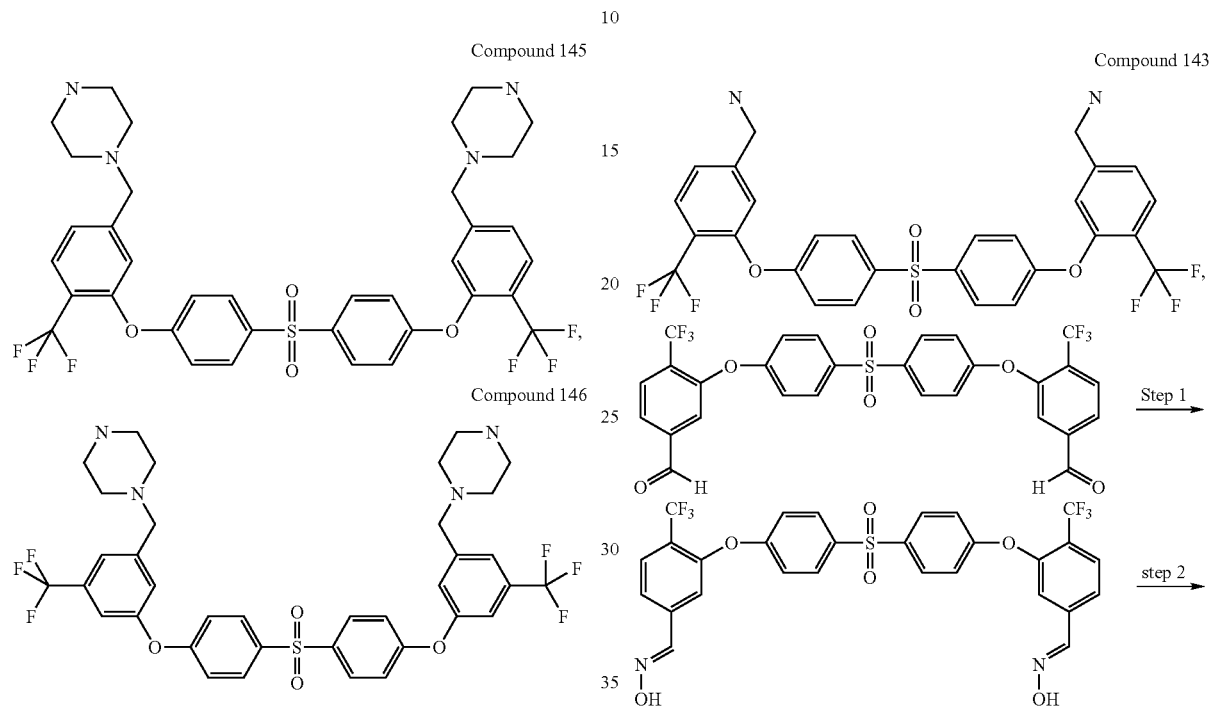

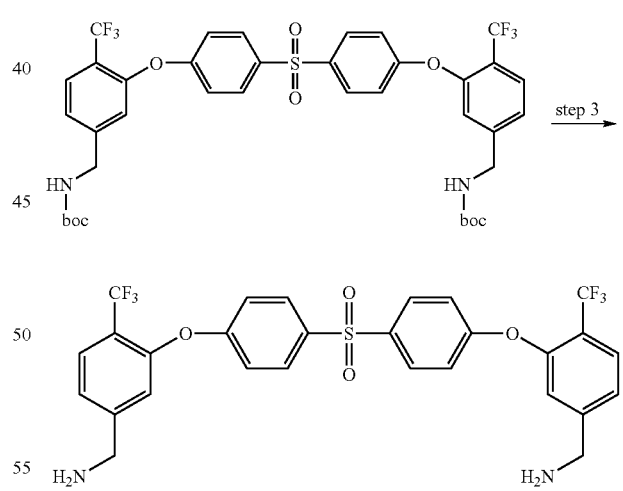

Step 1: The starting material was made using the same procedure as step 1 of the synthesis of compound 145. 60.6 mg of dialdehyde formed in coupling reaction in 2.0 ml of EtOH was sequentially added 220.3 mg of $NH_2OH \cdot HCl$, 0.5 ml of water, and 0.1 ml of pyridine. The reaction mixture was irradiated under microwave at 120° C. for 30 minutes. LCMS analysis indicated the starting material was consumed. The reaction mixture was concentrated and the residue was quenched with 2 ml of water. The crude product was filtered and used for the next step without further purification.

Step 2: The crude product formed in step 1 above was dissolved in 4 ml of HOAc. Zn dust (321.3 mg) was added in two portions. The resulting mixture was heated at 60° C. for 6 hours. The reaction mixture was filtered and concentrated. The residue was charged with 5 ml of tetrahydrofuran (THF), 0.3 ml of triethylamine (TEA) and 100.6 mg of Boc anhydride. The reaction mixture was stirred at room temperature for 4 hours and was quenched with Na₂CO₃ solution and extracted with EtOAc twice. The organic phase was washed with water, brine and dried with sodium sulfate before being concentrated under reduced pressure. The product was purified by column chromatography with a yield of 67.8 mg (82%, two steps).

Step 3: 42.1 mg of Boc-protected diamine formed in step 2 in 2.0 ml of DCM was added 2.0 ml of TFA and the reaction mixture was stirred at room temperature for 45 minutes. LCMS analysis indicated the starting material was consumed. The reaction mixture was concentrated and the residue was washed with ether twice. The white powder in 2 ml of ether was further sonicated for 10 minutes. The white solid was then washed with ether twice and was under high vacuum for 12 hours. The yield was 30.2 mg.

Example 6

Synthesis of Compounds 101, 102, 107, 113, 114, 121, 123, and 124

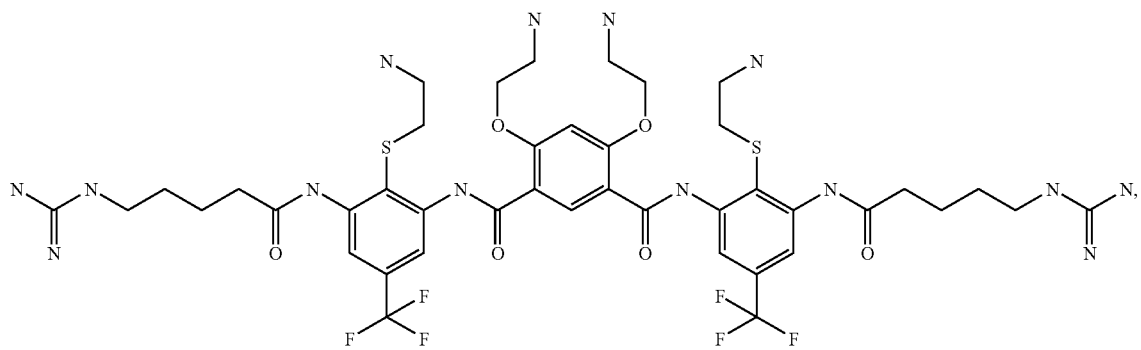

Compound 102

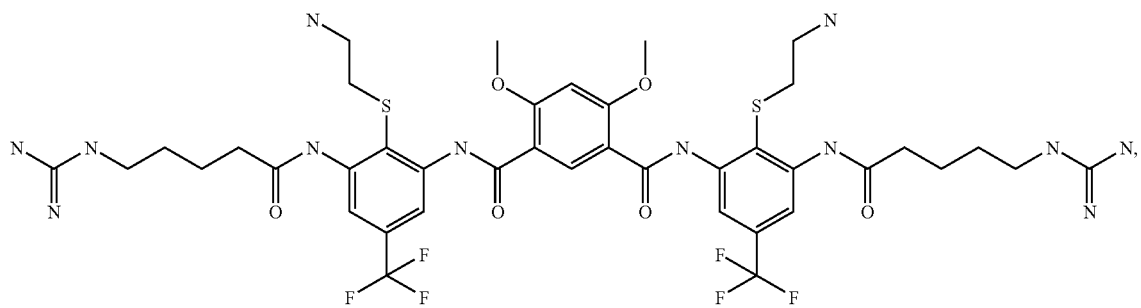

Compound 101

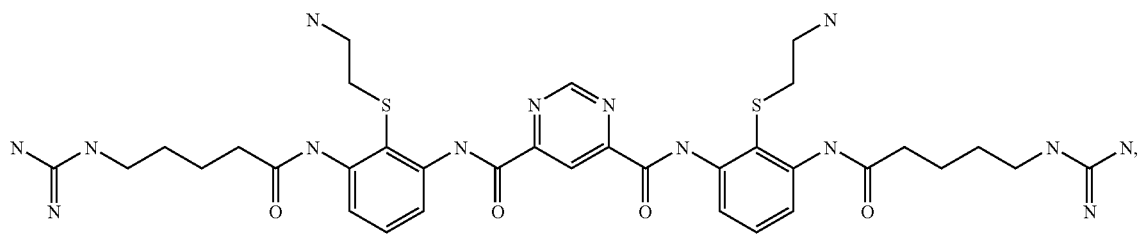

Compound 113

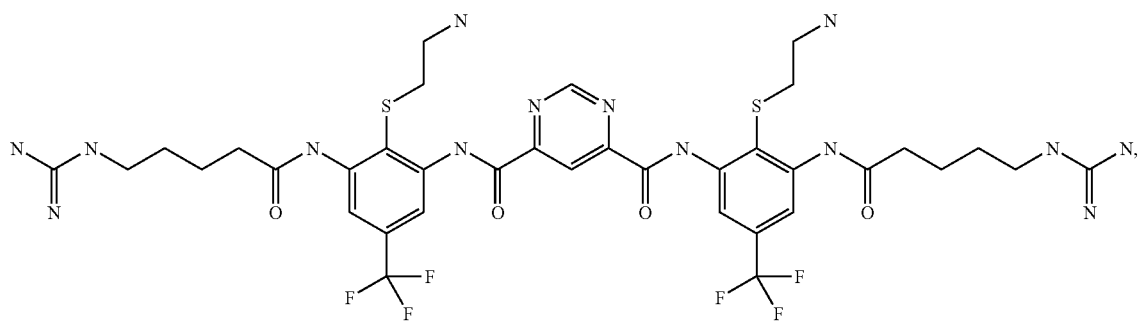

Compound 121

Compound 114
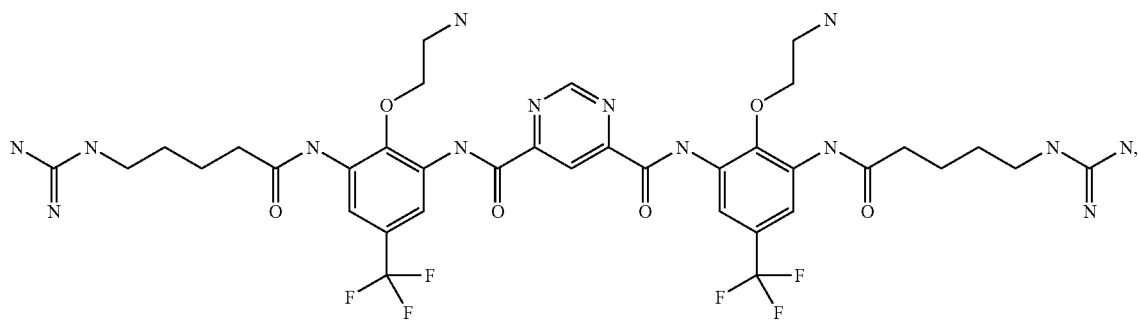
Compound 107
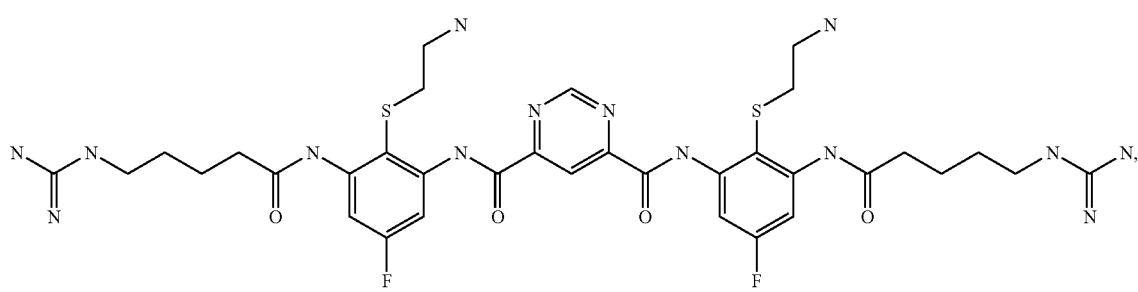
Compound 123
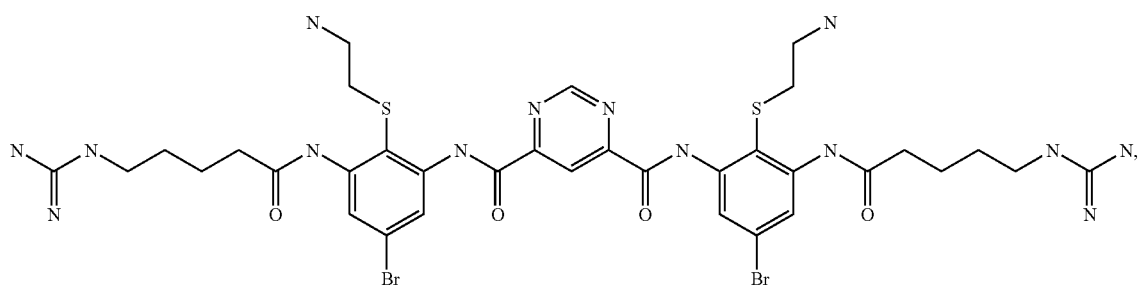
Compound 124
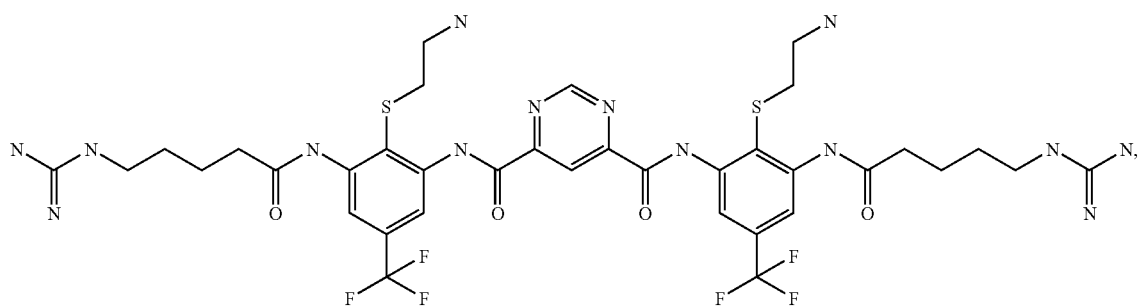
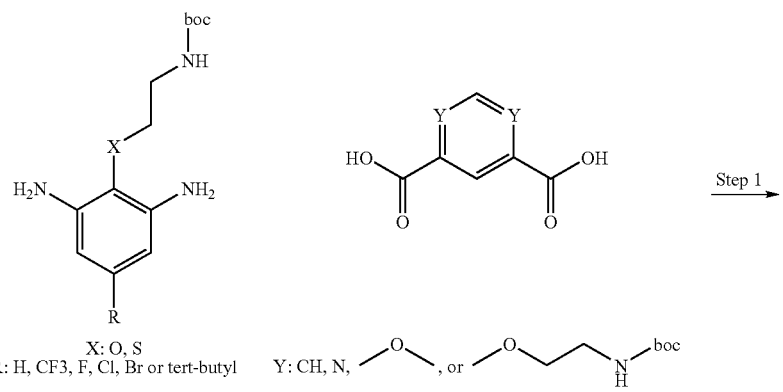
X: O, S
R: H, CF3, F, Cl, Br or tert-butyl    Y: CH, N,  
Step 1

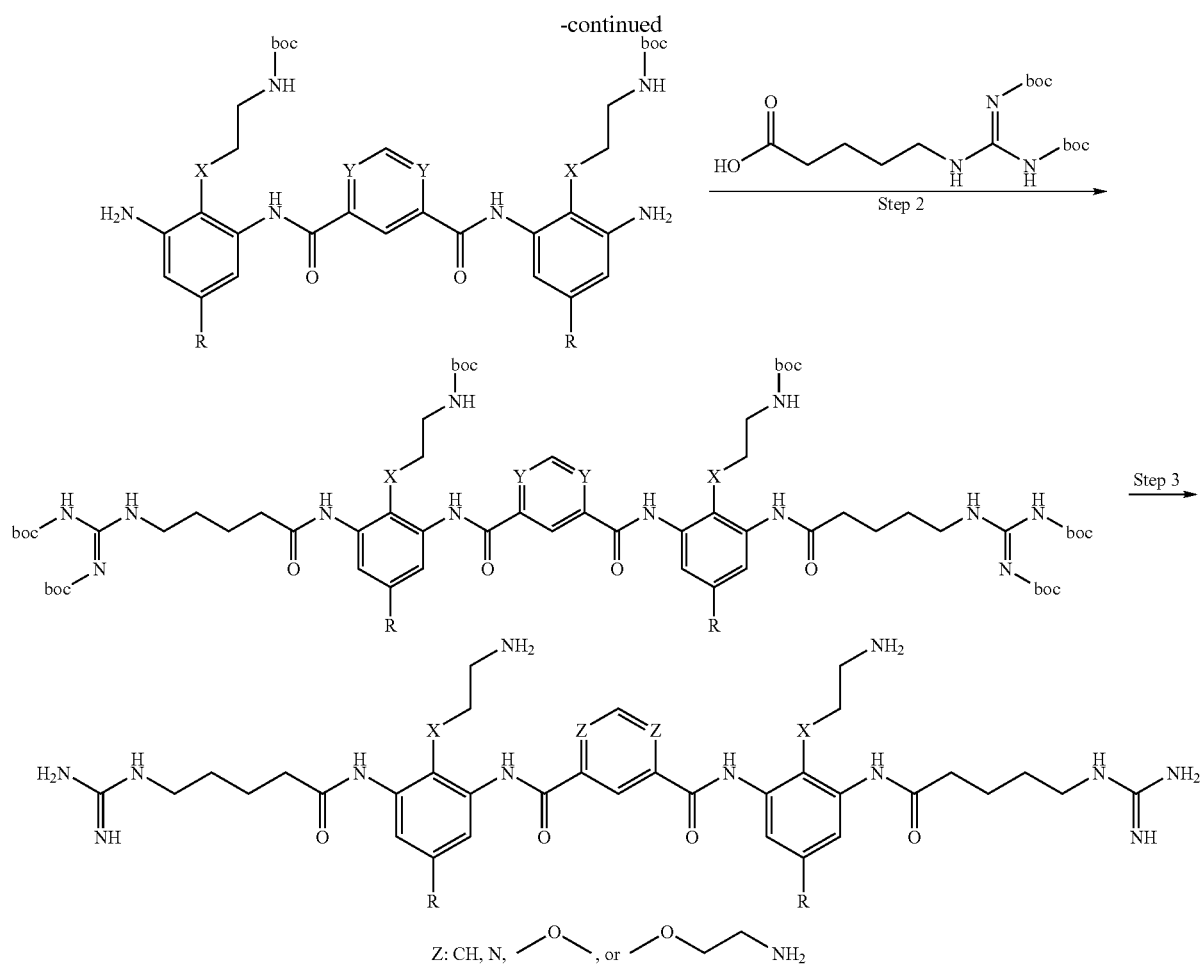

Step 1: Dianiline (0.15 mol) and diacid (0.062 mol) were combined with pyridine (121 mL) and a stir bar in a nitrogen purged 2 L RBF and stirred to a suspension with small pieces for 15 minutes. Then EDCI (0.185 mol) was added and the mixture was stirred at ambient temperature for 7.5 hours. The reaction was quenched with water (810 mL). The product was purified by column chromatography or trituration using heptane and ethyl acetate.

Step 2: Product from step 1 (0.179 mol) and ({[(tert-butoxycarbonyl)amino][(tert-butoxycarbonyl)imino]methyl}amino)pentanoic acid (0.734 mol) were dissolved in 2.1 L dry pyridine. The solution was cooled to −20° C. to 0° C. To the solution, POCl$_3$ (0.716 mol) was slowly added over 30 minutes. The reaction mixture was stirred for 2 hours at −20° C. to 0° C. and then it was allowed to warm to room temperature and stirred for another 2 hours. Ice water (8 L) was added to quench the reaction. The precipitated solid was collected and purified by either column chromatography or trituration.

Step 3: Product from step 3 (98.4 mmol) was dissolved in 465 mL of formic acid. The solution was added 246 mL of 4M HCl in dioxane and stirred at room temperature for 10 hours. To this reaction mixture was added 1-butanol (2.5 L). The resulting precipitate was collected by filtration and purified by reverse phase column chromatography.

Example 7

Synthesis of Compounds 122 and 126-129

Compound 122

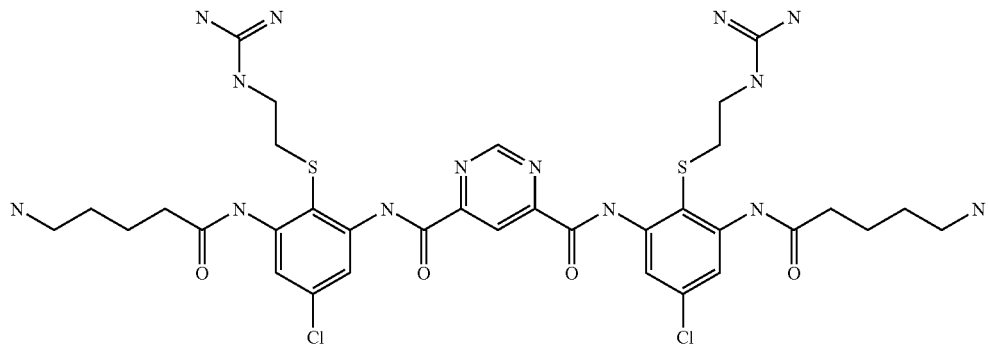

-continued
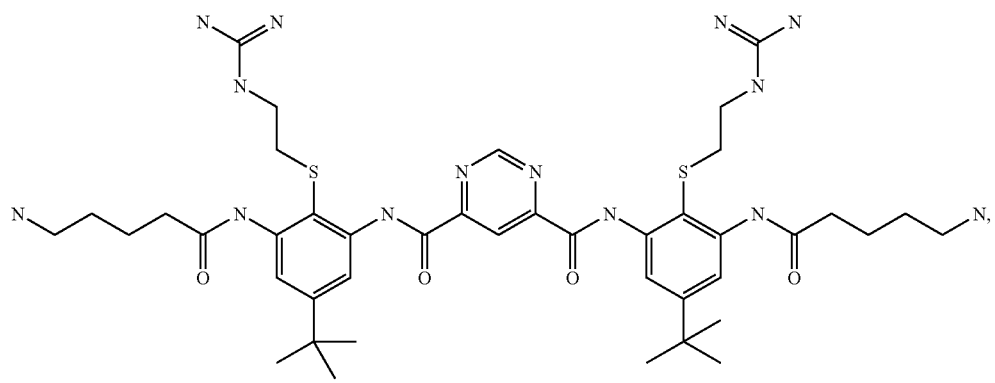
Compound 129
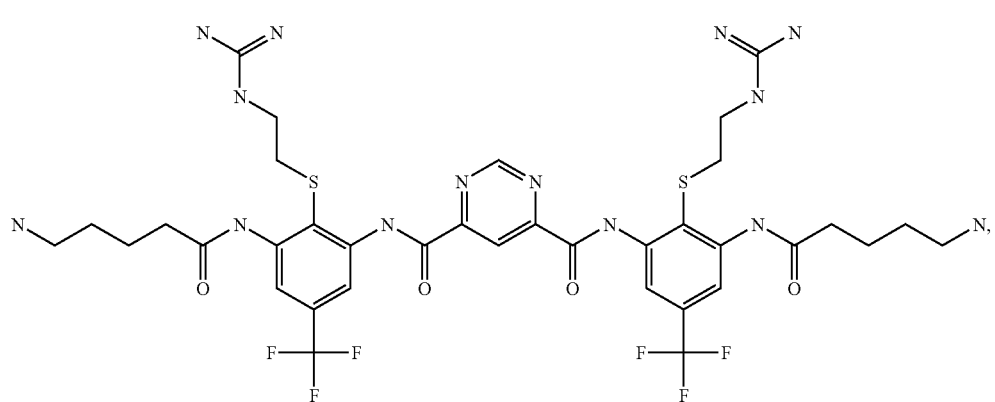
Compound 128
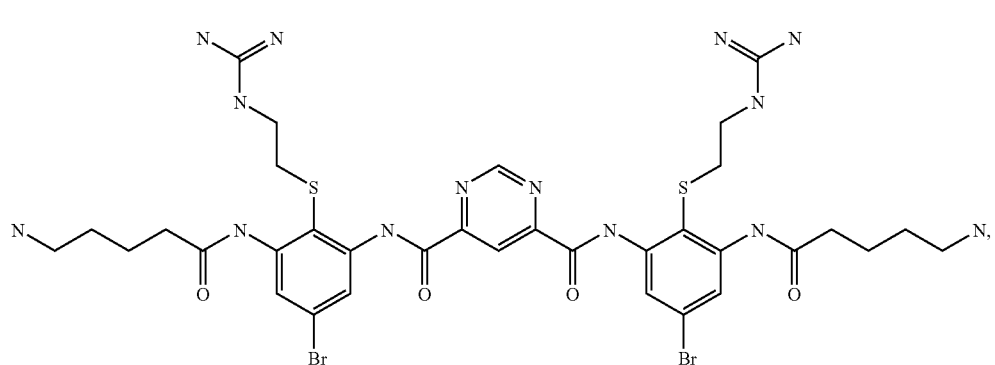
Compound 127
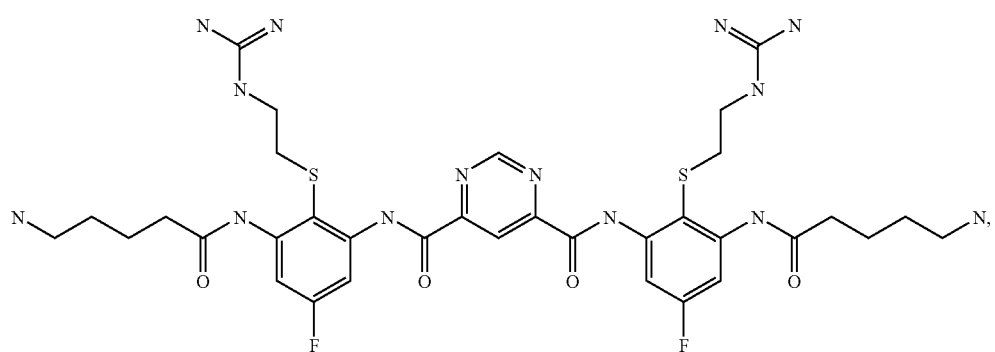
Compound 126

145
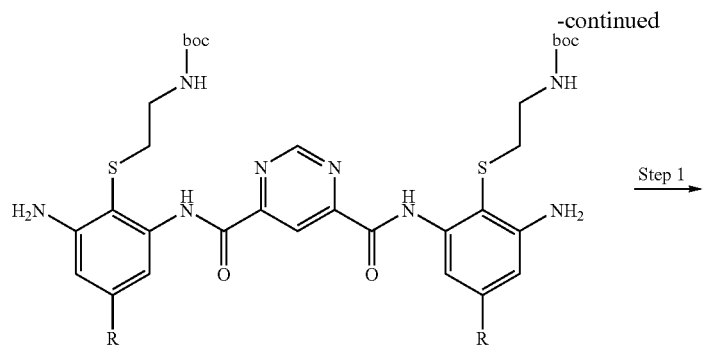
R: CF3, F, Cl, Br or tert-butyl
146
-continued
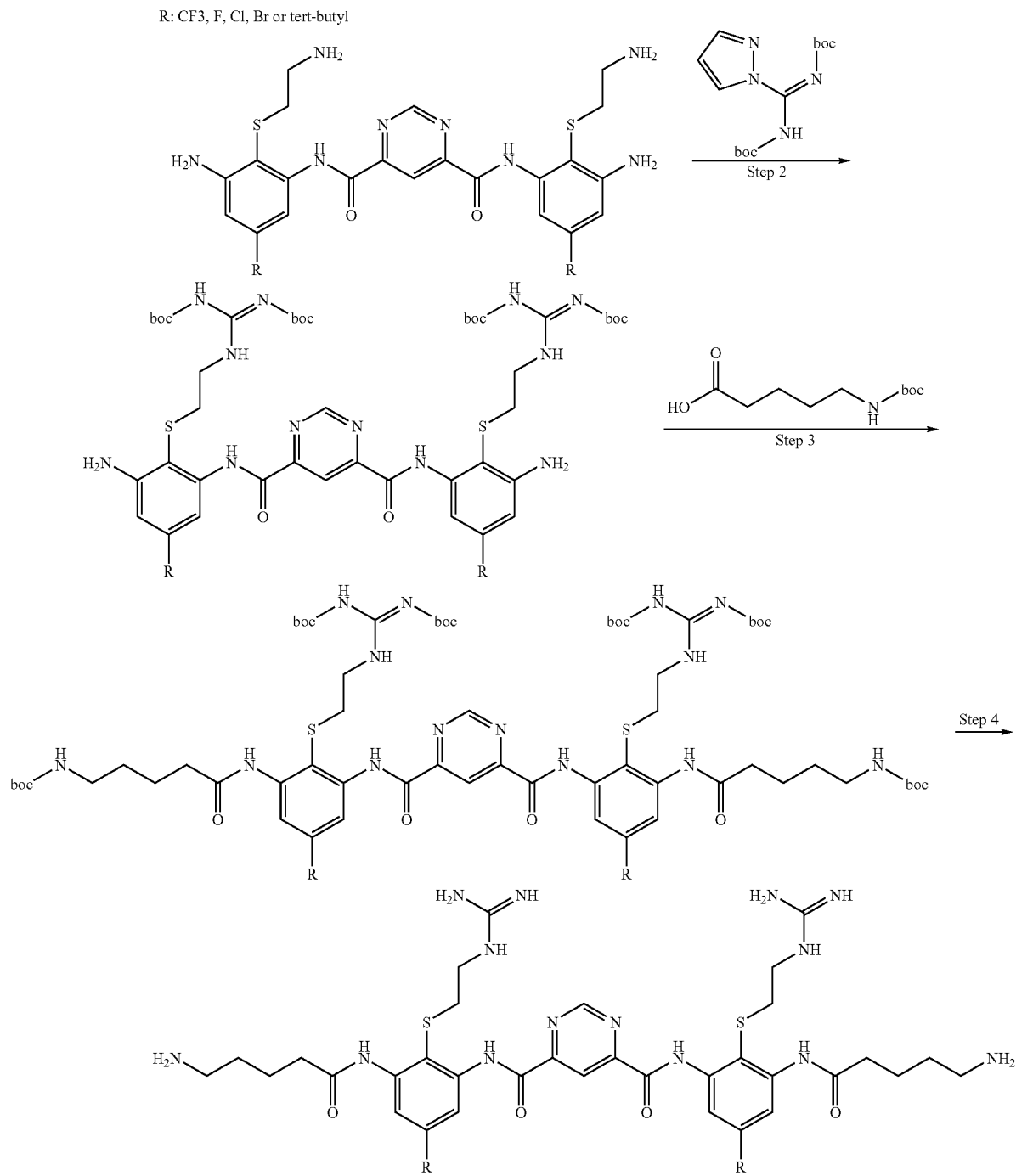

Step 1: The starting diamine is made using similar method as step 1 of common synthesis 2. Diamine was treated with 50% Trifluoroacetic acid in dichloromethane for 2 hours. The resulting solution was concentrated to an oil and triturated with cold diethyl ether. The solid was collected by filtration.

Step 2: Product from step 1 (1 mmol) and N,N'-bis-Boc-1-guanylpyrazole (2 mmol) were dissolved in 10 mL of methanol followed by 2 equivalence of mL of disopropylethylamine. The mixture was stirred overnight at room temperature before the solvent was removed by rotovap. The product was purified by column chromatography.

Step 3: This step was carried out similar as step 2 of common synthesis 2 using product from step 2 and N-tert-butoxycarbonylamino-pentanoic acid.

Step 4: This step is the same as step 3 in common synthesis 2.

Example 8

Synthesis of Compound 108

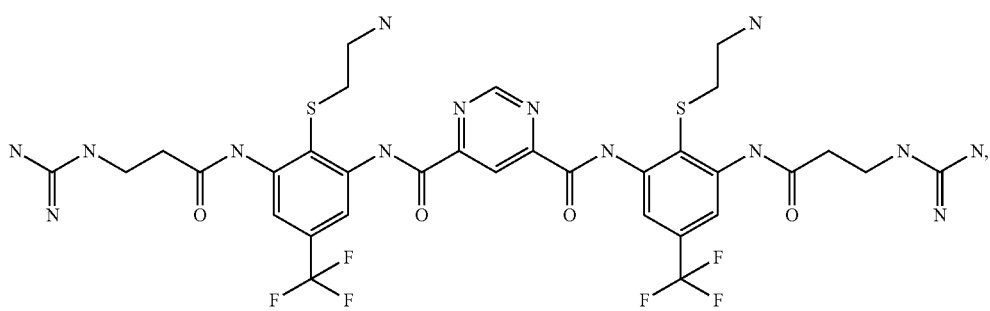

Compound 108

The synthesis is similar as common synthesis 2 except in step 3, ({[(tert-butoxycarbonyl)amino][(tert-butoxycarbonyl)imino]methyl}amino)propanoic acid was used.

Example 9

Synthesis of Compound 125

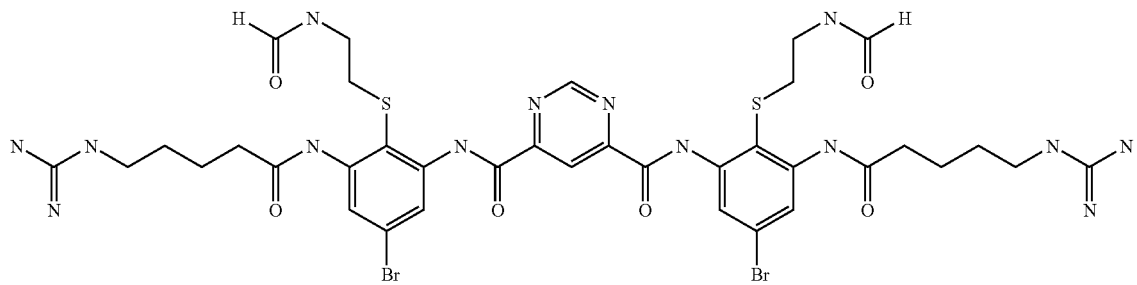

Compound 125

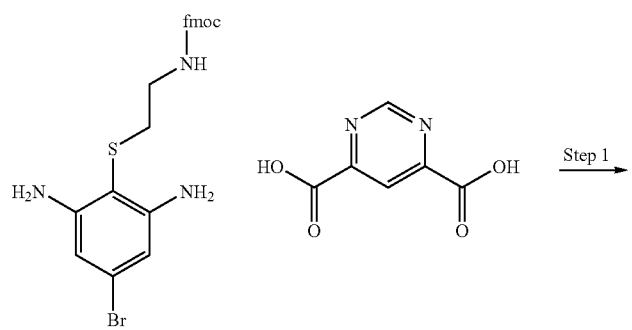

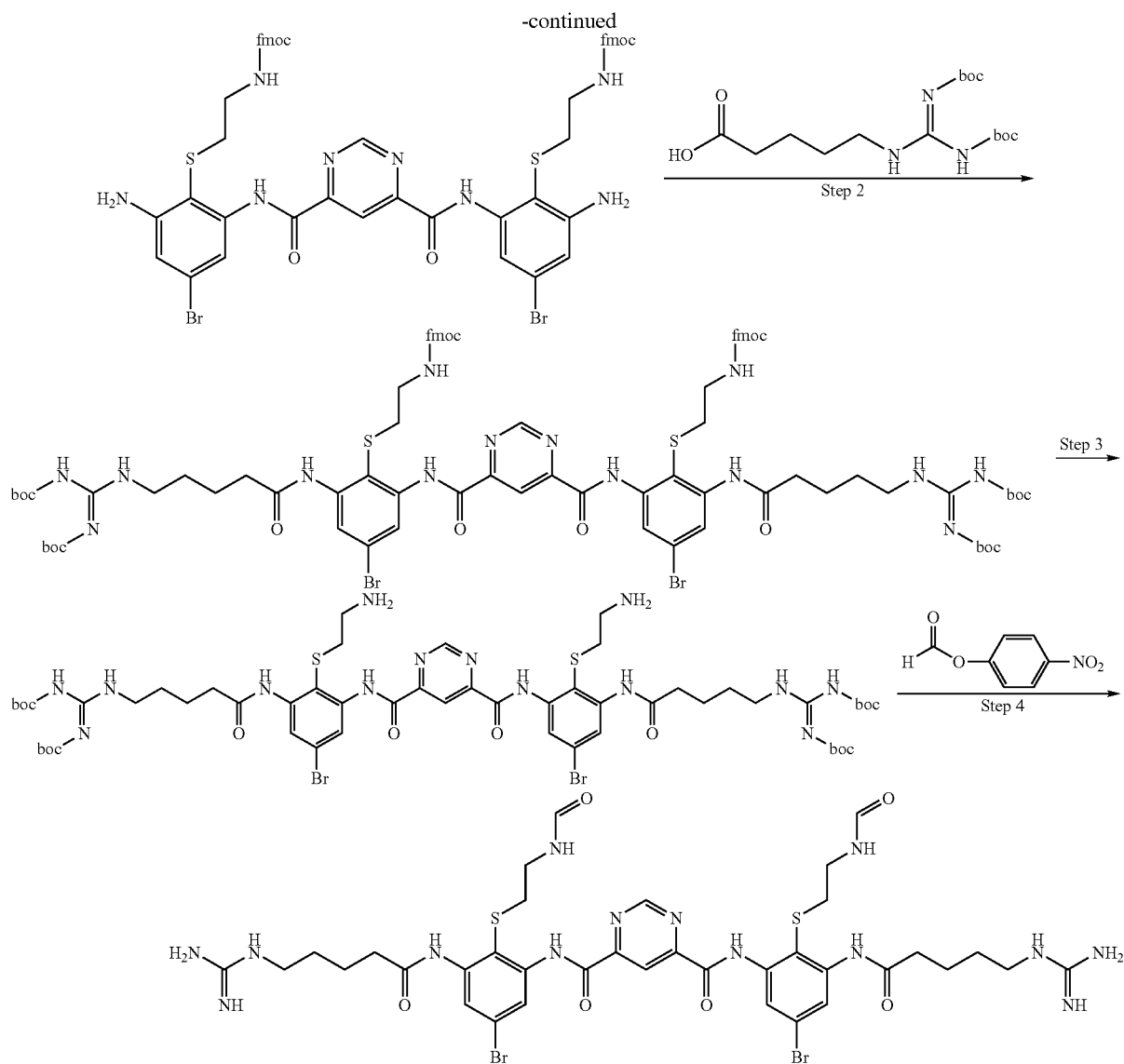

Step 1 and 2 are similar to step 1 and 2 of the synthesis of compound 101.

Step 3: Product from step 2 was treated with 20% piperidine in DMF. After diluted with ethyl acetate and washed with 10% citric acid and brine, the organic phase was concentrated and triturated with hexane.

Step 4: Product from step 3 (0.03 mmol) was mixed with 4-nitrophenyl formate (2 equiv.) in 3 mL of DMF, followed by the addition of DIEA (4 equiv.). The reaction mixture was stirred for 4 hours before was diluted with ethyl acetate. The organic layer was washed with saturated $K_2CO_3$, 10% citric acid and water before it was concentrated to a solid. The solid was treated with 50% TFA in DCM and purified by reverse phase column chromatography.

Example 10

Synthesis of Compound 152

Compound 152

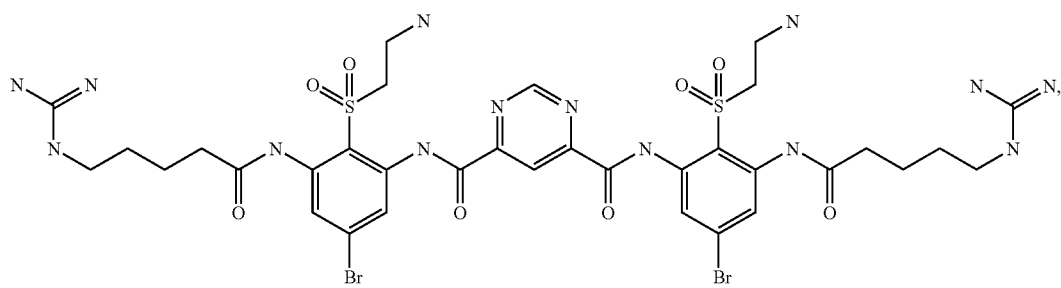

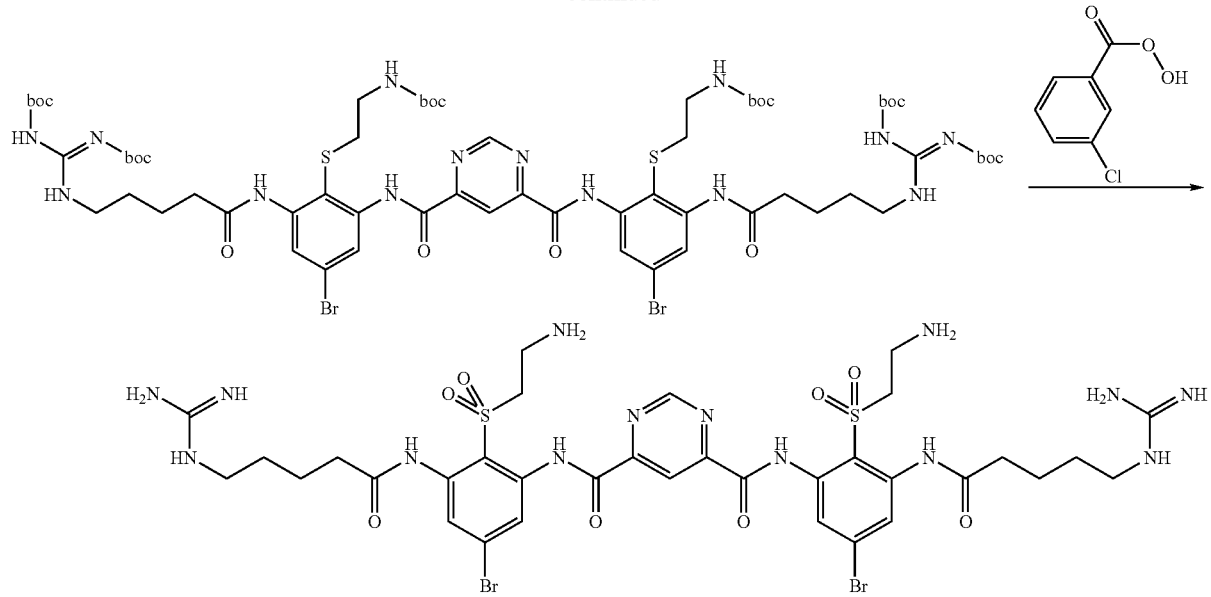

The starting material was made from step 1 to 2 in the synthesis of compound 123. The starting Boc-protected amide (0.023 mmol) and 3-chloroperoxybenzoic acid (MCPBA, 42.3 mg) were dissolved in DCM (0.8 mL) and stirred under Ar for 1 hour. The reaction mixture was diluted with DCM and washed with saturated $Na_2S_2O_3$, saturated $NaHCO_3$ and water. The organic layer was dried and concentrated to a solid. The solid was treated with 50% TFA in DCM. The final product was purified by reverse phase column chromatography.

Example 11

Synthesis of Compound 153

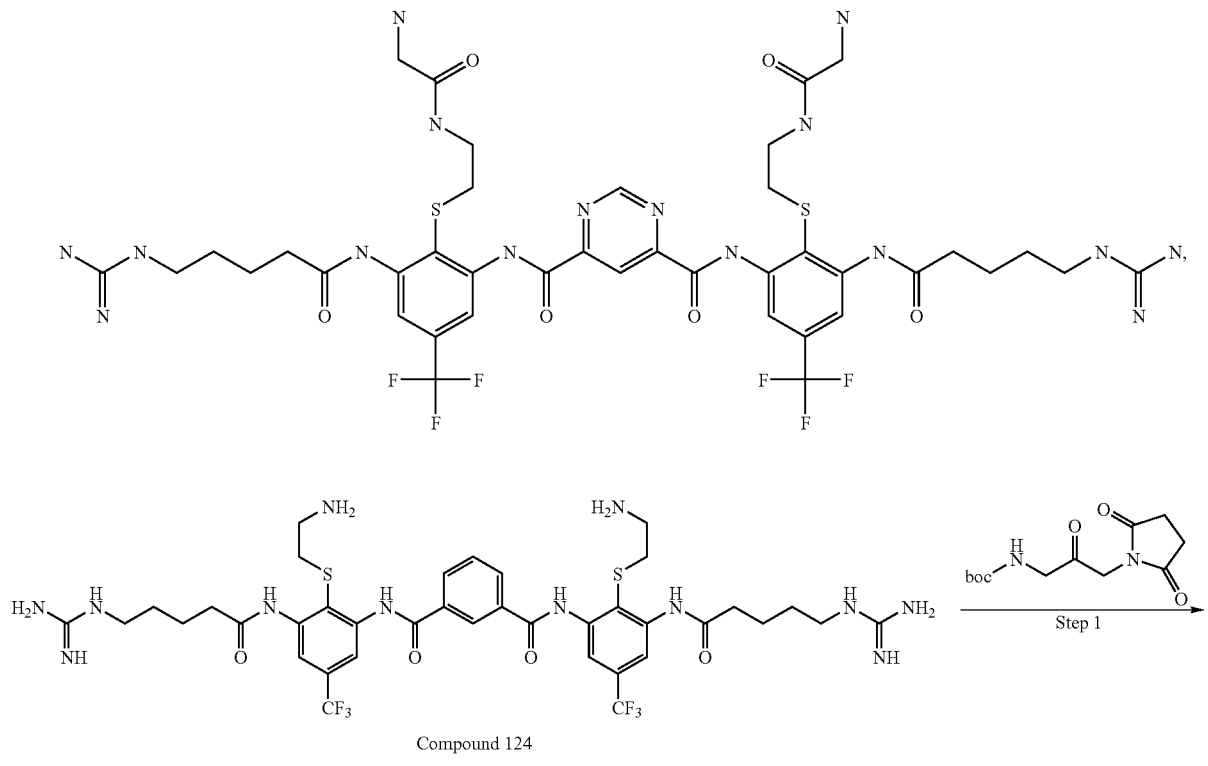

-continued

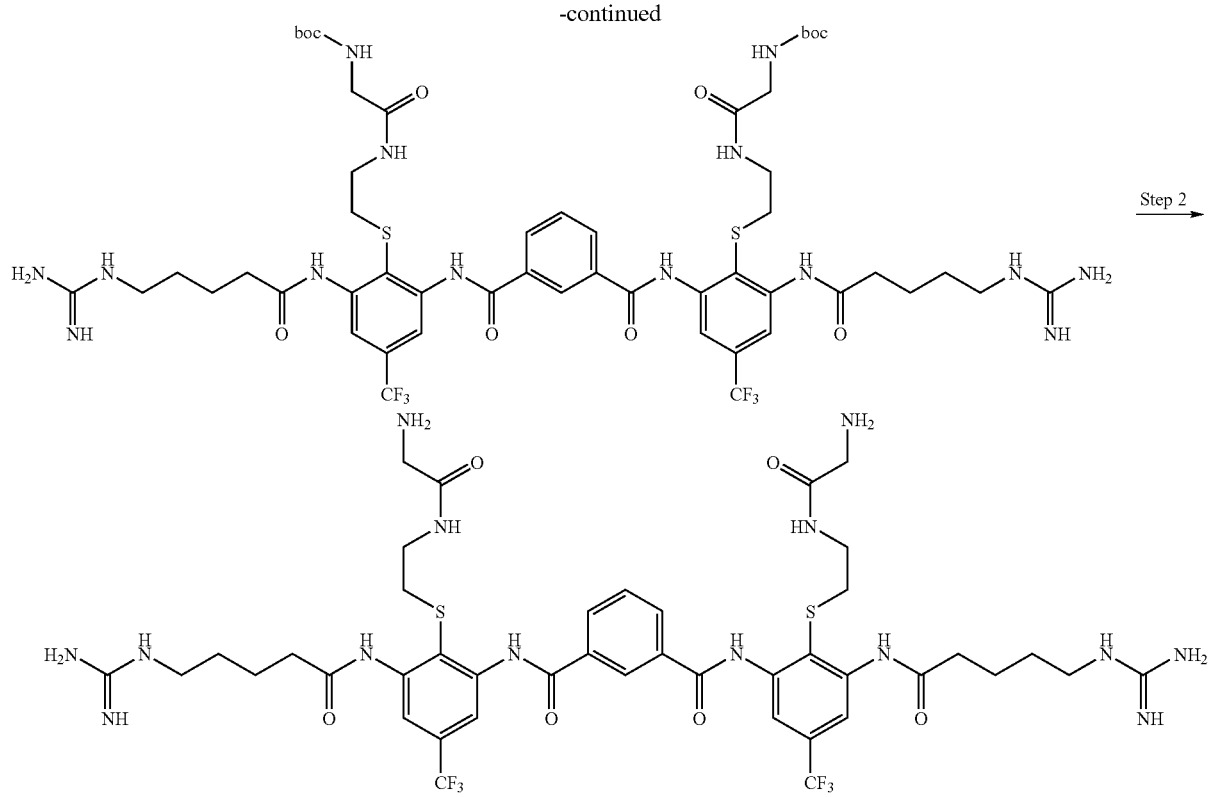

Step 1: Compound 124 (0.29 mmol) was dissolved in 10 mL of water and then was added N-methyl morpholine (NMM, 2.7 equiv.) and 5 mL of DMF. N-Boc-Gly-Osu (2.2 mmol) in 5 mL DMF was added to the solution dropwise. The reaction mixture was stirred at room temperature for 20 minutes before it was concentrated to a solid.

Step 2: The product from step 1 was treated with 4 N HCl in dioxane and purified with reverse phase column chromatography.

Example 12

Synthesis of Compounds 103-105 and 150

Compound 104

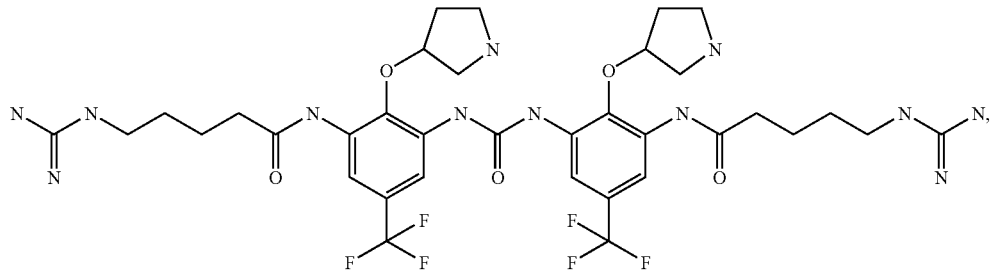

Compound 105

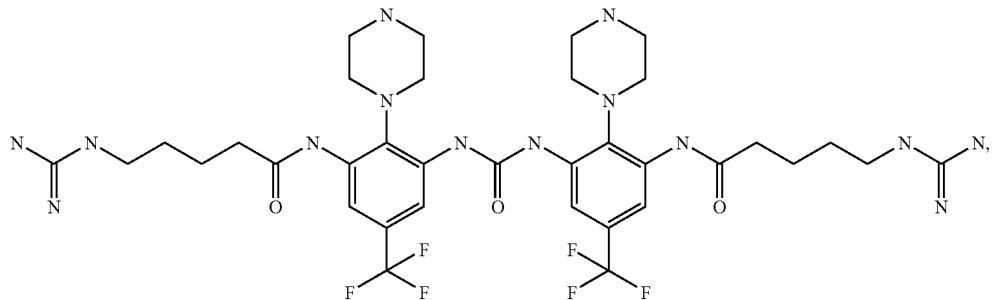

Compound 103
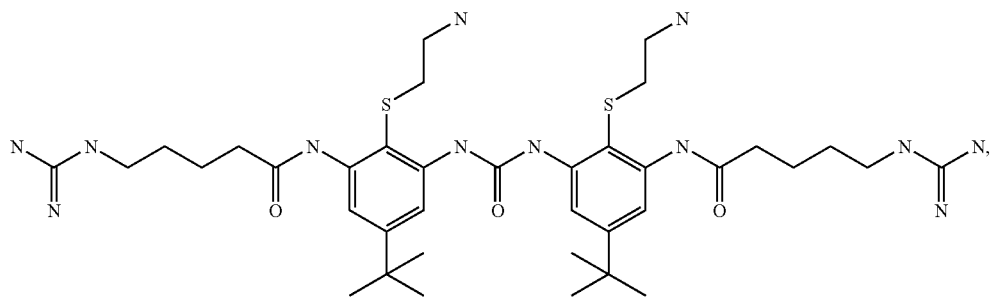
Compound 150
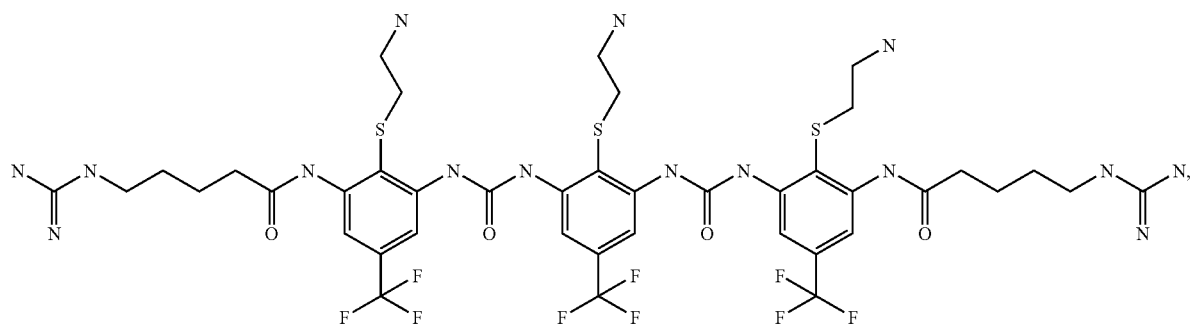
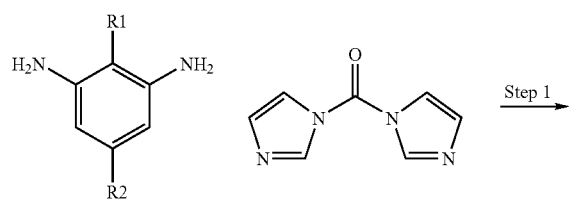 Step 1
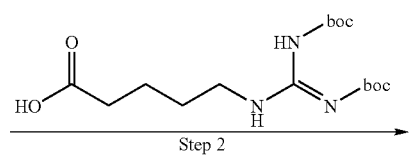 Step 2
n = 1, 2
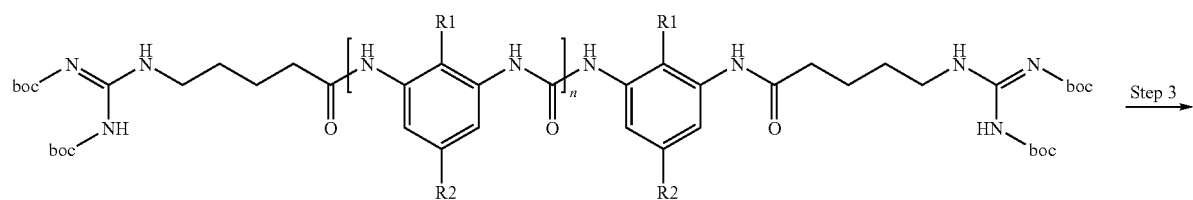 Step 3
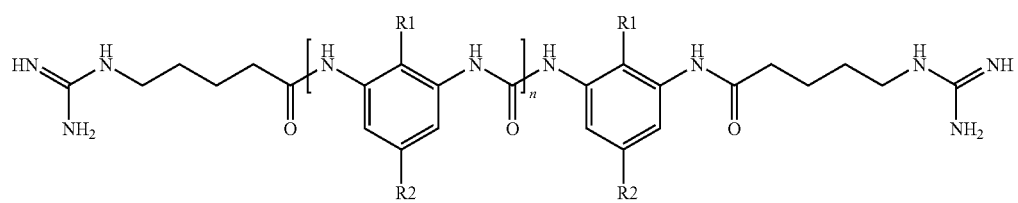

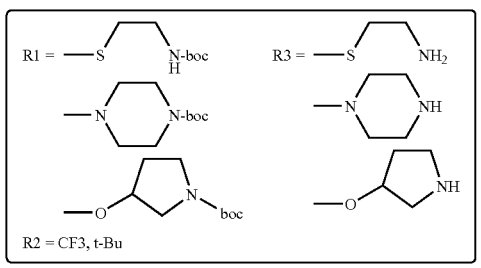

Step 1: Bisaniline and carbonyl diimidazole (CDI) were mixed in dry DMSO (with molar ratio bisaniline:CDI=4:1). The reaction mixture was stirred at 100° C. for 24 hours. After it cooled down, water was added to reaction mixture. The precipitate was filtered and dried under vacuum. The crude product was purified with silica gel column with dichloromethane and ethyl acetate as eluents.

Steps 2 and 3 are similar to steps 2 and 3 of the synthetic procedure for compound 101.

Example 13

Synthesis of Compound 151

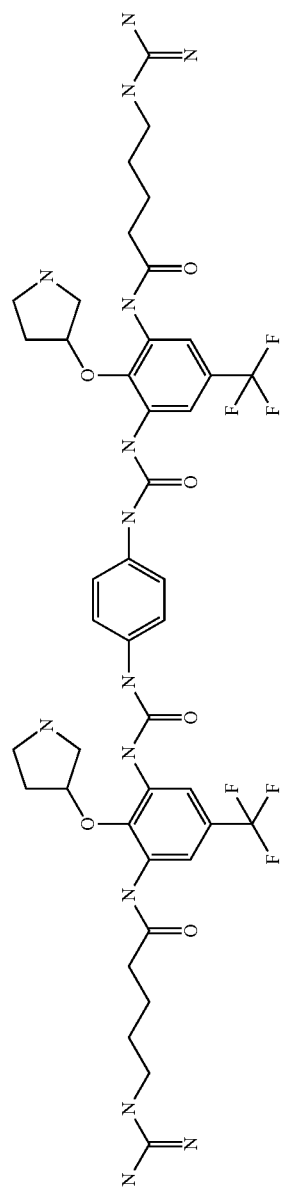
Compound 151
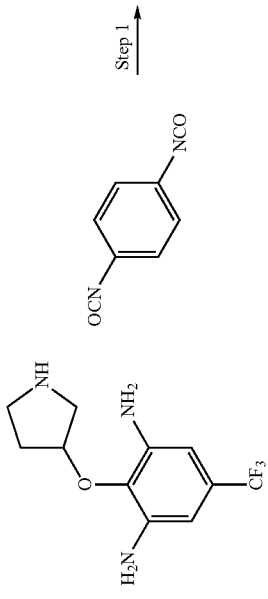
Step 1
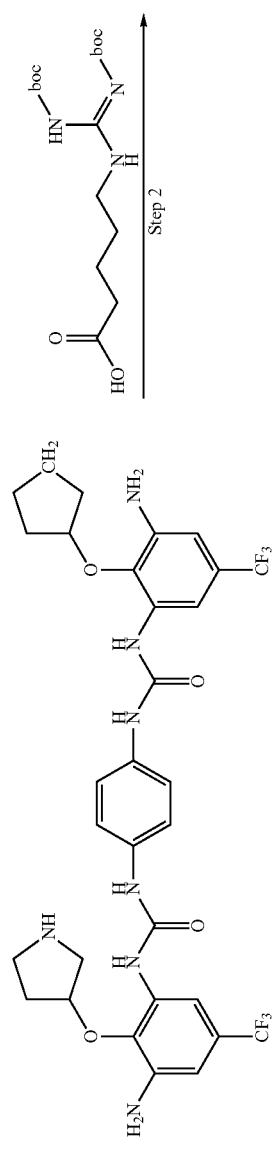
Step 2

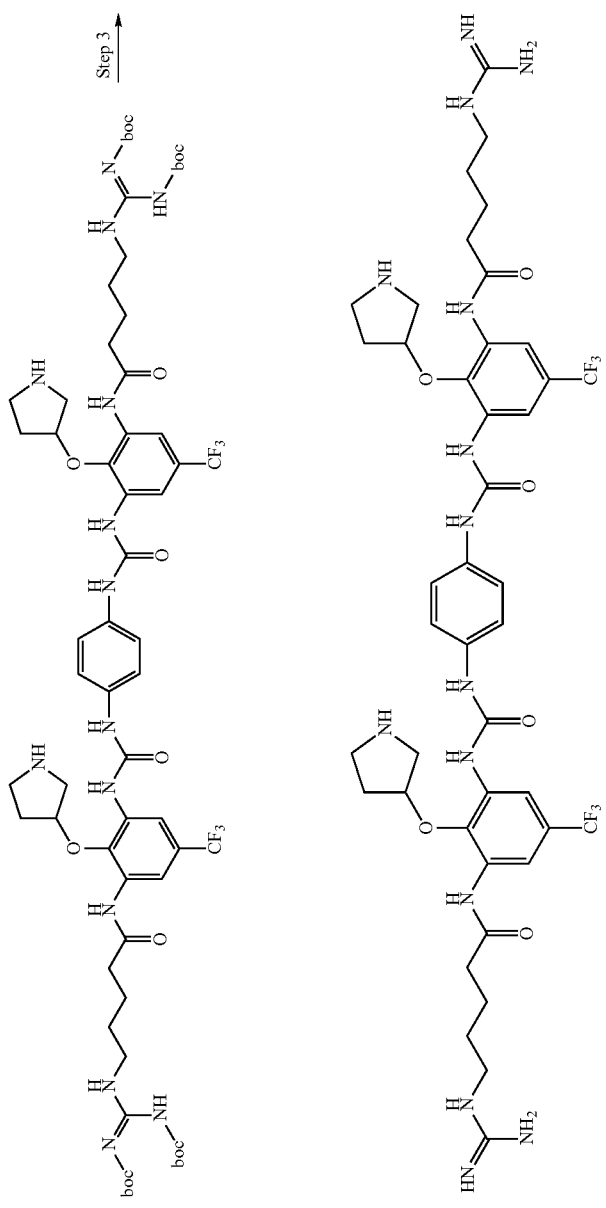

Step 1: Bisaniline (4 equiv.) and 1,4-benzenediisocyanate (1 equiv.) were mixed in dry DMSO. The reaction mixture was stirred at 100° C. for 24 hours. After it cooled down, water was added to the reaction mixture. The precipitate was filtered and dried under vacuum. The crude product was purified with silica gel column with dichloromethane and ethyl acetate as eluents.

Steps 2 and 3 are similar to steps 2 and 3 of the synthetic procedure for compound 101.

Example 14

Synthesis of Compound 112

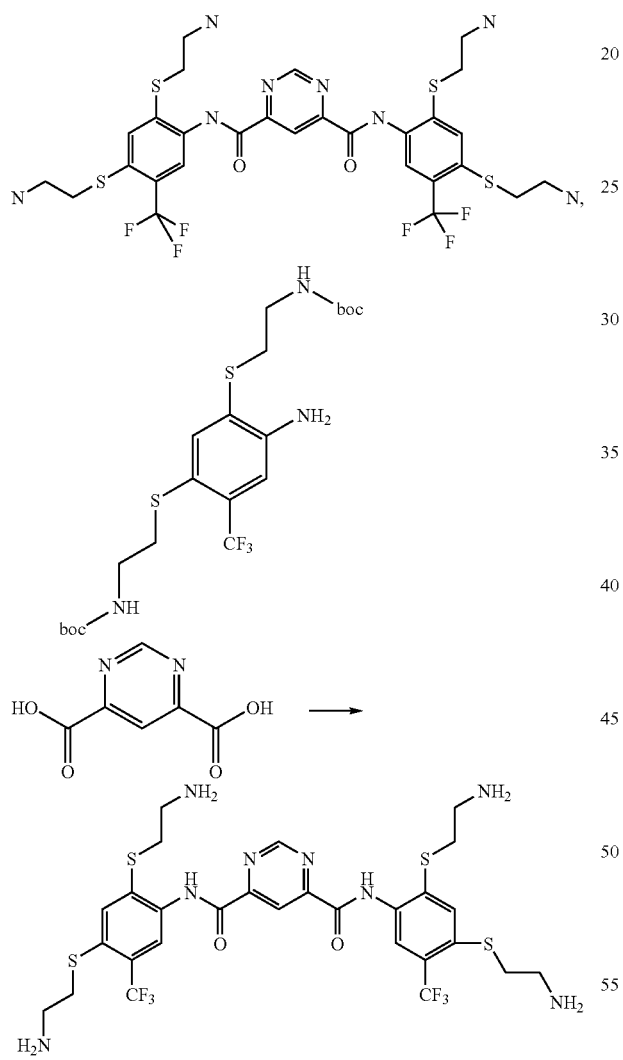

2-Chloro-4,6-dimethoxy-1,3,5-triazine was stirred in anhydrous THF. N-Methylmorpholine was added. The resulting mixture was stirred at room temperature for 30 minutes. Then aniline and pyrimidine-4,6-dicarboxylic acid were added. The mixture was stirred at room temperature for 24 hours. Then the solvent was evaporated completely in vacuum. Water was added and the mixture was stirred for 4 hours. The solid precipitate was collected and purified by silica gel column with dichloromethane and ethyl acetate as eluents. The Boc-protected compound was deprotected using 4N HCl dioxane solution overnight at room temperature to generate the final product.

Example 15

Synthesis of Compounds 116 and 133-141

Compound 116 has been synthesized utilizing three synthetic schemes.

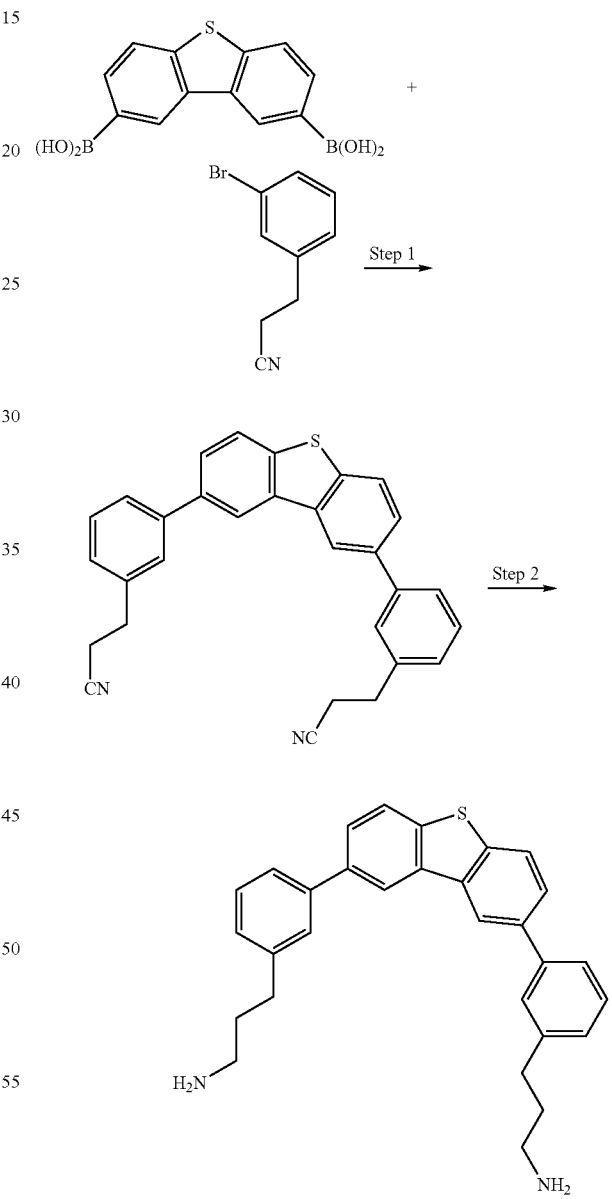

Step 1: 8-(dihydroxyboryl)dibenzo[b,d]thiophen-2-ylboronic acid (4 mmol, 1.08 g) and 3-(3-bromophenyl)propanenitrile (8.8 mmol, 1.875 g) were added into a microwave tube under Argon. Dioxane (10 mL), Pd(PPh$_3$)$_4$ (0.4 mmol, 0.46 g) and K$_2$CO$_3$ (16 mmol, 4 mL, 4M) were added. The mixture was under microwave irradiation (120° C., 15 minutes) with stirring. Then the reaction was cooled down to room temperature and extracted with EtOAc and brine. The organic layer was dried over NaSO₄ and evaporated under vacuum. The residue was purified with silica column (eluent: EtOAc/hexanes=1/2, v/v). A yellow solid (1.18 g, 70%) was obtained as product. ¹HNMR was acceptable.

Step 2: 2,8-di(3-phenylpropanenitrile)benzothiophene (1.33 mmol, 0.59 g) and platinum oxide hydrate (80 mg) were added into a mixture of MeOH (10 mL)/EtOAC (40 mL). HCl (2 mol, 0.5 mL, 4M in dioxane) was added. Hydrogen at 60 psi was introduced after removal of air. The mixture was shacked over night. Then the hydrogen was removed. The mixture was filtered through celite pad. The filtrate was evaporated under vacuum. The residue was purified by reverse phase HPLC. A white solid (70 mg, 12%) was obtained as product. LC-MS and ¹HNMR were acceptable.

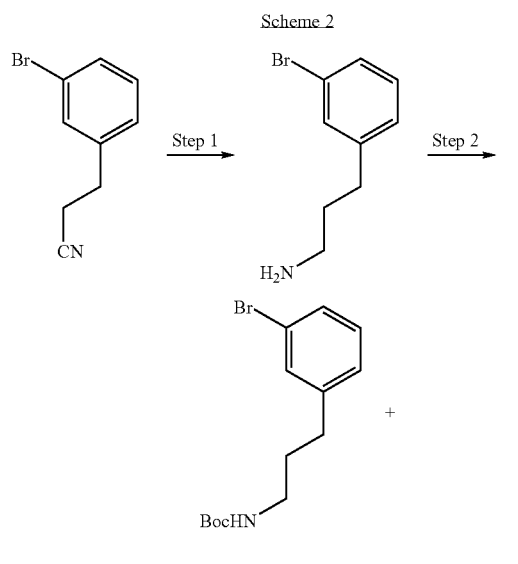

Scheme 2

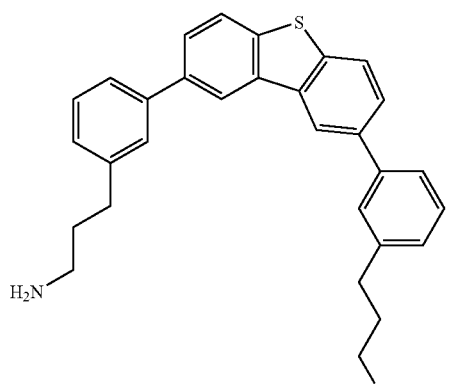

116

Step 1, 2 and 3: Synthesis of 2,8-di(tert-butyl 3-phenylpropylcarbamate) benzothiophene. The tert-butyl 3-(3-bromophenyl)propylcarbamate intermediate was synthesized from 3-(3-bromophenyl)propanenitrile by BH₃ reduction and Boc protection. tert-Butyl 3-(3-bromophenyl)propylcarbamate (2.2 mmol, 0.69 g), 8-(dihydroxyboryl)dibenzo[b,d]thiophen-2-ylboronic acid (1 mmol, 0.272 g) were added into a microwave tube under Argon. Dioxane (4 mL), Pd(PPh₃)₄ (0.1 mmol, 0.115 g) and K₂CO₃ (2 mmol, 2 mL, 4M) were added. The mixture was under microwave irradiation (120° C., 15 minutes) with stirring. Then the reaction was cooled down to room temperature and extracted with EtOAc and brine. The organic layer was dried over NaSO₄ and evaporated under vacuum. The residue was purified with silica column (eluent: EtOAc/hexanes=1/100-1/2, v/v). A yellow solid (1.0 g, 76.9%) was obtained as product. ¹HNMR was acceptable.

Step 4: The yellow solid from above reaction was stirred in 10 ml HCl in dioxane (4 M) at room temperature overnight. Then the mixture was filtrated and the cake was washed with ether. The solid was purified by reverse phase column. A white solid (0.376 g, 46.6%) was obtained. LC-MS and ¹HNMR were acceptable.

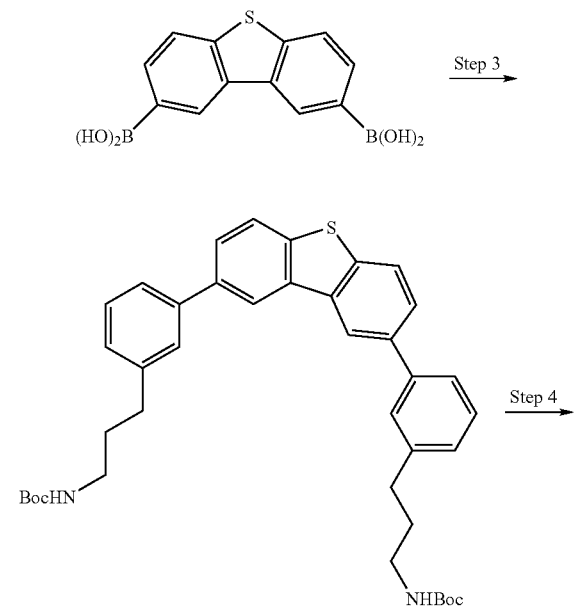

Scheme 3

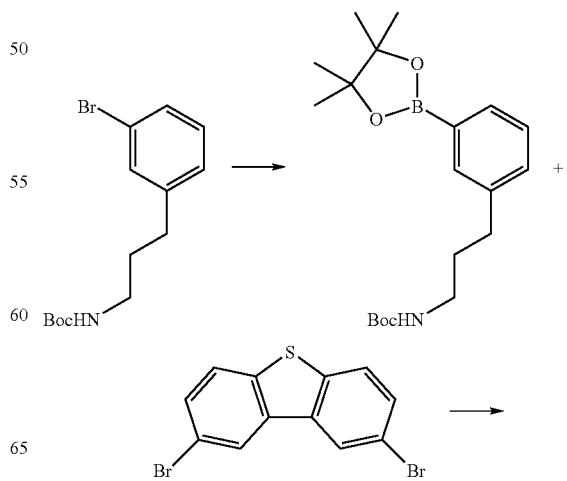

167

-continued

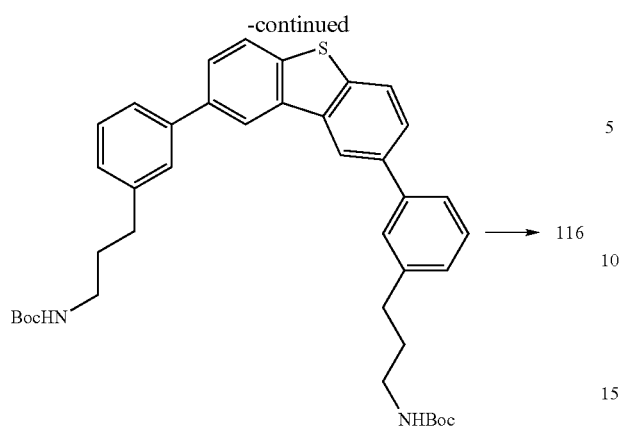

→ 116

Intermediate 2,8-di(tert-butyl 3-phenylpropylcarbamate) benzothiophene was synthesized by Suzuki reaction of 2,8-dibromodibenzothiophene and tert-butyl 3-(3-(4,4,5,5-tetramethyl-1,3,2-dioxaborolan-2-yl)phenyl)propylcarbamate, which was obtained from tert-butyl 3-(3-bromophenyl)propylcarbamate. Compound 116 was obtained following similar de-protection reaction condition in route 2.

Compounds 133-141 can be prepared based upon the above synthesis schemes, as well as the synthesis schemes shown below, using routine experimentation and knowledge of one skilled in the art.

Compound 133

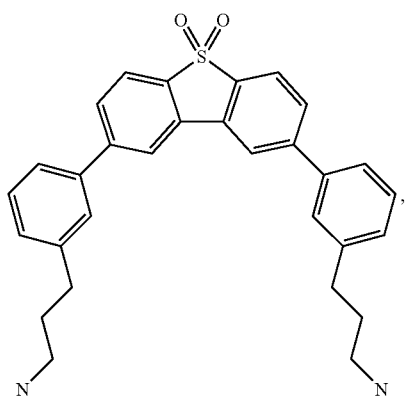

Compound 134

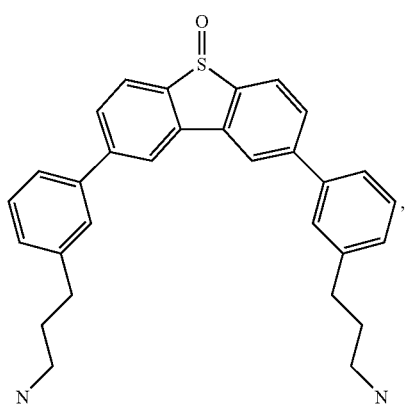

168

-continued

Compound 135

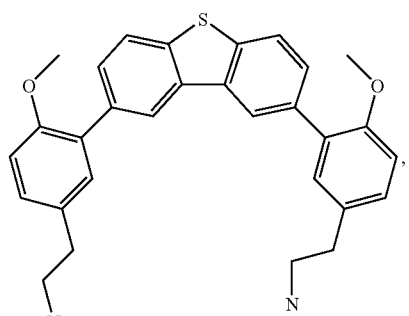

Compound 136

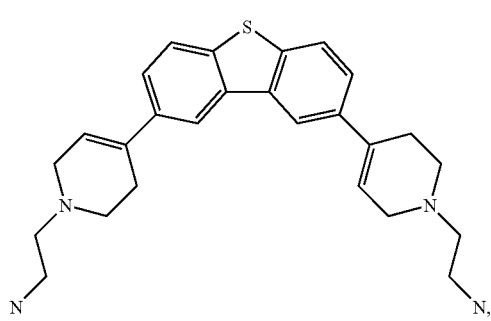

Compound 137

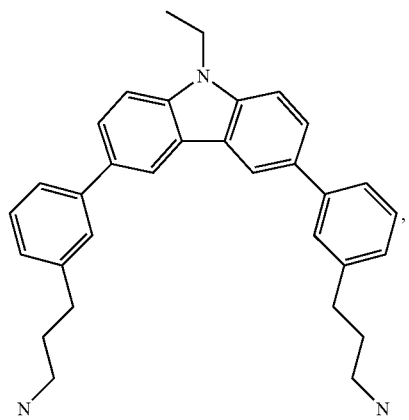

Compound 138

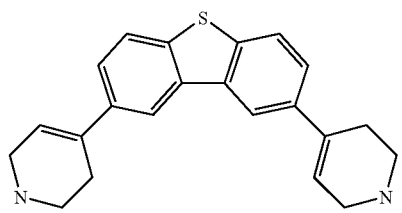

Compound 139
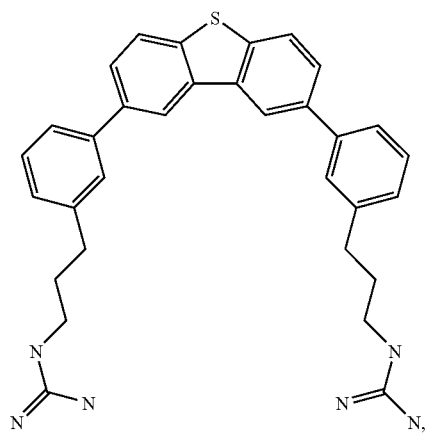
Compound 140
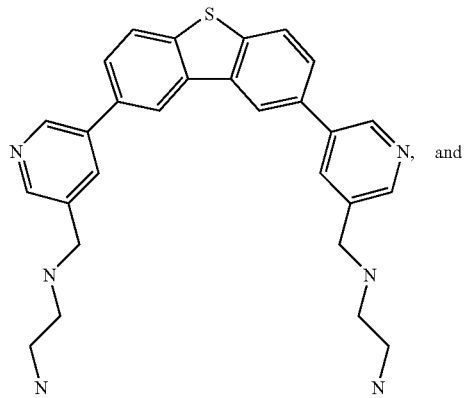
and
Compound 141
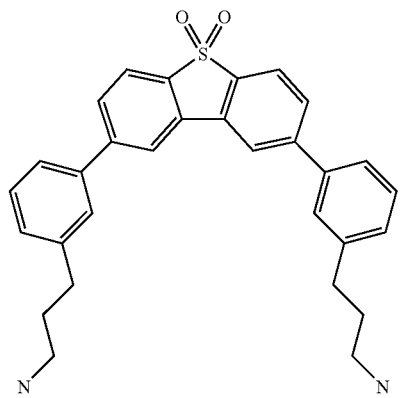
Compound 133 Scheme
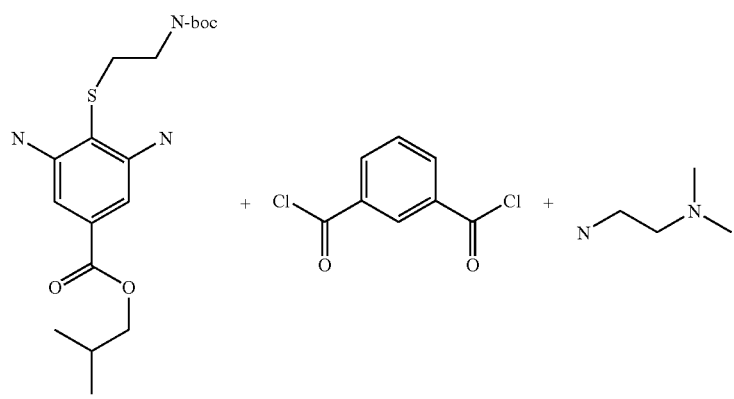
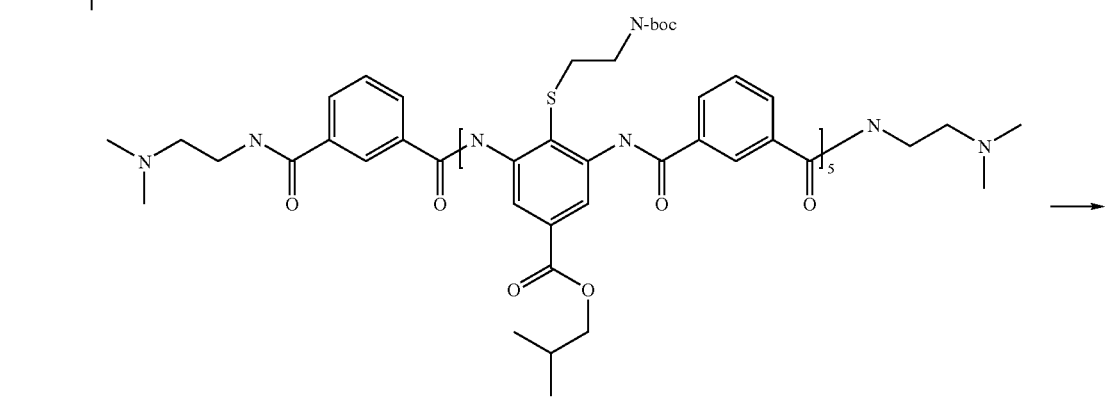

171 172
-continued
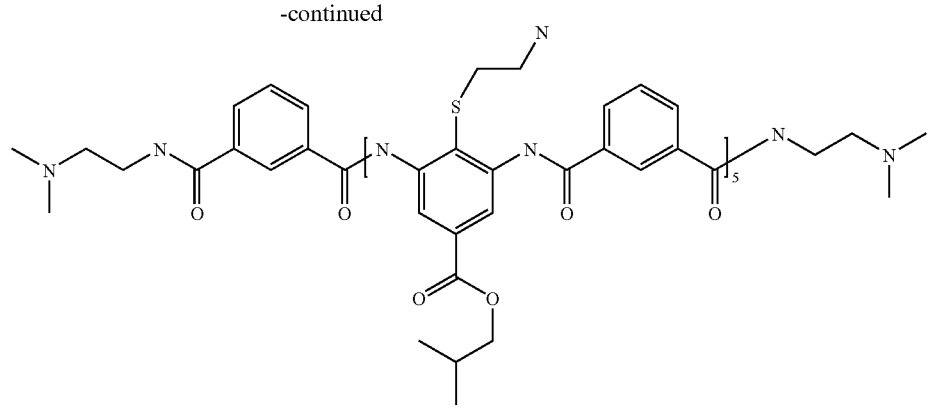
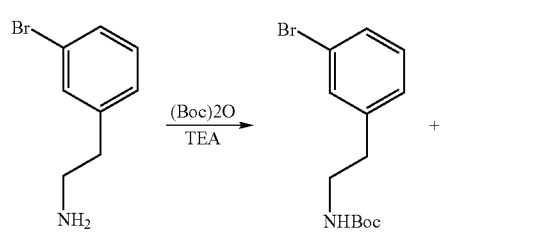
Compound 134 Scheme
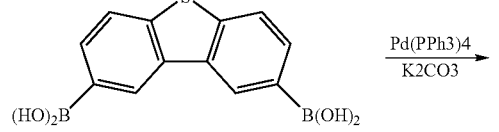
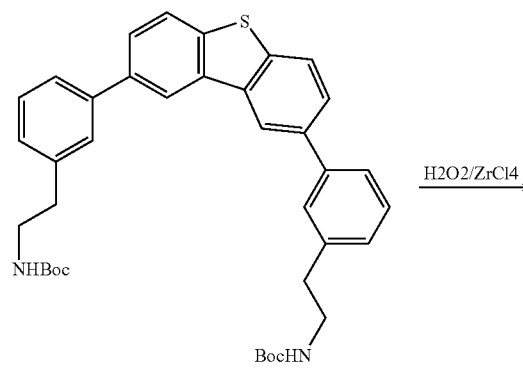
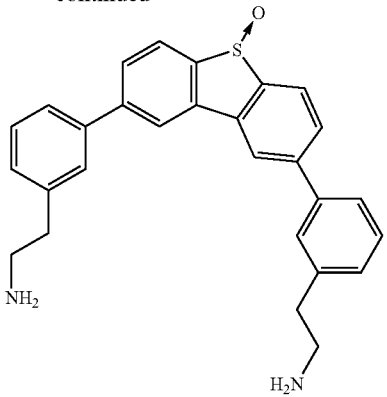
Compound 135 Scheme
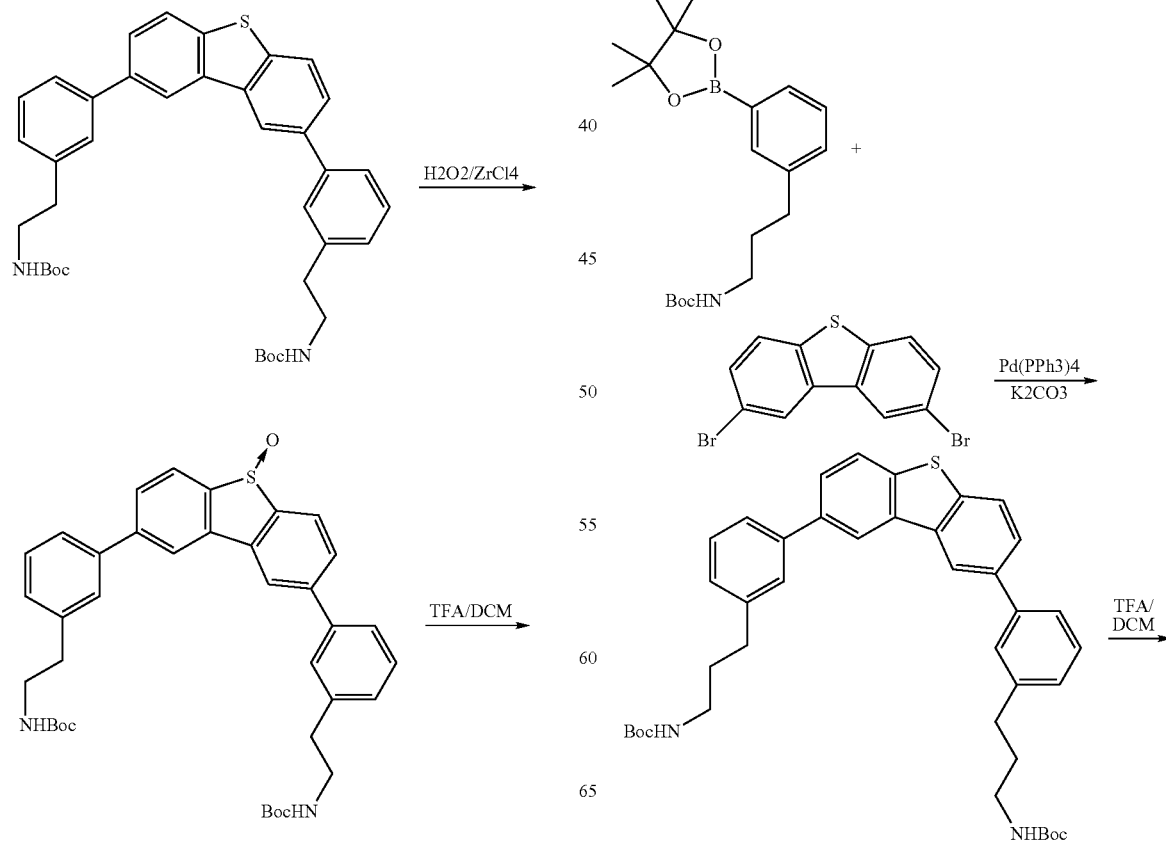

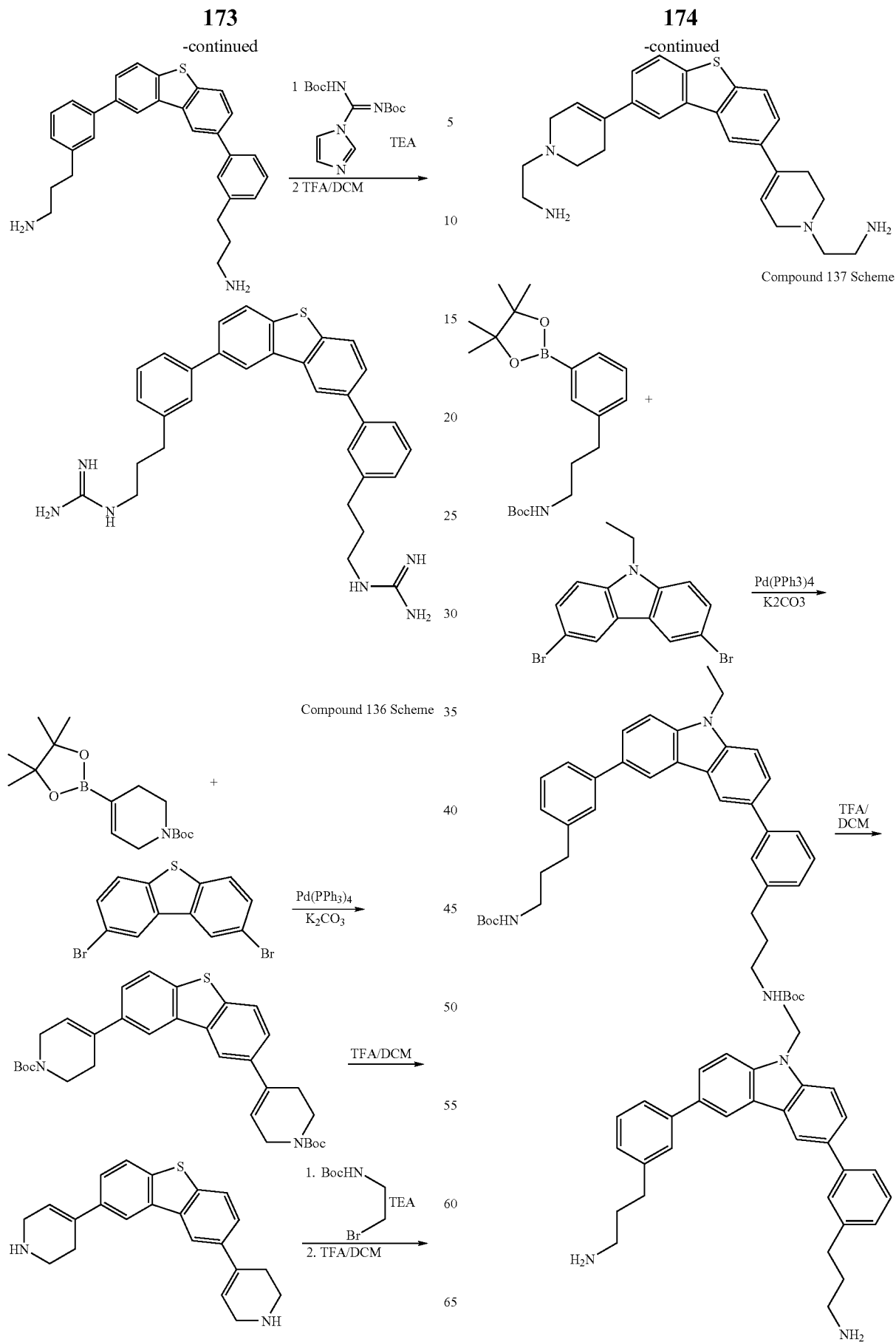

Compound 138 Scheme
Compound 140 Scheme
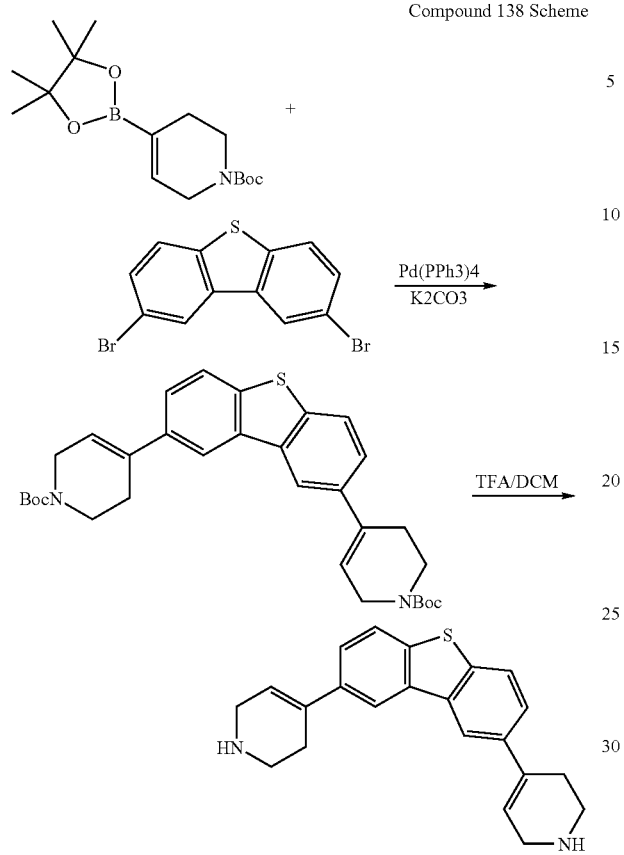
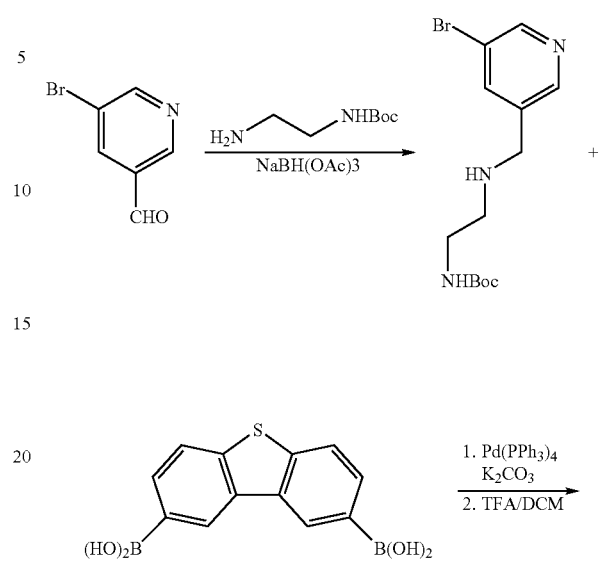
Compound 139 Scheme
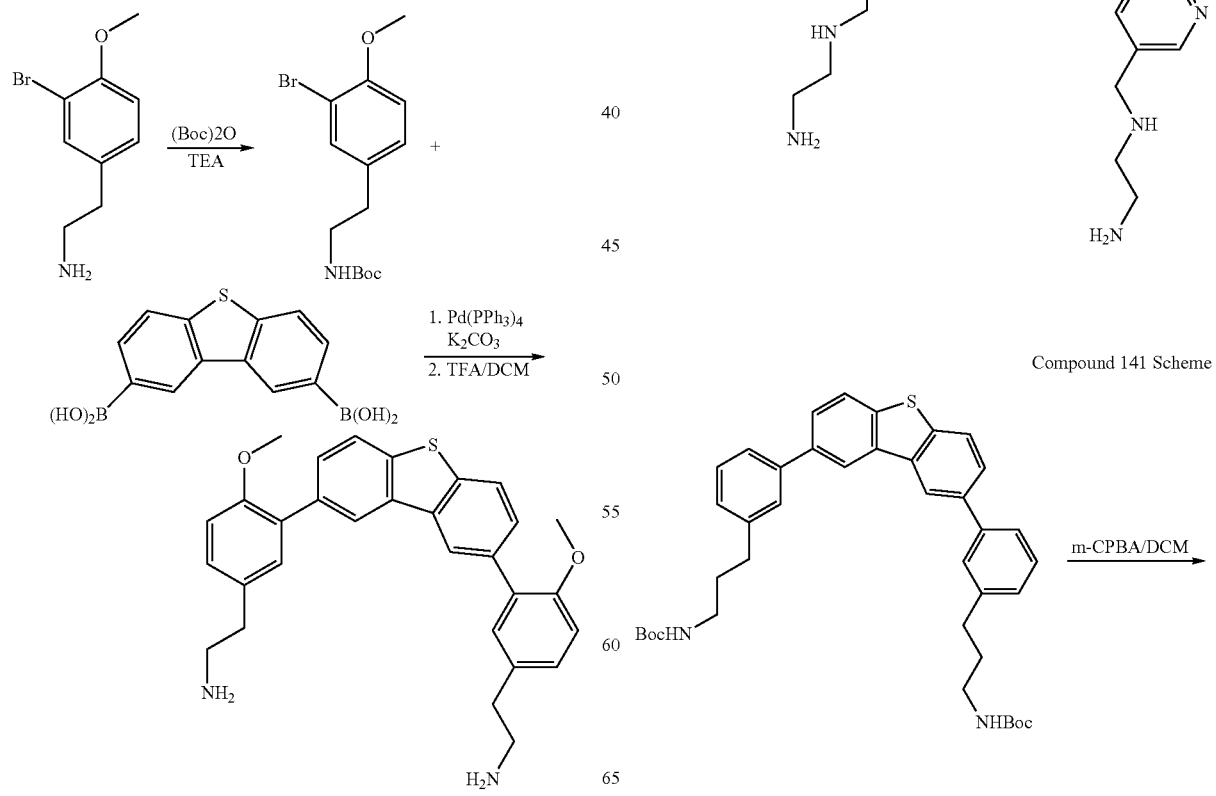
Compound 141 Scheme

177

-continued

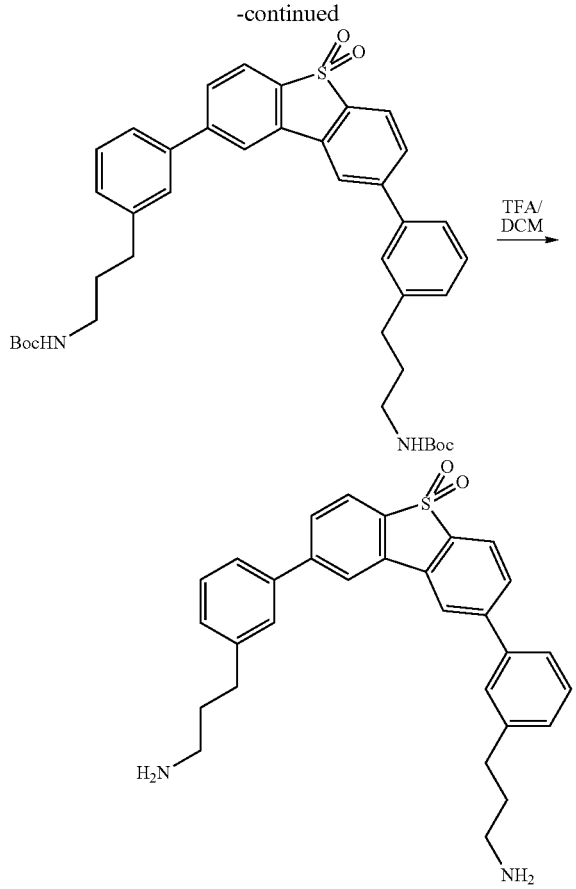

178

Example 16

Synthesis of Compound 106

Following similar procedure in route 2 of compound 116, compound 106 was synthesized in 45% overall yield as a white solid.

Example 17

Synthesis of Compounds 110, 117, 118, 119, 131, and 132

Following similar procedure in route 3 of compound 116, compounds 110, 117, 118, 119, 131, and 132 were obtained in 68%, 40%, 20%, 22%, 71%, and 15% overall yield, respectively.

Example 18

Synthesis of Compound 130

Following similar procedure in route 1 of compound 116, compound 130 was obtained in 7% overall yield.

Example 19

Synthesis of Compound 120

2,8-dibromodibenzo[b,d]furan was synthesized by bromination in 29% yield. Following similar procedure in route 3, compound 120 was obtained in 69% after two-step reaction.

Example 20

Synthesis of Compounds 154-156

Compound 156

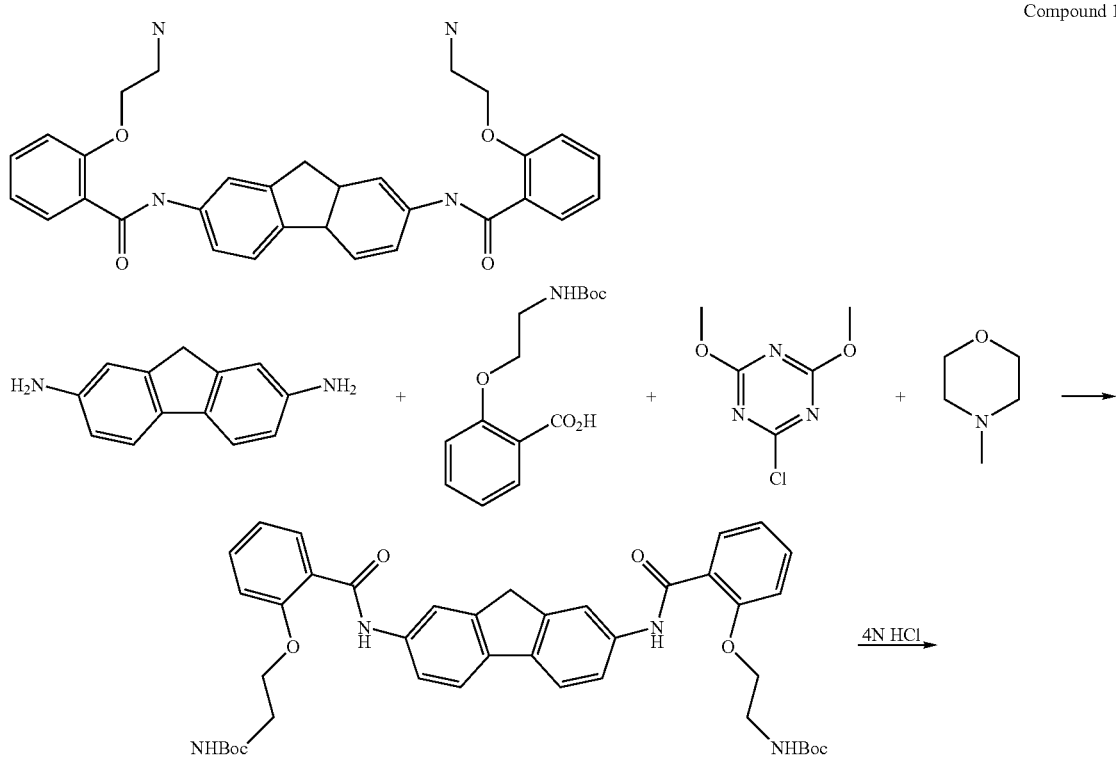

-continued

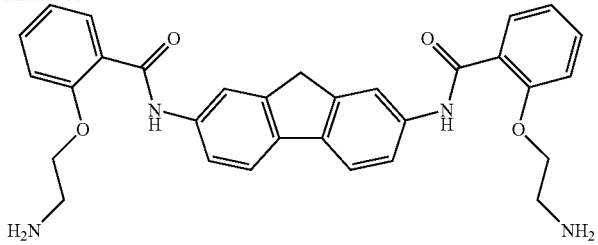

1.77 gram 2-Chloro-4,6-dimethoxy-1,3,5-triazine was stirred in anhydrous 50 ml THF. 2.02 gram N-Methylmorpholine was added. The resulting mixture was stirred at room temperature for 30 minutes. Then Bis-aniline and salicylic acid were added. The mixture was stirred at room temperature for 24 hours. Then the solvent was evaporated completely in vacuum. Water was added and the mixture was stirred for 4 hours. The solid precipitate was collected and dried in the vacuum. Then it was purified by crystallization with DCM and hexane. The Boc-protected compound was deprotected using 4N HCl dioxane solution overnight at room temperature.

Compounds 154 and 155 can be prepared based upon the above synthesis scheme, as well as the two synthesis schemes shown below, using routine experimentation and knowledge of one skilled in the art.

Compound 154

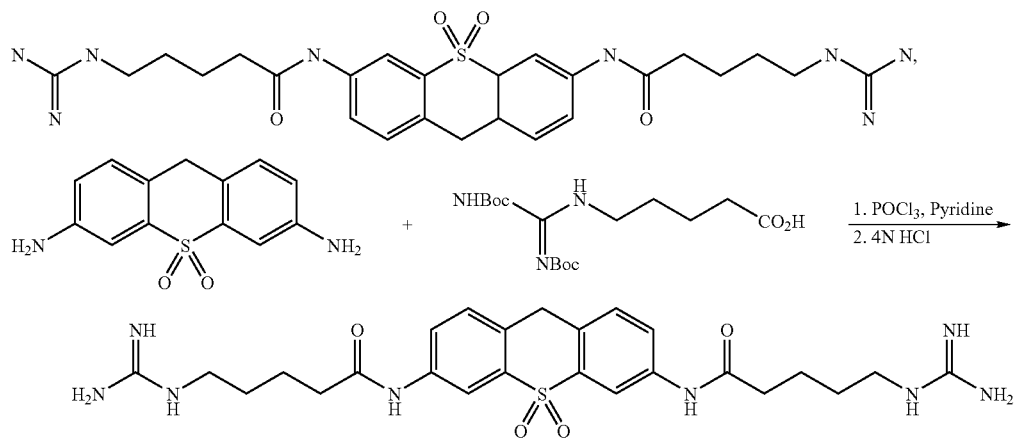

Compound 155

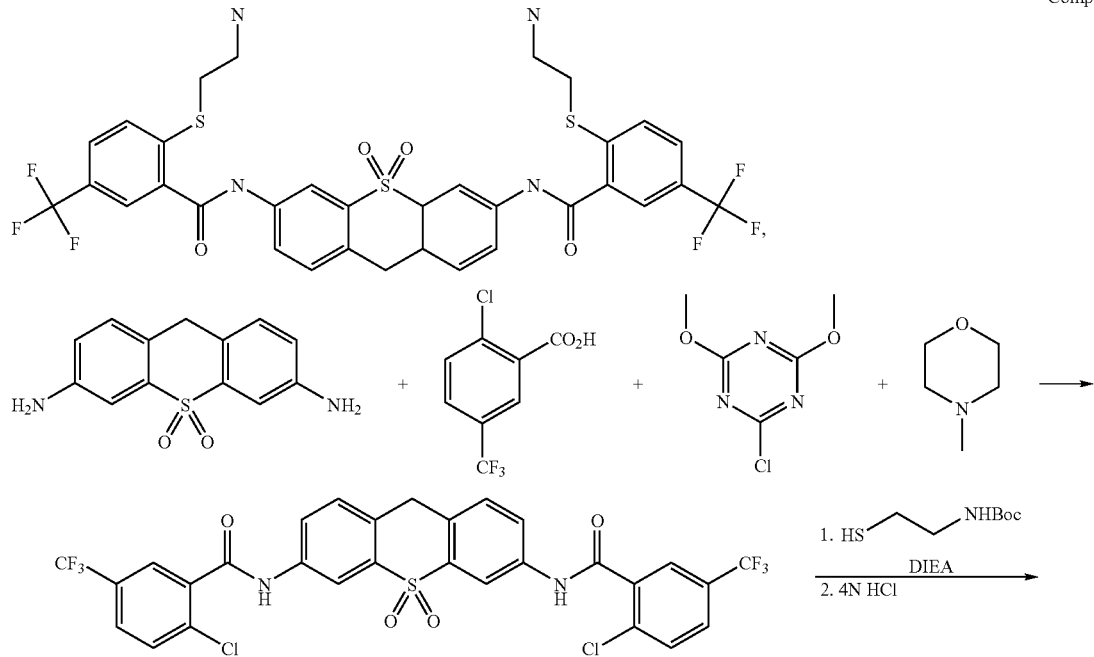

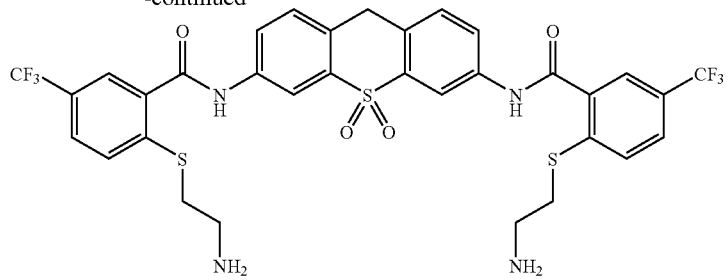
Example 21
Synthesis of Compound 115
Compound 115
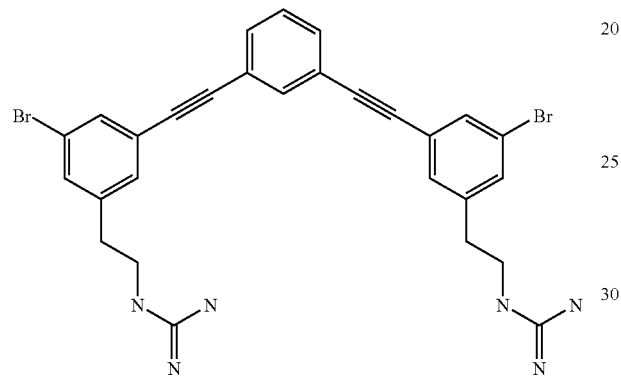
Compound 115 can be prepared based upon the synthesis scheme shown below, using routine experimentation and knowledge of one skilled in the art.
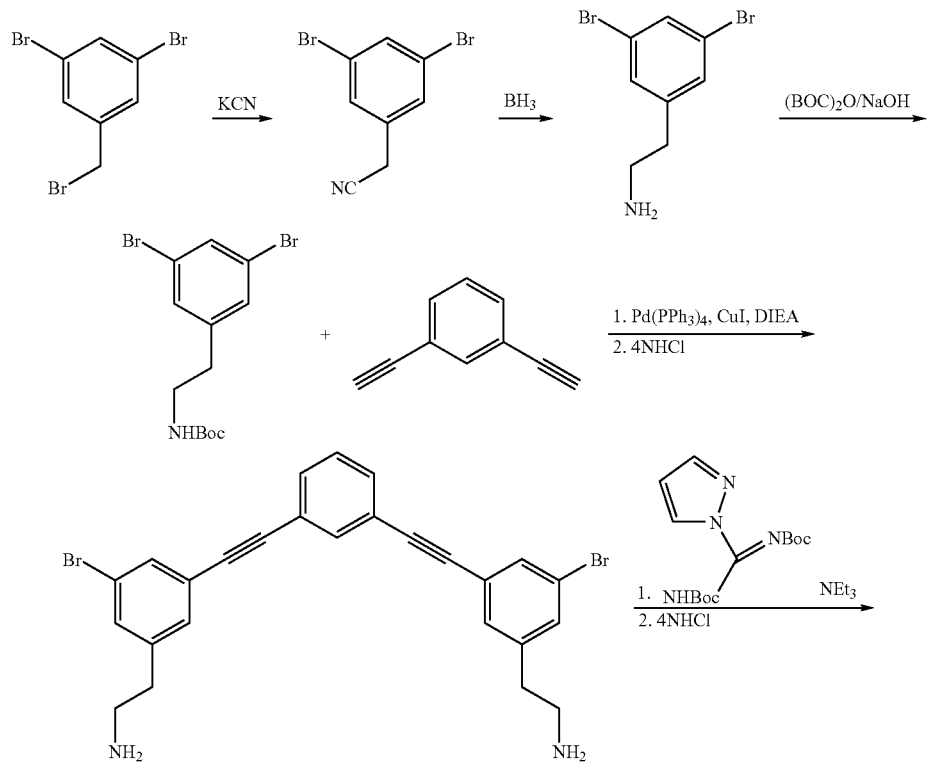

-continued

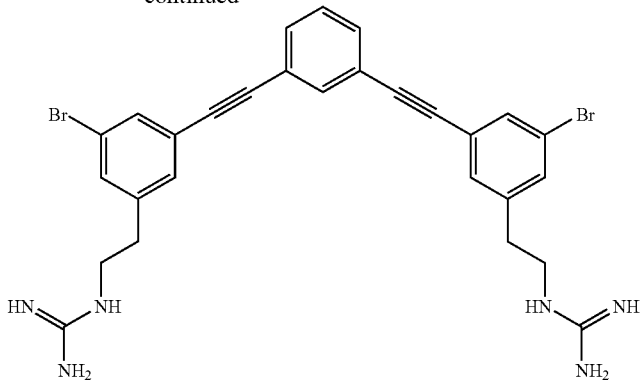

Recognizing the significant therapeutic limitations of peptides, a series of nonpeptidic mimics of these AMPs (SMAMPs) have been developed that represent a novel and powerful therapy against many microbes including, for example, malaria. A number of small molecules, sequence-specific oligomers, and polymers SMAMPs have been designed herein that have robust in vivo activity against *Staphyococcal aureus* in mouse models, suggesting a novel approach to the development of novel therapeutics. Six of these SMAMPs have been tested and demonstrated to kill *P. falciparum* parasites in culture with a range of $IC_{50}$s from 50 nM to 3 µM.

The present approach has several advantages. Anti-microbial peptides have remained an effective weapon against bacterial infection over evolutionary time indicating that their mechanism of action thwarts bacterial responses that lead to resistance against toxic substances. This premise is supported by direct experimental data showing that no appreciable resistance to the action of the anti-microbial peptides occurs after multiple serial passages of bacteria in the presence of sublethal concentrations of the peptides. Thus, targeting parasite membranes rather than proteins represents a highly innovative and novel approach to treating parasitic diseases and distinguishes the present invention from most others in this field.

To more fully evaluate the effects of SMAMP inhibitors on parasite growth through an entire life cycle, cytotoxic/cytostatic growth assays are performed. A synchronized population of parasites can be pulsed with the active SMAMPs for 8 hours during the ring, trophozoite, or schizont stages. The inhibitors can then removed by washing parasites and then parasites can be allowed to finish their cycle. To estimate successful parasite growth, a quantitative growth assay using luciferase expressing parasites can be used. The static effects can be differentiated from toxic effects and the timing of action of these compounds can be determined.

Morphological phenotypes arising from inhibition can be determined. All inhibitors can be evaluated using *P. falciparum* parasites in a culture model of the erythrocytic cycle. Phenotypes for all parasite treatments can be analyzed using Giemsa staining and standard light microscopy. After determining the timing of parasite death, time lapse DIC/fluorescent microscopy can be used to determine that after addition of SMAMPs, the plasma membrane becomes compromised. *P. falciparum* parasites expressing cytoplasmic GFP can be used to allow for the visualization of leakage of cytoplasmic contents after addition of SMAMPs.

To investigate the potential for parasites to develop resistance against the antiparasitic activity of the AMP compounds, *P. falciparum* can be serially passaged in $0.25 \times EC_{50}$, $0.5 \times EC_{50}$ and the $EC_{50}$ concentrations of the top three AMP compounds. Resulting $EC_{50}$ values can be determined at each passage for each inhibitor. As a control, parallel cultures can also be exposed to 0.5 $EC_{50}$ concentrations of the antifolate WR99210 and/or pyrimethamine, two well established antiparasitic agents for which resistance has been reported. If parasites that are resistant to SMAMPs are generated, tiling microarrays (REF) can be used to help determine any genes that contribute to resistance.

SMAMPs can be designed that can be used to probe mechanisms of action and resistance, and compounds that are active in vivo can be obtained. A very good correlation between the toxicity to mammalian cells and the overall hydrophobicity of the molecule has been observed. The activity against a particular bacterium has correlated with the overall amphiphilicity of the molecule as well as hydrophobicity, so long as the charge of the molecule was kept constant.

Example 22

Anti-protozoan Activity vs a Malarial Parasite

Seven compounds with diverse structures were screened in vitro against the malarial agent *Plasmodium falciparum*. *P. falciparum* is a protozoan parasite and is the infectious agent for the most prevalent and deadly forms of malaria. It accounts for 80% of all human malarial infections and 90% of deaths. More than 120 million clinical cases of malaria and between 1 to 1.5 million deaths occur worldwide every year. There is no vaccine for malaria and current therapies are plagued by rapid resistance which has become endemic in certain regions of the world. Several anti-microbial peptides possess anti-parasitic activities and appear to kill the parasites by interacting with the plasma membrane causing excessive permeability, lysis and death. Specificity for the parasite versus mammalian host cells is attributed to differences in phospholipid content and the lack of cholesterol in the protozoan membrane.

Anti-parasitic activities were measured in vitro using a human red blood cell assay. A single *P. falciparum* organism typically infects an erythrocyte and produces 24 progeny within 48 hours following infection. The progeny are released and rapidly infect neighboring red blood cells. The seven compounds (Table 1) were first screened at a single concentration and 6 of the 7 compounds killed *P. falciparum* progeny at a 10 µM concentration. Four of the active compounds were tested further to determine $IC_{50}$ and $IC_{100}$ values, or minimum concentrations resulting in 50% and 100% killing, respectively. Observations were also made during the 48 hour incubation period to assess the susceptibility of the parasite during lifecycle stages inside and outside the host erythrocyte. Two compounds, Compound 116 and Compound 107 possess sub-µM killing activities and Compound 116 potently kills with an $IC_{50}$ of 0.05 µM. Observations made during the infection cycle revealed that only parasitic organisms inside the erythrocyte were visible in the presence of active compounds and no extra-cellular organisms were apparent. Together, these data indicate that the compounds are rapidly killing the protozoa between the time of release and prior to re-infection. One goal of targeting parasite membranes, rather than proteins or metabolic pathways, represents a highly innovative and novel strategy for treating parasitic diseases and distinguishes this approach from most others in this field.

TABLE 1

Susceptibility of P. falciparum to compounds

| Compound | % Kill @ 10 µM | $IC_{50}$ (µM) | $IC_{100}$ (µM) |
|---|---|---|---|
| 116 | 100 | 0.050 | 0.850 |
| 107 | 100 | 0.200 | 0.850 |
| 102 | 100 | 1.5 | 3.5 |
| 103 | 100 | 0.200 | 1.5 |
| 101 | 100 | NT | NT |
| 108 | 100 | NT | NT |
| 102 | <10 | NT | NT |

Example 23

Anti-Malarial Activity

Several compounds were screened in cultures of P. falciparum at a concentration of 1.0 or 1.5 µM and showed strong efficacy. Of the compounds tested, Compounds 106 and 107 showed the best results. Compound 106 had an $IC_{50}$ in 3D7 cells of 150 nM with a cytotoxicity of about 40-50 µM in human HepG2 cells. Compound 107 had an $IC_{50}$ in 3D7 cells of 275 nM with a cytotoxicity of about 50-100 µM in human HepG2 cells. Parasite killing generally took place between 6 to 9 hours (data not shown). Neither compound, however, was hemolytic as determined by treatment of uninfected red blood cells using a standard absorbance assay for hemoglobin release (data not shown). In addition, both compounds disrupted food vacuoles as assayed by parasites expressing a marker for the food vacuole (plasmepsin II-YFP), with food vacuole integrity measured by standard fluorescence microscopy.

Example 24

Anti-Malarial Activity

Compounds 106 and 107 were also screened in cultures of P. falciparum 3D7 and DD2 and compared to chloroquine. Flow cytometry was used for quantitation of parasitemia using SYOX Green on an LSRII. The results are shown in Table 2.

TABLE 2

| Compound | $IC_{50}$ (3D7) | $IC_{50}$ (DD2) |
|---|---|---|
| chloroquine | 20 nM | 80 nM |
| Compound 107 | 275 nM | 200 nM |
| Compound 106 | 150 nM | 100 nM |

The DD2 strain of P. falciparum is 4 times as resistant to chloroquine as the 3D7 strain. Both Compounds 106 and 107 were effective in strain DD2. Thus, these compounds are effective in chloroquire-sensitive and/or chloroquire-resistant strains.

Example 25

Anti-Malarial Activity

Numerous compounds were initially screened using a high throughput quantitative parasite growth assay that makes use of a strain of parasites expressing a cytoplasmic firefly luciferase (obtained from Dr. Kirk Deitsch, Cornell Medical College). These parasites were transfected with a vector containing the firefly luciferase gene using the malarial HRPII promoter. To grow parasites, culture dishes ranging from 96 well plates to 30 ml dishes were used. The 3D7 strain of P. falciparum for assays and transfections was primarily used because it has become the standard chloroquine sensitive reference strain and was used for the genome sequencing project. Parasites were cultured in human RBCs under an atmosphere of 5% $O_2$/7% $CO_2$/88% $N_2$ in RPMI 1640 medium supplemented with 25 mM Hepes, 30 mg/L hypoxanthine, 0.225% (w/v) $NaHCO_3$ and 0.5% (w/v) Albumax II (Life Technologies, Grand Island, N.Y.). Parasite growth was normally synchronized by a combination of serial D-sorbitol treatment for selection of ring stage parasites followed by selective purification of mature schizonts using a Super Macs II magnetic separator (Miltenyi Biotec).

A standard luminescent readout was used to measure the growth of parasites. Parasites were grown under normal conditions, lysed in the presence of the luminescence reagents (Bright Glo, Promega) and then measured. To initially test for growth, luciferase expressing parasites were synchronized using serial sorbitol treatments and then parasitemia, the percentage of RBCS infected with parasites, was adjusted using uninfected RBCs. 100 µl of total media was used in a 96 well format. Parasitized RBCs were incubated in 96 well plates at 37° C. and gassed with 5% $CO_2$, 5% $O_2$, 90% $N_2$. Parasites were allowed to grow for approximately 60 hours, until they successfully divided, ruptured and reinvaded new RBCs. At 10-15 hours post invasion, the cells were lysed, and luciferase levels were measured using an Analyst HT luminometer (Molecular Devices). Results are shown in Table 3.

TABLE 3

| Compound | $IC_{50}$ µM |
|---|---|
| Artesunate | 0.009 |
| Compound 106 | 1.153 |
| Compound 118 | 0.364 |
| Compound 119 | 1.858 |
| Compound 110 | 0.584 |
| Compound 117 | 0.301 |
| Compound 104 | >10 |
| Compound 111 | 0.587 |
| Compound 113 | 0.241 |
| Compound 112 | >10 |
| Compound 120 | 0.604 |
| Compound 121 | 1.505 |
| Compound 114 | >10 |
| Compound 102 | 5.376 |
| Compound 103 | 0.783 |
| Compound 107 | 0.314 |
| Compound 116 | 0.318 |
| Compound 101 | 0.308 |
| Compound 122 | 0.260 |
| Compound 123 | 1.366 |

TABLE 3-continued

| Compound | IC$_{50}$ μM |
|---|---|
| Compound 124 | 1.582 |
| Compound 129 | 0.832 |
| Compound 128 | 1.725 |
| Compound 127 | 1.765 |
| Compound 126 | 1.420 |
| Compound 125 | 0.286 |
| Compound 130 | 2.559 |
| Compound 131 | 0.235 |
| Compound 132 | 0.236 |
| Compound 133 | 2.028 |
| Compound 134 | 2.438 |
| Compound 135 | 0.108 |
| Compound 136 | 0.958 |
| Compound 137 | 0.604 |
| Compound 138 | 0.213 |
| Compound 139 | 1.169 |
| Compound 140 | 1.674 |
| Compound 142 | 0.063 |
| Compound 154 | 0.200 |
| Compound 149 | 0.357 |
| Compound 141 | 1.344 |
| Compound 143 | 0.258 |
| Compound 144 | 3.399 |
| Compound 145 | 0.369 |
| Compound 146 | 0.127 |
| Compound 155 | 0.535 |
| Compound 152 | 0.783 |
| Compound 153 | 0.925 |
| Compound 150 | 6.608 |
| Compound 151 | 2.784 |
| Compound 147 | 0.221 |
| Compound 148 | 0.704 |
| Compound 156 | 0.107 |

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A compound of Formula I:

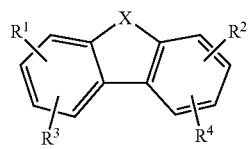

wherein:
X is N(R$^9$), O, S, S(=O), or S(=O)$_2$;
R$^9$ is H or C$_1$-C$_8$alkyl;
R$^1$ and R$^2$ are H;
R$^3$ and R$^4$ are, independently,

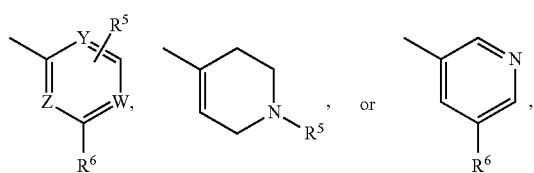

wherein each W, Y, and Z are, independently, C or N;
each R$^5$ is, independently, H or C$_1$-C$_8$alkoxy; and
each R$^6$ is, independently, the free base or salt form of —(CH$_2$)$_n$—NH$_2$, or —(CH$_2$)$_n$—NH—(CH$_2$)$_n$—NH$_2$, or —(CH$_2$)$_n$—NH—C(=NH)NH$_2$, where each n is, independently, 1 to 8;
or a pharmaceutically acceptable salt thereof.

2. The compound of claim 1 wherein X is N(R$^9$), O, S, or S(=O)$_2$.

3. The compound of claim 1 wherein R$^3$ and R$^4$ are, independently

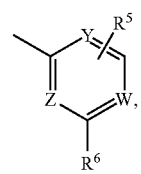

wherein each W, Y, and Z are C; or each Y and Z are C and each W is N.

4. The compound of claim 1 wherein:
X is NH, O, S, or S(=O)$_2$;
R$^1$ and R$^2$ are H;
R$^3$ and R$^4$ are, independently,

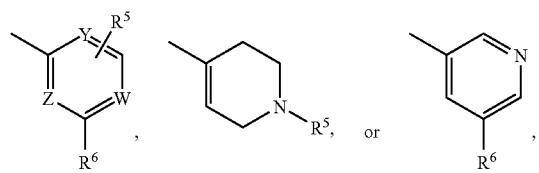

wherein each W, Y, and Z are, independently, C or N;
each R$^5$ is H; and
each R$^6$ is, independently, the free base or salt form of —(CH$_2$)$_n$—NH$_2$, where each n is, independently, 1 to 3.

5. The compounds of claim 1 chosen from:

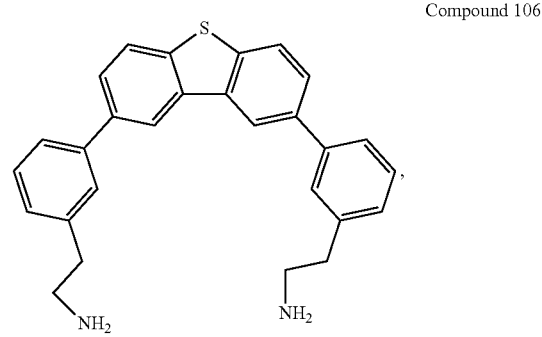

Compound 106

-continued
Compound 118
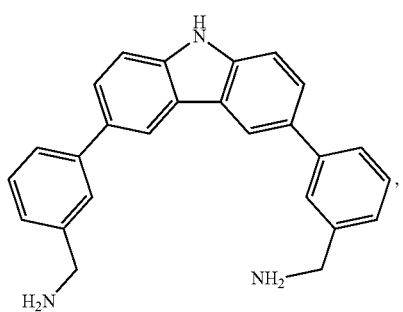
Compound 119
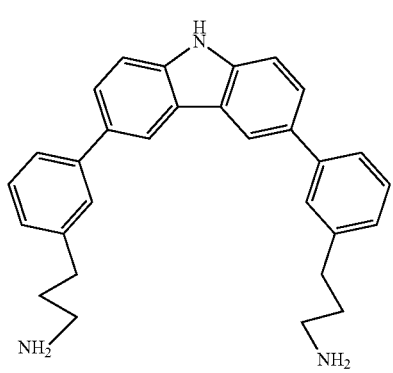
Compound 120
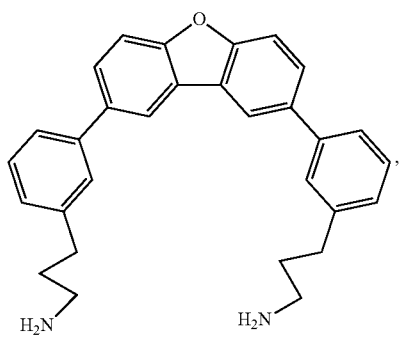
Compound 116
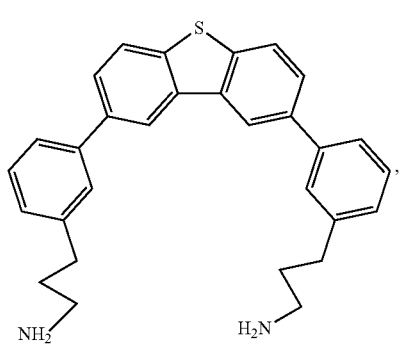
-continued
Compound 130
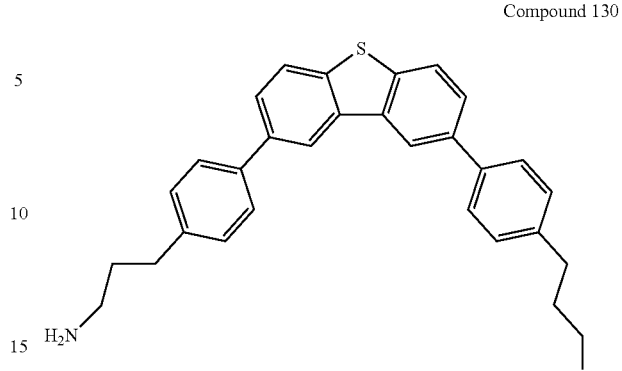
Compound 131
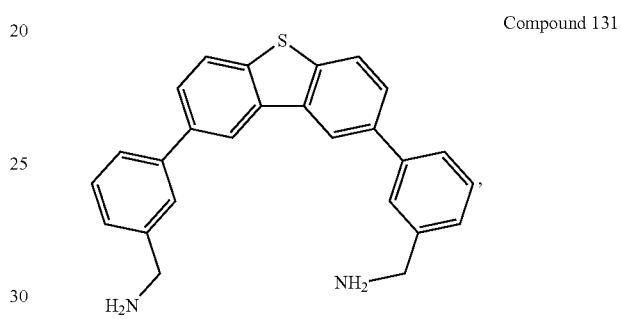
Compound 133
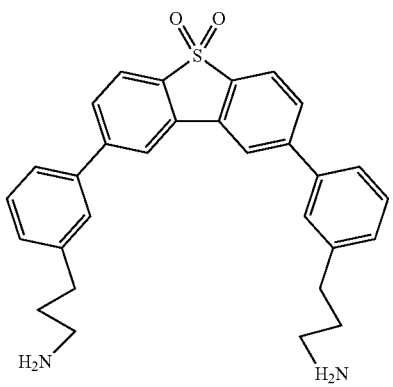
Compound 134
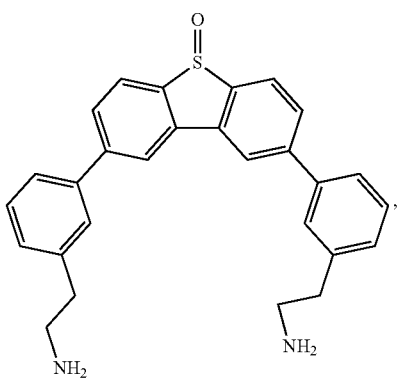

Compound 135
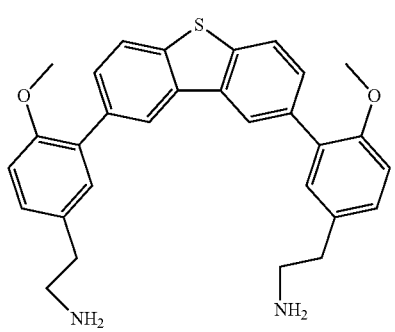
Compound 136
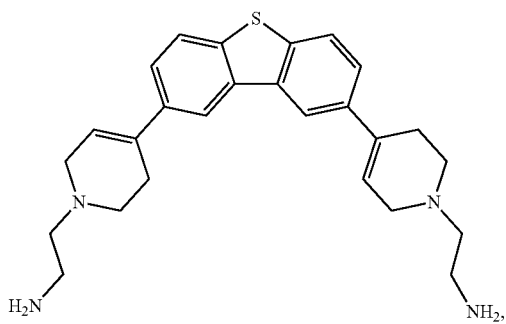
Compound 137
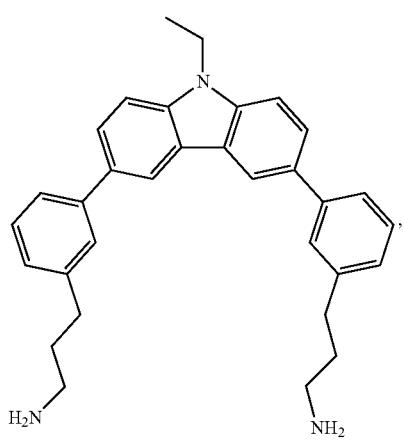
Compound 138
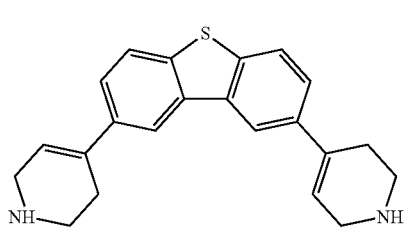
Compound 139
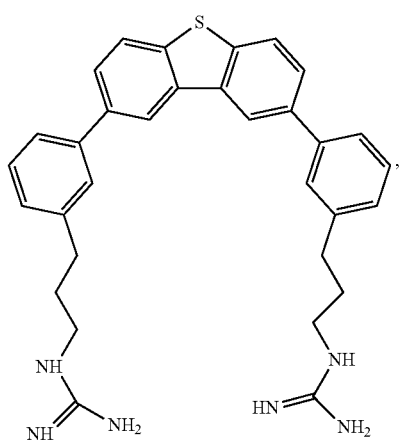
Compound 140
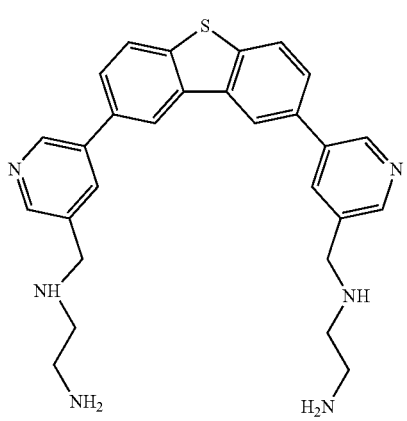
Compound 141
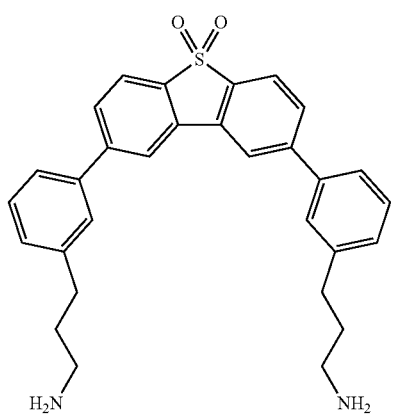
or pharmaceutically acceptable salt thereof.

6. The compound of claim 1 which is:

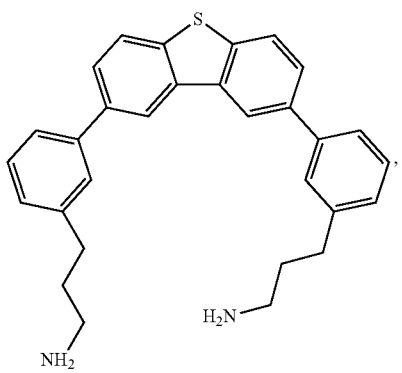

or pharmaceutically acceptable salt thereof.

7. A compound of Formula I:

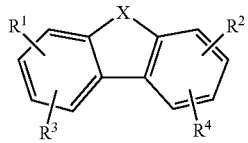

wherein:
X is NH or S;
$R^1$ and $R^2$ are H;
$R^3$ and $R^4$ are, independently,

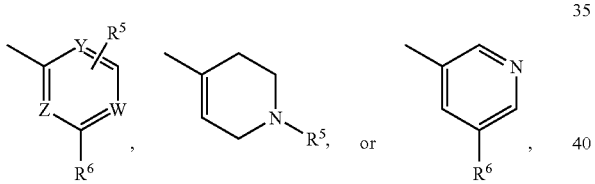

wherein each W, Y, and Z are, independently, C or N;
each $R^5$ is, independently, H or $C_1$-$C_8$alkoxy; and
each $R^6$ is, independently, heterocycle, or the free base or salt form of —$(CH_2)_n$—$NH_2$, or —$(CH_2)_n$—NH—$(CH_2)_n$—$NH_2$, or —$(CH_2)_n$—NH—C(=NH)$NH_2$, where each n is, independently, 1 to 8;
or a pharmaceutically acceptable salt thereof.

8. The compound of claim 7 which is

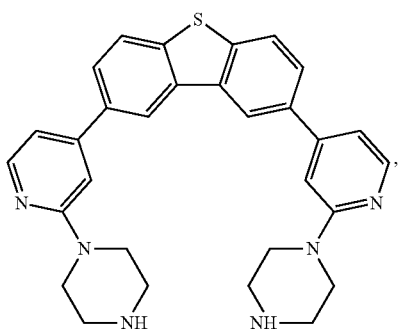 [SMILES: c1cc(-c2ccc3sc4ccc(-c5ccnc(N6CCNCC6)c5)cc4c3c2)cc(N2CCNCC2)n1]

or a pharmaceutically acceptable salt thereof.

9. A compound of Formula I:

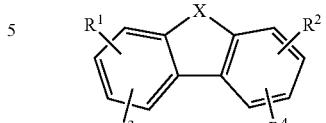

wherein:
X is N($R^9$), O, S, S(=O), or S(=O)$_2$;
$R^9$ is H or $C_1$-$C_8$alkyl;
$R^1$ and $R^2$ are H;
$R^3$ and $R^4$ are, independently,

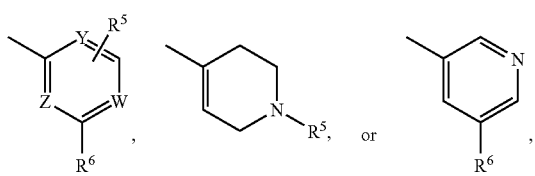

wherein each W, Y, and Z are, independently, C or N;
each $R^5$ is, independently, H or $C_1$-$C_8$alkoxy; and
each $R^6$ is piperazinyl or the free base or salt form of —$(CH_2)_n$—$NH_2$ where each n is, independently, 1 to 3.

10. A compound of Formula I:

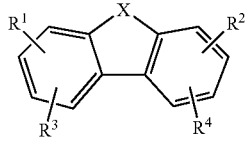

wherein:
X is NH, O, or S;
$R^1$ and $R^2$ are H;
$R^3$ and $R^4$ are

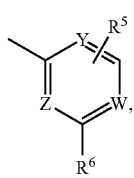

where each Z and Y are C, and each W is N; or each W, Y, and Z are C; each $R^5$ is H, and each $R^6$ is piperazinyl or the free base or salt form of —$(CH_2)_n$—$NH_2$, where each n is, independently, 1 to 3.

11. A pharmaceutical composition comprising the compound

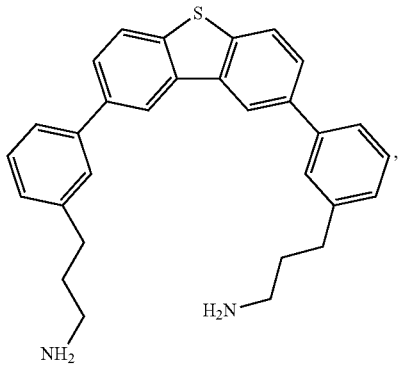 [SMILES: NCCCc1cccc(-c2ccc3sc4ccc(-c5cccc(CCCN)c5)cc4c3c2)c1]

or pharmaceutically acceptable salt thereof, and a pharmaceutically acceptable carrier.

12. A method of treating malaria in an animal or killing or inhibiting the growth of a *Plasmodium* species comprising administering to the animal a therapeutically effective amount of a compound of Formula I or contacting the species with an effective amount of a compound of Formula I:

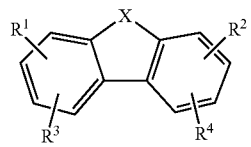

wherein:
X is $N(R^9)$, O, S, $S(=O)$, or $S(=O)_2$;
$R^9$ is H, $C_1$-$C_8$alkyl, $C_1$-$C_8$alkoxy, halo, OH, or $CF_3$;
$R^1$ and $R^2$ are, independently, H, $C_1$-$C_8$alkyl, $C_1$-$C_8$alkoxy, halo, OH, halo$C_1$-$C_8$alkyl, or CN;
$R^3$ and $R^4$ are, independently,

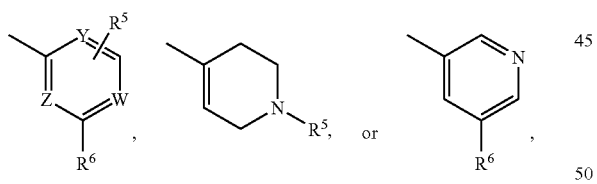

wherein each W, Y, and Z are, independently, C or N;
each $R^5$ and each $R^6$ are, independently, H, $C_1$-$C_8$alkyl, $C_1$-$C_8$alkoxy, halo, OH, $CF_3$, aromatic group, heterocycle, or the free base or salt form of —$(CH_2)_n$—$NH_2$, —$(CH_2)_n$—NH—$(CH_2)_n$—$NH_2$, or —$(CH_2)_n$—NH—C(=NH)$NH_2$, where each n is, independently, 1 to 8;
or a pharmaceutically acceptable salt thereof.

13. The method of claim 12 wherein X is $N(R^9)$, O, S, or $S(=O)_2$.

14. The method of claim 12 wherein $R^1$ and $R^2$ are, independently, H, $C_1$-$C_3$alkyl, $C_1$-$C_3$alkoxy, halo, OH, halo$C_1$-$C_3$alkyl, or CN.

15. The method of claim 12 wherein each $R^5$ is, independently, H, $C_1$-$C_8$alkyl, $C_1$-$C_8$alkoxy, halo, OH, $CF_3$, or the free base or salt form of —$(CH_2)_n$—$NH_2$, —$(CH_2)_n$—NH—$(CH_2)_n$—$NH_2$, or —$(CH_2)_n$—NH—C(=NH)$NH_2$, where each n is, independently, 1 to 8, and each $R^6$ is, independently, heterocycle or the free base or salt form of —$(CH_2)_n$—$NH_2$, —$(CH_2)_n$—NH—$(CH_2)_n$—$NH_2$, or —$(CH_2)_n$—NH—C(=NH)$NH_2$, where each n is, independently, 1 to 8.

16. The method of claim 12 wherein:
X is NH, O, S, or $S(=O)_2$;
$R^1$ and $R^2$ are H;
$R^3$ and $R^4$ are, independently,

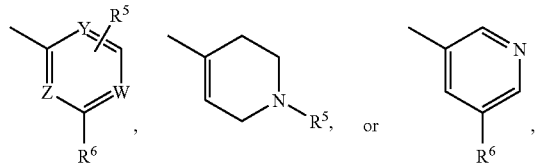

wherein each W, Y, and Z are, independently, C or N; and each $R^5$ and each $R^6$ are, independently, H, heterocycle, or the free base or salt form of —$(CH_2)_n$—$NH_2$, where each n is, independently, 1 to 3.

17. The method of claim 12 wherein the malaria is chloroquine-sensitive or chloroquine-resistant.

18. The method of claim 12 wherein the compound is chosen from:

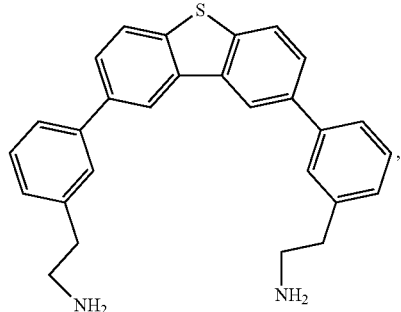

Compound 106

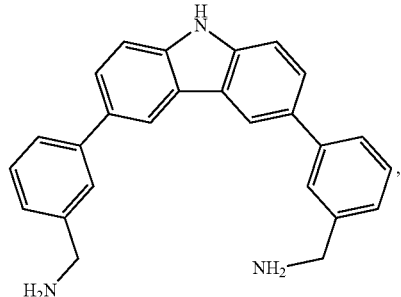

Compound 118

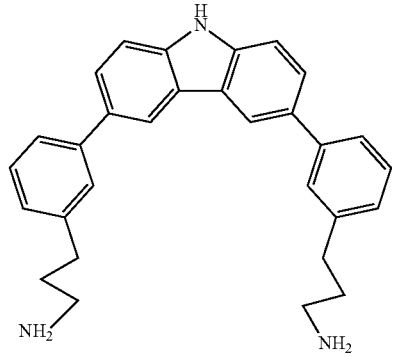

Compound 119

Compound 110
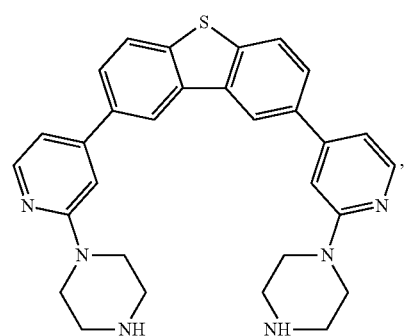
Compound 117
Compound 120
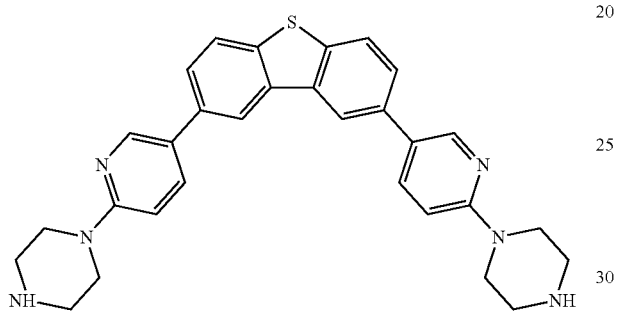
Compound 116
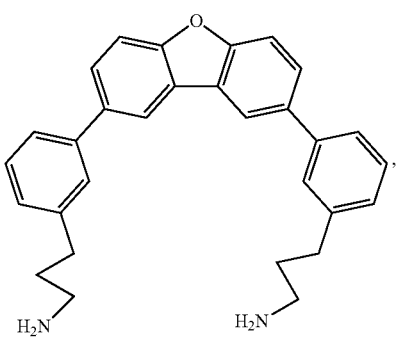
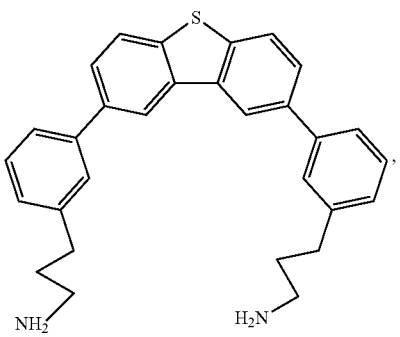
Compound 130
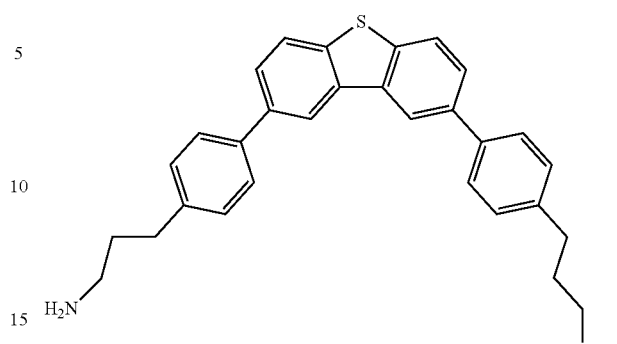
Compound 131
Compound 132
Compound 133
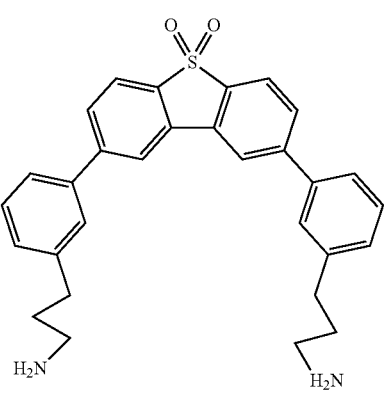

-continued
Compound 134
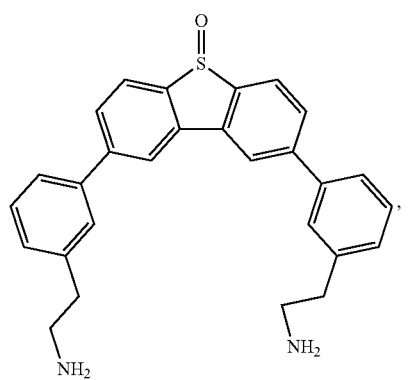
Compound 135
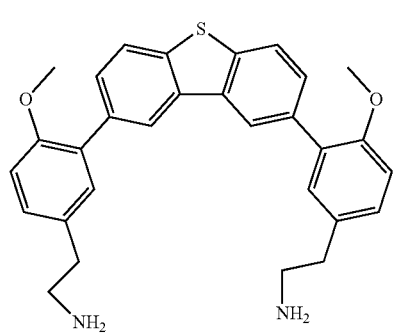
Compound 136
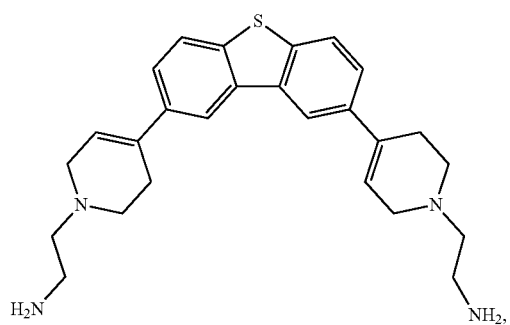
Compound 137
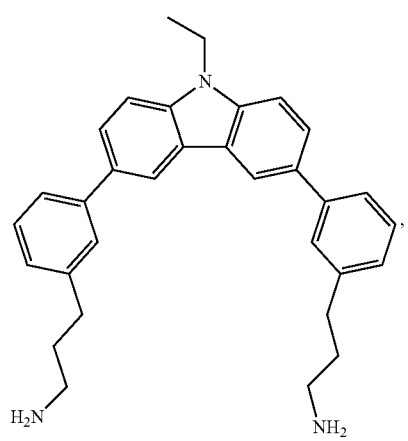
-continued
Compound 138
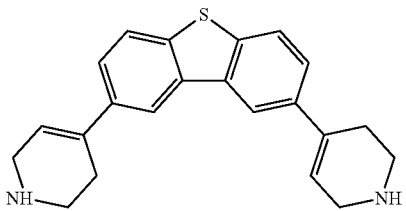
Compound 139
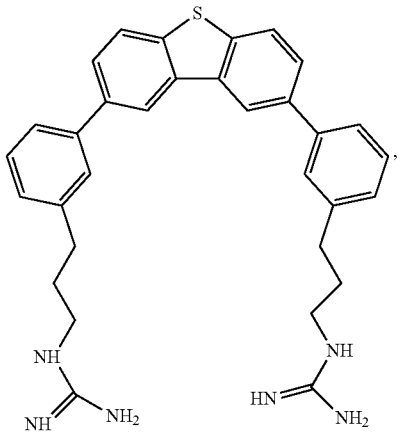
Compound 140
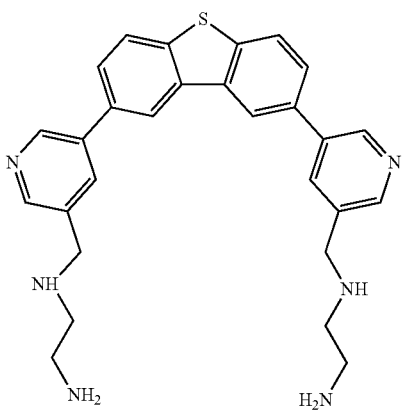
Compound 141
or pharmaceutically acceptable salt thereof.

19. The method of claim 12 wherein the compound is:

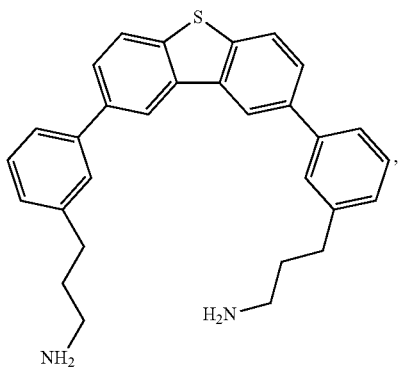

or pharmaceutically acceptable salt thereof.

20. The method of claim 12 wherein:

X is $N(R^9)$, O, S, S(=O), or $S(=O)_2$;
$R^9$ is H or $C_1$-$C_8$alkyl;
$R^1$ and $R^2$ are H;
$R^3$ and $R^4$ are, independently,

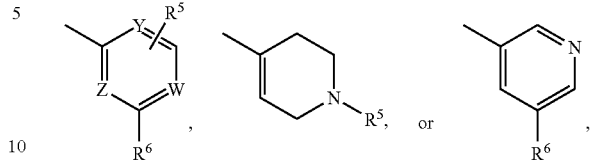

wherein each W, Y, and Z are, independently, C or N; each $R^5$ is, independently, H or $C_1$-$C_8$alkoxy; and each $R^6$ is, independently, the free base or salt form of —(CH$_2$)$_n$—NH$_2$, or —(CH$_2$)$_n$—NH—(CH$_2$)$_n$—NH$_2$, or —(CH$_2$)$_n$—NH—C(=NH)NH$_2$, where each n is, independently, 1 to 8;

or a pharmaceutically acceptable salt thereof.

\* \* \* \* \*

UNITED STATES PATENT AND TRADEMARK OFFICE
CERTIFICATE OF CORRECTION

| | | |
|---|---|---|
| PATENT NO. | : 8,796,275 B2 | Page 1 of 1 |
| APPLICATION NO. | : 12/510593 | |
| DATED | : August 5, 2014 | |
| INVENTOR(S) | : Scott et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 597 days.

Signed and Sealed this
Fifteenth Day of March, 2016

Michelle K. Lee
*Director of the United States Patent and Trademark Office*